US011618926B2

(12) United States Patent
Goel et al.

(10) Patent No.: US 11,618,926 B2
(45) Date of Patent: Apr. 4, 2023

(54) METHODS FOR DIAGNOSING, PROGNOSING, AND TREATING COLORECTAL CANCER USING BIOMARKER EXPRESSION

(71) Applicant: BAYLOR RESEARCH INSTITUTE, Dallas, TX (US)

(72) Inventors: Ajay Goel, Dallas, TX (US); Raju Kandimalla, Dallas, TX (US); Shusuke Toden, Dallas, TX (US); Roshni Roy, Baltimore, MD (US); Tsuyoshi Ozawa, Dallas, TX (US); Takatoshi Matsuyama, Dallas, TX (US); Wenhao Weng, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 440 days.

(21) Appl. No.: 16/489,597

(22) PCT Filed: Feb. 28, 2018

(86) PCT No.: PCT/US2018/020191
§ 371 (c)(1),
(2) Date: Aug. 28, 2019

(87) PCT Pub. No.: WO2018/160675
PCT Pub. Date: Sep. 7, 2018

(65) Prior Publication Data
US 2020/0140953 A1    May 7, 2020

Related U.S. Application Data

(60) Provisional application No. 62/464,781, filed on Feb. 28, 2017.

(51) Int. Cl.
*C12Q 1/6886*    (2018.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2012/0108446 | A1* | 5/2012 | Wu | C12Q 1/6886 435/6.12 |
| 2015/0238564 | A1 | 8/2015 | Lee et al. | |
| 2016/0090636 | A1 | 3/2016 | Ju et al. | |

FOREIGN PATENT DOCUMENTS

WO    WO 2014/145612    *  9/2014

OTHER PUBLICATIONS

Figueredo (Cochrane Database of Systemic Reviews 2008 Issue 3 Art No. CD005390).*
Slattery (Carcinogenesis 2016 vol. 37 No. 3 pp. 245-261, advance access publication Jan. 6, 2016).*
Wu (Molecular Cancer 2013 12:30 pp. 1-11).*
Bovell (Proceedings of the 101st Annual Meeting of the American Association for Cancer Research; Apr. 17-21, 2010; Washington DC. AACR; Cancer Res 2010;70(8Suppl):abstract 4037).*
Pinchler (Clin Cancer Res 23(5) 1323-33).*
Guo (Am J Cancer Res 2016;6(11):2463-2475).*
Wang (Med Oncol 2012 29:919-927).*
Liu (Biomedicine & Pharmacotherapy 69 2015 214-220).*
Aragane, et al., "Chromosomal Aberrations in Colorectal Cancers and Liver Metastases Analyzed by Comparative Genomic Hybridization," *International Journal of Cancer*, 94: 623-629, 2001.
Cheng, et al., "piRNA, The New Non-Coding RNA, Is Aberrantly Expressed in Human Cancer Cells," *Clinica Chimica Acta International Journal of Clinical Chemistry and Diagnostic Laboratory Medicine*, 412(17-18): 1621-1625, 2011.
Douglas, et al., "Array Comparative Genomic Hybridization Analysis of Colorectal Cancer Cell Lines and Primary Carcinomas," *Cancer Research*, 64(14): 4817-4825, 2004.
Ghadimi, et al., "Gain of Chromosome 8q23-24 is a Predictive Marker for Lymph Node Positivity in Colorectal Cancer," *Clinical Cancer Research*, 9(5): 1808-1814, 2003.
Gibb, et al., "The Functional Role of Long Non-Coding RNA in Human Carcinomas," *Molecular Cancer*, 10: 38, 2011.
Grisanzio & Freeman, "Chromosome 8q24-Associated Cancers and MYC," *Genes & Cancer*, 1(6): 555-559, 2010.
Han, et al., "MicroRNA-29c Mediates Initiation of Gastric Carcinogenesis by Directly Targeting ITGB1," *Gut*, 64(2): 203-214, 2015.
Hur, et al., "Identification of a Metastasis-Specific MicroRNA Signature in Human Colorectal Cancer," *Journal of the National Cancer Institute*, 107(3): 1-11, 2015.
International Preliminary Report on Patentability Issued in Corresponding PCT Patent Application No. PCT/US2018/020191, dated Sep. 3, 2019.
International Search Report and Written Opinion Issued in Corresponding PCT Patent Application No. PCT/US2018/020191, dated Jul. 30, 2018.
Kim, et al., "Long-Range Interaction and Correlation Between MYC Enhancer and Oncogenic Long Noncoding RNA CARLo-5," *PNAS*, 111(11): 4173-4178, 2014.

(Continued)

*Primary Examiner* — Amanda Haney
(74) *Attorney, Agent, or Firm* — Norton Rose Fulbright US LLP

(57) ABSTRACT

Dysregulated expression of microRNAs (miRNAs) has emerged as a hallmark feature in human cancers. Aspects of the disclosure relate to methods for selecting optimal therapy for a patient from several alternative treatment options. A major clinical challenge in cancer treatment is to identify the subset of patients who will benefit from a therapeutic regimen, both in metastatic and adjuvant settings. The number of anti-cancer drugs and multi-drug combinations has increased substantially in the past decade, however, treatments continue to be applied empirically using a trial-and-error approach. Here methods and compositions are provided to determine the optimal treatment option for cancer patients.

10 Claims, 110 Drawing Sheets

Specification includes a Sequence Listing.

(56) References Cited

OTHER PUBLICATIONS

Krishnan, et al., "Piwi-Interacting RN As and PIWI Genes as Novel Prognostic Markers for Breast Cancer," *Oncotarget*, 7(25): 2016.

Ling, "CCAT2, A Novel Noncoding RNA Mapping to 8q24, Underlies Metastatic Progression and Chromosomal Instability in Colon Cancer," *Genome Research*, 23(9): 1446-1461, 2013.

Ling, "Junk DNA and the Long Non-Coding RNA Twist in Cancer Genetics," *Oncogene*, 34(39): 5003-5011, 2015.

Mei, et al., "Novel Dimensions of piRNAs in Cancer," *Cancer Letters*, 336(1), 46-52, 2013.

O'Connor, et al., "Adjuvant Chemotherapy for Stage II Colon Cancer with Poor Prognostic Features," *Journal of Clinical Oncology*, 29(25): 3381-3388, 2011.

Okugawa, et al., "Clinical Significance of SNORA42 as an Oncogene and a Prognostic Biomarker in Colorectal Cancer," *Gut*, 66(1): 2015.

Pomerantz, et al., "The 8q24 Cancer Risk Variant rs6983267 Shows Long Range Interaction with MYC in Colorectal Cancer," *Nature Genetics*, 41: 882-884, 2009.

Ross, et al., "PIWI Proteins and PIWI-Interacting RNAs in the Soma," *Nature*, 505(7483): 353-359, 2014.

Siddiqi & Matushansky, "Piwis and Piwi-Interacting RNAs in the Epigenetics of Cancer," *Journal of Cell Biochemistry*, 113(2): 373-380, 2012.

Sonnenberg, et al., "Cost-Effectiveness of Colonoscopy in Screening for Colorectal Cancer," *Annals of Internal Medicine*, 133(8): 573-584, 2000.

Stiegelbauer, et al., "MicroRNAs as Novel Predictive Biomarkers and Therapeutic Targets in Colorectal Cancer," *World Journal of Gastroenterology*, 20(33), 11727-11735, 2014.

Takahashi, et al., "Amplification of PVT-1 is Involved in Poor Prognosis Via Apoptosis Inhibition in Colorectal Cancers," *British Journal of Cancer*, 110(1): 164-171, 2014.

Tuupanen, et al., "Characterization of the Colorectal Cancer-Associated Enhancer MYC-335 at 8q24: The Role of rs67491583," *Cancer Genetics*, 205(1-2): 25-33, 2012.

Weng, et al., "An Update on miRNAs as Biological and Clinical Determinants in Colorectal Cancer: A Bench-to-Bedside Approach," *Future Oncology*, 11(12), 1791-1808, 2015.

\* cited by examiner

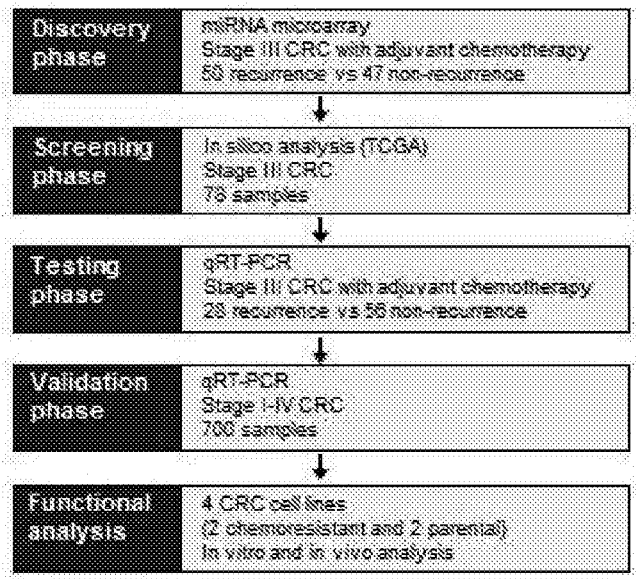
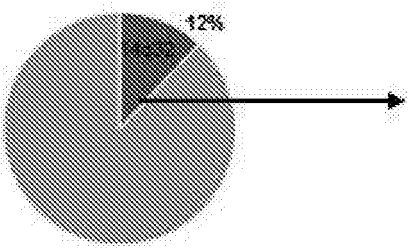
FIG. 1A-C

A
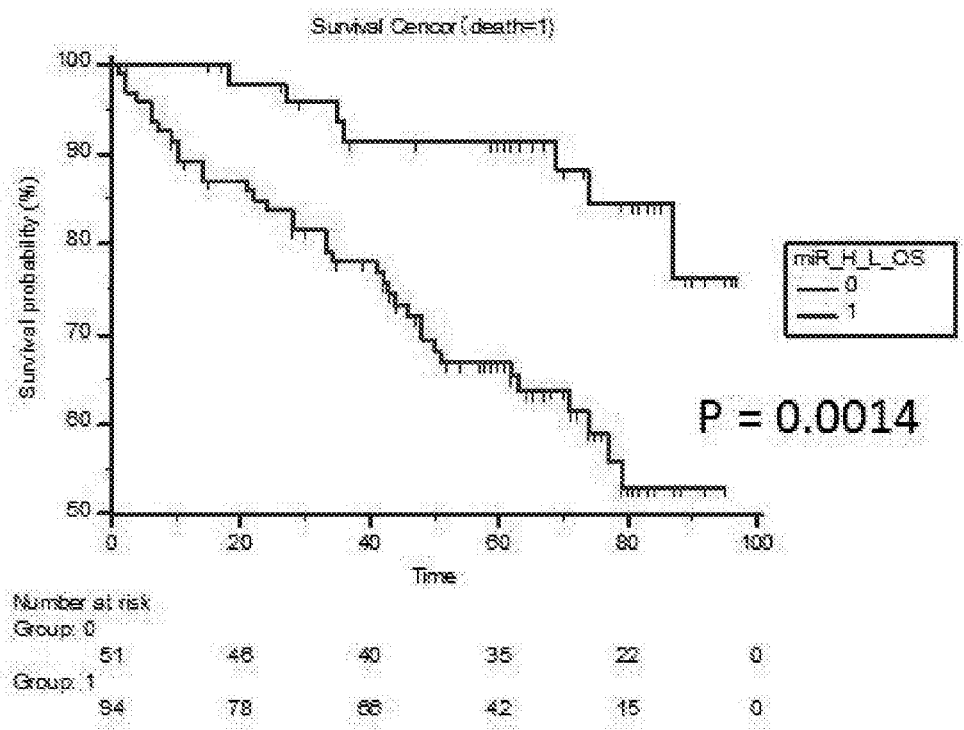
B
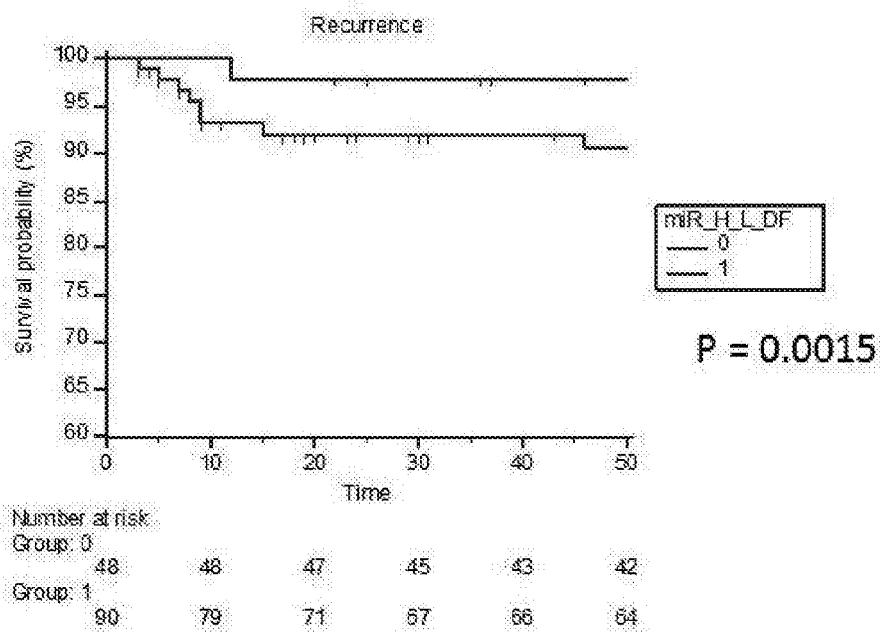
FIG. 15A-B

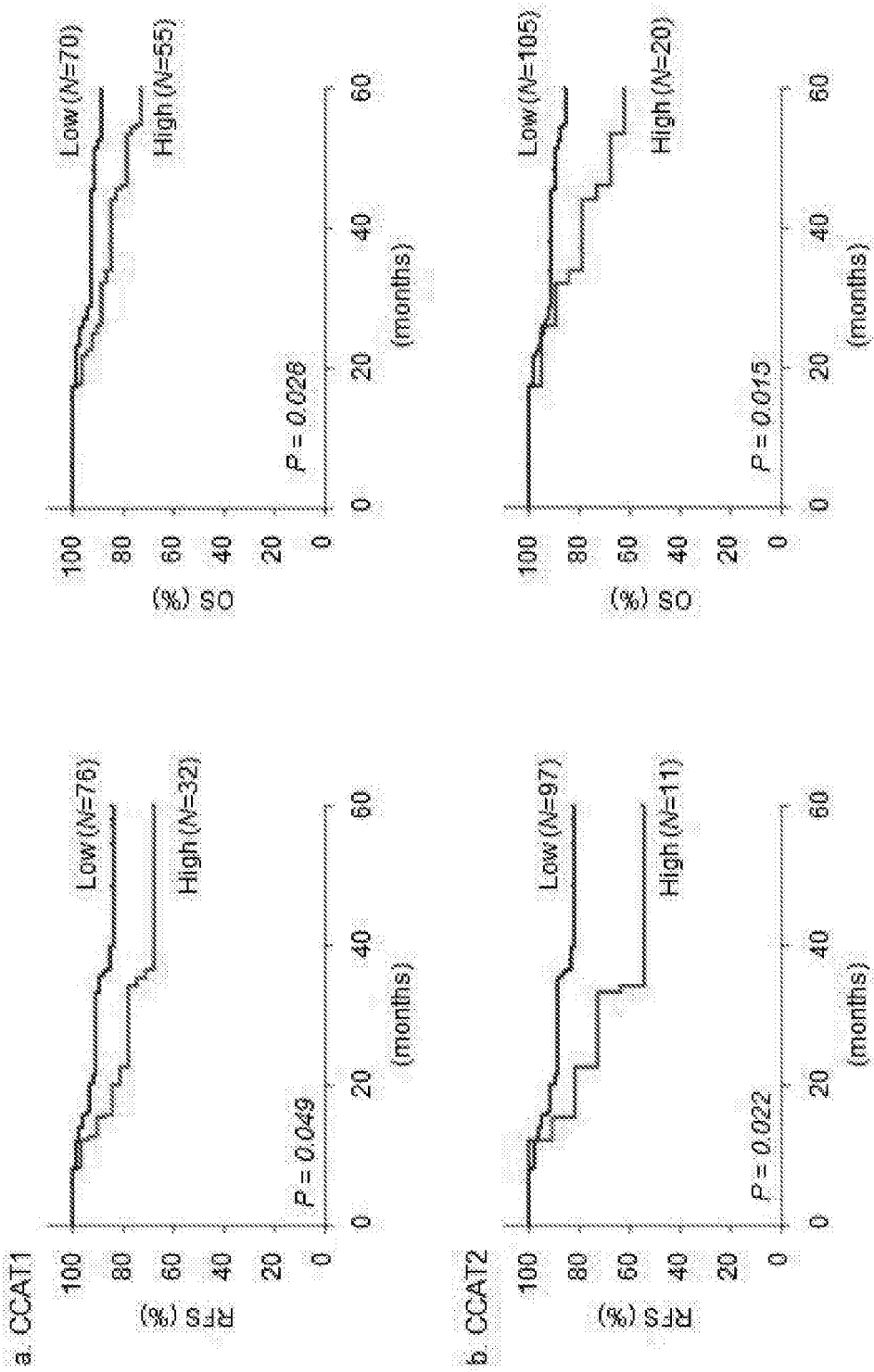
FIG. 33A-B

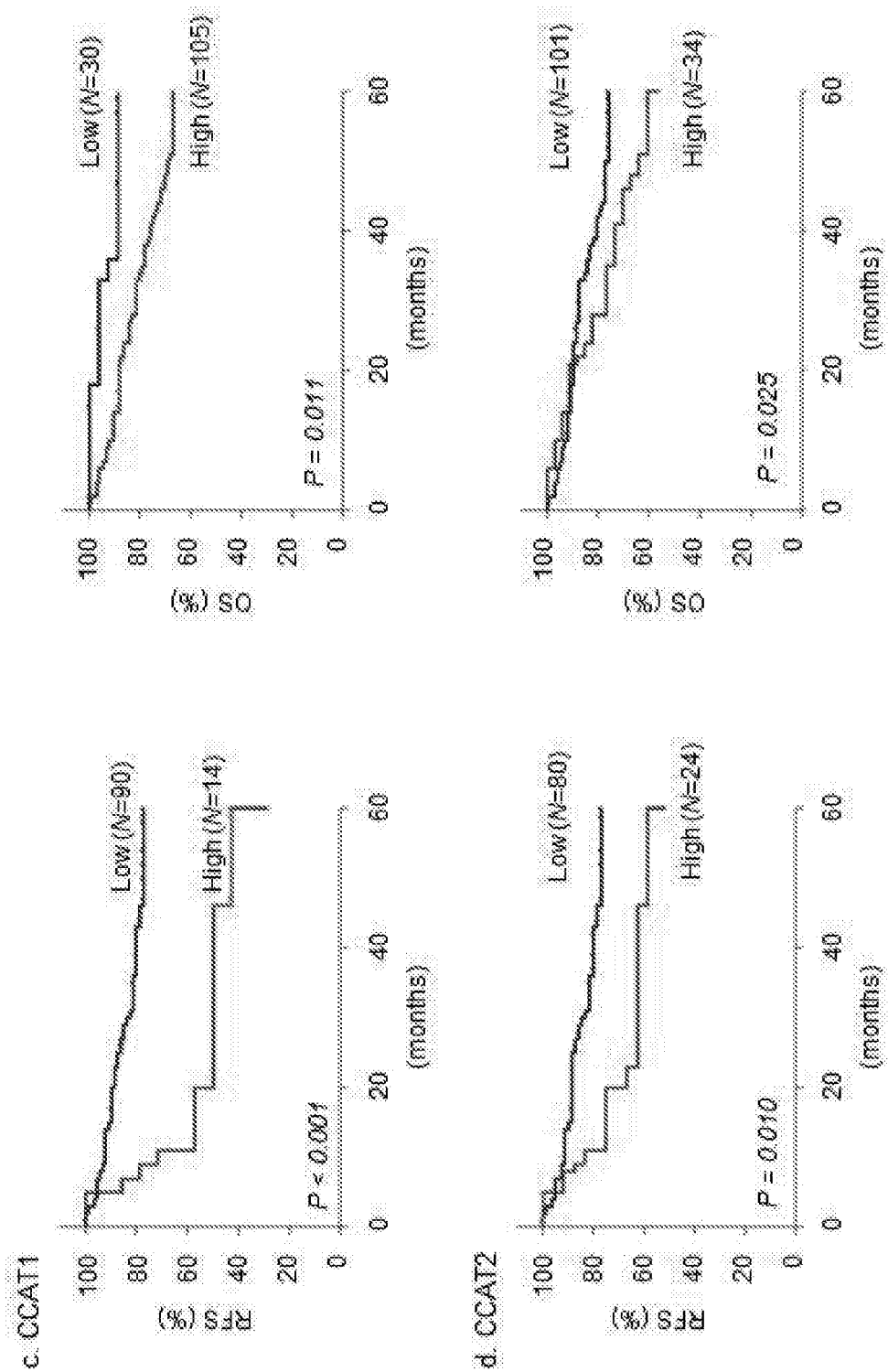
FIG. 33C-D

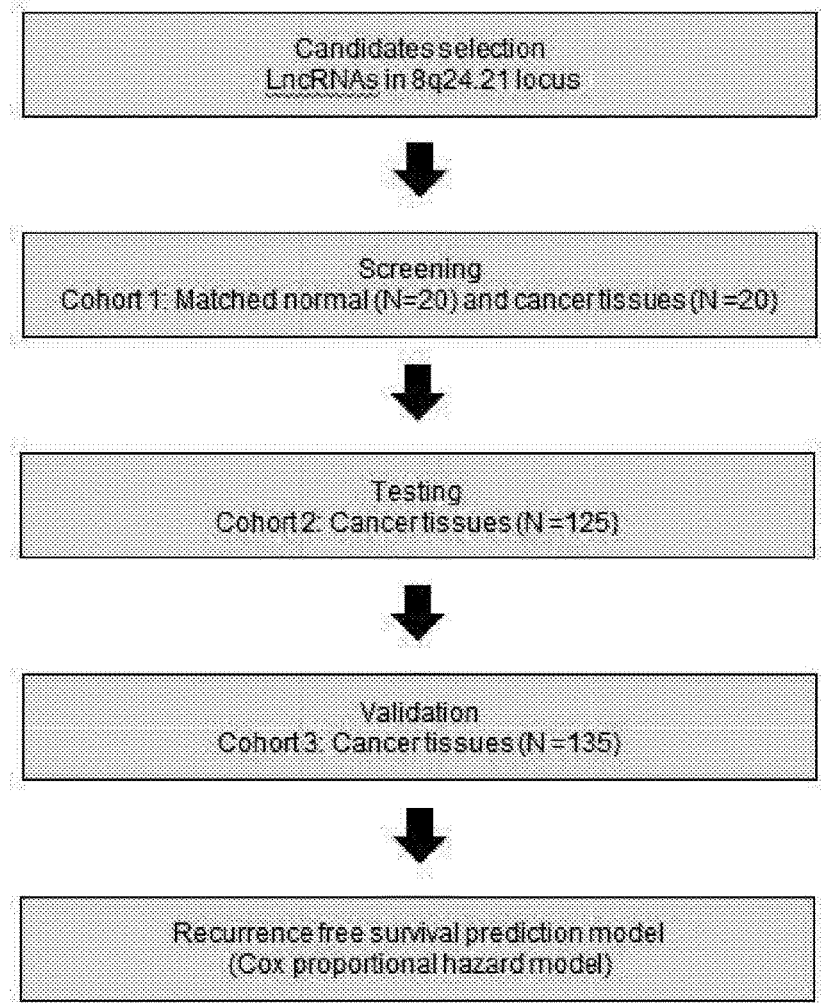
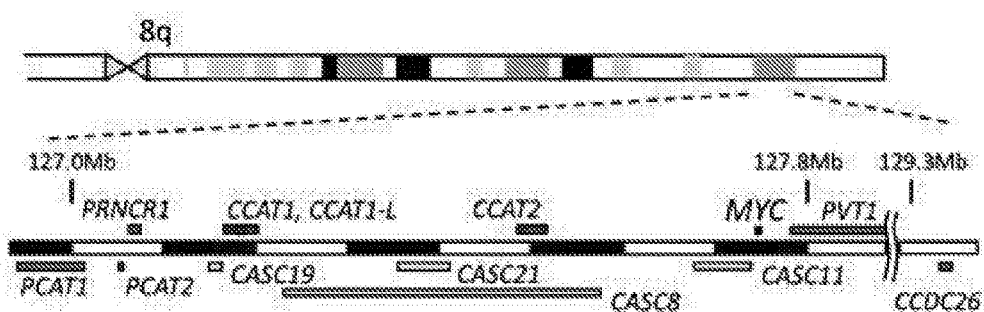
FIG. 35A-B

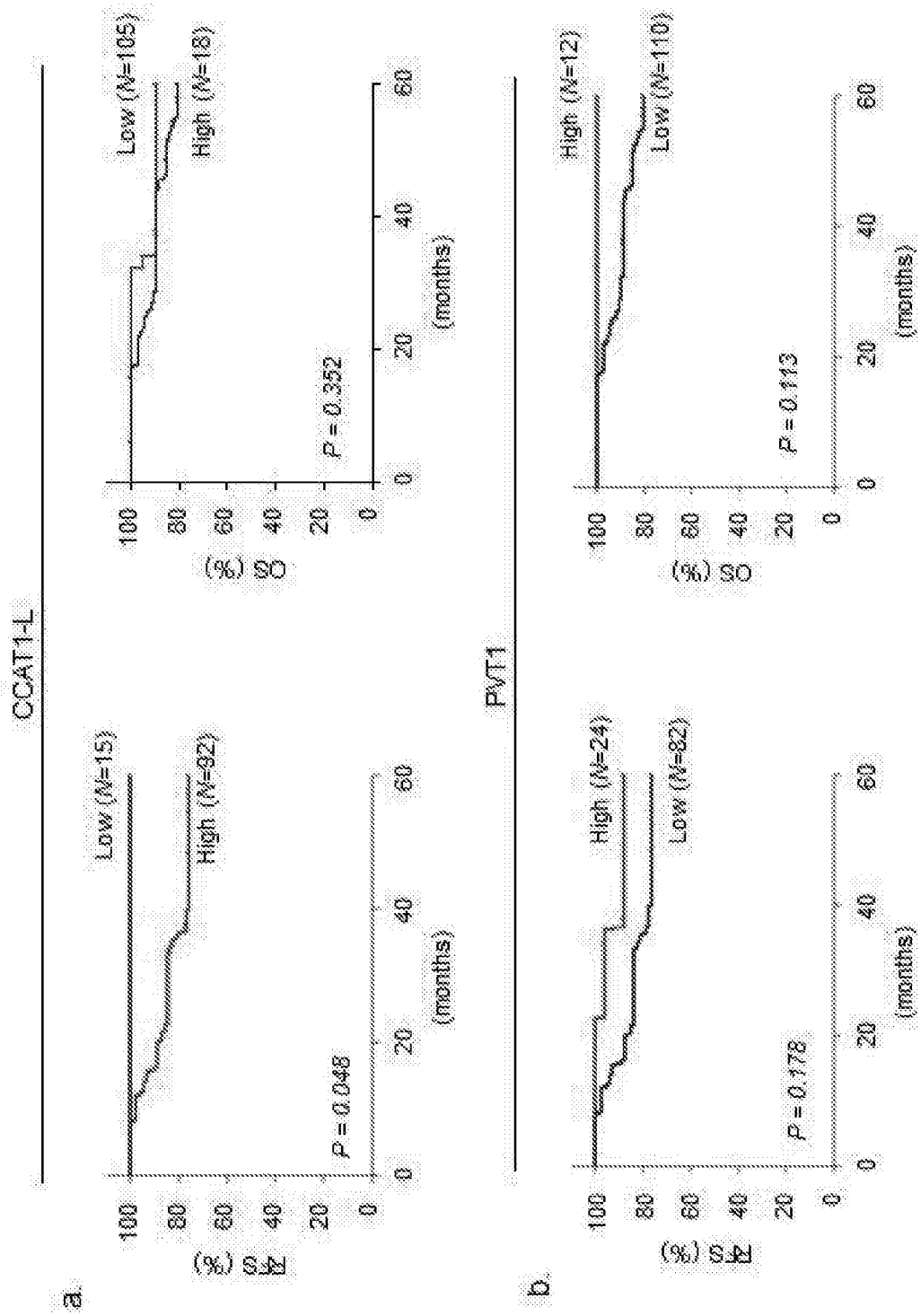
FIG. 37A-B

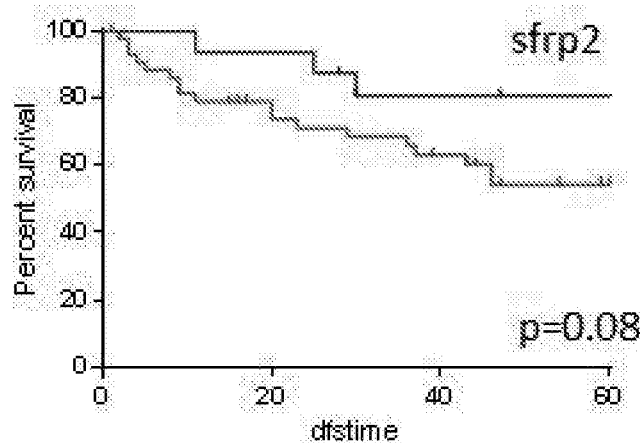
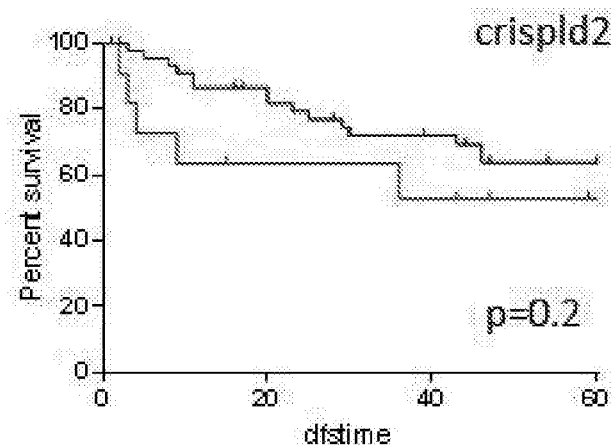
FIG. 44B

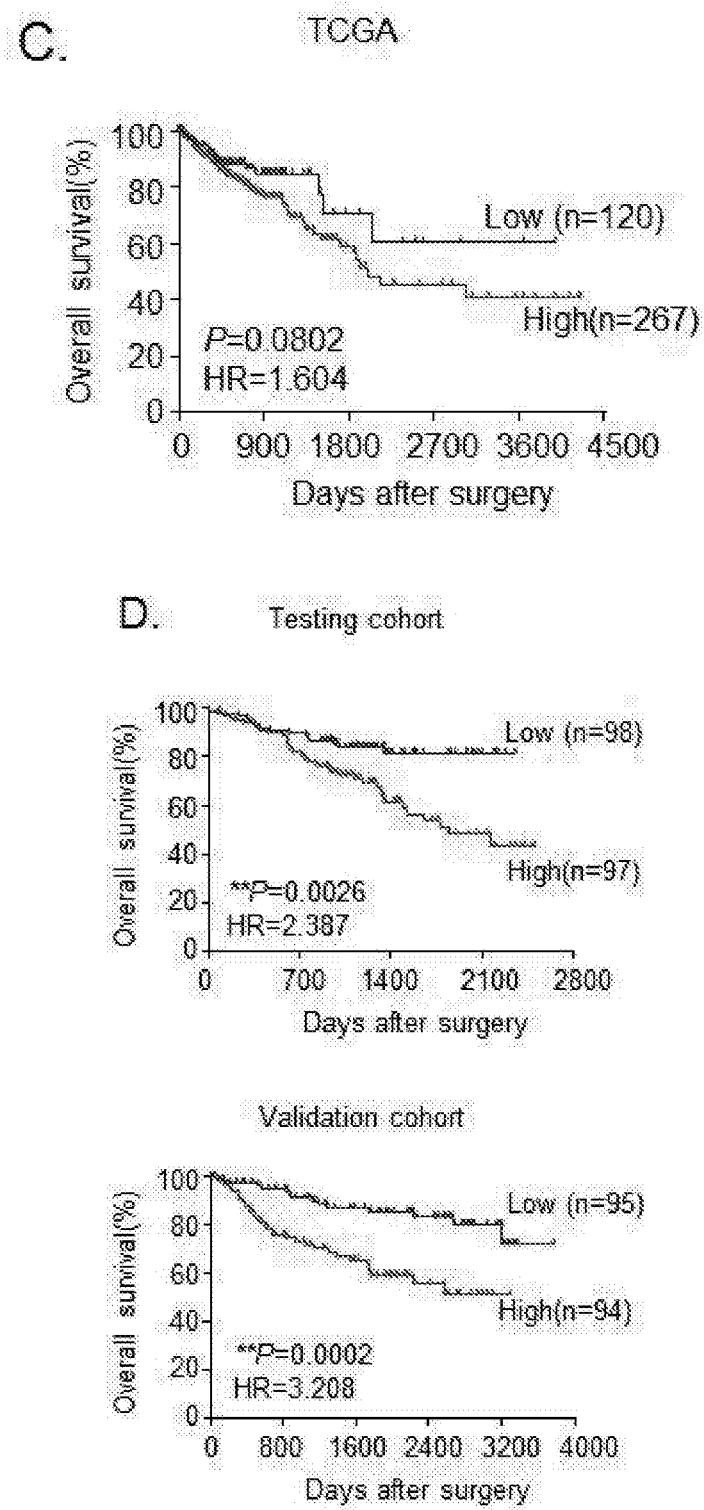
FIG. 52C-D

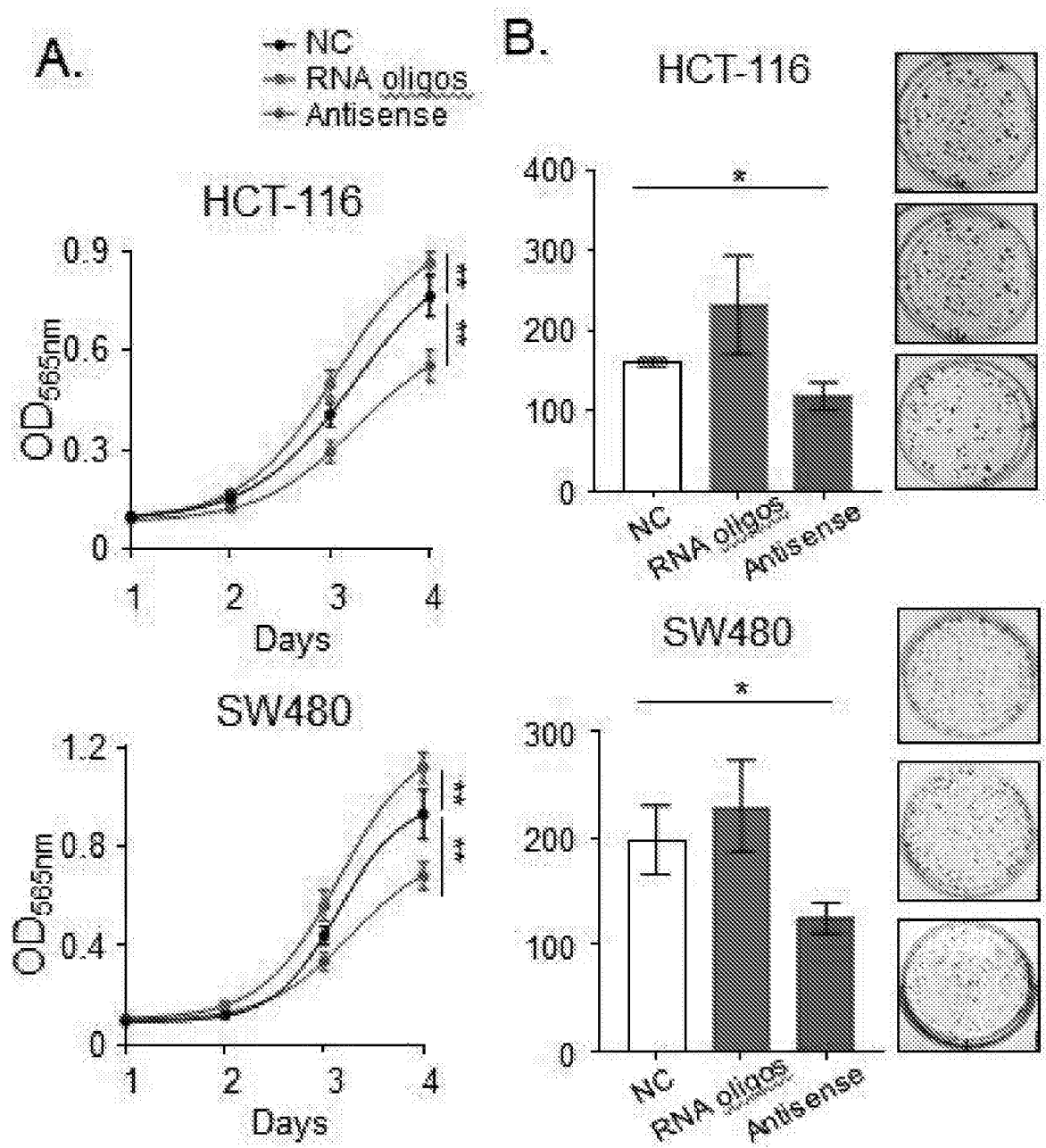
FIG. 53A-B

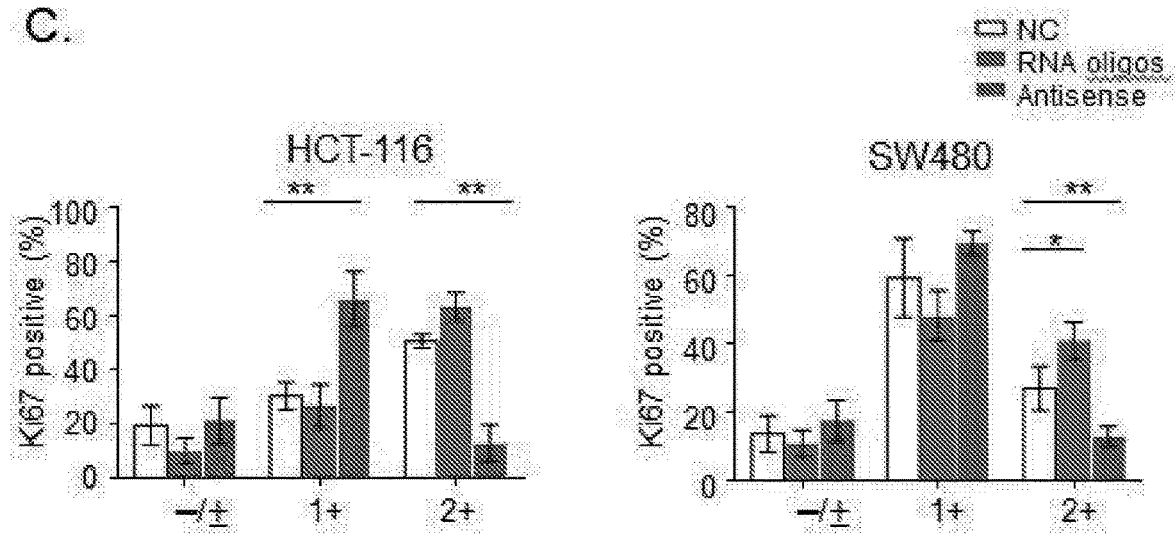
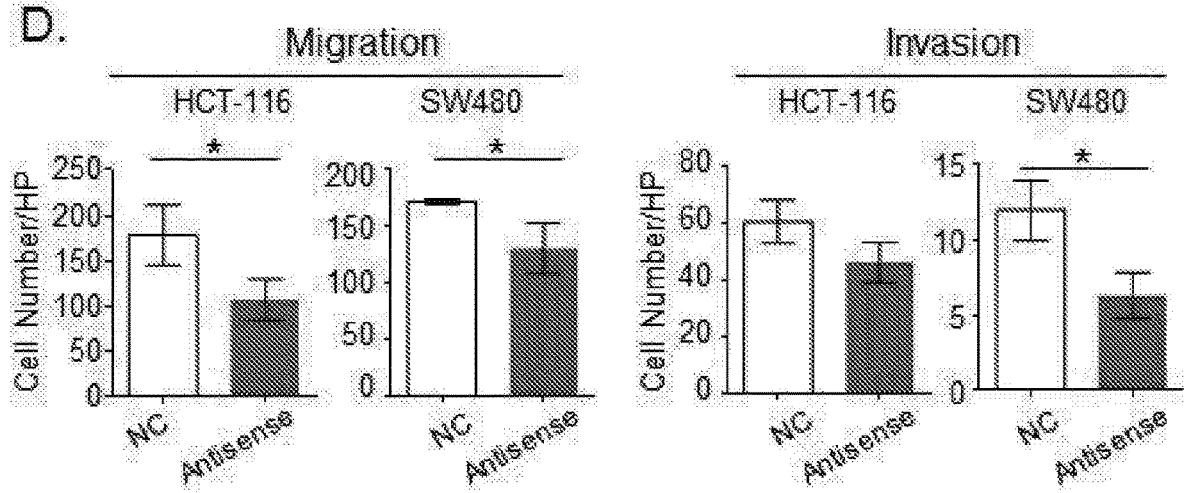
FIG. 53C-D

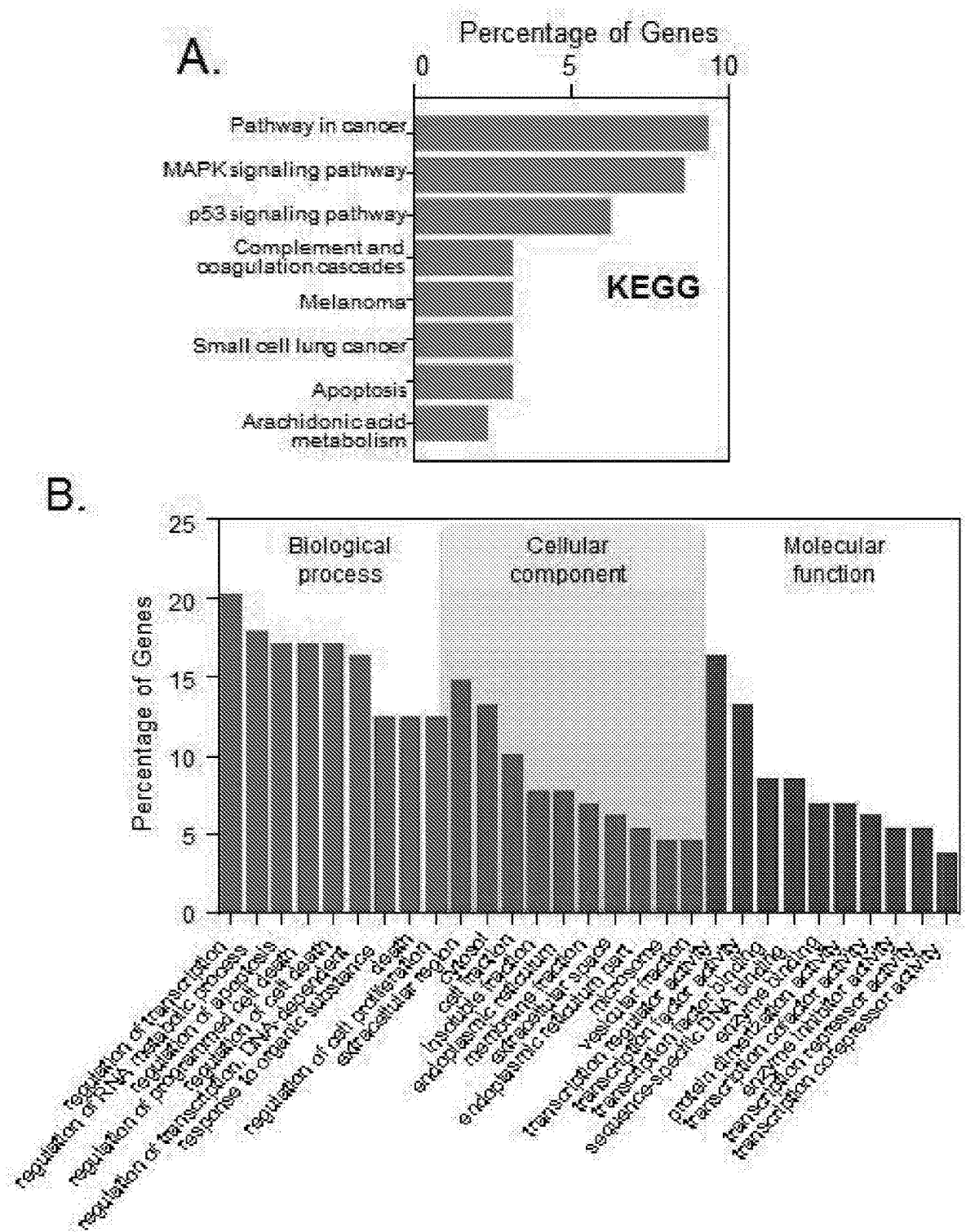
FIG. 54A-B

ATF3

```
piRACC  3'-CGAGTCCTCACCCGT-AGTAGTCCCGA-5'
            : |  | | | | | | |    | | | | | | | |:
ATF3    5'-TGGTAAGAGTGGCAATTCCTCAGGGTT-3' piRACC  3'-CGAGTCCTCACCCGTAGTA--GTCCCGA-5'
           | | | | : | | | : | |    | | | | | :
ATF3    5'-CTCCAGGGG-GAGTTTGAAGTCAGGGTA-3' piRACC  3'-CGAGTCCTCACCCGTAG-TAGTCCCGA-5'
            | |  | | | | | | |: | :   | | | | | |
ATF3    5'-CCCCA-GAGTGGGTCTTGGACCAGGGCA-3' piRACC  3'-CGAGTCCTCACCCGTAGTAGTCCCGA-5'
           | : |    | | | | | | |  | | | : | | | |
ATF3    5'-CGTTGGATATGGGCAGCATTAGGGAA-3' piRACC  3'-CGAGTCCTCA-CCCGTAGTAGTCCCGA-5'
           | |   | | |   | | |       | | | | | | | |
ATF3    5'-CTGTGGAAGGGGGC--TCAGGGCA-3' piRACC  3'-CGAGTCCTCACCCGTAGTAGTCCCGA-5'
           | | | | : |   : | |  | | | | | | | :
ATF3    5'-TTTCAGGGTT--TTAT-ATCAGGGTC-3' piRACC  3'-CGAGTCCTCACCCGTAGTAGTCCCGA-5'
             | | | | | | | :   | | | | | | :
ATF3    5'-GAGTCTCTGGGGGCATT-TCAGGGTT-3'
```

TP53INP1

```
piRACC    3'-CGAGTCCTCACCCGTAGTAGTCCCGA-5'
             | | |   |  |  : | |   | | | | | | | |
TP53INP1  5'-TCTCACTTGCAGCTATGCTCAGGGCC-3' piRACC    3'-CGAGTCCTCACCCGTAGTAGTCCCGA-5'
             | |   |   |     | | | | | | | | | |
TP53INP1  5'-ATCTAATTGTAGCCTGAATCAGGGCT-3' piRACC    3'-CGAGTCCTCACCCGTAGTAGTCCCGA-5'
             | | : | | |   | |   | : | |: | | | | |
TP53INP1  5'-CTTCGGGACTCGG---CGTCGGGGCT-3' piRACC    3'-CGAGTCCTC--ACCCGTAGT-AGTCCCGA-5'
             | | | : |   |   | | | | |  | | | | | | | |
TP53INP1  5'-TCCCAGTGGCTTTAGC-TGATTCAGGGCT-3' piRACC    3'-CGAGTCCTCACCCGTAGTAGTCCCGA-5'
             | | | | | | |  |   | | | | | | :
TP53INP1  5'-TAATTACAGTGGGC-T--TCAGGGTA-3'
```

FIG. 59A

NFKBIA

```
piRACC  3'-CGAGTCCTCACCCGTAGTAGTCCCGA-5'
                          | | | | | | |
NFKBIA  5'-CCCAGATCCTTTCTGAATTCAGGGCC-3'
```

SESN2

```
piRACC  3'-CGAGTCCT-CACCCGTAGT-AGTCCCGA-5'
           | | | | | |   | | | | | | | | | | | |
SESN2   5'-TGTCAGGATCGGGGAAGCATTCAGGGTA-3' piRACC  3'-CGAGTCCTCACCCGTAGTAGTCCCGA-5'
                    |        | | | | | | | |
SESN2   5'-GACGAGTCACTTCCTAGCTCAGGGCT-3' piRACC  3'-CGAGTCCTCACCCGTA--GTAGTCCCGA-5'
           | | |   |   |   | | | | | | | | |
SESN2   5'-AAATCTACTTGGTTTTGCCTTCAGGGCT-3'
```

BTG1

```
piRACC  3'-CGAGTCCTCA-CCCGTAGTAGTCCCGA-5'
           | | |  | | | |   | | |   | · | |  | | | | |
BTG1    5'-GGTCA-GAGTCCGGC--CGTCGGGGCT-3' piRACC  3'-CGAGTCCTC-AC--CCGT---AGTAGTCCCGA-5'
           | | | | | |  | |   | | | |   |  |   | | | | | |
BTG1    5'-CTGCAGGAGCTGCTGGCAGGTGAGCAGGGCG-3' piRACC  3'-CGAGTCCTCACC--C---GTAGTAGTCCCGA-5'
           |  | | · | | | |   |    | ·  | · | | · | | | |
BTG1    5'-AGCCCGGGGTGGCTGCTCCGCCGTCGGGCC-3'
```

DUSP5

```
piRACC  3'-CGAGTCCTCACCCGTAGTAGTCCCGA-5'
           | | |      | | |  |  · ·   : | | | | | | | |
DUSP5   5'-TCGCCGCTGTCGCTGGGGTCAGGGCT-3' piRACC  3'-CGAGTCCTC--AC----CCGTAGTAGTCCCGA-5'
           : | | | | |   | |       | | · |   :  | | | | | | |
DUSP5   5'-GCATAGGAGATTGCCCTGGTACTCTCAGGGCA-3'
```

FIG. 59B

MXD1

```
piRACC  3'-CGAGTCCTCACCCGTAGTAGTCCCGA-5'
           ||||  |||    |||      |||||||
MXD1    5'-CTTCAGAAGT-TGCAGATTCAGGGCA-3' piRACC  3'-CGAGTCCTCACCCGTAGTAGTCCCGA-5'
              |||||:| |  |||||||||
MXD1    5'-GGAGCTCCGTGGGTA-C-TCAGGGCT-3' piRACC  3'-CGAGTCCTCACCCGTAG-TAGTCCCGA-5'
           |||    |:|||  |||||||:
MXD1    5'-AGGTGAGAGCTGATATCTATCAGGGTT-3'
```

FAS

```
piRACC  3'-CGAGTCCTCACCC---GTAGTAGTCCCGA-5'
            :|||  |   ||    ||||  |||||||
FAS     5'-TTTCATGTTTAGGTCCCATC-TCAGGGCA-3' piRACC  3'-CGAGTCCTCACCCGTAG-TAGTCCCGA-5'
           ||||   |||  ||||||||:
FAS     5'-TTTTTGACATGGGAATCTATCAGGGTG-3' piRACC  3'-CGAGTCCTCACCCGTAGTAGTCCCGA-5'
                        |  |  ||||||||
FAS     5'-TCAGCTTCTTCCCAAGCTTCAGGGCA-3'
```

UPP1

```
piRACC  3'-CGAGTCCTCACCCGTAGTAGTCCCGA-5'
              ||  |::   |   ||||||||
UPP1    5'-ATGCTCCATGTGTG-CCTCAGGGCA-3' piRACC  3'-CGAGTCCTCACCCGTAGTAGTCCCGA-5'
                              ||||||||
UPP1    5'-CTCGTCTCCTGTCCCAATTCAGGGCT-3' piRACC  3'-CGAGTCCTCACCCGT-AGTA-GTCCCGA-5'
           |||  ||||||  |   |  ||  |||||||
UPP1    5'-GAATAGG-GTGGGTATTTATGCAGGGCT-3' piRACC  3'-CGAGTCCTCACCCGTA---GT------AGTCCCGA-5'
           | |||||   |   |||    ||       |||||||
UPP1    5'-AATGAGGAGGAGACATGACCACGGGGTTCAGGGCA-3'
```

FIG. 59C

BTG1 piRACC 3'-CGAGTCCTCACCCGTAGTAGTCCCGA-5'
          |:|||              ||   |:||||
BTG1    5'-GTTCAATTAGAAATTTCCCCGGGGCA-3' piRACC 3'-CGAGTCCTCACCCGTAGT--AGTCCCGA-5'
          :|:      | ||||: |||    ||| |||
BTG1    5'-GTTTTTAAATGGGTCTCACCCCAGTGCT-3'

DUSP5 piRACC 3'-CGAGTCCTC-ACCCGTAGTAGTCCCGA-5'
          ||||:||  |    ||||   |:||: |||
DUSP5   5'-GCTCGGGCGCCGGGCTCCGTCGCGGCC-3'

FAS piRACC 3'-CGAGTCCTC-ACCCGTAGTAGTCCCGA-5'
          ||   |  ||     |||||||  | |||
FAS     5'-ACTTGGAAGGCCTGCATCATGATGGCC-3'

NFKBIA piRACC 3'-CGAGTCCTCACCCGTAGTAGTCCCGA-5'
          |    ||  ||:  ||   :||||
NFKBIA  5'-CTGACGTTATGAGCG-CAAAGGGCT-3' piRACC 3'-CGAGTCCTCACCCGTAGTAGTCCCGA-5'
          ||:|   ||||  :|   ||||||    ||
NFKBIA  5'-TCTTA-TTGTGG-TAGGATCAGCCCT-3'

FIG. 60A

SESN2 piRACC    3'-CGAGTCC - TCACCCGTAGTAGTCCCGA-5'
          | | | | | | |   |       |   |   |   | | | |
SESN2     5'-GCTCAGGCACCCCTACCTTCCGGGCC-3' piRACC    3'-CGAGTCCTCACCCGTAGTAGTCCCGA-5'
          | |   | | |     | | | |   |           : | | | | |
SESN2     5'-GC - CTCGAG - CAGCACC - - - GGGGCT-3' piRACC    3'-CGAGTCCTCACCCGTAGTAGTCCCGA-5'
          | |   | |     |         | |         | | | |   | | | |
SESN2     5'-GC - CACTACATTGC -- GATCATGGCT-3' piRACC    3'-CGAGT - CCTCACCC - GTAGTAGTCCCGA-5'
          | | | | |               | |           | | | |     | | |
SESN2     5'-GCTCATCACCAAGGAACACATCCAGGCC-3'

TP53INP1 piRACC    3'-CGAGTCCTCACCCGTAGTAGTCCCGA-5'
            | | | | | : :       : | | | |     | |
TP53INP1  5'-AAATGTTTGTGGGTGAAGTCAGTTCT-3' piRACC    3'-CGAGTCCTCACCCG -- TAGTAGTCCCGA-5'
          |   |     | | | | :           | | | | | | |     | |
TP53INP1  5'-CACAATGGCTGGGTTGTTCATCAGCCCT-3'

MXD1 piRACC    3'-CGAGTCCTCACCCGTAGTAGTCCCGA-5'
          | |   | | |   | |     | | |       |   | | | | |   | |
MXD1      5'-GC-CAG-AG-AGGCTCCCTCAGCCCT-3' piRACC    3'-CGAGTCCTCACC - CGTAGTAGTCCCGA-5'
          | |   | | |   | | |     | | |   | |   | | |   | :
MXD1      5'-GATCTGGACTGGAGCAGCAGCAGTGTG-3' piRACC    3'-CGAGTCCTCACCCGTAGTAGT CCCGA-5'
          | | :                     | | |   | |         | | | |
MXD1      5'-ACTTTTTCAAAAGCAACAAAGGGGCC-3'

FIG. 60B

SEQUENCE LISTING

<160> NUMBER OF SEQ ID NOS: 99

<210> SEQ ID NO 1
<211> LENGTH: 20
<212> TYPE: DNA
<213> ORGANISM: Artificial Sequence
<220> FEATURE:
<223> OTHER INFORMATION: CCAT1 forward primer

<400> SEQUENCE: 1
agaaacacta tcacctacgc                                              20

<210> SEQ ID NO 2
<211> LENGTH: 22
<212> TYPE: DNA
<213> ORGANISM: Artificial Sequence
<220> FEATURE:
<223> OTHER INFORMATION: CCAT1 reverse primer

<400> SEQUENCE: 2
cttaacaggg cattgctaat ct                                           22

<210> SEQ ID NO 3
<211> LENGTH: 22
<212> TYPE: DNA
<213> ORGANISM: Artificial Sequence
<220> FEATURE:
<223> OTHER INFORMATION: CCAT1-L forward primer

<400> SEQUENCE: 3
ccacgtgcac atatttgaat tg                                           22

<210> SEQ ID NO 4
<211> LENGTH: 22
<212> TYPE: DNA
<213> ORGANISM: Artificial Sequence
<220> FEATURE:
<223> OTHER INFORMATION: CCAT1-L reverse primer

<400> SEQUENCE: 4
tgcattccct gcttaatact ca                                           22

<210> SEQ ID NO 5
<211> LENGTH: 22
<212> TYPE: DNA
<213> ORGANISM: Artificial Sequence
<220> FEATURE:
<223> OTHER INFORMATION: CCAT2 forward primer

<400> SEQUENCE: 5
ccctggtcaa attgcttaac ct                                           22

<210> SEQ ID NO 6
<211> LENGTH: 25
<212> TYPE: DNA
<213> ORGANISM: Artificial Sequence
<220> FEATURE:
<223> OTHER INFORMATION: CCAT2 reverse primer

<400> SEQUENCE: 6
ttattcgtcc ctctgtttta tggat                                        25

<210> SEQ ID NO 7
<211> LENGTH: 20
<212> TYPE: DNA
<213> ORGANISM: Artificial Sequence

```
<220> FEATURE:
<223> OTHER INFORMATION: PVT1 forward primer

<400> SEQUENCE: 7
ttgggtctcc ctatggaatg                                         20

<210> SEQ ID NO 8
<211> LENGTH: 20
<212> TYPE: DNA
<213> ORGANISM: Artificial Sequence
<220> FEATURE:
<223> OTHER INFORMATION: PVT1 reverse primer

<400> SEQUENCE: 8
ggagaaggct ccagggagta                                         20

<210> SEQ ID NO 9
<211> LENGTH: 24
<212> TYPE: DNA
<213> ORGANISM: Artificial Sequence
<220> FEATURE:
<223> OTHER INFORMATION: PCAT1 forward primer

<400> SEQUENCE: 9
tgagaagaga aatctattgg aacc                                    24

<210> SEQ ID NO 10
<211> LENGTH: 20
<212> TYPE: DNA
<213> ORGANISM: Artificial Sequence
<220> FEATURE:
<223> OTHER INFORMATION: PCAT1 reverse primer

<400> SEQUENCE: 10
ggtttgtctc cgctgcttta                                         20

<210> SEQ ID NO 11
<211> LENGTH: 21
<212> TYPE: DNA
<213> ORGANISM: Artificial Sequence
<220> FEATURE:
<223> OTHER INFORMATION: PCAT2 forward primer

<400> SEQUENCE: 11
cttaaggcac tgatgctctc a                                       21

<210> SEQ ID NO 12
<211> LENGTH: 20
<212> TYPE: DNA
<213> ORGANISM: Artificial Sequence
<220> FEATURE:
<223> OTHER INFORMATION: PCAT2 reverse primer

<400> SEQUENCE: 12
gtgctgatgc ctctggaaat                                         20

<210> SEQ ID NO 13
<211> LENGTH: 20
<212> TYPE: DNA
<213> ORGANISM: Artificial Sequence
<220> FEATURE:
<223> OTHER INFORMATION: CASC8 forward primer

<400> SEQUENCE: 13
tccagctttg tgctgatgaa                                         20
```

```
<210> SEQ ID NO 14
<211> LENGTH: 20
<212> TYPE: DNA
<213> ORGANISM: Artificial Sequence
<220> FEATURE:
<223> OTHER INFORMATION: CASC8 reverse primer

<400> SEQUENCE: 14
cttgcaacgt cagtccaaaa                                                   20

<210> SEQ ID NO 15
<211> LENGTH: 20
<212> TYPE: DNA
<213> ORGANISM: Artificial Sequence
<220> FEATURE:
<223> OTHER INFORMATION: CASC11 forward primer

<400> SEQUENCE: 15
ccccaacacc ttctttgaac                                                   20

<210> SEQ ID NO 16
<211> LENGTH: 19
<212> TYPE: DNA
<213> ORGANISM: Artificial Sequence
<220> FEATURE:
<223> OTHER INFORMATION: CASC11 reverse primer

<400> SEQUENCE: 16
cgtccagttg ctttccatc                                                    19

<210> SEQ ID NO 17
<211> LENGTH: 20
<212> TYPE: DNA
<213> ORGANISM: Artificial Sequence
<220> FEATURE:
<223> OTHER INFORMATION: CASC19 forward primer

<400> SEQUENCE: 17
attggagtgc ctgggttaga                                                   20

<210> SEQ ID NO 18
<211> LENGTH: 20
<212> TYPE: DNA
<213> ORGANISM: Artificial Sequence
<220> FEATURE:
<223> OTHER INFORMATION: CASC19 reverse primer

<400> SEQUENCE: 18
tttggacagc accttgaatg                                                   20

<210> SEQ ID NO 19
<211> LENGTH: 20
<212> TYPE: DNA
<213> ORGANISM: Artificial Sequence
<220> FEATURE:
<223> OTHER INFORMATION: CASC21 forward primer

<400> SEQUENCE: 19
ccagaggagc caagagaaga                                                   20

<210> SEQ ID NO 20
<211> LENGTH: 20
<212> TYPE: DNA
<213> ORGANISM: Artificial Sequence
<220> FEATURE:
<223> OTHER INFORMATION: CASC21 reverse primer
```

```
<400> SEQUENCE: 20
ccaatgctgt cccactctgt                                              20

<210> SEQ ID NO 21
<211> LENGTH: 20
<212> TYPE: DNA
<213> ORGANISM: Artificial Sequence
<220> FEATURE:
<223> OTHER INFORMATION: PRNCR1 forward primer

<400> SEQUENCE: 21
ccagattcca agggctgata                                              20

<210> SEQ ID NO 22
<211> LENGTH: 20
<212> TYPE: DNA
<213> ORGANISM: Artificial Sequence
<220> FEATURE:
<223> OTHER INFORMATION: PRNCR1 reverse primer

<400> SEQUENCE: 22
gatgtttgga ggcatctggt                                              20

<210> SEQ ID NO 23
<211> LENGTH: 20
<212> TYPE: DNA
<213> ORGANISM: Artificial Sequence
<220> FEATURE:
<223> OTHER INFORMATION: CCDC26 forward primer

<400> SEQUENCE: 23
ggtgatgtgg tgcatctgag                                              20

<210> SEQ ID NO 24
<211> LENGTH: 20
<212> TYPE: DNA
<213> ORGANISM: Artificial Sequence
<220> FEATURE:
<223> OTHER INFORMATION: CCDC26 reverse primer

<400> SEQUENCE: 24
gcaacaacgg gaactctgat                                              20

<210> SEQ ID NO 25
<211> LENGTH: 21
<212> TYPE: DNA
<213> ORGANISM: Artificial Sequence
<220> FEATURE:
<223> OTHER INFORMATION: MYC forward primer

<400> SEQUENCE: 25
cgtctccaca catcagcaca a                                            21

<210> SEQ ID NO 26
<211> LENGTH: 22
<212> TYPE: DNA
<213> ORGANISM: Artificial Sequence
<220> FEATURE:
<223> OTHER INFORMATION: MYC reverse primer

<400> SEQUENCE: 26
tcttggcagc aggatagtcc tt                                           22

<210> SEQ ID NO 27
```

```
<211> LENGTH: 20
<212> TYPE: DNA
<213> ORGANISM: Artificial Sequence
<220> FEATURE:
<223> OTHER INFORMATION: ACTB forward primer

<400> SEQUENCE: 27
agagctacga gctgcctgac                                              20

<210> SEQ ID NO 28
<211> LENGTH: 20
<212> TYPE: DNA
<213> ORGANISM: Artificial Sequence
<220> FEATURE:
<223> OTHER INFORMATION: ACTB reverse primer

<400> SEQUENCE: 28
agcactgtgt tggcgtacag                                              20

<210> SEQ ID NO 29
<211> LENGTH: 21
<212> TYPE: DNA
<213> ORGANISM: Artificial Sequence
<220> FEATURE:
<223> OTHER INFORMATION: MXD1 forward primer

<400> SEQUENCE: 29
gctgaacatg gttatgcctc c                                            21

<210> SEQ ID NO 30
<211> LENGTH: 24
<212> TYPE: DNA
<213> ORGANISM: Artificial Sequence
<220> FEATURE:
<223> OTHER INFORMATION: MXD1 reverse primer

<400> SEQUENCE: 30
agcccgtcta ttcttctcca tttc                                         24

<210> SEQ ID NO 31
<211> LENGTH: 20
<212> TYPE: DNA
<213> ORGANISM: Artificial Sequence
<220> FEATURE:
<223> OTHER INFORMATION: DUSP5 forward primer

<400> SEQUENCE: 31
tcctgagtgt tgcgtggatg                                              20

<210> SEQ ID NO 32
<211> LENGTH: 19
<212> TYPE: DNA
<213> ORGANISM: Artificial Sequence
<220> FEATURE:
<223> OTHER INFORMATION: DUSP5 reverse primer

<400> SEQUENCE: 32
gggccaccct ggtcataag                                               19

<210> SEQ ID NO 33
<211> LENGTH: 21
<212> TYPE: DNA
<213> ORGANISM: Artificial Sequence
<220> FEATURE:
<223> OTHER INFORMATION: BTG1 forward primer
```

```
<400> SEQUENCE: 33
ggagctgctg gcagaacatt a                                              21

<210> SEQ ID NO 34
<211> LENGTH: 20
<212> TYPE: DNA
<213> ORGANISM: Artificial Sequence
<220> FEATURE:
<223> OTHER INFORMATION: BTG1 reverse primer

<400> SEQUENCE: 34
gtgctgcctg tccaatcaga                                                20

<210> SEQ ID NO 35
<211> LENGTH: 21
<212> TYPE: DNA
<213> ORGANISM: Artificial Sequence
<220> FEATURE:
<223> OTHER INFORMATION: TP53INP1 forward primer

<400> SEQUENCE: 35
ctcacgggca cagaagtgga a                                              21

<210> SEQ ID NO 36
<211> LENGTH: 19
<212> TYPE: DNA
<213> ORGANISM: Artificial Sequence
<220> FEATURE:
<223> OTHER INFORMATION: TP53INP1 reverse primer

<400> SEQUENCE: 36
atccactggg aagggcgaa                                                 19

<210> SEQ ID NO 37
<211> LENGTH: 20
<212> TYPE: DNA
<213> ORGANISM: Artificial Sequence
<220> FEATURE:
<223> OTHER INFORMATION: FAS forward primer

<400> SEQUENCE: 37
gtacggagtt ggggaagctc                                                20

<210> SEQ ID NO 38
<211> LENGTH: 21
<212> TYPE: DNA
<213> ORGANISM: Artificial Sequence
<220> FEATURE:
<223> OTHER INFORMATION: FAS reverse primer

<400> SEQUENCE: 38
acagacgtaa gaaccagagg t                                              21

<210> SEQ ID NO 39
<211> LENGTH: 20
<212> TYPE: DNA
<213> ORGANISM: Artificial Sequence
<220> FEATURE:
<223> OTHER INFORMATION: SENS2 forward primer

<400> SEQUENCE: 39
tcgctctcct ccttcgtgtt                                                20

<210> SEQ ID NO 40
```

```
<211> LENGTH: 21
<212> TYPE: DNA
<213> ORGANISM: Artificial Sequence
<220> FEATURE:
<223> OTHER INFORMATION: SENS2 reverse primer

<400> SEQUENCE: 40
tcaaagcccc cagagttgtt c                                              21

<210> SEQ ID NO 41
<211> LENGTH: 19
<212> TYPE: DNA
<213> ORGANISM: Artificial Sequence
<220> FEATURE:
<223> OTHER INFORMATION: NFKBIA forward primer

<400> SEQUENCE: 41
cccctacacc ttgcctgtg                                                 19

<210> SEQ ID NO 42
<211> LENGTH: 21
<212> TYPE: DNA
<213> ORGANISM: Artificial Sequence
<220> FEATURE:
<223> OTHER INFORMATION: NFKBIA reverse primer

<400> SEQUENCE: 42
cacgtgtggc cattgtagtt g                                              21

<210> SEQ ID NO 43
<211> LENGTH: 19
<212> TYPE: DNA
<213> ORGANISM: Artificial Sequence
<220> FEATURE:
<223> OTHER INFORMATION: UPP1 forward primer

<400> SEQUENCE: 43
gagtgggctt ggtgaggtg                                                 19

<210> SEQ ID NO 44
<211> LENGTH: 20
<212> TYPE: DNA
<213> ORGANISM: Artificial Sequence
<220> FEATURE:
<223> OTHER INFORMATION: UPP1 reverse primer

<400> SEQUENCE: 44
caggacccgt cagaggagag                                                20

<210> SEQ ID NO 45
<211> LENGTH: 21
<212> TYPE: DNA
<213> ORGANISM: Artificial Sequence
<220> FEATURE:
<223> OTHER INFORMATION: ATF3 forward primer

<400> SEQUENCE: 45
gccgaaacaa gaagaaggag a                                              21

<210> SEQ ID NO 46
<211> LENGTH: 21
<212> TYPE: DNA
<213> ORGANISM: Artificial Sequence
<220> FEATURE:
<223> OTHER INFORMATION: ATF3 reverse primer
```

```
<400> SEQUENCE: 46
tcgttcttga gctcctcaat c                                            21

<210> SEQ ID NO 47
<211> LENGTH: 22
<212> TYPE: DNA
<213> ORGANISM: Artificial Sequence
<220> FEATURE:
<223> OTHER INFORMATION: GAPDH forward primer

<400> SEQUENCE: 47
tgtagttgag gtcaatgaag gg                                           22

<210> SEQ ID NO 48
<211> LENGTH: 19
<212> TYPE: DNA
<213> ORGANISM: Artificial Sequence
<220> FEATURE:
<223> OTHER INFORMATION: GAPDH reverse primer

<400> SEQUENCE: 48
acatcgctca gacaccatg                                               19

<210> SEQ ID NO 49
<211> LENGTH: 26
<212> TYPE: RNA
<213> ORGANISM: Artificial Sequence
<220> FEATURE:
<223> OTHER INFORMATION: single-stranded RNA oligonucleotides

<400> SEQUENCE: 49
agcccugaug augcccacuc cugagc                                       26

<210> SEQ ID NO 50
<211> LENGTH: 24
<212> TYPE: RNA
<213> ORGANISM: Artificial Sequence
<220> FEATURE:
<223> OTHER INFORMATION: single-stranded scrambled RNA control

<400> SEQUENCE: 50
ucacaaccuc cuagaaagag uaga                                         24

<210> SEQ ID NO 51
<211> LENGTH: 35
<212> TYPE: DNA
<213> ORGANISM: Artificial Sequence
<220> FEATURE:
<223> OTHER INFORMATION: 2'-O-Me-modified antisense sequence

<400> SEQUENCE: 51
cuuagctcag gagtgggcat catcagggct accuu                             35

<210> SEQ ID NO 52
<211> LENGTH: 35
<212> TYPE: DNA
<213> ORGANISM: Artificial Sequence
<220> FEATURE:
<223> OTHER INFORMATION: negative scrambled control

<400> SEQUENCE: 52
cuuatcagga ctgctactgg tgcggacgcg accuu                             35

<210> SEQ ID NO 53
```

```
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 53
agccctgatg atgcccactc ctgagc                                          26

<210> SEQ ID NO 54
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 54
tggtaagagt ggcaattcct cagggtt                                         27

<210> SEQ ID NO 55
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 55
ctccaggggg agtttgaagt cagggta                                         27

<210> SEQ ID NO 56
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 56
ccccagagtg ggtcttggac cagggca                                         27

<210> SEQ ID NO 57
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 57
cgttggatat gggcagcatt agggaa                                          26

<210> SEQ ID NO 58
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 58
ctgtggaagg gggctcaggg ca                                              22

<210> SEQ ID NO 59
<211> LENGTH: 23
<212> TYPE: DNA
<213> ORGANISM: Artificial Sequence
<220> FEATURE:
<223> OTHER INFORMATION: Synthetic polynucleotide
```

<400> SEQUENCE: 59
tttcagggtt ttatatcagg gtc                                           23

<210> SEQ ID NO 60
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 60
gagtctctgg gggcatttca gggtt                                         25

<210> SEQ ID NO 61
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 61
tctcacttgc agctatgctc agggcc                                        26

<210> SEQ ID NO 62
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 62
atctaattgt agcctgaatc agggct                                        26

<210> SEQ ID NO 63
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 63
cttcgggact cggcgtcggg gct                                           23

<210> SEQ ID NO 64
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 64
tcccagtggc tttagctgat tcagggct                                      28

<210> SEQ ID NO 65
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 65
taattacagt gggcttcagg gta                                           23

<210> SEQ ID NO 66

```
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 66
cccagatcct ttctgaattc agggcc                                           26

<210> SEQ ID NO 67
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 67
tgtcaggatc ggggaagcat tcagggta                                         28

<210> SEQ ID NO 68
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 68
gacgagtcac ttcctagctc agggct                                           26

<210> SEQ ID NO 69
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 69
aaatctactt ggttttgcct tcagggct                                         28

<210> SEQ ID NO 70
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 70
ggtcagagtc cggccgtcgg ggct                                             24

<210> SEQ ID NO 71
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 71
ctgcaggagc tgctggcagg tgagcagggg cg                                    32

<210> SEQ ID NO 72
<211> LENGTH: 31
<212> TYPE: DNA
<213> ORGANISM: Artificial Sequence
<220> FEATURE:
<223> OTHER INFORMATION: Synthetic polynucleotide
```

```
<400> SEQUENCE: 72
agcccggggt ggctgctccg ccgtcggggc c                                31

<210> SEQ ID NO 73
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 73
tcgccgctgt cgctggggtc agggct                                      26

<210> SEQ ID NO 74
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 74
gcataggaga ttgccctggt acttctcagg gca                              33

<210> SEQ ID NO 75
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 75
cttcagaagt tgcagattca gggca                                       25

<210> SEQ ID NO 76
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 76
ggagctccgt gggtactcag ggct                                        24

<210> SEQ ID NO 77
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 77
aggtgaagag ctgatatcta tcagggtt                                    28

<210> SEQ ID NO 78
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 78
tttcatgttt aggtcccatc tcagggca                                    28

<210> SEQ ID NO 79
```

```
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 79
tttttgacat gggaatctat cagggtg                                           27

<210> SEQ ID NO 80
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 80
tcagcttctt cccaagcttc agggca                                            26

<210> SEQ ID NO 81
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 81
atgctccatg tgtgcctcag ggca                                              24

<210> SEQ ID NO 82
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 82
ctcgtctcct gtcccaattc agggct                                            26

<210> SEQ ID NO 83
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 83
gaatagggtg ggtatttatg cagggct                                           27

<210> SEQ ID NO 84
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 84
aatgaggagg agacatgacc acggggttca gggca                                  35

<210> SEQ ID NO 85
<211> LENGTH: 26
<212> TYPE: DNA
<213> ORGANISM: Artificial Sequence
<220> FEATURE:
<223> OTHER INFORMATION: Synthetic polynucleotide
```

<400> SEQUENCE: 85
gttcaattag aaatttcccc ggggca                    26

<210> SEQ ID NO 86
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 86
gtttttaaat gggtctcacc ccagtgct                  28

<210> SEQ ID NO 87
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 87
gctcgggcgc cgggtccgtc gcggcc                    26

<210> SEQ ID NO 88
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 88
acttggaagg cctgcatcat gatggcc                   27

<210> SEQ ID NO 89
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 89
ctgacgttat gagcgcaagg ggct                      24

<210> SEQ ID NO 90
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 90
tcttattgtg gtaggatcag ccct                      24

<210> SEQ ID NO 91
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 91
gctcaggcac cccctacctt ccgggcc                   27

<210> SEQ ID NO 92

```
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 92
gcctcgagca gcaccggggc t                                              21

<210> SEQ ID NO 93
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 93
gccactacat tgcgatcatg gct                                            23

<210> SEQ ID NO 94
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 94
gctcatcacc aaggaacaca tccaggcc                                       28

<210> SEQ ID NO 95
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 95
aaatgtttgt gggtgaagtc agttct                                         26

<210> SEQ ID NO 96
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 96
cacaatggct gggttgttca tcagccct                                       28

<210> SEQ ID NO 97
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 97
gccagagagg ctccctcagc cct                                            23

<210> SEQ ID NO 98
<211> LENGTH: 27
<212> TYPE: DNA
<213> ORGANISM: Artificial Sequence
<220> FEATURE:
<223> OTHER INFORMATION: Synthetic polynucleotide
```

```
<400> SEQUENCE: 98
gatctggact ggagcagcag cagtgtg                                          27

<210> SEQ ID NO 99
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 99 acttttcaa aagcaacaaa ggggcc                                            26
```

METHODS FOR DIAGNOSING, PROGNOSING, AND TREATING COLORECTAL CANCER USING BIOMARKER EXPRESSION

This application is a national phase under 35 U.S.C. § 371 of International Application No. PCT/US2018/020191, filed Feb. 28, 2018, which claims the benefit of priority to U.S. Provisional Patent Application Ser. No. 62/464,781, filed Feb. 28, 2017, the entire contents of each of which are hereby incorporated by reference in their entirety.

This invention was made with government support under Grant Nos. R01CA202797, U01CA187956, R01CA184792, R01CA072851 and R01CA181572 awarded by the National Cancer Institute, National Institutes of Health. The government has certain rights in the invention.

The instant application contains a Sequence Listing which has been submitted in ASCII format and is hereby incorporated by reference in its entirety. Said ASCII copy, created on Jun. 28, 2022, is named BHCSP0577US_ST25.txt and is 19300 bytes in size.

BACKGROUND

1. Field of the Invention

The present invention relates generally to the fields of molecular biology and oncology. More particularly, it concerns methods and compositions involving cancer prognosis, diagnosis, and treatment.

2. Description of Related Art

Colorectal cancer (CRC) is one of the most frequently diagnosed malignancies and a leading cause of cancer-related deaths worldwide. High degree of mortality associated with CRC is largely due to late disease detection and lack of availability of adequate prognostic biomarkers, including the currently used tumor-node-metastasis (TNM) classification system from the American Joint Committee on Cancer for predicting tumor prognosis and recurrence. This highlights the need to develop robust prognostic biomarkers for CRC, and the expectations are that such biomarkers must offer a superior prognostic clinical usefulness compared to existing TNM staging classification. In addition, such biomarkers must perform independent of the existing classification criteria, and possess adequate prognostic significance for specific subgroups defined by node-negative (stage II) or node-positive (stage III) CRC patients.

SUMMARY OF THE DISCLOSURE

The current disclosure fulfills a need in the art by providing more effective therapeutic treatments and diagnostic/prognostic methods for colorectal cancer based on the expression or activity level of biomarkers. Aspects of the disclosure relate to a method for treating a patient determined to have colorectal cancer comprising: administering adjuvant therapy to the patient; wherein the patient was determined to have one or more of the following: differential expression of one or more miRNA, lncRNA, piRNA, mRNA, protein, or 5hmC DNA-modified gene biomarkers compared to a control sample, wherein the one or more biomarkers are selected from: i) differential expression of miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, miR-4326, CCAT1, CCAT2; piRNA: DQ596309, DQ570994 (piRACC), DQ595807 (piR61919), piR30652 (DQ570540), and/or piR31111 (DQ570999); ii) differential levels of 5hmC DNA modification of genes: P2RX4, CRISPLD2, and/or FKBP4; and iii) differential mRNA gene expression and/or protein level of: CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1. In some embodiments, the subject was determined to have differential expression of at least, at most, or exactly one, two, three, four, five, six, seven, eight, nine, ten, eleven, twelve, thirteen, fourteen, fifteen, sixteen, seventeen, eighteen, nineteen, or twenty (or any derivable range therein) of the biomarkers described herein.

In some embodiments, the expression level of lncRNAs: CCAT1 and/or CCAT2 were increased compared to the control; the expression level of piRNAs: DQ596309, DQ570994 (piRACC), DQ595807, DQ570540, and/or DQ570999 were increased compared to the control; and/or the level of 5hmC of genes: P2RX4, CRISPLD2, and/or FKBP4 is decreased compared to the control. In some embodiments, the expression level of miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, and/or -4326 were increased compared to the control. In some embodiments, miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, and/or miR-4326 were decreased compared to the control. In some embodiments, CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1 were increased compared to control. In some embodiments, CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1 were decreased compared to control.

A further aspect of the disclosure relates to a method for determining whether a patient diagnosed with Stage I, II, III, or IV colorectal cancer is high or low risk, wherein the method comprises: determining that the patient is high risk when one or more miRNA, lncRNA, piRNA, mRNA, protein, or 5hmC modified gene biomarkers are determined to be differentially expressed in a biological sample from the patient compared to a control; or determining that the patient is low risk when one or more of a miRNA, lncRNA, piRNA, mRNA, protein, or 5hmC modified gene biomarkers are determined to be not significantly different in expression in a biological sample from the patient compared to a control; wherein the one or more biomarkers are selected from: i) differential expression of miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, miR-4326, CCAT1, CCAT2; piRNA: DQ596309, DQ570994 (piRACC), DQ595807, DQ570540, and/or DQ570999; ii) differential 5hmC DNA modification levels of genes: P2RX4, CRISPLD2, and/or FKBP4; and iii) differential mRNA gene expression and/or protein level of:

CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1.

In some embodiments, the patient is determined as high risk when the expression level of lncRNAs: CCAT1 and/or CCAT2 were determined to be increased compared to the control; the expression level of piRNAs: DQ596309, DQ570994 (piRACC), DQ595807, DQ570540, and/or DQ570999 were determined to be increased compared to the control; and/or the level of 5hmC of genes: P2RX4, CRISPLD2, and/or FKBP4 were determined to be decreased compared to the control. In some embodiments, the patient is determined to be high risk when the expression level of miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, and/or -4326 were increased compared to the control. In some embodiments, the patient was determined to be high risk when the expression level of miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, and/or miR-4326 were decreased compared to the control. In some embodiments, the patient was determined to be high risk when the expression level of CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1 were increased compared to control. In some embodiments, the patient was determined to be high risk when the expression level of CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1 were decreased compared to control.

In some embodiments, the method further comprises administering adjuvant therapy to a patient determined to be high risk.

In some embodiments, the method further comprises measuring the expression level of the miRNAs in a biological sample from the patient. In some embodiments, the method further comprises comparing the expression level of the biomarker in the biological sample from the patient to the expression level of the same biomarker in a control biological sample.

In some embodiments, the patient has, is determined to have, or is diagnosed with stage I, II, III, or IV colorectal cancer. In some embodiments, the patient was determined to have stage I, II, III, or IV colorectal cancer on the basis of a clinical measurement or biomarker measurement described herein. In some embodiments, the patient is diagnosed with Stage I or II colorectal cancer and does not have lymph node metastasis. In some embodiments, the patient diagnosed with high risk is identified as one likely to have or develop distant metastasis, liver metastasis, and/or lymph node metastasis. In some embodiments, the patient diagnosed with high risk is identified as one likely to develop chemoresistance.

In some embodiments, the expression level is normalized. In some embodiments, the biological sample from the patient is a sample from a primary colorectal cancer tumor. In some embodiments, the biological sample from the patient is a blood sample. In some embodiments, the biological sample from the patient is a serum or plasma sample. In some embodiments, the biological sample from the patient is a biopsy sample. In some embodiments, the biological sample is a biological sample described herein.

In some embodiments, the control is the level of expression or the biomarker or level of 5hmC DNA modification in a control biological sample. In some embodiments, the control biological sample comprises normal mucosal tissue. In some embodiments, the control comprises the level of expression or the biomarker or level of 5hmC DNA modification in a non-metastatic colorectal cancer tissue. In some embodiments, the tissue is a primary colorectal cancer tumor. In some embodiments, the control comprises a biological sample from a stage I, II, III, or IV patient. In some embodiments, the control comprises a level of expression or the biomarker or level of 5hmC DNA modification in a biological sample from a patient with non-metastatic or non-progressive colorectal cancer. In some embodiments, non-progressive colorectal cancer is one that is not classified as having T1, T2 T3, T4, N1, N2, and/or M1. In some embodiments, non-progressive colorectal cancer comprises one that is not characterized by lymph node metastasis. In some embodiments, non-progressive colorectal cancer comprises one that is not characterized by distant metastasis. In some embodiments, non-progressive colorectal cancer comprises one that is not characterized by lung, liver, breast, or bone metastasis.

In some embodiments, the adjuvant therapy comprises cetuximab, 5-fluorouracil, oxaliplatin, irinotecan, bevacizumab, panitumumab, afibercept, leucovorin, and/or radiotherapy. In some embodiments, the method further comprises surgical resection of the primary tumor or metastatic tumor. In some embodiments, the patient does not have and/or has not been diagnosed with lymph node metastasis and/or distant metastasis. In some embodiments, the method further comprises calculating a risk score based on the expression levels of the miRNAs in the biological sample from the patient. In some embodiments, the risk score is compared to a cut-off value.

In some embodiments, the patient was determined to have differential expression of one or more (or all of) miR-409, miR-432, and miR-758. In some embodiments, the patient was determined to have differential expression of miR-758. In some embodiments, the patient was determined to have differential express of one or more of (or all of) miR-191, miR-200b, miR-30b, miR-33a, miR-362, miR-429, and miR-744. In some embodiments, the patient was determined to have differential expression of miR-191, miR-200b, miR-33a, miR-429, and miR-744. In some embodiments, the patient was determined to have differential expression of one or more of (or all of) miR-32, miR-181b, miR-188, miR-193b, miR-195, miR-424, miR-425, miR-592, miR-3677, and/or miR-4326. In some embodiments, the patient was determined to have differential expression of miR-32, miR-181b, miR-188, miR-193b, miR-195, miR-424, miR-425, miR-592, miR-3677, and miR-4326. In some embodiments, the patient was determined to have one or more risk factors selected from poorly differentiated tissues, increased tumor depth; lymphatic invasion, and venous invasion. In some embodiments, the patient was determined to not have one or more risk factors selected from poorly differentiated tissues, increased tumor depth; lymphatic invasion, and venous invasion. In some embodiments, the patient was determined to have differential expression of one or more of (or all of) miR-32, miR-181b, miR-188, miR-193b, miR-195, miR-424, miR-425, and miR-592. In some embodiments, the patient was determined to have differential expression of one or more of miR-1246; miR-34a, miR-101, miR-200, miR-3605, miR-3182, and miR-4284. In some embodiments, the patient was determined to have increased expression of CD44v6 compared to a control. In some embodiments, the patient was determined to have differential expression of one or more of (or all of) AMT, C2CD4A, CYP2B6, DEFA6, FOXA1, GSTT1, LYZ, MGAT5, MMP1, MMP9, NOS2, PIGR, PRAC1, RPL39L, RCC1, and SPAG16. In some embodiments, the patient was determined to have differential expression of one or more of C2CD4A, DEFA6, MGAT5, MMP9, SPAG16, FOXA1, AMT, PRAC1, and RCC1. In some embodiments, the patient was determined to have differential expression of C2CD4A, DEFA6, MGAT5, MMP9, SPAG16, FOXA1, AMT, PRAC1, and RCC1. In some embodiments, the patient was determined to have differential expression of one or more of (or all of) AMT2, MMP9, DEFA6, FOXA1, MGAT5, C2CD4A, RCC1, LYZ, MMP1, NOS2, PIGR, and CYP2B6. In some embodiments, the patient was determined to have differential expression of AMT2, MMP9, DEFA6, FOXA1, MGAT5, C2CD4A, RCC1, LYZ, MMP1, NOS2, PIGR, and CYP2B6. In some embodiments, the patient was determined to have differential expression of one or more of AMT2, MMP9, FOXA1, C2CD4A, RCC1, LYZ, MMP1, and PIGR. In some embodiments, the patient was determined to have differential expression of AMT2, MMP9, FOXA1, C2CD4A, RCC1, LYZ, MMP1, and PIGR. In some embodiments, the patient was determined to have differential expression of one or more of AMT2, MMP9, FOXA1, RCC1, LYZ, MMP1, and PIGR. In some embodiments, the patient was determined to have differential expression of AMT2, MMP9, FOXA1, RCC1, LYZ, MMP1, and PIGR. In some embodiments, the patient was determined to have differential expression of one or more of (or all of) CCAT1 and CCAT2. In some embodiments, the patient was determined to have increased CEA expression compared to the expression in a control. In some embodiments, the patient was determined to have differential expression of one or more of (or all of) DQ595807, DQ570540, and DQ570999. In some embodiments, the patient was determined to have a low level of 5hmC modified DNA at one or more of (or all of) P2RX4, CRISPLD2, and FKBP4. In some embodiments, the patient was determined to have an increased level of expression of ITGBL1. In some embodiments, the patient was determined to have an increased level of expression of DQ596309 and/or DQ570994 (piRACC).

In some embodiments, the method further comprises predicting that the patient is likely to survive, likely to have disease free survival, and/or likely to have recurrence free survival when the expression level of the biomarker in the biological sample from the patient is not significantly different than the expression level of the biomarker in a control.

In some embodiments, the patient was determined to be high risk when one or more of (or all of) miR-409, miR-432, and miR-758 were determined to be differentially expressed in the biological sample from the patient. In some embodiments, the patient was determined to be high risk when miR-758 was determined to be differentially expressed in the biological sample from the patient. In some embodiments, the patient was determined to be high risk when one or more of (or all of) miR-191, miR-200b, miR-30b, miR-33a, miR-362, miR-429, and/or miR-744 were determined to be differentially expressed in the biological sample from the patient. In some embodiments, the patient was determined to be high risk when miR-191, miR-200b, miR-33a, miR-429, and miR-744 were determined to be differentially expressed in the biological sample from the patient. In some embodiments, the patient was determined to be high risk when miR-32, miR-181b, miR-188, miR-193b, miR-195, miR-424, miR-425, miR-592, miR-3677, and/or miR-4326 were determined to be differentially expressed in the biological sample from the patient. In some embodiments, the patient was determined to be high risk when miR-32, miR-181b, miR-188, miR-193b, miR-195, miR-424, miR-425, miR-592, miR-3677, and miR-4326 were determined to be differentially expressed in the biological sample from the patient. In some embodiments, the patient was determined to be high risk when the biological sample from the patient demonstrates poor tissue differentiation, increased tumor depth; lymphatic invasion, and/or venous invasion in the biological sample from the patient. In some embodiments, the patient was determined to be high risk when one or more of (or all of) miR-32, miR-181b, miR-188, miR-193b, miR-195, miR-424, miR-425, and miR-592 were determined to be differentially expressed in the biological sample from the patient. In some embodiments, the patient was determined to be high risk when one or more of (or all of) miR-1246; miR-34a, miR-101, miR-200, miR-3605, miR-3182, and miR-4284 were determined to be differentially expressed in the biological sample from the patient. In some embodiments, the patient was determined to be high risk when the expression of CD44v6 was determined to be increased in the biological sample from the patient. In some embodiments, the patient was determined to be high risk when one or more of AMT, C2CD4A, CYP2B6, DEFA6, FOXA1, GSTT1, LYZ, MGAT5, MMP1, MMP9, NOS2, PIGR, PRAC1, RPL39L, RCC1, and SPAG16 were determined to be differentially expressed in the biological sample from the patient. In some embodiments, the patient was determined to be high risk when one or more of C2CD4A, DEFA6, MGAT5, MMP9, SPAG16, FOXA1, AMT, PRAC1, and RCC1 was determined to be differentially expressed in the biological sample from the patient. In some embodiments, the patient was determined to be high risk when C2CD4A, DEFA6, MGAT5, MMP9, SPAG16, FOXA1, AMT, PRAC1, and RCC1 were determined to be differentially expressed in the biological sample from the patient. In some embodiments, the patient was determined to be high risk when one or more of AMT2, MMP9, DEFA6, FOXA1, MGAT5, C2CD4A, RCC1, LYZ, MMP1, NOS2, PIGR, and CYP2B6 was determined to be differentially expressed in the biological sample from the patient. In some embodiments, the patient was determined to be high risk when AMT2, MMP9, DEFA6, FOXA1, MGAT5, C2CD4A, RCC1, LYZ, MMP1, NOS2, PIGR, and CYP2B6 was determined to be differentially expressed in the biological sample from the patient. In some embodiments, the patient was determined to have differential expression of one or more of AMT2, MMP9, FOXA1, C2CD4A, RCC1, LYZ, MMP1, and PIGR was determined to be differentially expressed in the biological sample from the patient. In some embodiments, the patient was determined to have differential expression of AMT2, MMP9, FOXA1, C2CD4A, RCC1, LYZ, MMP1, and PIGR was determined to be differentially expressed in the biological sample from the patient. In some embodiments, the patient was determined to be high risk when one or more of AMT2, MMP9, FOXA1, RCC1, LYZ, MMP1, and PIGR was determined to be differentially expressed in the biological sample from the patient. In some embodiments, the patient was determined to be high risk when AMT2, MMP9, FOXA1, RCC1, LYZ, MMP1, and PIGR was determined to be differentially expressed in the biological sample from the patient. In some embodiments, the patient was determined to be high risk when one or more of CCAT1 and CCAT2 was determined to be differentially expressed in the biological sample from the patient. In some embodiments, the patient was determined to be high risk when CCAT1 and CCAT2 was determined to be differentially expressed in the biological sample from the patient. In some embodiments, the method further comprises determining serum CEA expression. In some embodiments, the patient was determined to be high risk when CEA expression is increased in the biological sample from the patient. In some embodiments, the patient was determined to be high risk when one or more of DQ595807, DQ570540, and DQ570999 were determined to be differentially expressed in the biological sample from the patient. In some embodiments, the patient was determined to be high risk when DQ595807, DQ570540, and DQ570999 were determined to be differentially expressed in the biological sample from the patient. In some embodiments, the patient was determined to be high risk when one or more of (or all of) P2RX4, CRISPLD2, and FKBP4 were determined to have decreased levels of 5hmC in the biological sample from the patient. In some embodiments, the patient was determined to be high risk when ITGBL1 was determined to be increased in the biological sample from the patient. In some embodiments, the patient was determined to be high risk when DQ596309 and/or DQ570994 (piRACC) was determined to be differentially expressed in the biological sample from the patient.

Further aspects relate to a method for treating colorectal cancer in a patient, the method comprising administering one or more of miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, miR-4326, CCAT1, CCAT2; piRNA: DQ596309, DQ570994 (piRACC), DQ595807 (DQ595807), DQ570540 (DQ570540), DQ570999 (DQ570999); CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1 or antagonist, agonists, or modifiers thereof.

In some embodiments, the method further comprises determining a risk score based on the expression levels of the miRNAs in the biological sample from the patient. In some embodiments, the risk score is compared to a cut-off value.

In some embodiments, the adjuvant therapy comprises or the method further comprises administration of one or more of cetuximab, fluorouracil, oxaliplatin, irinotecan, bevacizumab, panitumuman, afibercept, leucovorin, and radiotherapy. In some embodiments, the method excludes administration of one or more of cetuximab, fluorouracil, oxaliplatin, irinotecan, bevacizumab, panitumuman, afibercept, leucovorin, and radiotherapy. In some embodiments, the adjuvantherapy comprises or the method further comprises administration of one or more of cetuximab, fluorouracil, oxaliplatin, irinotecan, bevacizumab, panitumuman, afibercept, leucovorin, and radiotherapy. In some embodiments, the treatment for advanced colorectal cancer excludes administration of one or more of cetuximab, fluorouracil, oxaliplatin, irinotecan, bevacizumab, panitumuman, afibercept, leucovorin, and radiotherapy. In some embodiments, the adjuvant therapy comprises or the method further comprises administration of one or more of cetuximab, fluorouracil, oxaliplatin, irinotecan, bevacizumab, panitumuman, afibercept, leucovorin, and radiotherapy. In some embodiments, the adjuvant therapy excludes or the method excludes administration of one or more of cetuximab, fluorouracil, oxaliplatin, irinotecan, bevacizumab, panitumuman, afibercept, leucovorin, and radiotherapy.

The expression level or activity level from a control sample may be an average value, a normalized value, a cut-off value, or an average normalized value. The expression level or activity level may be an average or mean obtained from a significant proportion of patient samples. The expression or activity level may also be an average or mean from one or more samples from the patient.

In some embodiments, the method further comprises surgical incision of the primary tumor. In some embodiments, the elevated level/increased expression or reduced level/decreased expression is at least 1, 1.5, 2, 2.5, 3, 3.5, 4, 4.5, 5, 5.5, 6, 7, 8, 9, 10, 12, 14, 16, 18, 20, 50, 100, 150, 200, 250, 500, or 1000 fold (or any derivable range therein) or at least 10, 20, 30, 40, 50, 60, 70, 80, 90, 100, 200, 300, 400, 500, 600, 700, 800, or 900% different than the control, or any derivable range therein.

In some embodiments, the biological sample from the patient is a sample from a primary colorectal cancer tumor. In some embodiments, the biological sample is from a tissue or organ as described herein. In still further embodiments, the method may comprise obtaining a sample of the subject or patient. Non-limiting examples of the sample include a tissue sample, a whole blood sample, a urine sample, a saliva sample, a serum sample, a plasma sample, or a fecal sample. In particular embodiments, the sample is a rectum sample, a colon sample or a cecum sample.

In some embodiments the subject or patient is one that has previously been treated for colorectal cancer. In some embodiments, the colorectal cancer is recurrent.

The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy.

In certain embodiments the sample is obtained from a biopsy from rectal, cecum, or colon tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, intestine, brain, prostate, esophagus, or thyroid tissue.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In certain aspects the sample is obtained from cystic fluid or fluid derived from a tumor or neoplasm. In yet other embodiments the cyst, tumor or neoplasm is in the digestive system. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. Further embodiments include isolating or analyzing protein expression in a biological sample for the expression of the biomarker.

In certain embodiments, a microarray may be used to measure or assay the level of the biomarkers in a sample. The methods may further comprise recording the biomarker expression or activity level in a tangible medium or reporting the expression or activity level to the patient, a health care payer, a physician, an insurance agent, or an electronic system.

In some embodiments, methods will involve determining or calculating a prognosis score based on data concerning the expression or activity level of one or more of the biomarkers, meaning that the expression or activity level of one or more of the biomarkers is at least one of the factors on which the score is based. A prognosis score will provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor response to a particular treatment. Alternatively, the probability may be expressed generally in percentiles, quartiles, or deciles.

A difference between or among weighted coefficients or expression or activity levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression or activity levels in a biomarker, gene, or protein.

Further aspects relate to a kit comprising nucleic acid probes for detecting the expression level of differentially expressed biomarkers in a biological sample; wherein the differentially expressed biomarkers comprise one or more of: miRNAs: miR-30b, miR-32, miR-33a, miR-34a, miR-101, miR-181b, miR-188, miR-191, miR-193b, miR-195, miR-200, miR-200b, miR-362, miR-409, miR-424, miR-425, miR-429, miR-432, miR-592, miR-744, miR-758, miR-1246, miR-3182, miR-3605, miR-3677, miR-4284, and/or miR-4326; lncRNA: CCAT1 and/or CCAT2; piRNA: DQ596309, DQ570994 (piRACC), DQ595807, DQ570540, and/or DQ570999; 5hmC DNA modification levels of genes: P2RX4, CRISPLD2, and/or FKBP4; and mRNA gene expression and/or protein level of: CD44v6, AMT, C2CD4A, CYP2B6, DEFA6, FOXA1, GSTT1, LYZ, MGAT5, MMP1, MMP9, NOS2, PIGR, PRAC1, RPL39L, RCC1, SPAG16, AMT2, and/or ITGBL1.

In some embodiments, the differentially expressed biomarkers consist of miR-409, miR-432, and miR-758. In some embodiments, the differentially expressed biomarkers consist of miR-758. In some embodiments, the differentially expressed biomarkers consist of miR-191, miR-200b, miR-30b, miR-33a, miR-362, miR-429, and miR-744. In some embodiments, the differentially expressed biomarkers consist of miR-191, miR-200b, miR-33a, miR-429, and miR-744. In some embodiments, the differentially expressed biomarkers consist of miR-32, miR-181b, miR-188, miR-193b, miR-195, miR-424, miR-425, miR-592, miR-3677, and miR-4326. In some embodiments, the differentially expressed biomarkers consist of miR-32, miR-181b, miR-188, miR-193b, miR-195, miR-424, miR-425, and miR-592. In some embodiments, the differentially expressed biomarkers consist of miR-1246; miR-34a, miR-101, miR-200, miR-3605, miR-3182, and miR-4284. In some embodiments, the differentially expressed biomarker consists of CD44v6. In some embodiments, the differentially expressed biomarkers consist of AMT, C2CD4A, CYP2B6, DEFA6, FOXA1, GSTT1, LYZ, MGAT5, MMP1, MMP9, NOS2, PIGR, PRAC1, RPL39L, RCC1, and SPAG16. In some embodiments, the differentially expressed biomarkers consist of C2CD4A, DEFA6, MGAT5, MMP9, SPAG16, FOXA1, AMT, PRAC1, and RCC1. In some embodiments, the differentially expressed biomarkers consist of AMT2, MMP9, DEFA6, FOXA1, MGAT5, C2CD4A, RCC1, LYZ, MMP1, NOS2, PIGR, and CYP2B6. In some embodiments, the differentially expressed biomarkers consist of AMT2, MMP9, FOXA1, C2CD4A, RCC1, LYZ, MMP1, and PIGR. In some embodiments, the differentially expressed biomarkers consist of AMT2, MMP9, FOXA1, RCC1, LYZ, MMP1, and PIGR. In some embodiments, the differentially expressed biomarkers consist of CCAT1 and CCAT2. In some embodiments, the differentially expressed biomarkers consist of DQ595807, DQ570540, and DQ570999. In some embodiments, the differentially expressed biomarkers consist of P2RX4, CRISPLD2, and FKBP4. In some embodiments, the differentially expressed biomarker consists of ITGBL1. In some embodiments, the differentially expressed biomarkers consist of DQ596309 and DQ570994 (pi-RACC).

In some embodiments, the probes are labeled. In some embodiments, the kit further comprises nucleic acid probes for detecting a control. In some embodiments, the control comprises a RNA, miRNA, or protein not differentially expressed in colorectal cancer. In some embodiments, the probe comprises nucleic acid primers that are capable of amplifying the RNA or a cDNA made from the RNA by PCR. In some embodiments, the kit further comprises reagents for performing one or more of reverse transcriptase PCR, DNA amplification by PCR, and real-time PCR. In some embodiments, the kit further comprises instructions for use.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression or activity level of a gene, biomarker or protein in a sample from a patient; and b) determining a difference value in the expression or activity levels using the information corresponding to the expression or activity levels in the sample compared to a control or reference expression or activity level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for colorectal cancer, administering the same treatment as the first treatment to the patient if the patient does not have increased expression or activity level; administering a different treatment from the first treatment to the patient if the patient has increased expression or activity level.

In some embodiments, receiving information comprises receiving from a tangible data storage device information corresponding to the expression or activity levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional colorectal therapy if the patient does not have expression or activity levels, and/or or treating the patient with an alternative colorectal therapy if the patient has increased expression or activity levels.

The tangible, computer-readable medium further comprise computer-readable code that, when executed by a computer, causes the computer to perform one or more additional operations comprising calculating a prognosis score for the patient. The operations may further comprise making recommendations comprising: administering a treatment comprising a thymidylate synthase inhibitor to a patient that is determined to have a decreased expression or activity level.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-D: Schematic design of miRNA discovery (a-c); Log 2 expression level of differentially expressed miRNAs in recurrent and non-recurrent colorectal cancer tissues. These results are further discussed in Example 1.

FIG. 15A-C: High miR-1246 expression resulted in poor overall (a) and poor disease free survival (b). The expression of CD44v6 positively correlated with miR-1246 in CRC tissues (c). These results are further discussed in Example 4.

(ROC), 1.0 (Precision); and (d) CIT/GSE39582 cohort with T1 and T2 CRC patients (18 LN+, 38 LN−); AUC=0.86 (ROC), 0.74 (precision) using 9 gene classifier described in Example 5.

FIG. 33A-D: The testing and validation phase of this study. a) CCAT1 expression and association with recurrence free survival (RF S) and overall survival (OS) in cohort 2. High CCAT1 expression was associated with poor RFS and poor OS (P=0.049 and 0.028, respectively). b) CCAT2 expression and association with RFS and OS in cohort 2. High CCAT2 expression was associated with poor RFS and poor OS (P=0.022 and 0.015, respectively). c) CCAT1 expression and association with RFS and OS in cohort 3. High CCAT1 expression was significantly association with RFS and OS (P<0.001 and 0.011, respectively). d) CCAT2 expression and association with RFS and OS in cohort 3. High CCAT2 expression was significantly association with RFS and OS (P=0.010 and 0.025, respectively). These results are further discussed in Example 6.

Figure 34A:
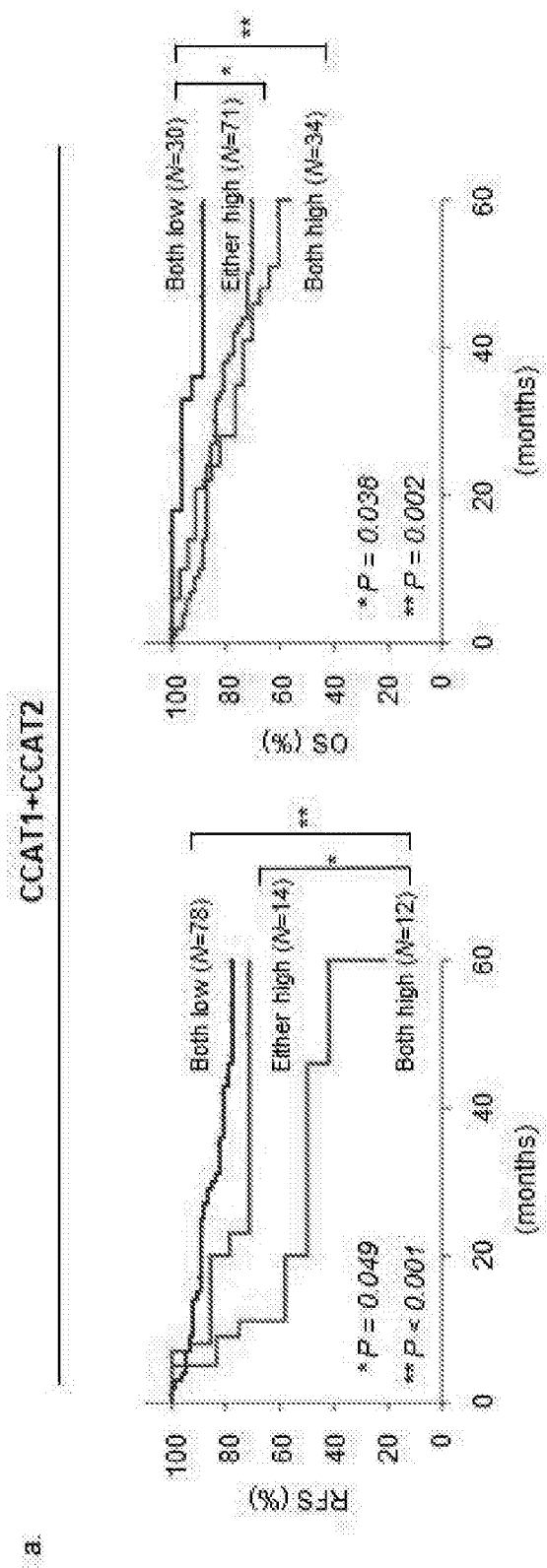
Figure 34B:
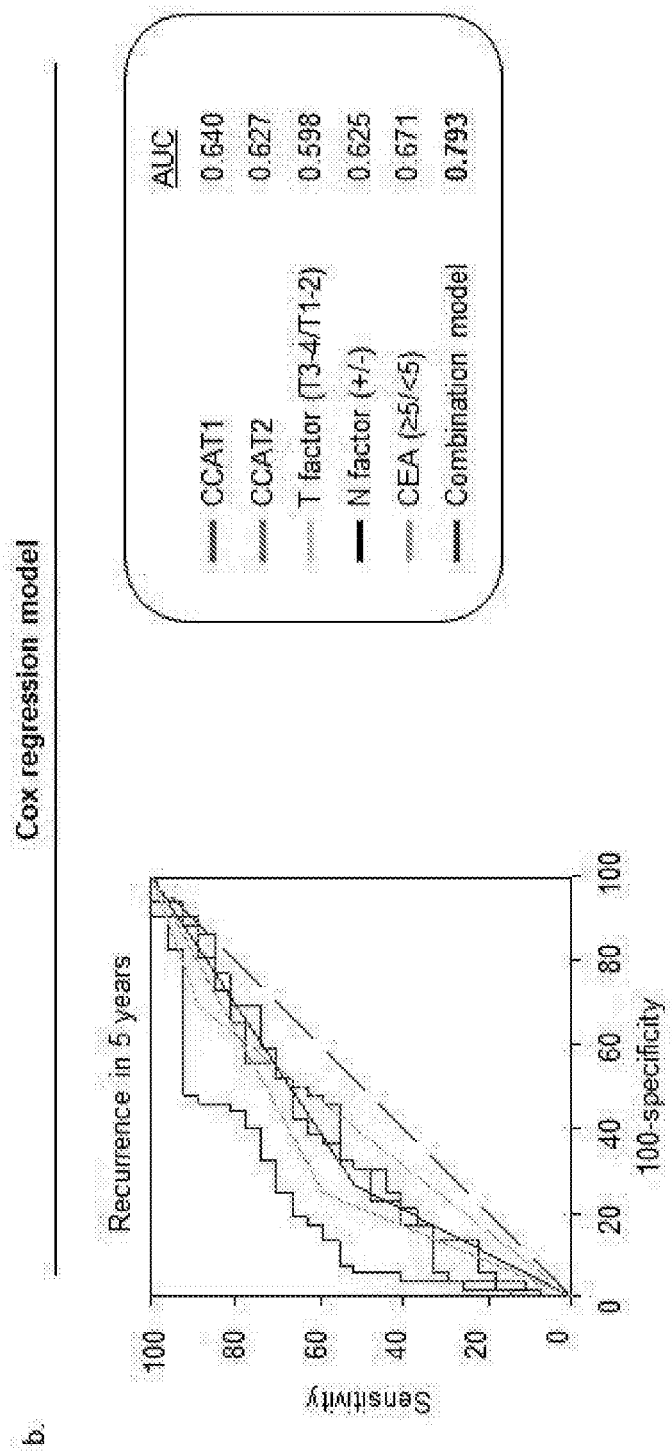
Figure 34C:
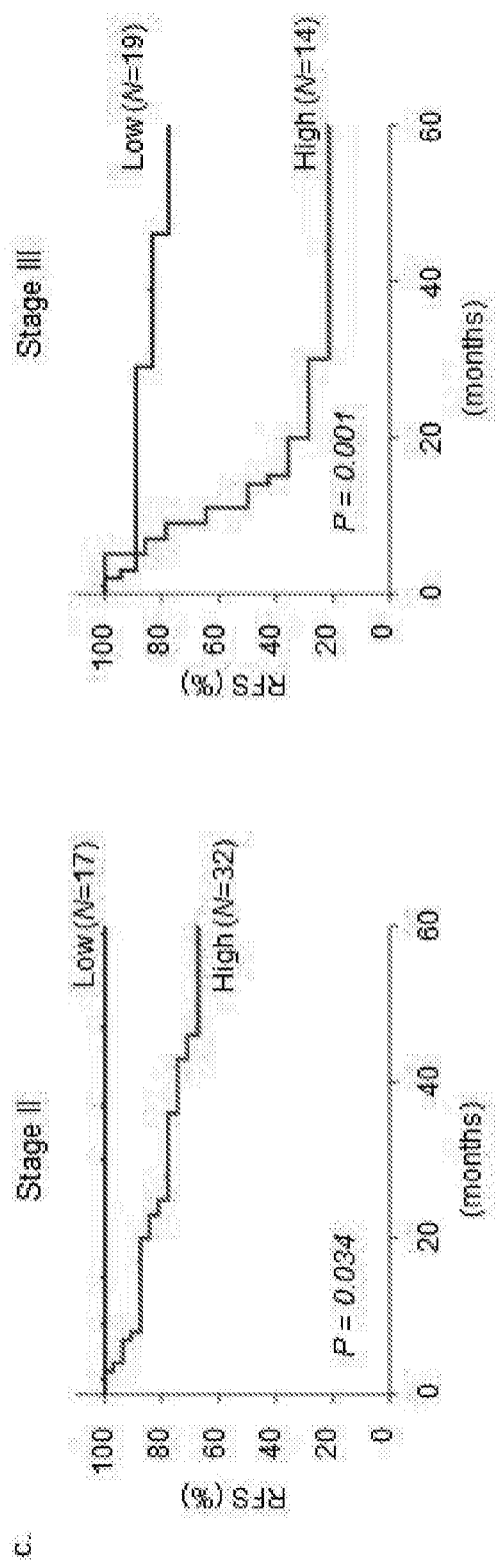

FIG. 34A-C: Combination of CCAT1, CCAT2 expression and association with RFS, OS. a) Survival curves plotting co-expression of CCAT1 and CCAT2 lncRNAs versus recurrence free survival (RFS) and overall survival (OS) in 135 patients with colorectal cancer. Patients whose tumors expressed high levels of both CCAT1 and CCAT2 had poorer RFS compared with those who express high levels of either CCAT1 or CCAT2 (P=0.049) and those who express low levels of CCAT1 and CCAT2 lncRNAs (P<0.001). OS showed the same trends, with patients expressing low levels of CCAT1 and CCAT2 having a better OS than those expression high levels of CCAT1 or CCAT2 (P=0.038) and those with high levels of expression of both lncRNAs (P=0.002). b) Receiver operating characteristic analysis comparing the accuracy of predicting recurrence in 5 years for patients with stage I-III CRC. Expression of CCAT1, CCAT2, and several clinicopathological factors, and combination model of CCAT1, CCAT2 and CEA expression were investigated. Combination model showed the highest area under the curve (AUC) of 0.793. c) The association of RFS with combination model of CCAT1, CCAT2, and CEA expression in tumor tissues from stage II and stage III colorectal cancer patients. High levels of combination model showed poorer RFS than those with low expression in both stage II and stage III patients (P=0.034 and 0.001, respectively). These results are further discussed in Example 6.

FIG. 35A-B: The study design, and the screening phase of the study. a) Study design. b) The long non-coding RNAs (lncRNAs) located in the 8q24.21 locus. These results are further discussed in Example 6.

Figure 36A:
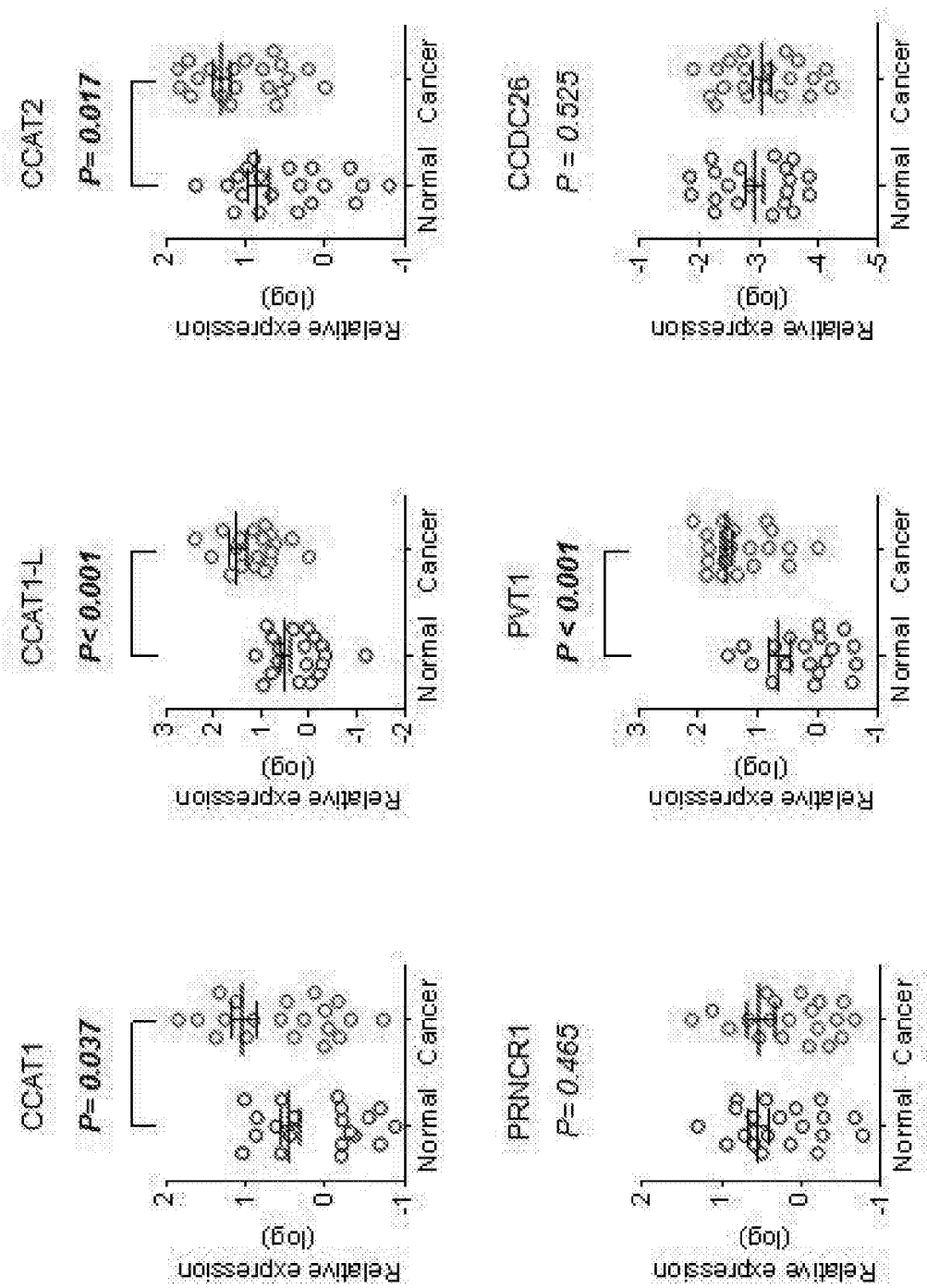
Figure 36B:
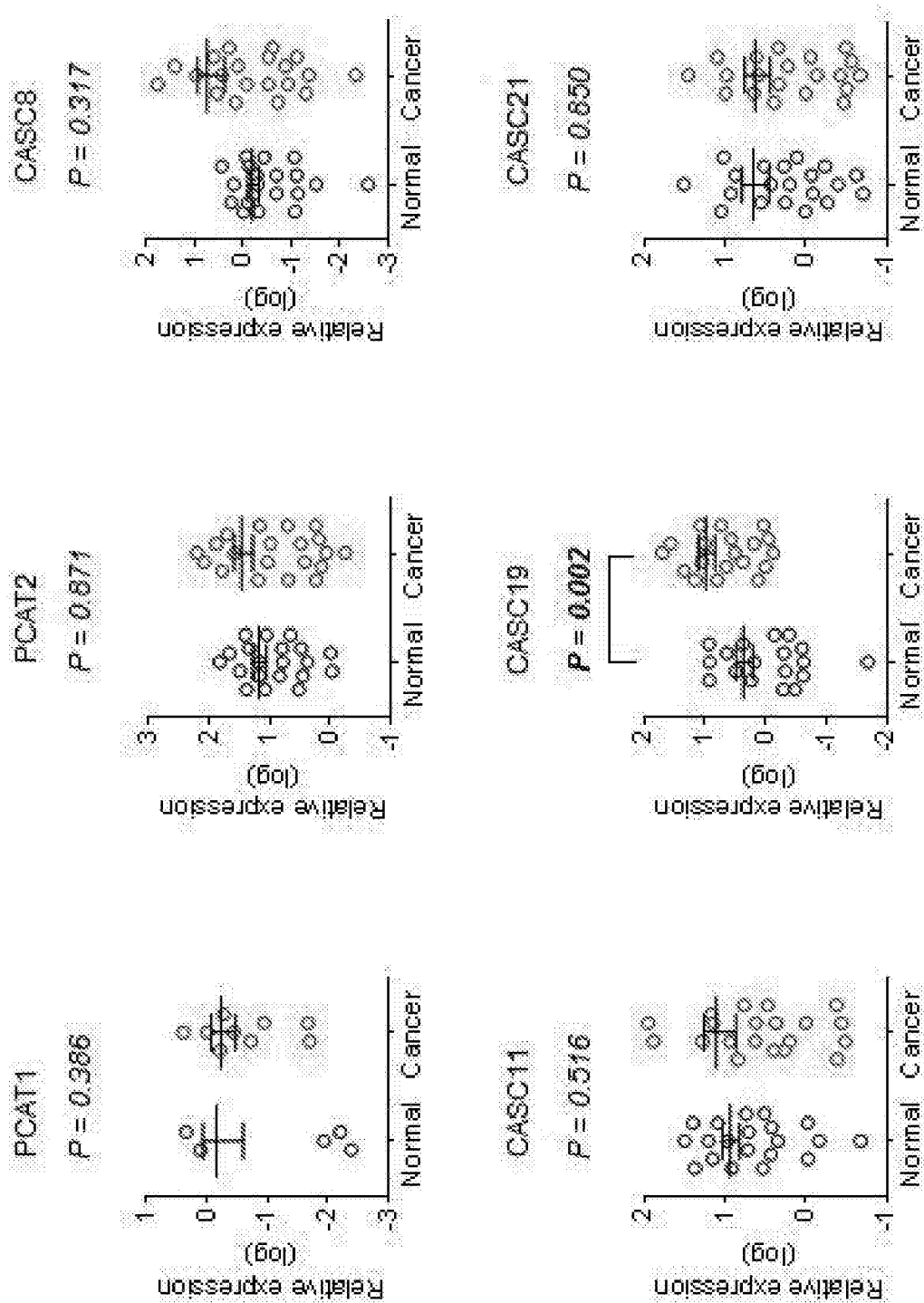

FIG. 36A-B: The screening phase of the study. Expression of twelve lncRNAs was compared between 20 CRC tissues and their matched adjacent normal mucosa. CCAT1, CCAT1-L, CCAT2, PVT1, and CASC19 lncRNAs were significantly overexpressed in cancer tissues compared to the matched controls (P=0.039, <0.001, 0.018, <0.001, 0.002, respectively). These results are further discussed in Example 6.

Figure 37C:
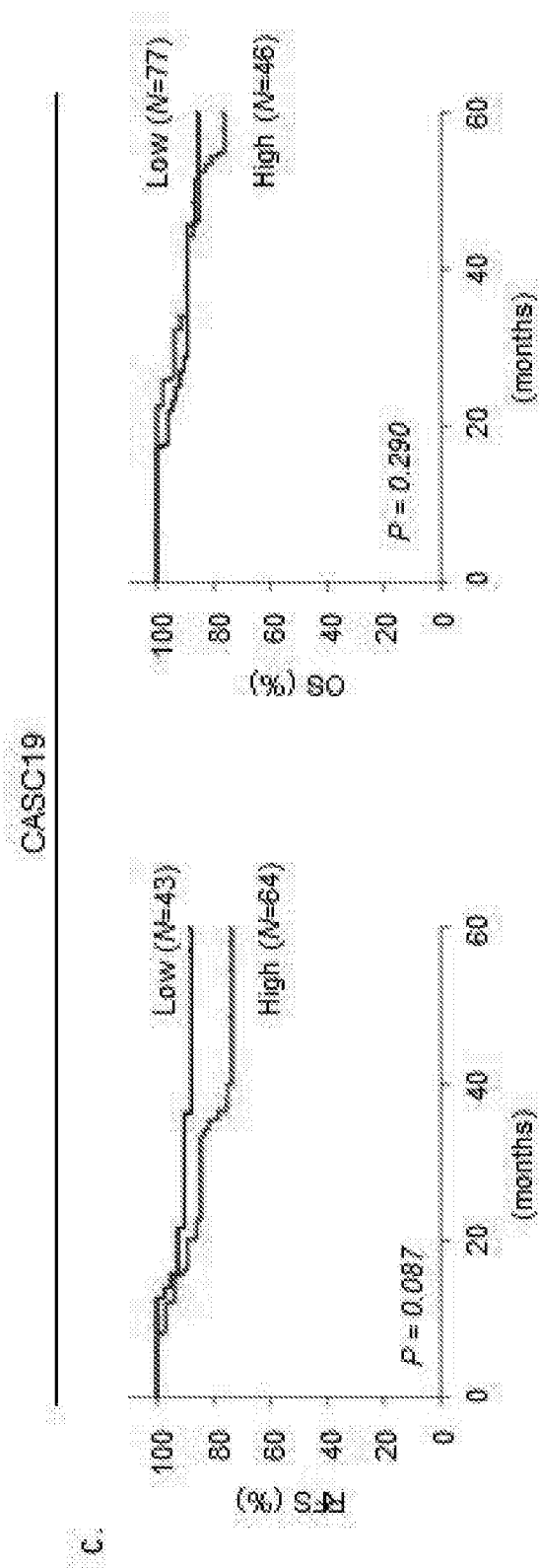

FIG. 37A-C: The testing phase of the study. CCAT1-L, PVT1, and CASC19 lncRNA expressions were evaluated in 125 colorectal cancer tissues, and their associations with recurrence free survival (RFS) and overall survival (OS) were compared using Kaplan-Meier curve. a) High levels of CCAT1-L were significantly associated with poor RFS (P=0.048), although not with OS (P=0.352). b) c) PVT1 and CASC19 showed no significant association with RFS (P=0.178 and 0.087, respectively) or OS (P=0.113 and 0.290, respectively). These results are further discussed in Example 6.

Figure 38:
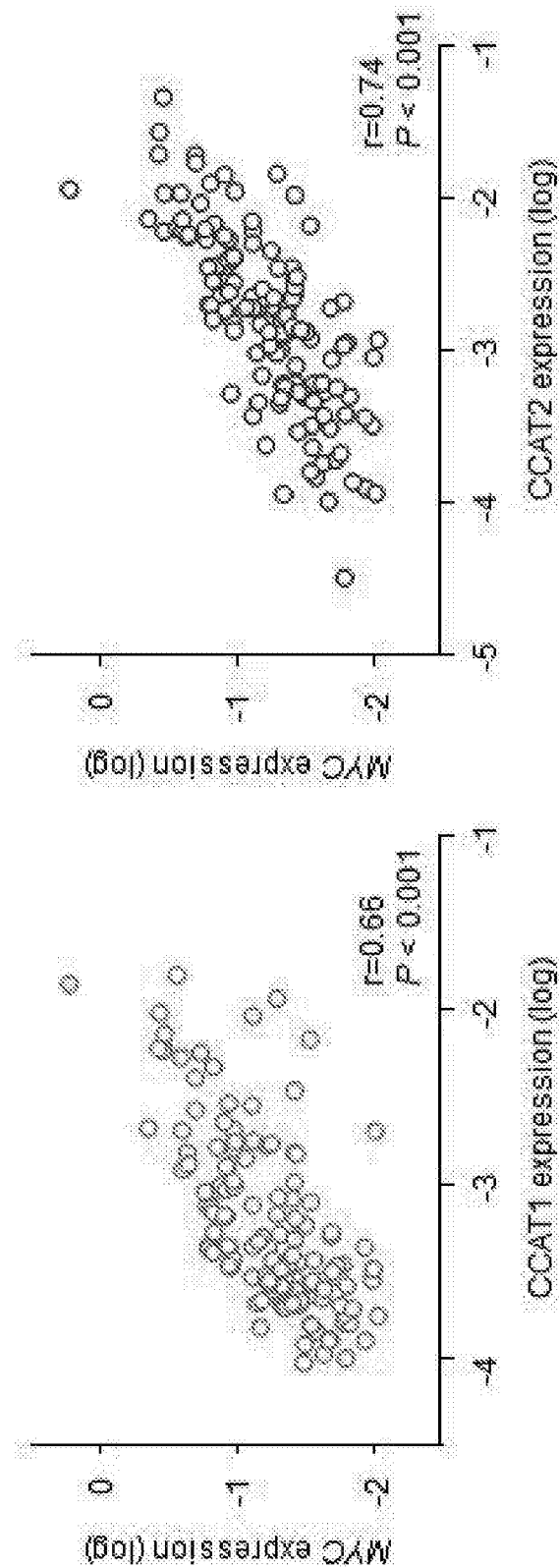

FIG. 38: The association between MYC expression and CCAT1 and CCAT2 expressions. Correlation between MYC expression and expression of CCAT1 and CCAT2 lncRNA levels. Expression of both CCAT1 and CCAT2 were highly correlated with MYC expression (r=0.66; P<0.001, r=0.74; P<0.001, Pearson's correlation). These results are further discussed in Example 6.

Figure 39:
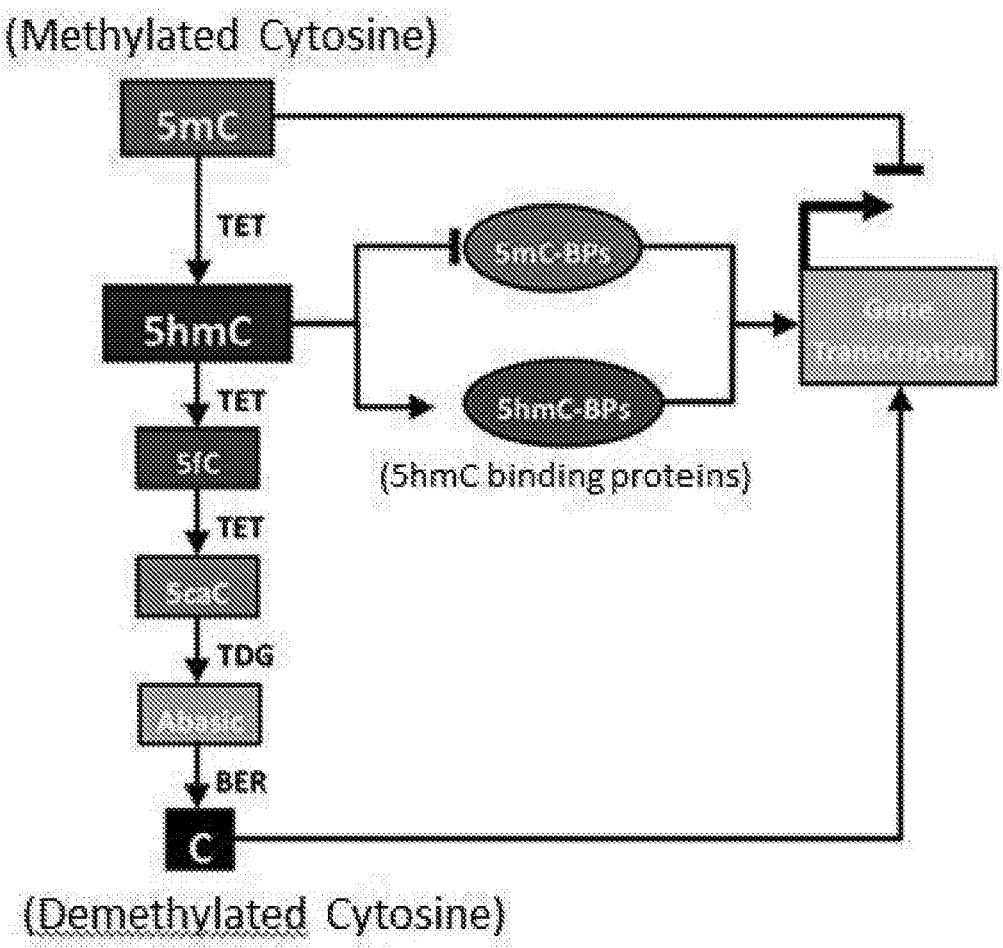
Figure 40A:
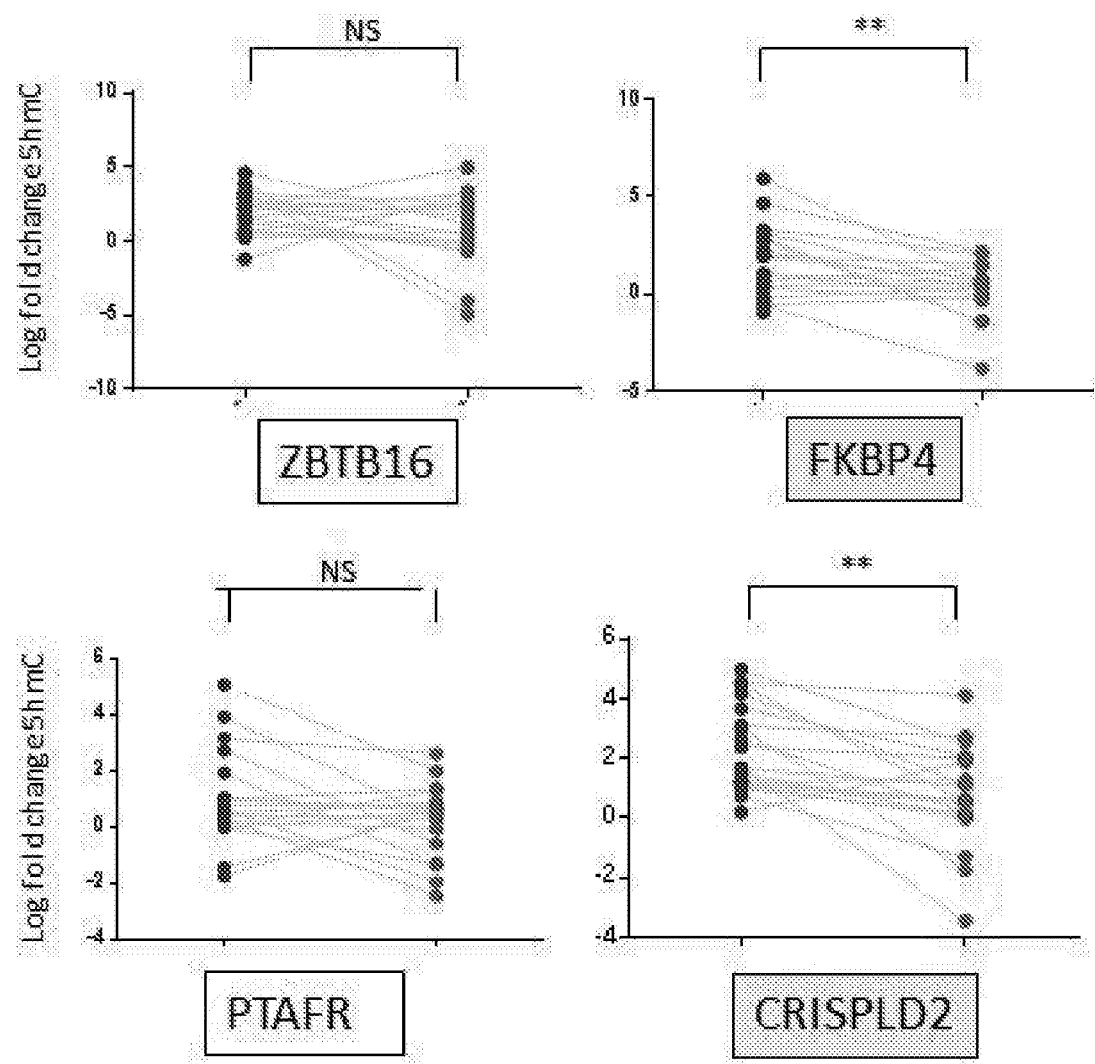
Figure 40B:
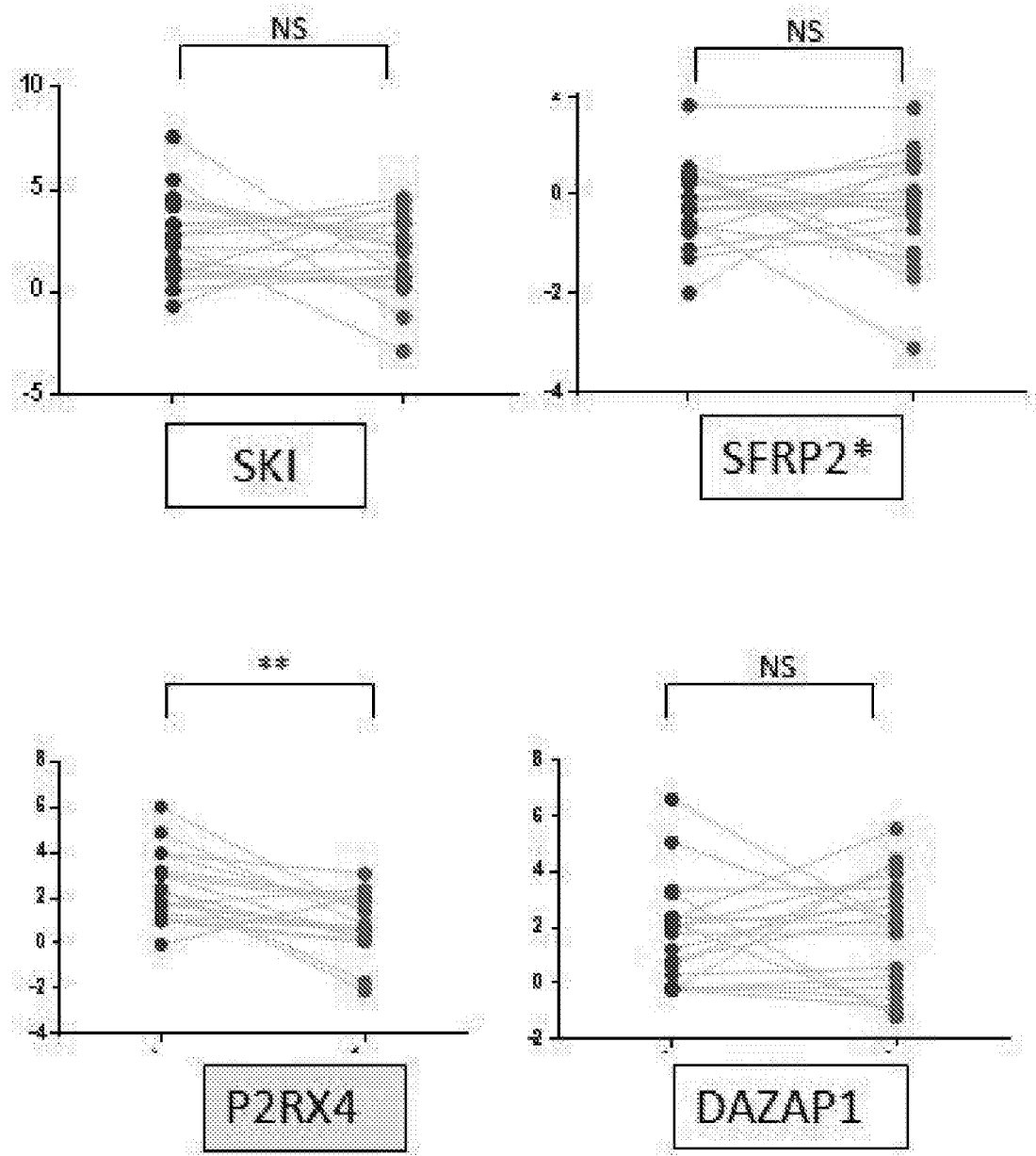
Figure 40C:
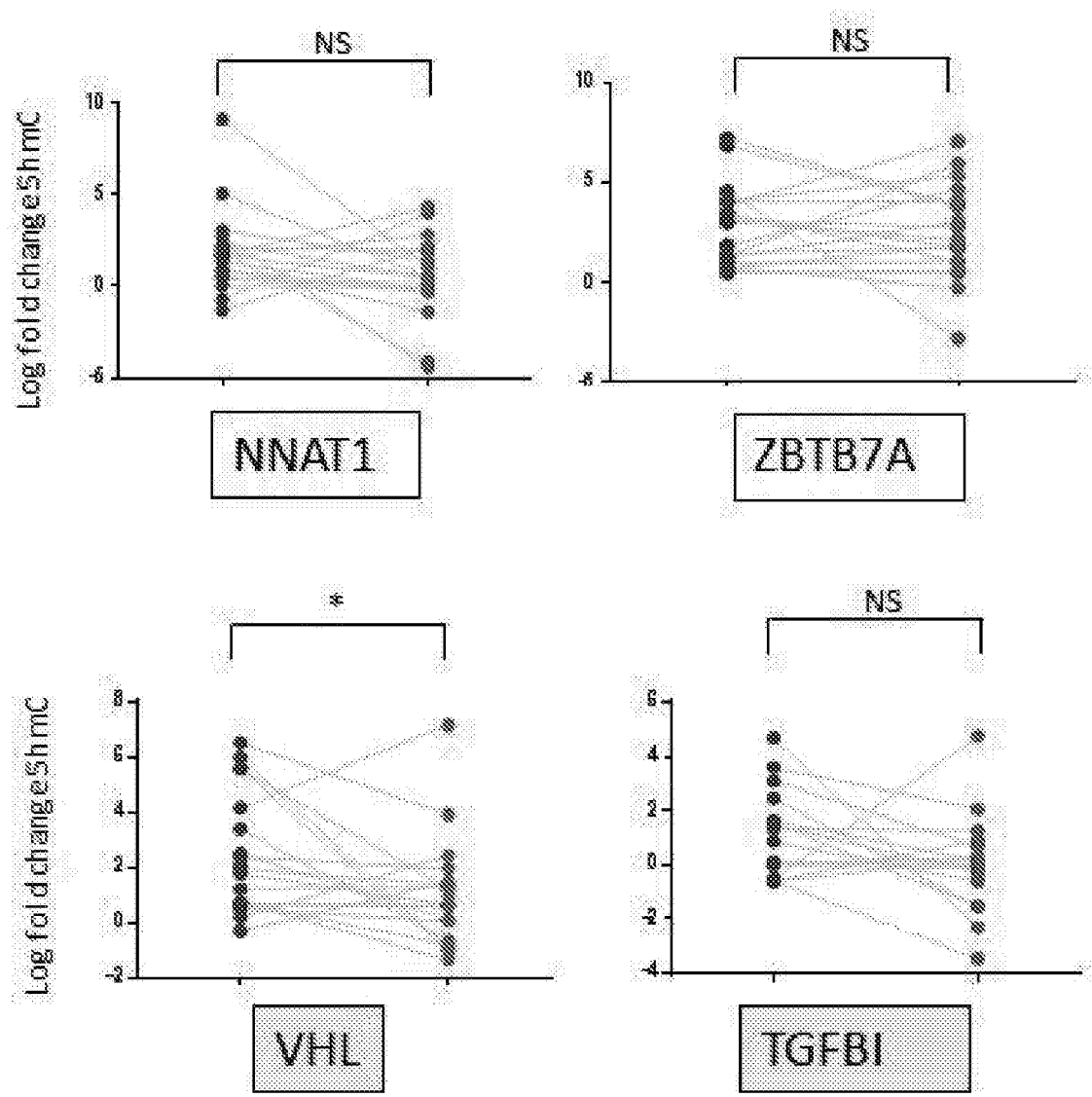
Figure 40D:
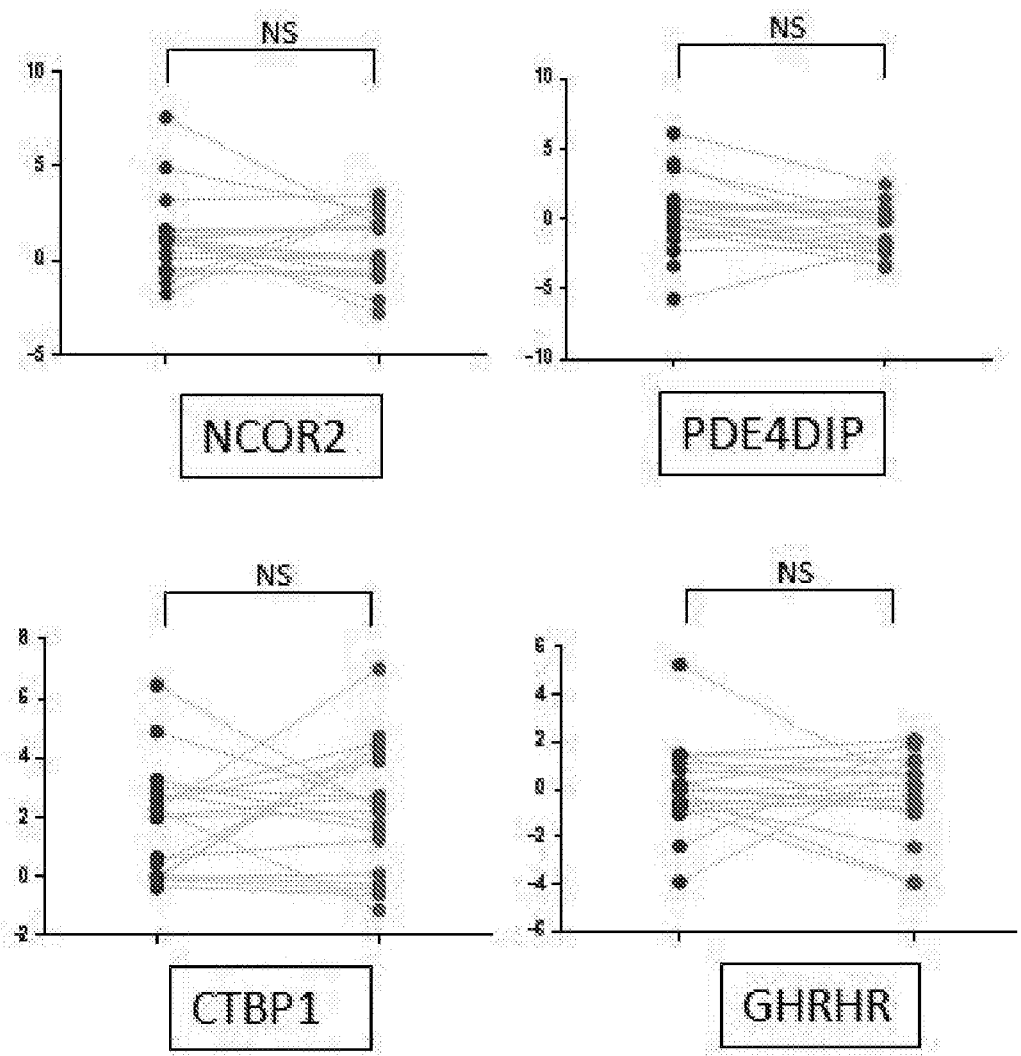
Figure 40E:
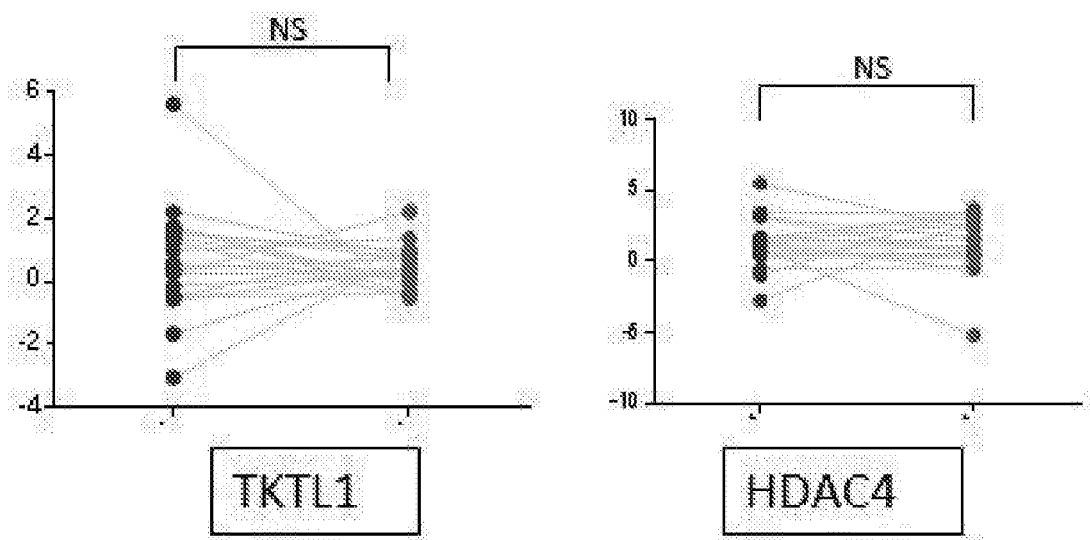

FIG. 39 depicts the 5mC demethylation pathway. These results are further discussed in Example 8.

FIG. 40A-E shows the log fold change of 5hmC in each of the indicated genes in the paired cohort (25 samples). Shown in each graph is the fold change in normal (left) and cancer (right) samples. These results are further discussed in Example 8.

Figure 41:
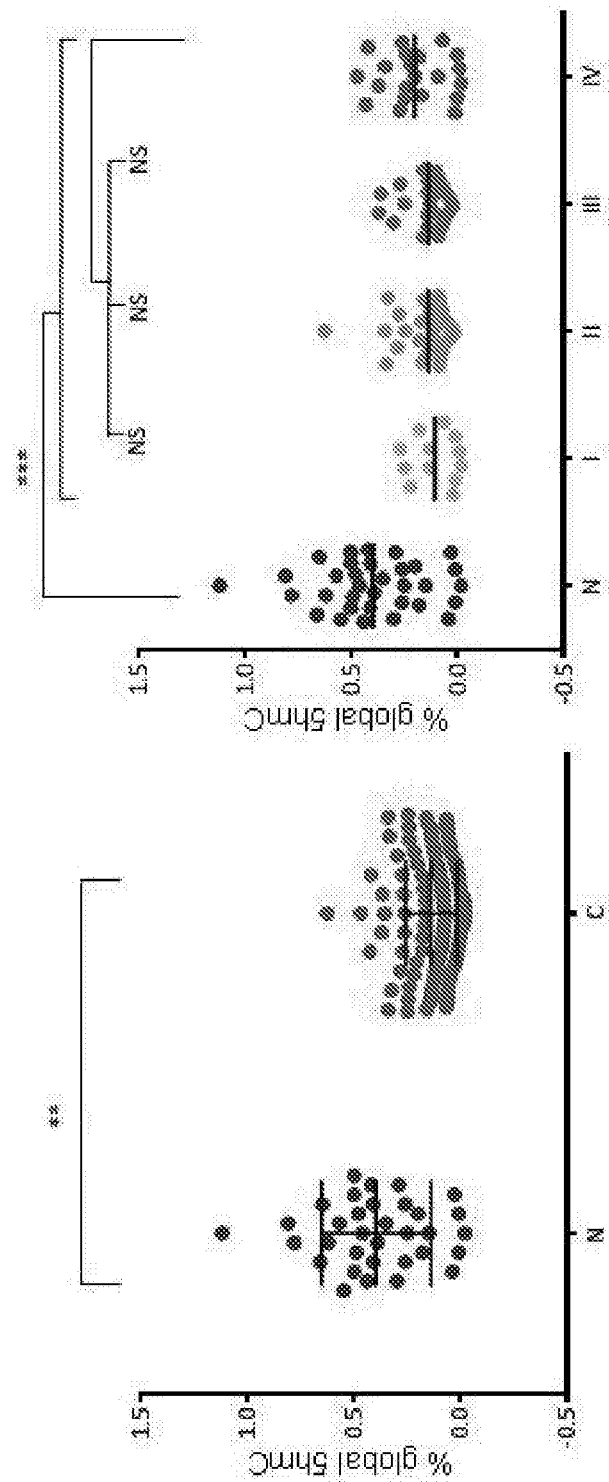

FIG. 41 shows the global 5hmC level in tumor (c) and normal (n) samples (left) and the stage specific global 5hmC levels (right) of independent cohort 1. 100 colorectal cancer samples and 48 normal samples were in cohort 1. These results are further discussed in Example 8.

Figure 42:
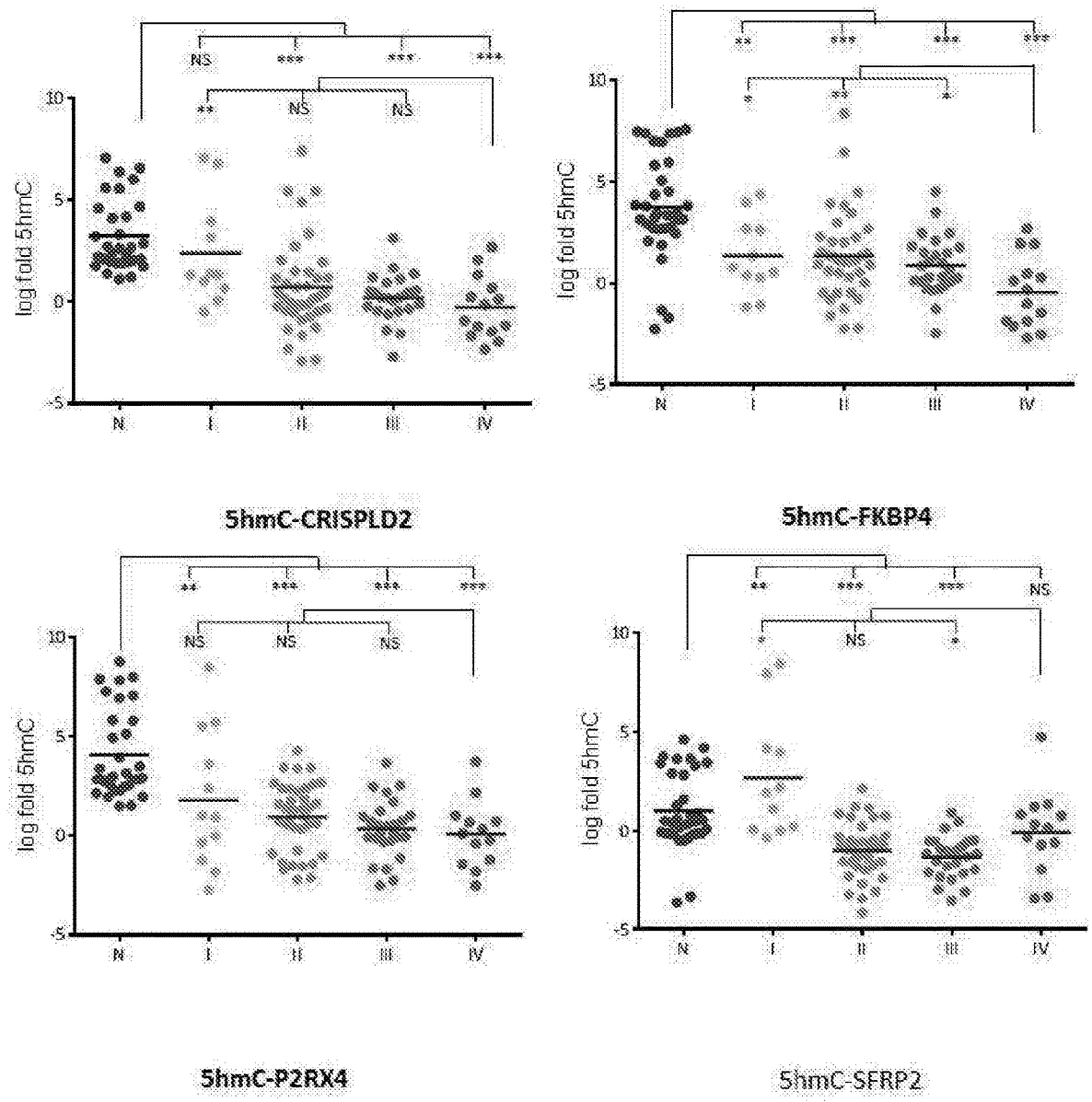

FIG. 42 shows the 5hmC levels of the indicated genes in each stage of samples from paired cohort. These results are further discussed in Example 8.

Figure 43A:
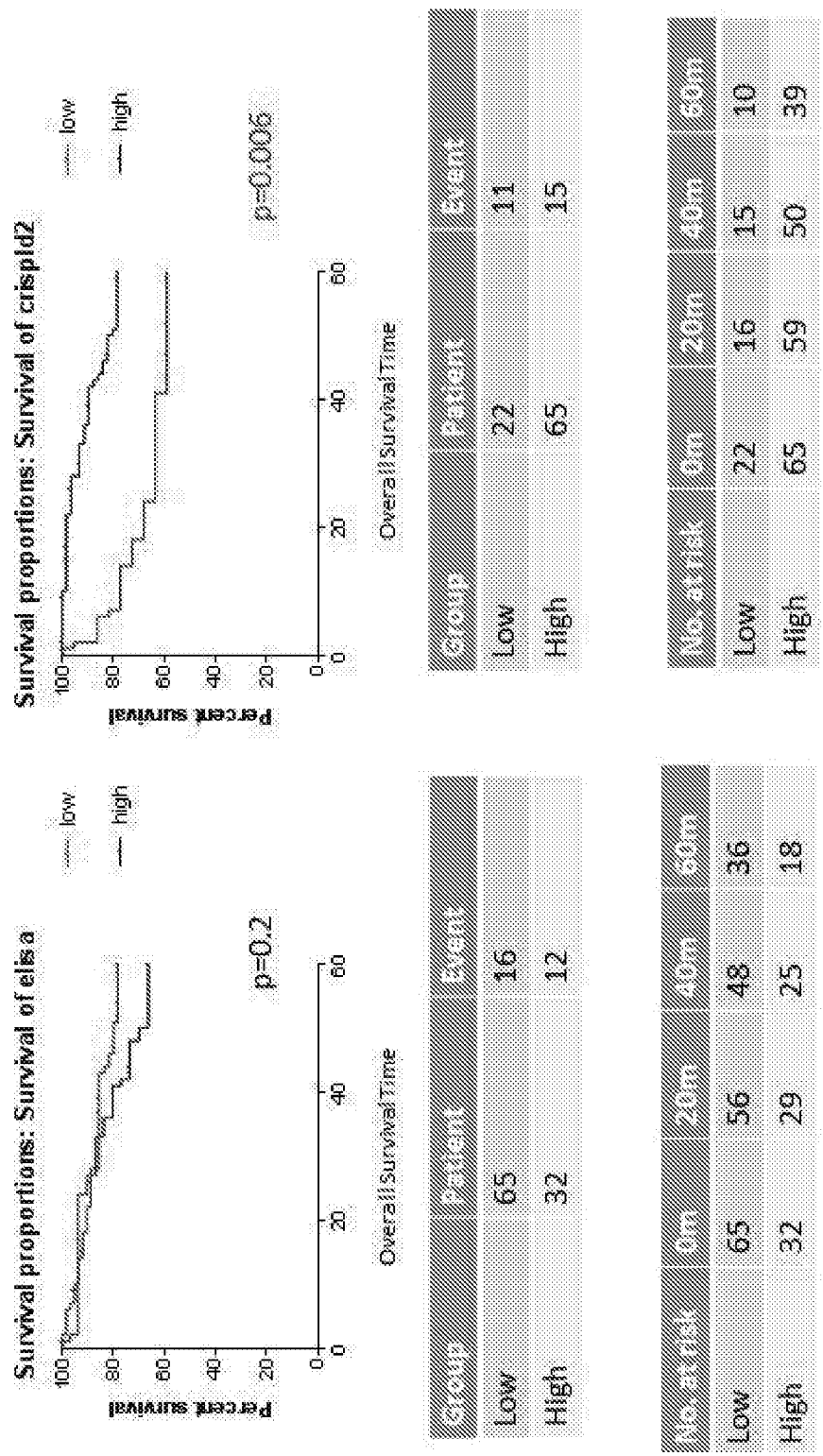
Figure 43B:
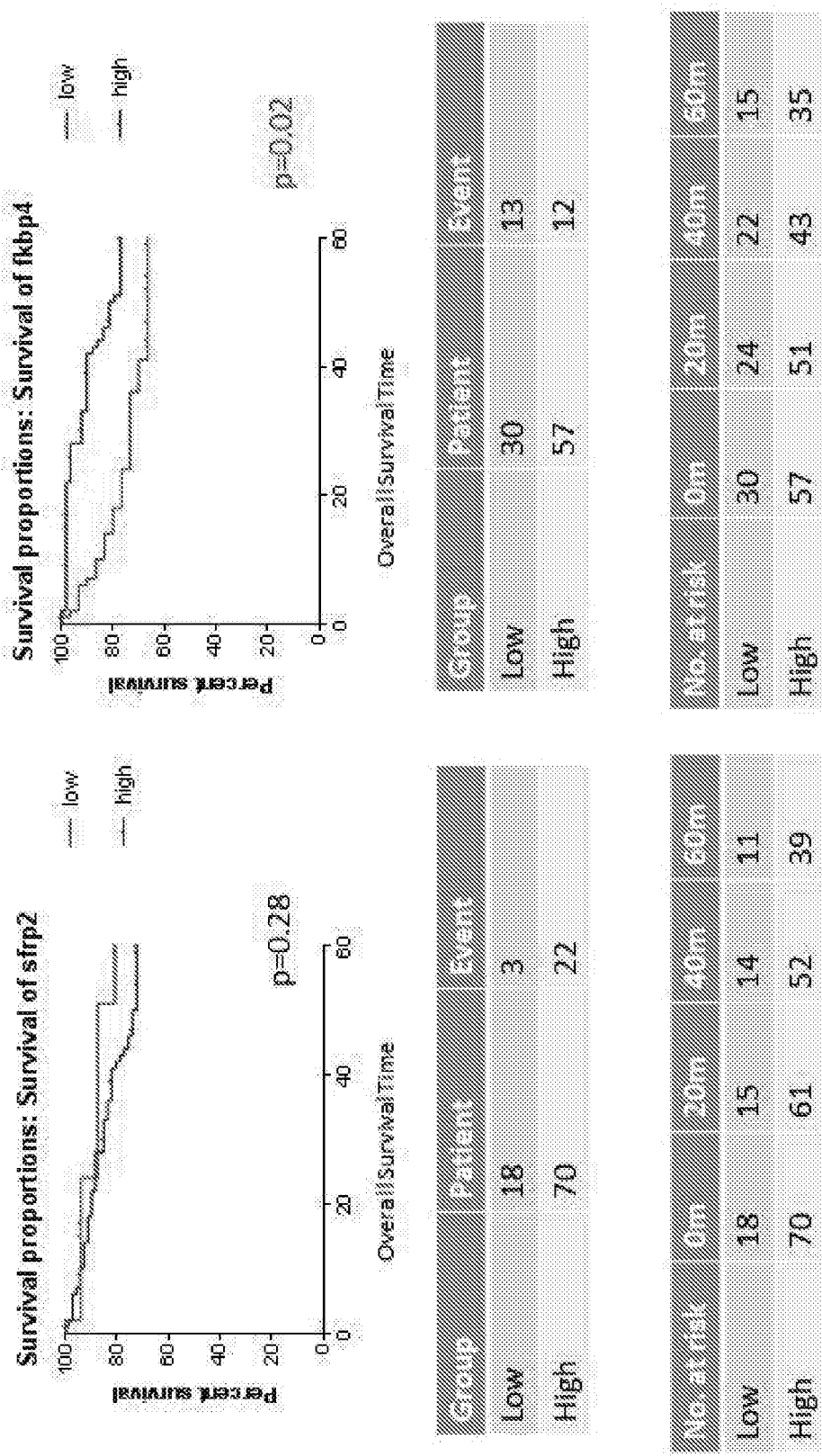
Figure 43C:
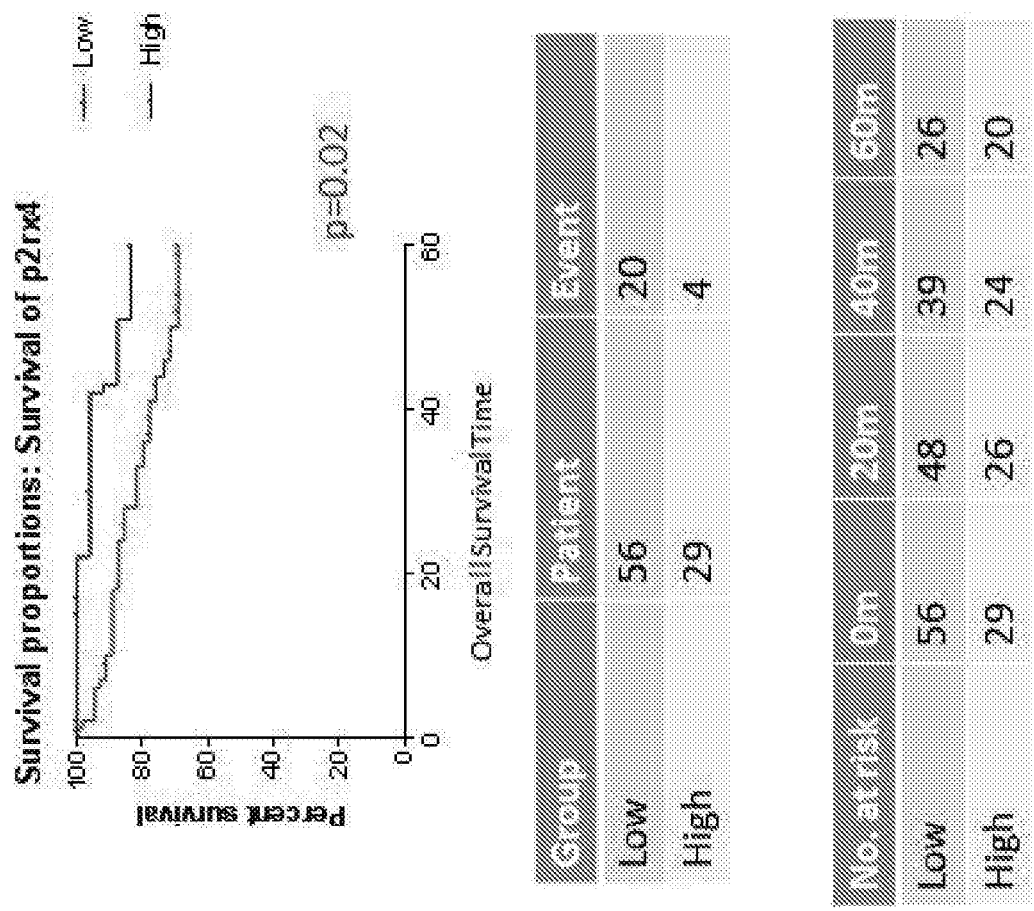

FIG. 43A-C shows the ability of the indicated gene biomarkers to be predictive of overall survival in colorectal cancer (paired cohort). These results are further discussed in Example 8.

Figure 44A:
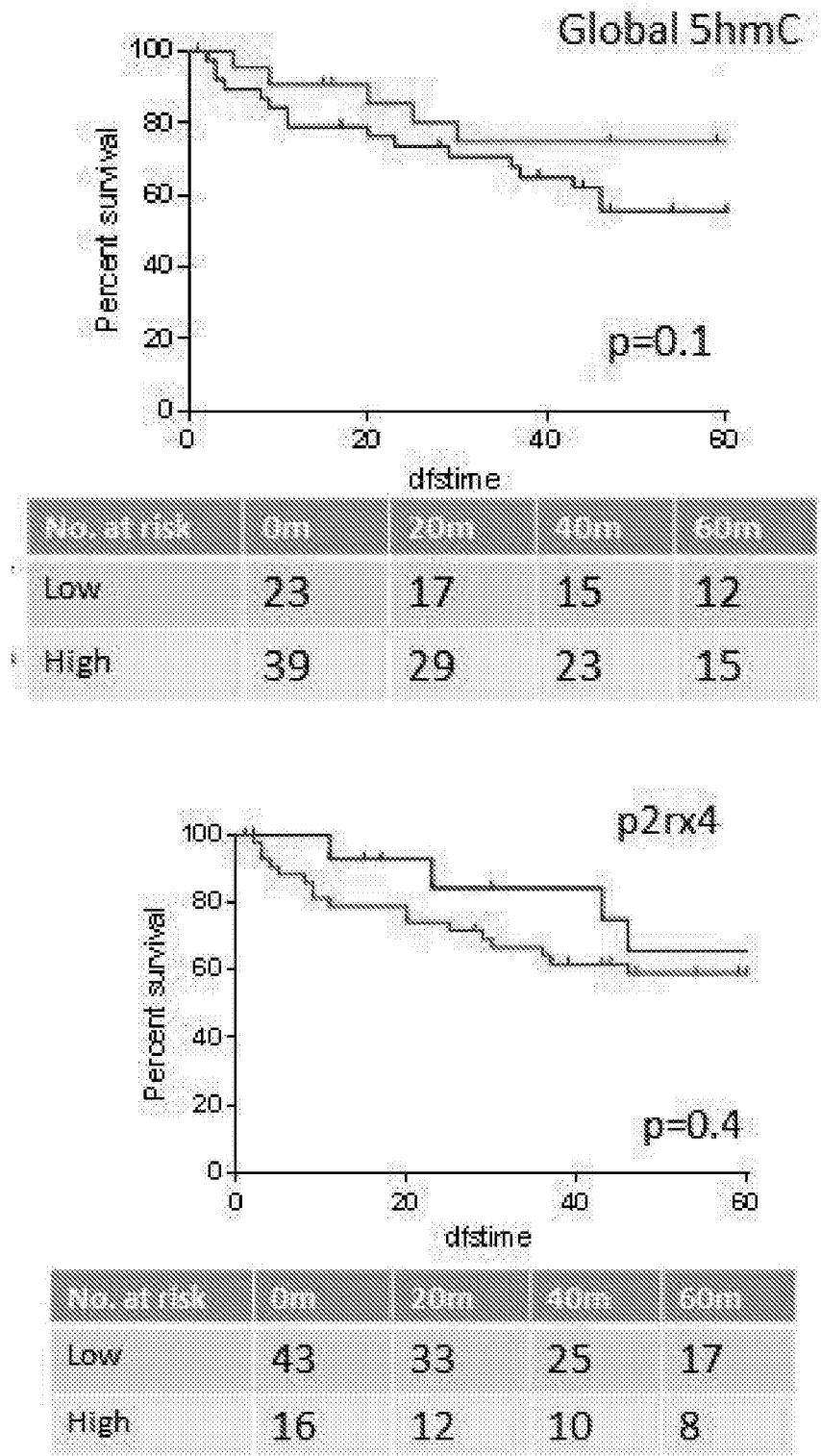
Figure 44C:
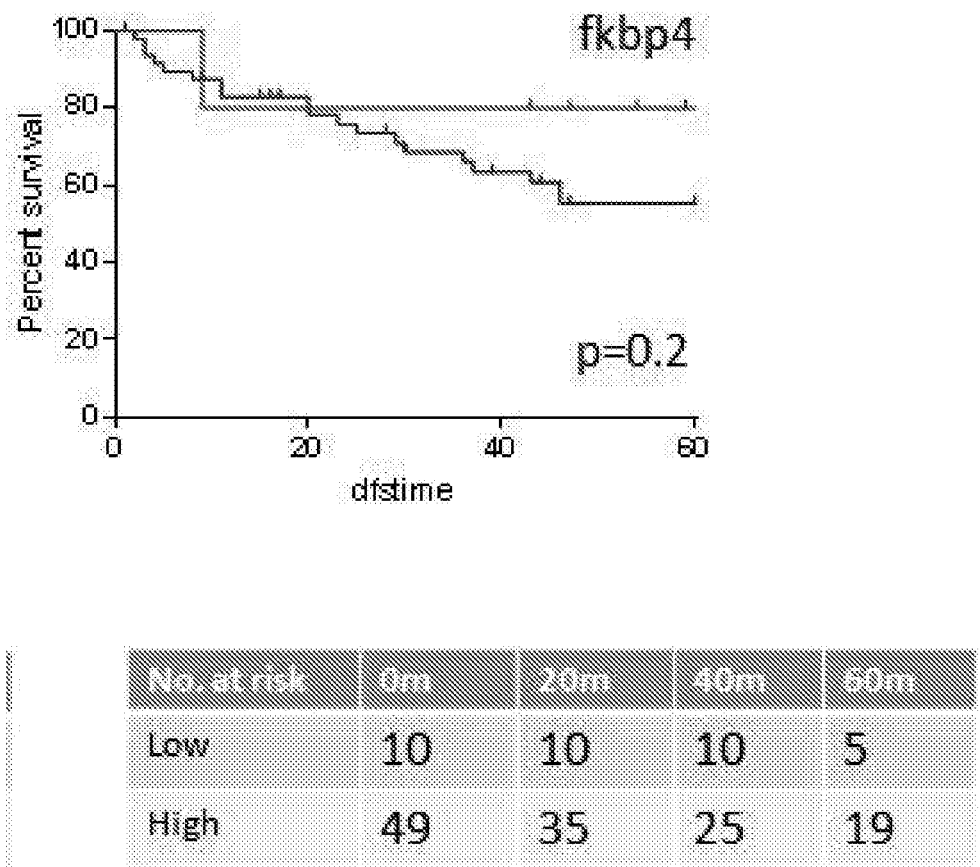

FIG. 44A-C shows the ability of the indicated gene biomarkers to be predictive of disease free survival in colorectal cancer (paired cohort). These results are further discussed in Example 8.

Figure 45:
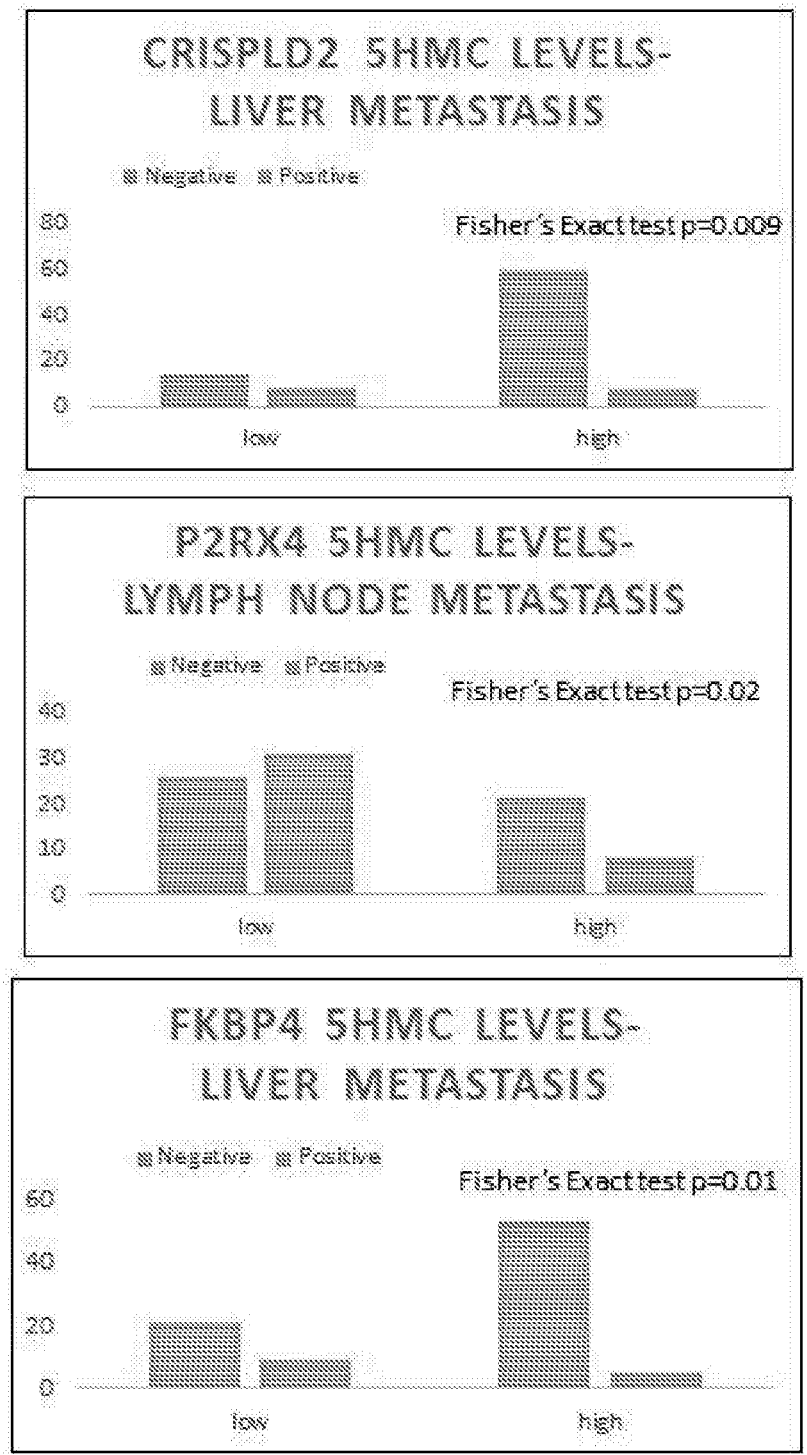

FIG. 45: The association of the indicated gene biomarkers metastasis in colorectal cancer paired cohort). These results are further discussed in Example 8.

Figure 46:
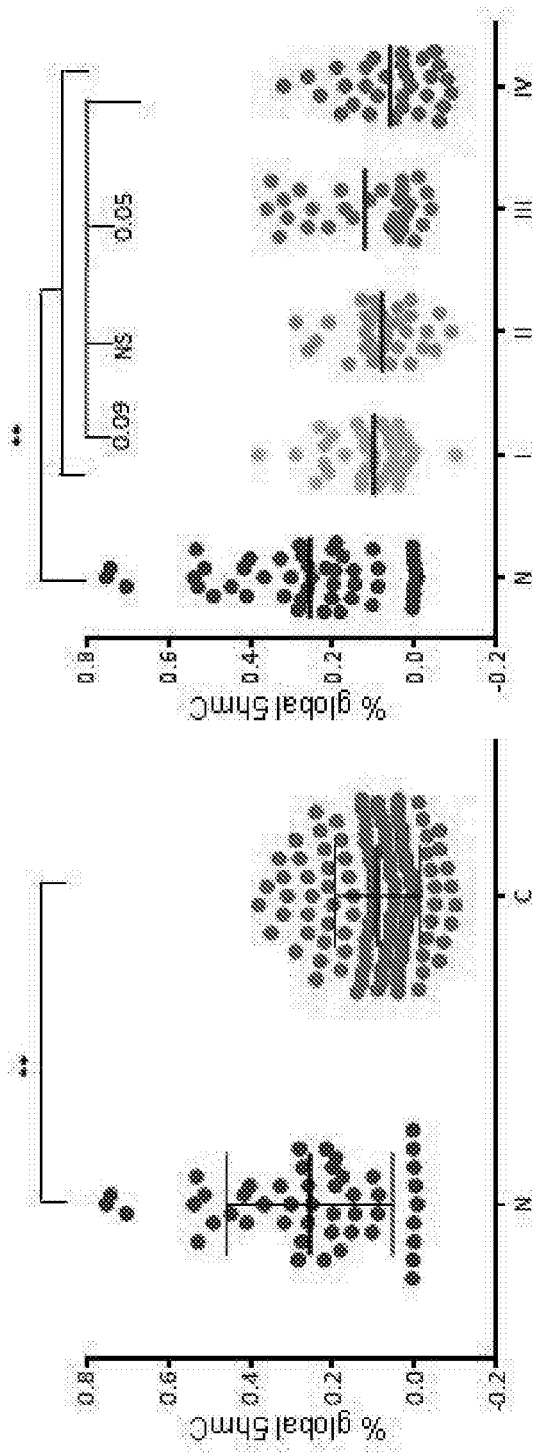

FIG. 46: Global 5hmC level in tumor (c) and normal (n) samples (left) and the stage specific global 5hmC levels (right) of the cohort 2 (152 samples; Normal=48). These results are further discussed in Example 8.

Figure 47:
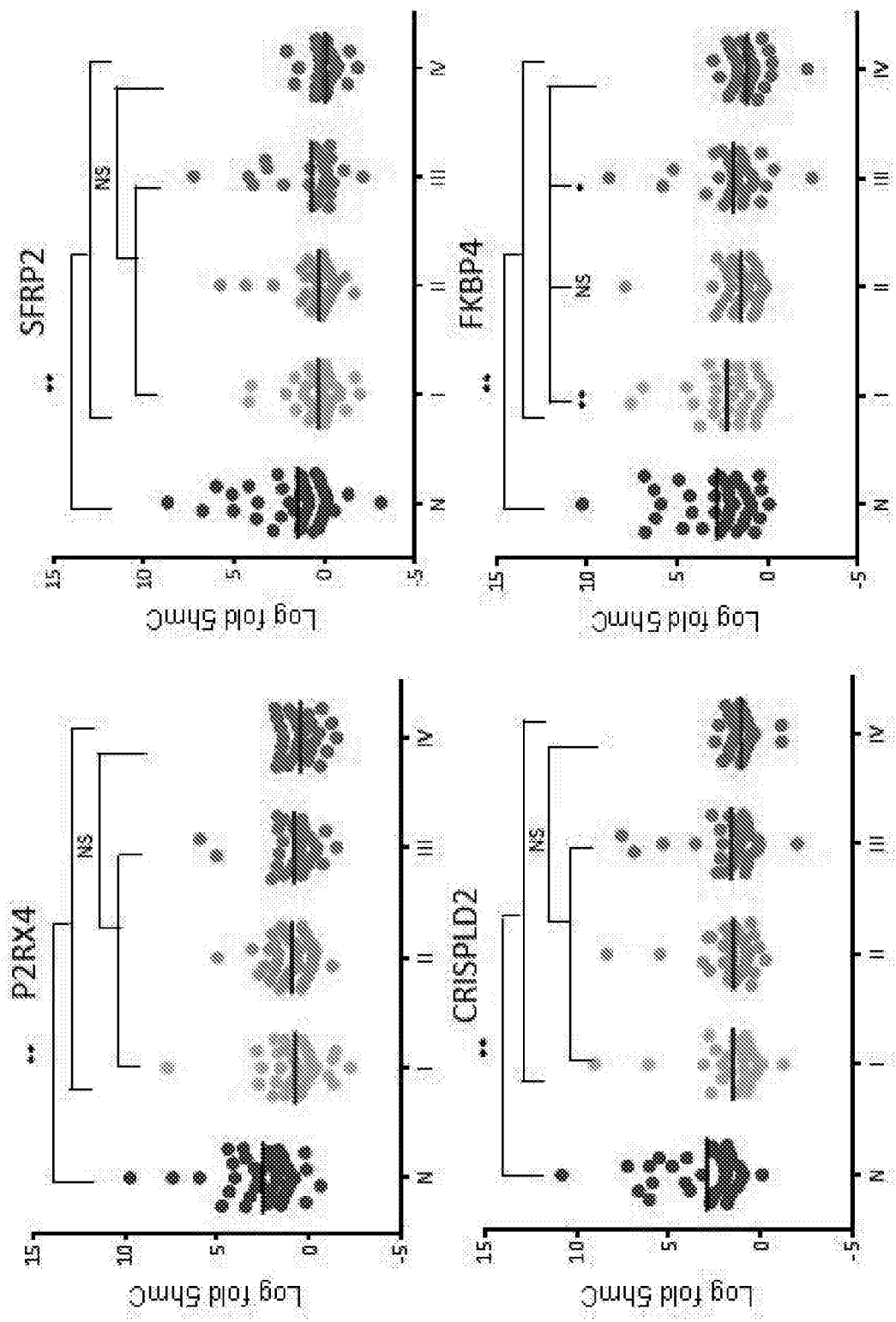

FIG. 47 shows the 5hmC levels of the indicated genes in each CRC stage of samples from the larger cohort 2. These results are further discussed in Example 8.

Figure 48A:
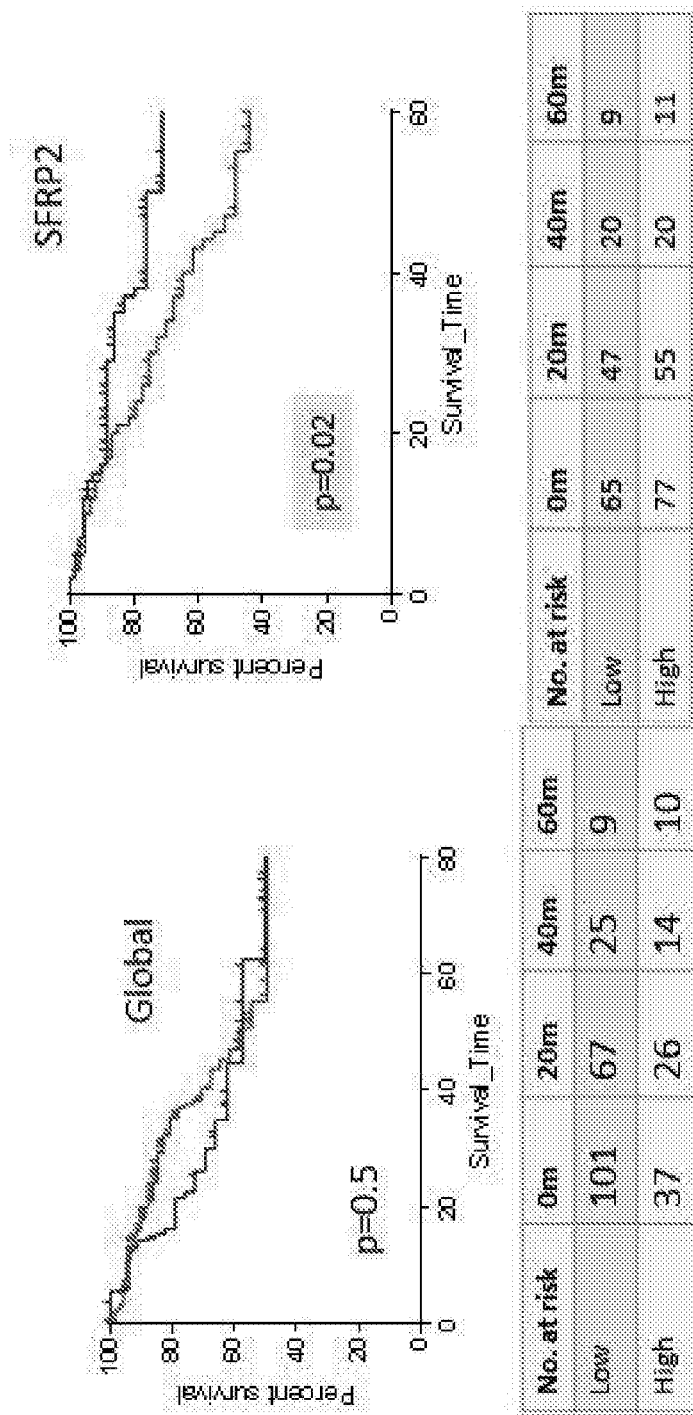
Figure 48B:
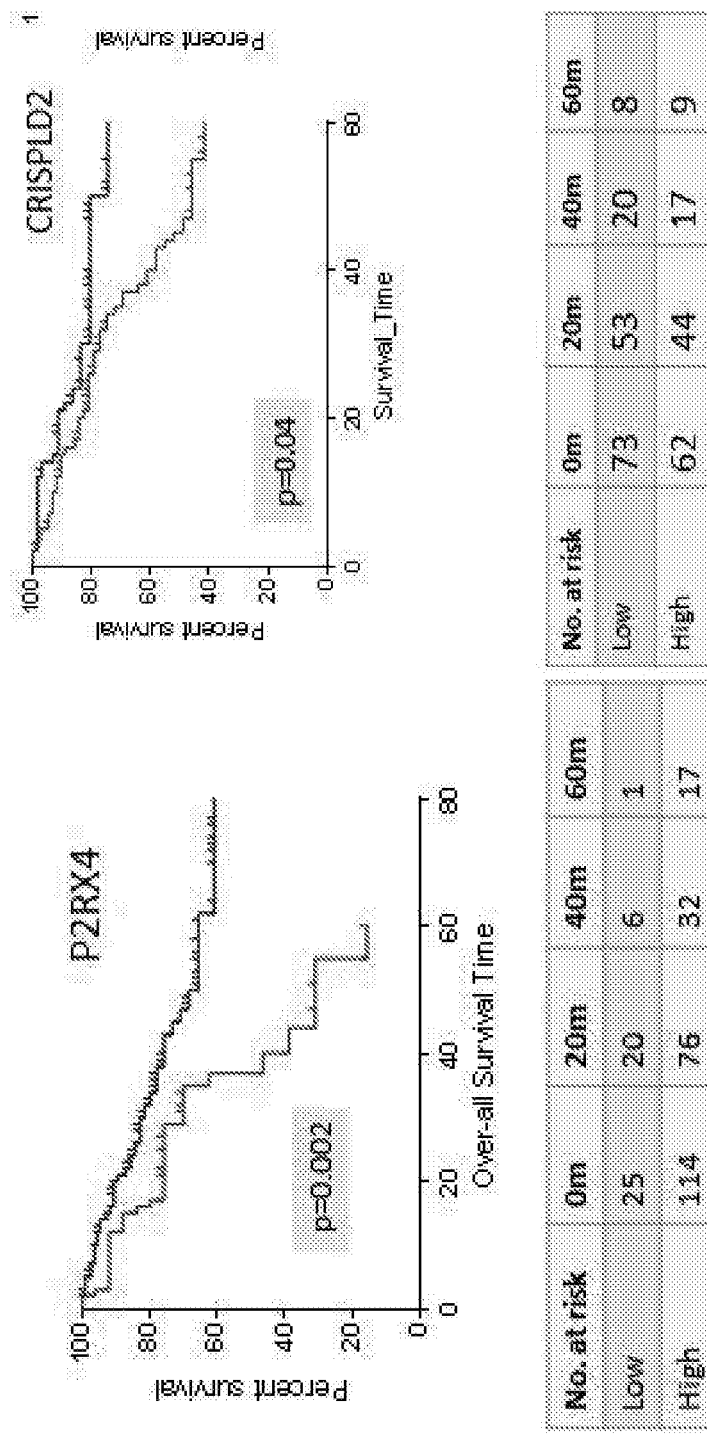
Figure 48C:
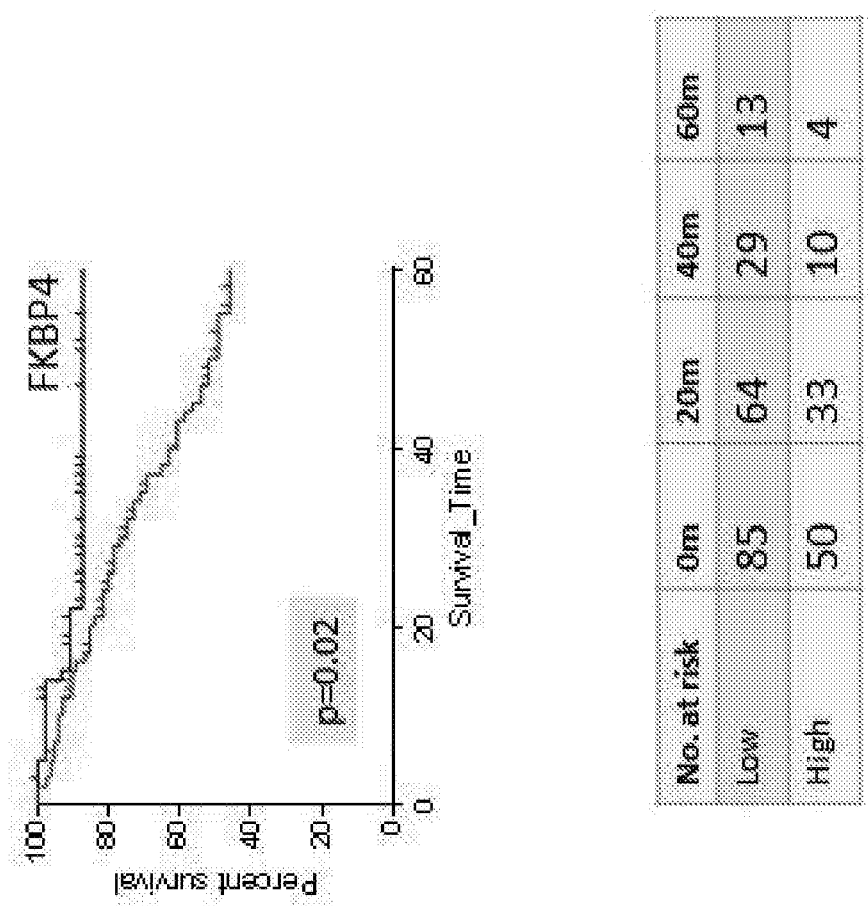

FIG. 48A-C shows the ability of the indicated gene biomarkers to be predictive of overall survival in colorectal cancer Larger cohort 2. These results are further discussed in Example 8.

Figure 49A:
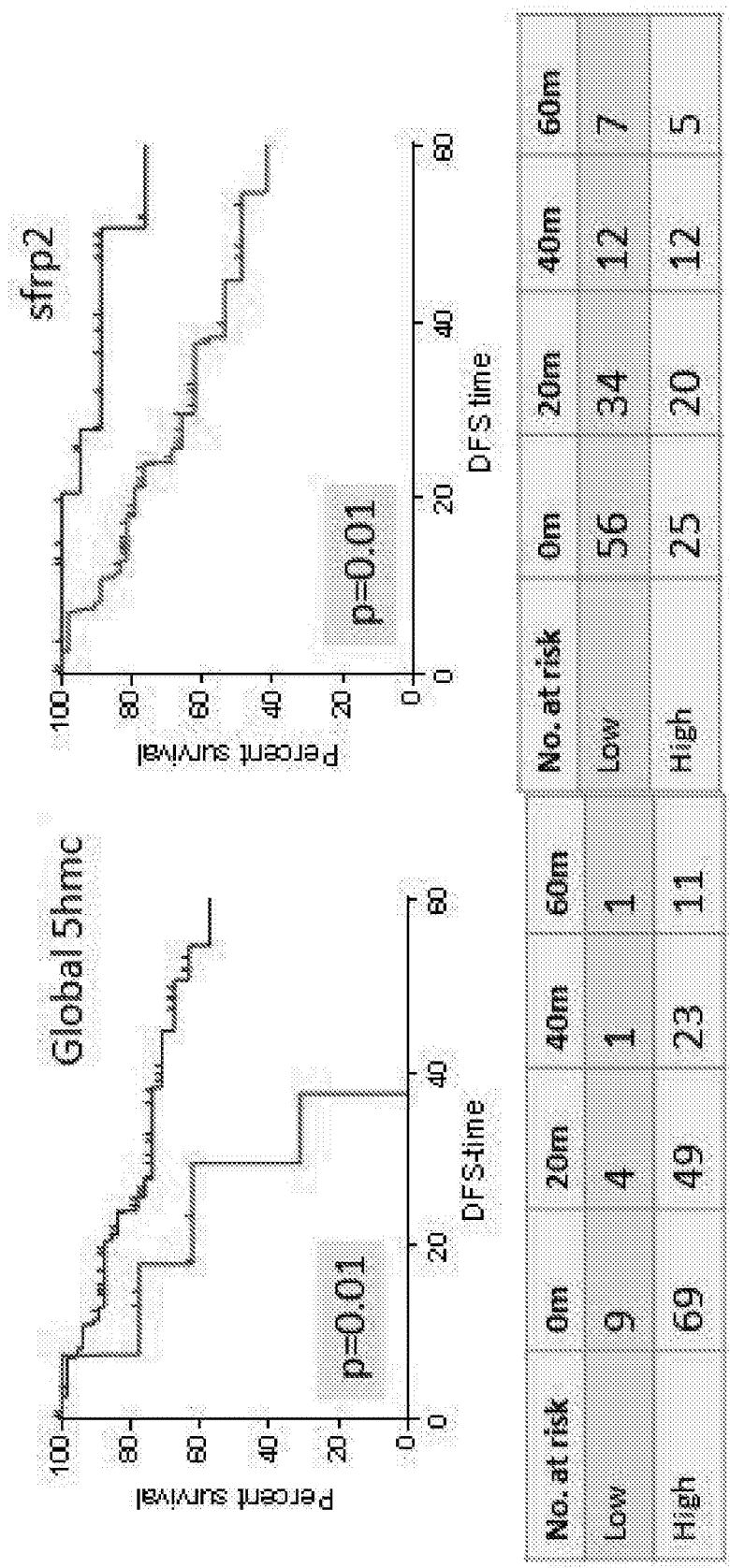
Figure 49B:
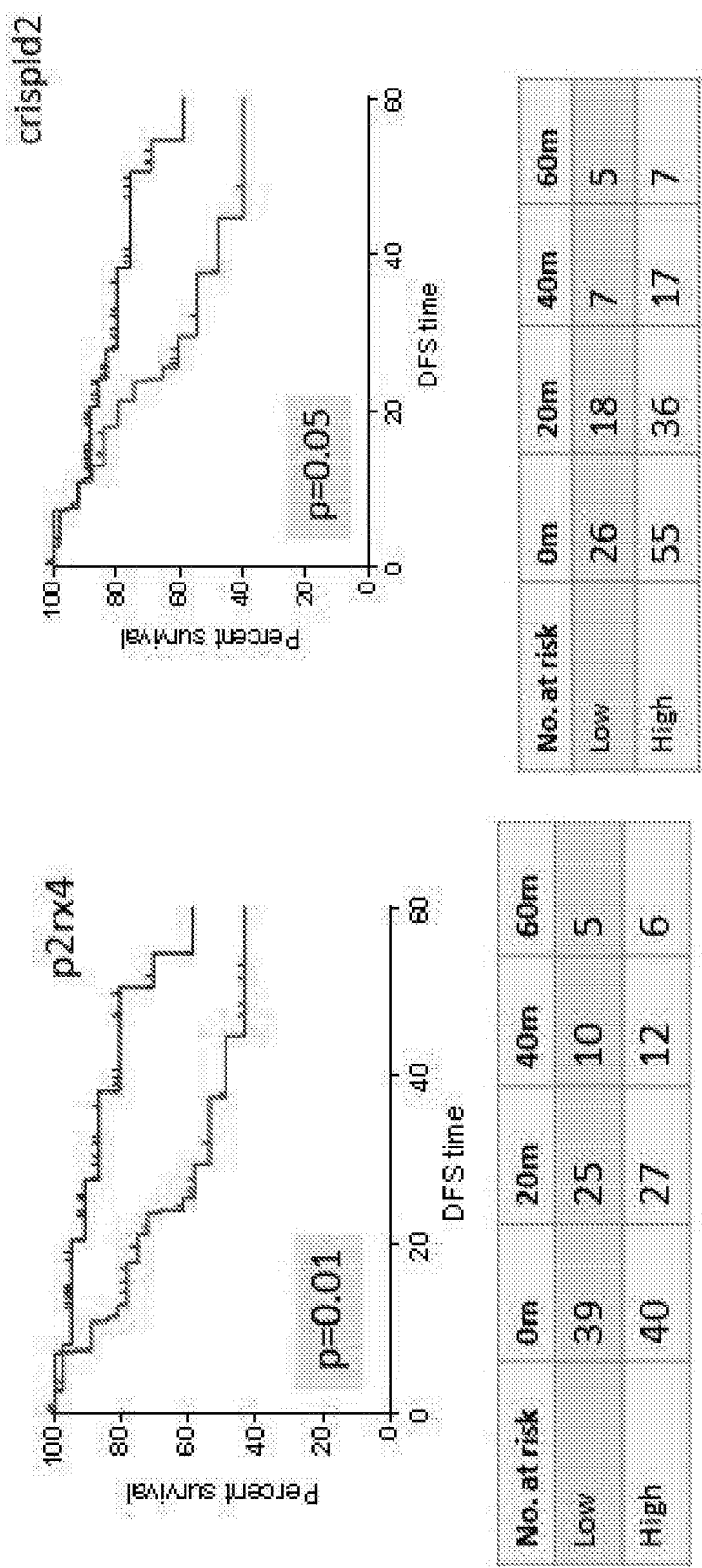
Figure 49C:
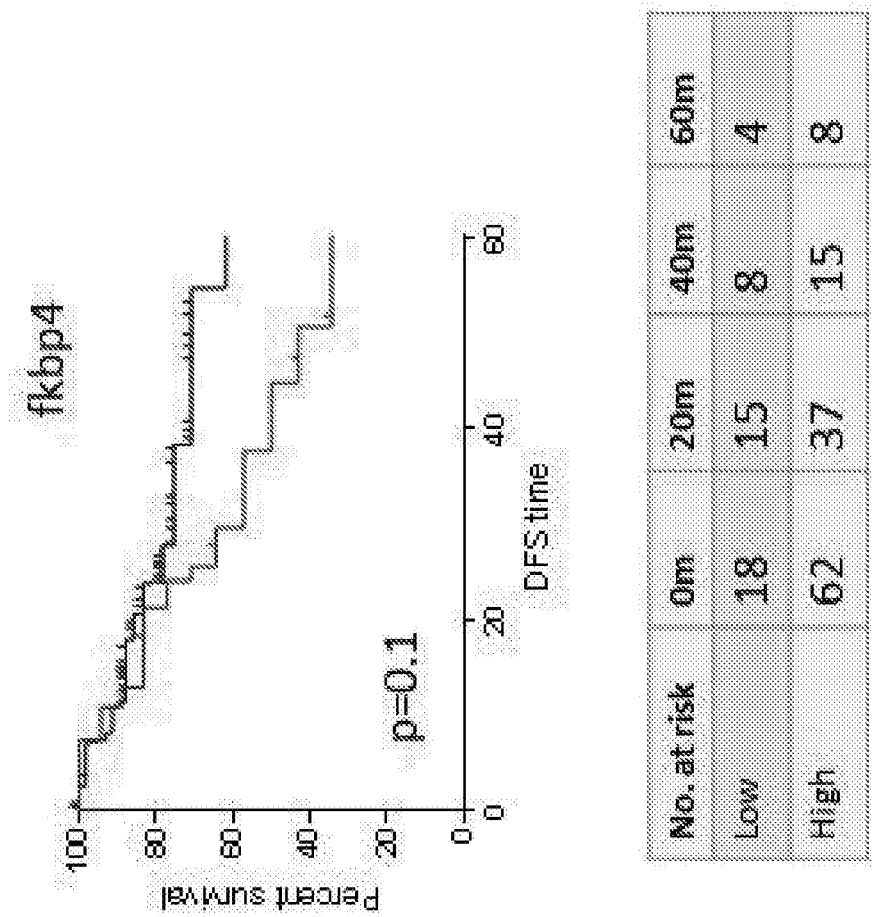

FIG. 49A-C shows the ability of the indicated gene biomarkers to be predictive of disease free survival in colorectal cancer (cohort 2). These results are further discussed in Example 8.

Figure 50:
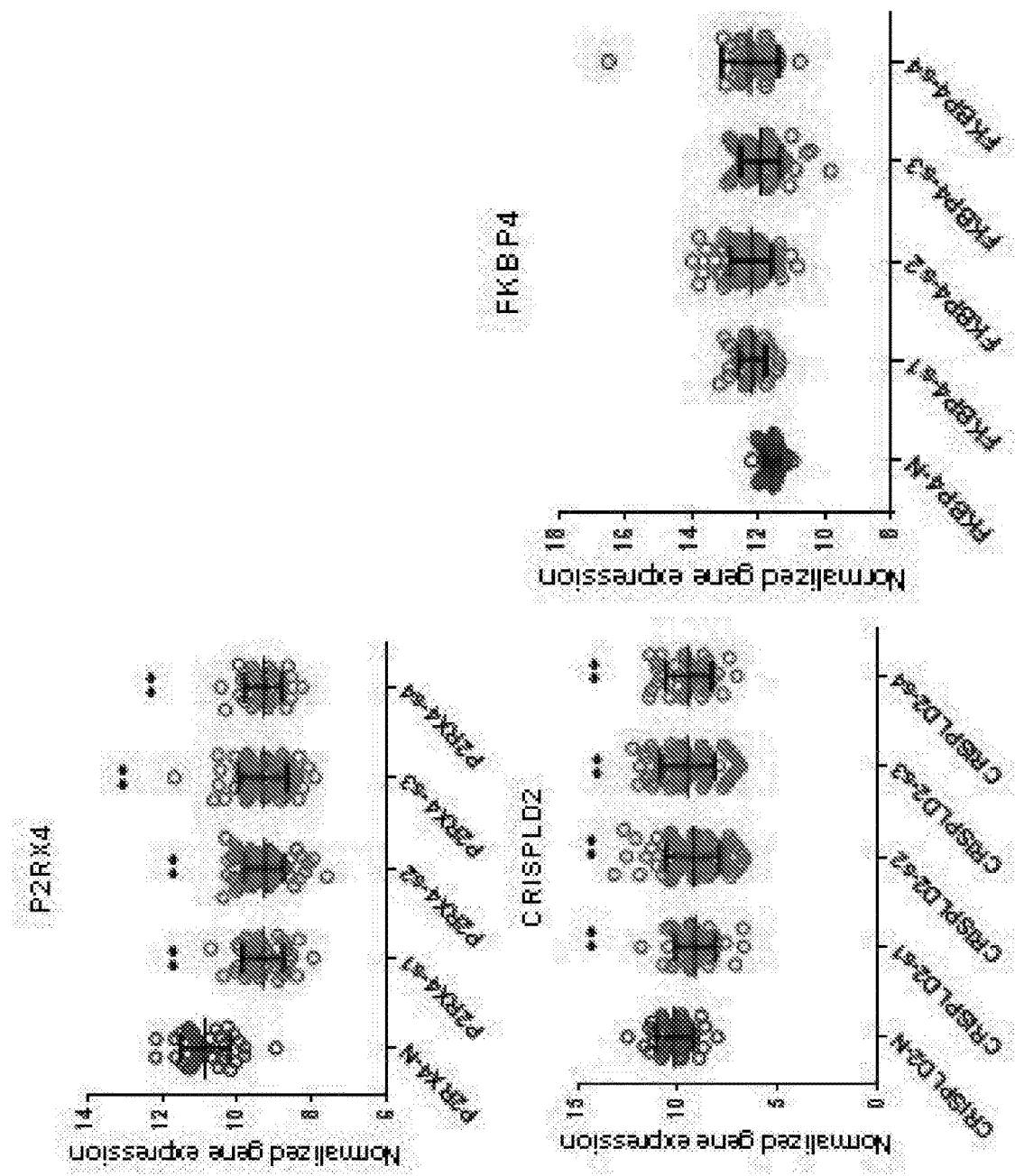

FIG. 50: TCGA data RNASeq expression. TCGA dataset was used to examine the expression pattern of these genes. 2 out of 3 genes (P2RX4 and CRISPLD2) had reduced expression in CRC tissues compared to normal tissue, which corroborated with the finding of reduced 5hmC levels in these tissues. These results are further discussed in Example 8.

Figure 51A:
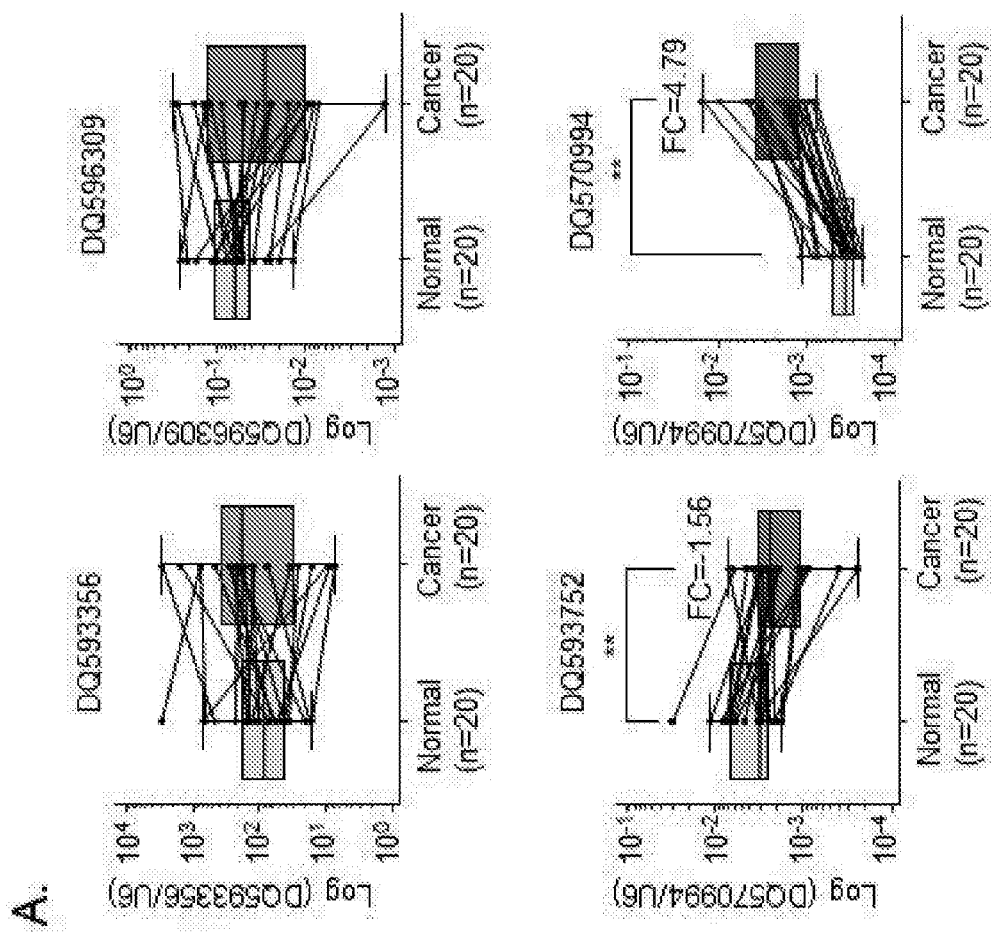
Figure 51B:
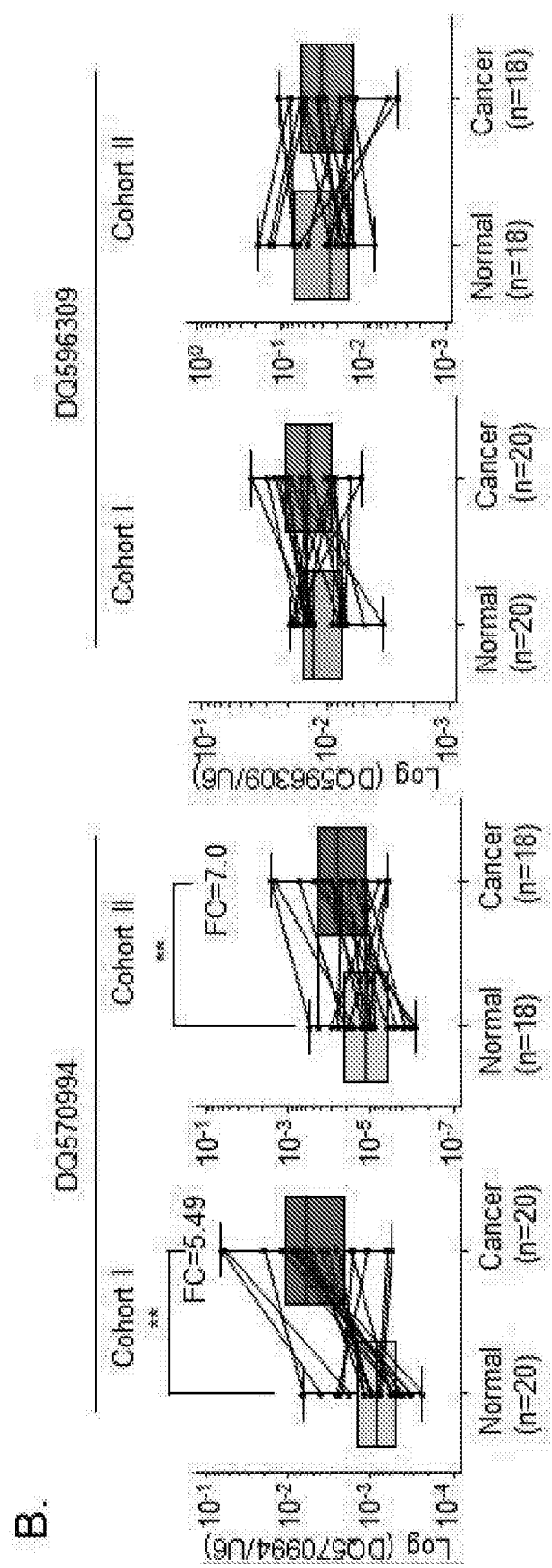

FIG. 51A-B: Identification of cancer-related piRNAs in CRC. (A) The expression of candidate piRNAs were validated in a subset of 20 cancer and paired NM specimens from Mie cohort. (B) The expression of DQ570994 and DQ596309 were further confirmed in Shanghai (cohort I) and Okayama cohort (cohort II). DQ570994 were consistently higher in cancer versus normal tissues in each cohort, and we named this piRNA as piRNA DQ570994 associated with colorectal cancer (piRACC). **P<0.01, Wilcoxon paired test. These results are further discussed in Example 10.

FIG. 52A-D: piRACC exhibits pan-cancer pattern expression and correlates with poor prognosis in CRC patients. (A-B) TCGA datasets showed piRACC is significantly upregulated in different cancer types. P<0.01, Wilcoxon paired test. The prognostic significance of piRACC was evaluated in colorectal cancer patients from TCGA datasets (C) and clinical testing and validation cohorts (D). ROC curve analysis yielded optimal cutoff expression values to discriminate dead or alive patients. Colorectal cancer patients were thereafter divided into high- and low expression groups based upon these cut off values. The OS analysis was performed by Kaplan-Meier test and the log-rank method (P<0.05, HR: Hazard Ratio). These results are further discussed in Example 10.

FIG. 53A-E: piRACC promotes cell growth, colony formation, migration and invasion and inhibits apoptosis in vitro. HCT116 and SW480 cells were transfected with either piRACC RNA oligos, antisense or scrambled control. The treated cells or control cells were subsequently used for MTT assay (A), colony formation assay (B), Ki-67 staining (C), Migration and invasion assay (D) and apoptosis assay (E). All the experiments were performed biological triplicate. (*P<0.05, **P<0.01; independent t-test was used to compare control and treated cells). These results are further discussed in Example 10.

Figure 54C:
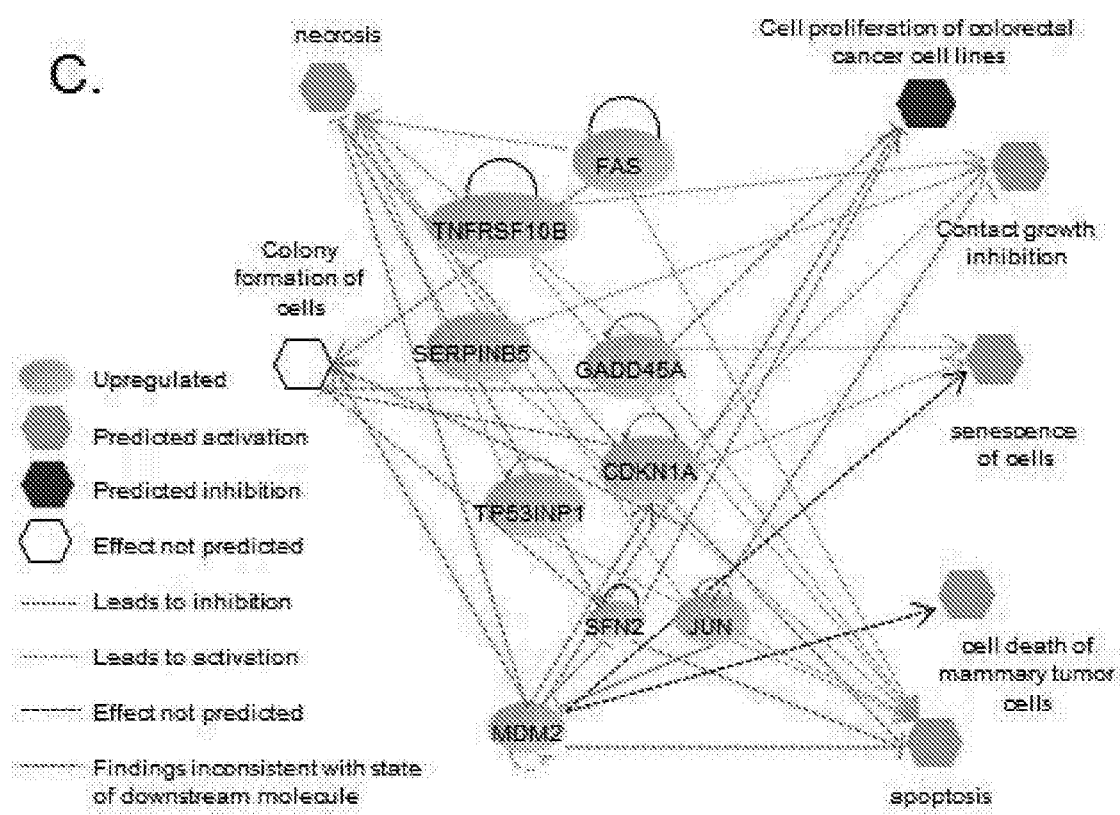

FIG. 54A-C: KEGG, Gene Ontology (GO) and Ingenuity Pathway Analysis (IPA) for the differentially expressed genes between piRACC inhibition HCT116 cells and control cells. (A) KEGG analysis for the up-regulated genes (B) Go annotation of up-regulated genes with top 10 enrichment pathways covering domains of biological processes, cellular components and molecular functions. (C) IPA analysis for the upregulated genes to interrogate the function of piRACC in CRC. These results are further discussed in Example 10.

Figure 55A:
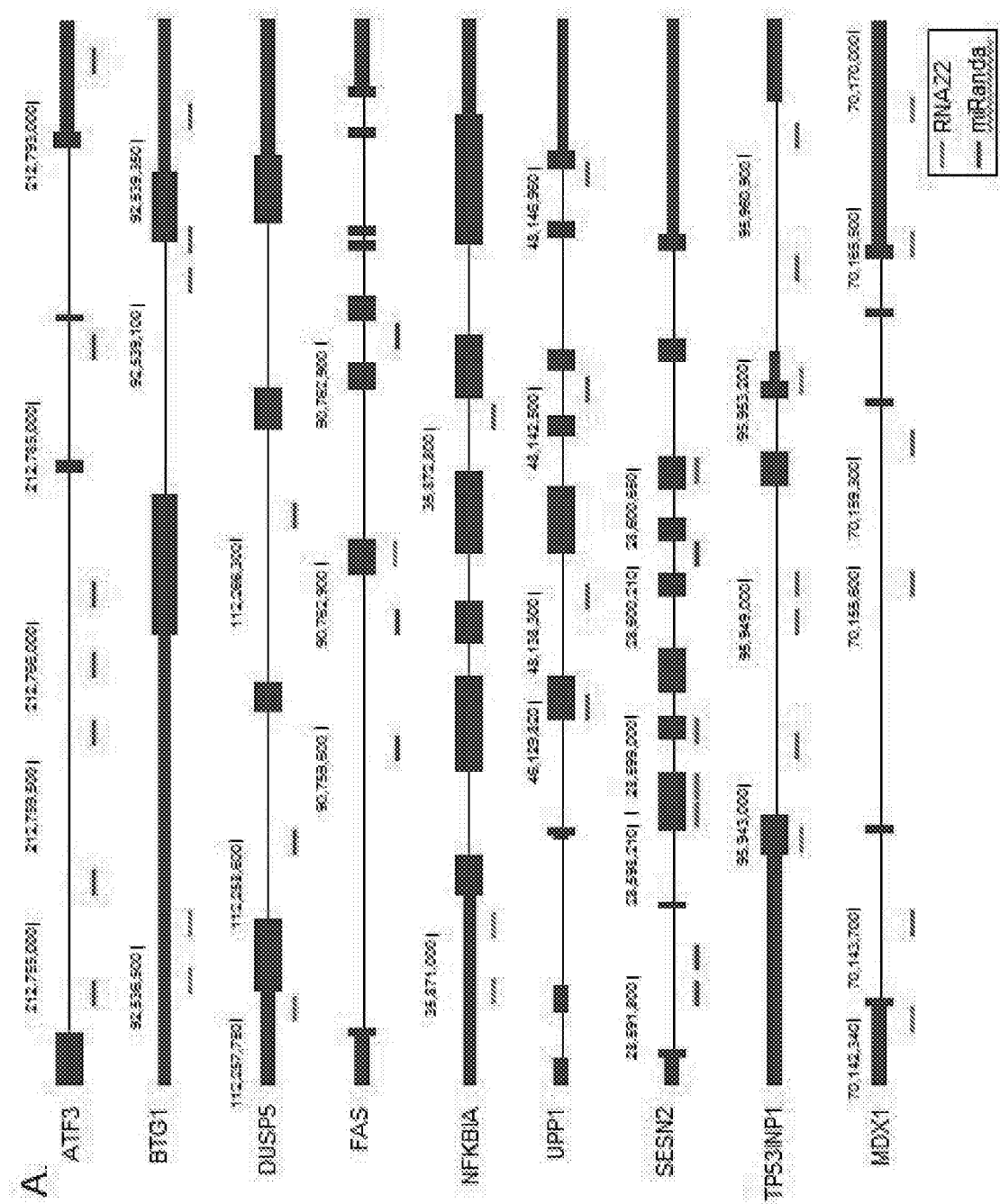
Figure 55B:
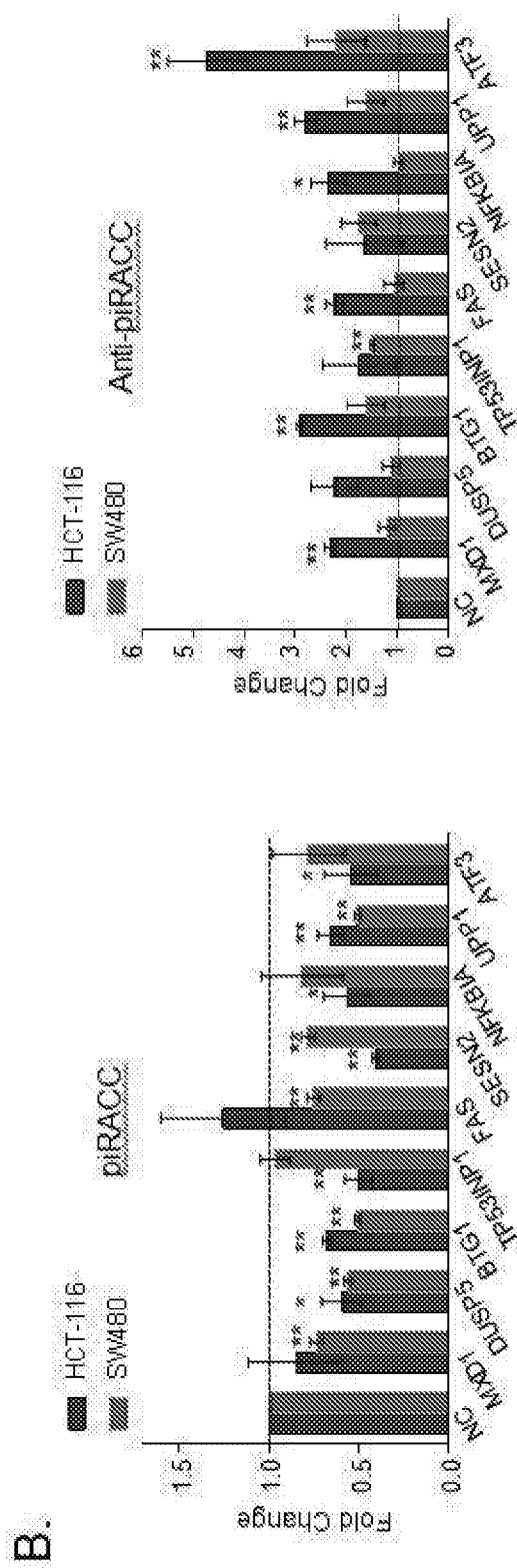

FIG. 55A-B: Identification of piRACC target mRNAs. (A) miRANDA and RNA22 was used to predict the binding of piRACC to potential targets. (B) qPCR was performed to confirm the expression change of target genes after piRACC overexpression or knockdown in HCT116 and SW480 cells. (n=3, *P<0.05, **P<0.01, independent t-test was used to compare control and treated cells). These results are further discussed in Example 10.

Figure 56A:
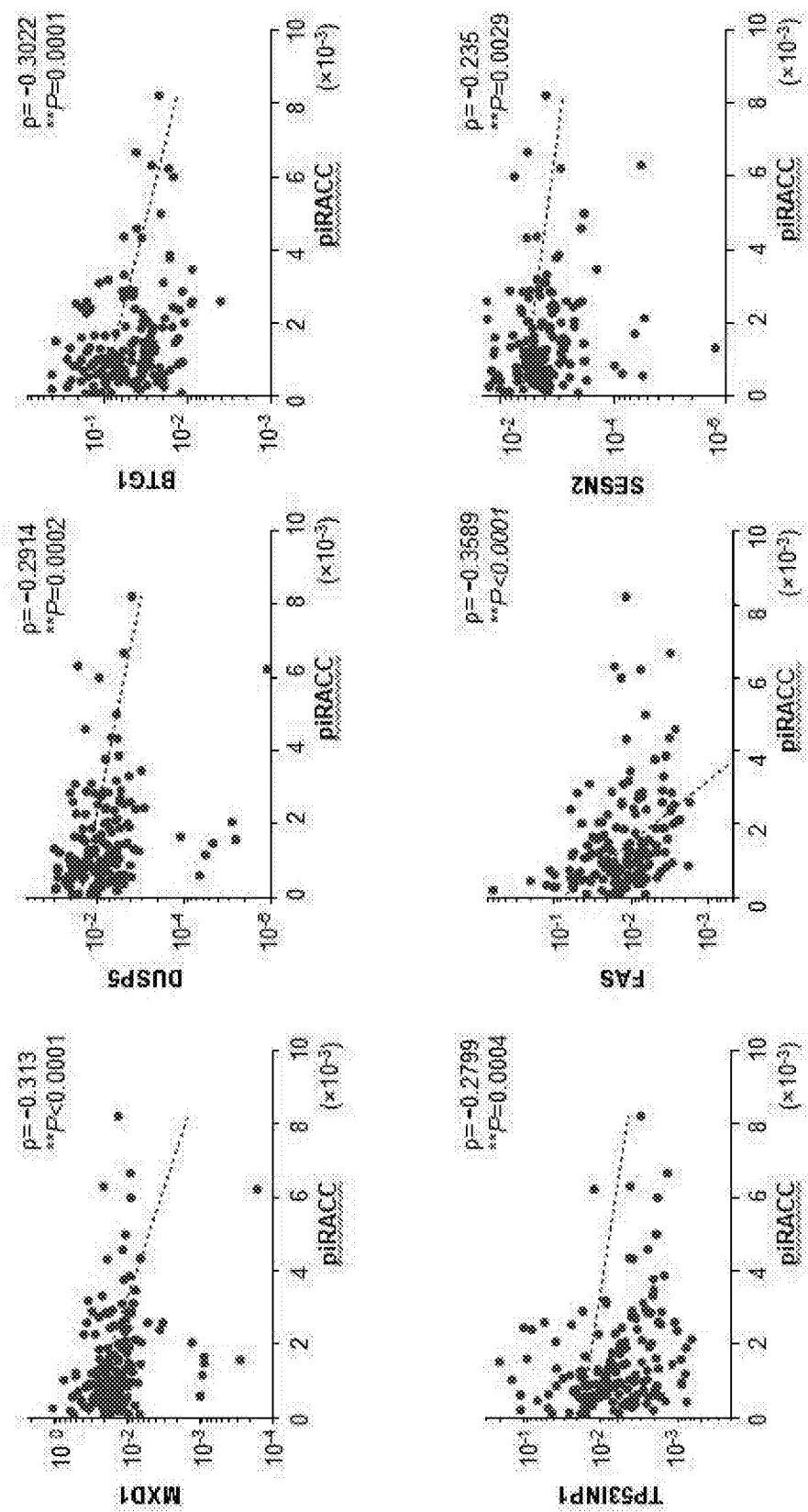
Figure 56B:
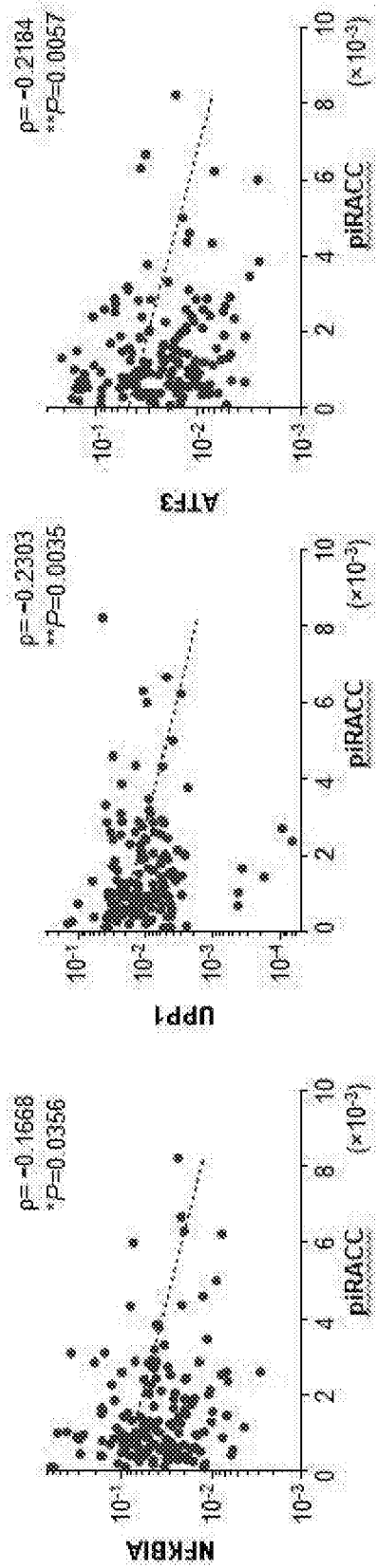

FIG. 56A-B: The correlation between piRACC and its target genes in CRC tissues. qPCR was performed to evaluate the expression correlation between piRACC and its targets in CRC tissues. (n=159, *P<0.05, **P<0.01; Spearman's rank correlation (p) was used for the correlation analysis). These results are further discussed in Example 10.

Figure 57:
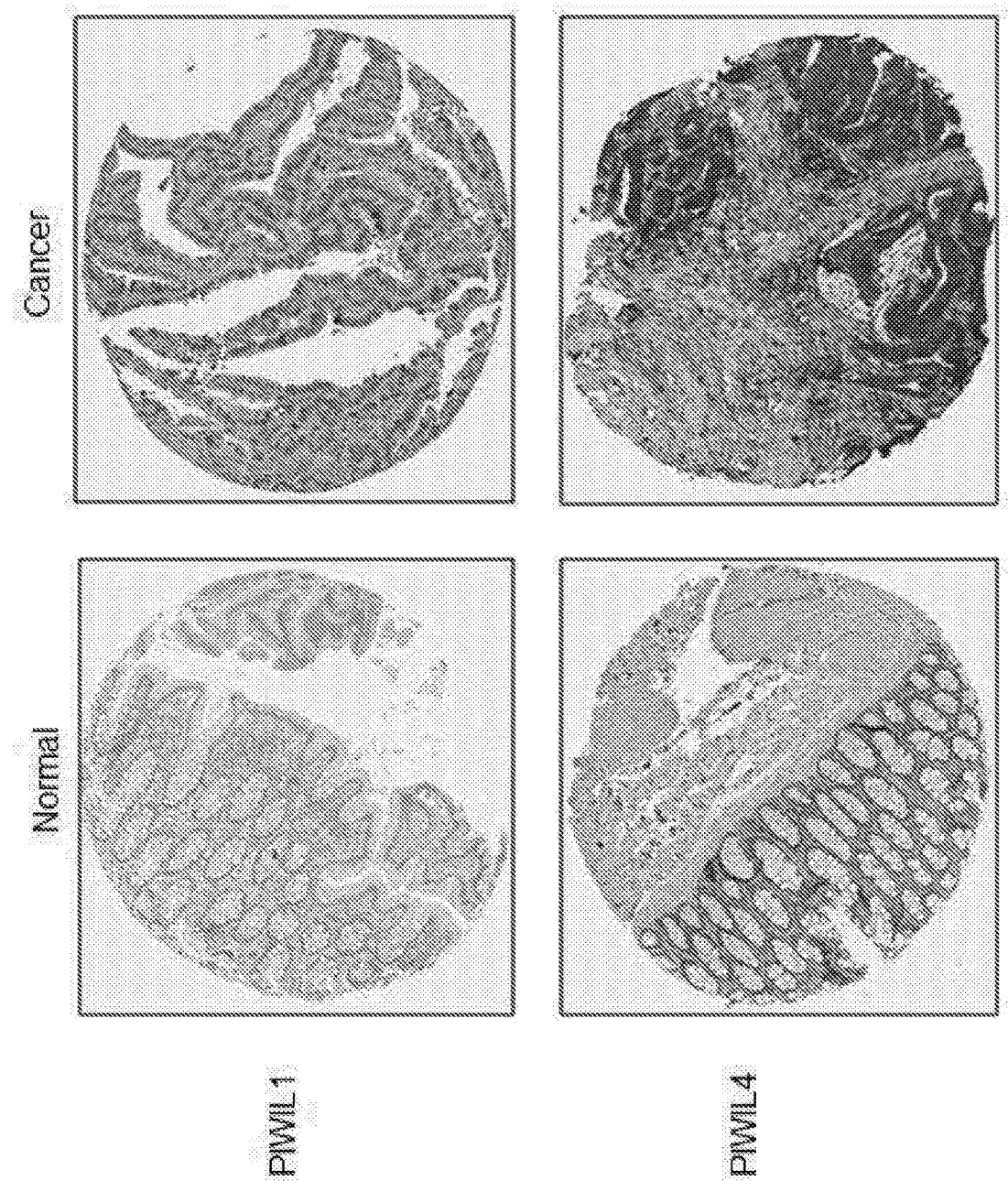

FIG. 57: PIWIL1 and PIWIL4 are overexpressed in CRC. The representative IHC staining of PIWIL1 and PIWIL4 in CRC and normal tissues (provided by Protein atlas database). These results are further discussed in Example 10.

Figure 58:
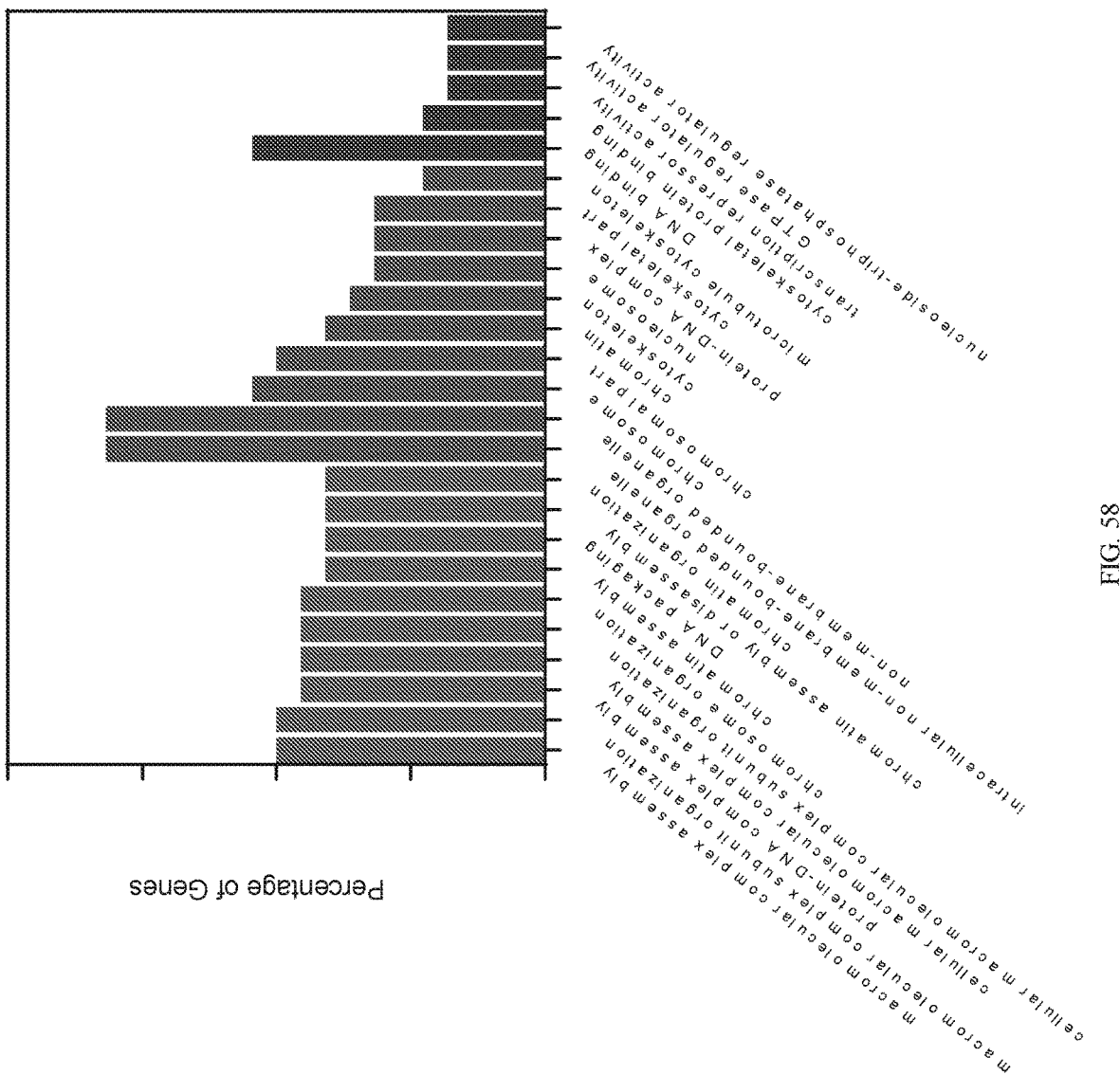

FIG. 58: Gene Ontology (GO) analysis for the downregulated genes. Go annotation of top 10 enrichment pathways covering domains of biological processes, cellular components and molecular functions. These results are further discussed in Example 10.

FIG. 59A-C: Prediction of piRACC's target by miRanda. The representative images showed the binding sites between piRACC and its targets. These results are further discussed in Example 10. The sequences (from top to bottom) in each of FIGS. 59A-C correspond to the following SEQ ID NOS, respectively:

| FIG. | SEQ ID NO: |
| --- | --- |
| 59A | 53 |
| 59A | 54 |
| 59A | 53 |
| 59A | 55 |
| 59A | 53 |
| 59A | 56 |
| 59A | 53 |
| 59A | 57 |
| 59A | 53 |
| 59A | 58 |
| 59A | 53 |
| 59A | 59 |
| 59A | 53 |
| 59A | 60 |
| 59A | 53 |
| 59A | 61 |
| 59A | 53 |
| 59A | 62 |
| 59A | 53 |
| 59A | 63 |
| 59A | 53 |
| 59A | 53 |
| 59A | 64 |
| 59A | 53 |
| 59A | 65 |
| 59B | 53 |
| 59B | 66 |
| 59B | 53 |
| 59B | 67 |
| 59B | 53 |
| 59B | 68 |
| 59B | 53 |
| 59B | 69 |
| 59B | 53 |
| 59B | 70 |
| 59B | 53 |
| 59B | 71 |
| 59B | 53 |
| 59B | 72 |
| 59B | 53 |
| 59B | 73 |
| 59B | 53 |
| 59B | 74 |
| 59C | 53 |
| 59C | 75 |
| 59C | 53 |
| 59C | 76 |
| 59C | 53 |
| 59C | 77 |
| 59C | 53 |
| 59C | 78 |
| 59C | 53 |
| 59C | 79 |
| 59C | 53 |
| 59C | 80 |
| 59C | 53 |
| 59C | 81 |
| 59C | 53 |
| 59C | 82 |
| 59C | 53 |
| 59C | 83 |
| 59C | 53 |
| 59C | 84 |

FIG. 60A-B: Prediction of piRACC's target by RNA22. The representative images showed the binding sites between piRACC and its targets. These results are further discussed in Example 10. The sequences (from top to bottom) in each of FIGS. 60A-B correspond to the following SEQ ID NOS, respectively:

| FIG. | SEQ ID NO: |
| --- | --- |
| 60A | 53 |
| 60A | 85 |

-continued

| FIG. | SEQ ID NO: |
|------|------------|
| 60A  | 53 |
| 60A  | 86 |
| 60A  | 53 |
| 60A  | 87 |
| 60A  | 53 |
| 60A  | 88 |
| 60A  | 53 |
| 60A  | 89 |
| 60A  | 53 |
| 60A  | 90 |
| 60B  | 53 |
| 60B  | 91 |
| 60B  | 53 |
| 60B  | 92 |
| 60B  | 53 |
| 60B  | 93 |
| 60B  | 53 |
| 60B  | 94 |
| 60B  | 53 |
| 60B  | 95 |
| 60B  | 53 |
| 60B  | 96 |
| 60B  | 53 |
| 60B  | 97 |
| 60B  | 53 |
| 60B  | 98 |
| 60B  | 53 |
| 60B  | 99 |

DESCRIPTION OF ILLUSTRATIVE EMBODIMENTS

Dysregulated expression of microRNAs (miRNAs) has emerged as a hallmark feature in human cancers. Aspects of the disclosure relate to methods for selecting optimal therapy for a patient from several alternative treatment options. A major clinical challenge in cancer treatment is to identify the subset of patients who will benefit from a therapeutic regimen, both in metastatic and adjuvant settings. The number of anti-cancer drugs and multi-drug combinations has increased substantially in the past decade, however, treatments continue to be applied empirically using a trial-and-error approach. Here methods and compositions are provided to determine the optimal treatment option for cancer patients.

I. Definitions

As used herein, the term "antibody" encompasses antibodies and antibody fragments thereof, derived from any antibody-producing mammal (e.g., mouse, rat, rabbit, and primate including human), that specifically bind to an antigenic polypeptide. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

"Prognosis" refers to as a prediction of how a patient will progress, and whether there is a chance of recovery. "Cancer prognosis" generally refers to a forecast or prediction of the probable course or outcome of the cancer, with or without a treatment. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis also includes prediction of favorable responses to cancer treatments, such as a conventional cancer therapy. A response may be either a therapeutic response (sensitivity or recurrence-free survival) or a lack of therapeutic response (residual disease, which may indicate resistance or recurrence).

The term substantially the same or not significantly different refers to a level of expression that is not significantly different than what it is compared to. Alternatively, or in conjunction, the term substantially the same refers to a level of expression that is less than 2, 1.5, or 1.25 fold different than the expression or activity level it is compared to.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

The term "disease free survival" is a clinical endpoint and is usually used to analyze the results of the treatment for the localized disease which renders the patient apparently disease free, such as surgery or surgery plus adjuvant therapy. In the disease-free survival, the event is relapse rather than death. The people who relapse are still surviving but they are no longer disease-free. Just as in the survival curves not all patients die, in "disease-free survival curves" not all patients relapse and the curve may have a final plateau representing the patients who didn't relapse after the study's maximum follow-up. Because the patients survive for at least some time after the relapse, the curve for the actual survival would look better than disease free survival curve.

The term "primer" or "probe" as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased expression" or "elevated expression" or "decreased expression" refers to an expression level of a biomarker in the subject's sample as compared to a reference level representing the same biomarker or a different biomarker. In certain aspects, the reference level may be a reference level of expression from a non-cancerous tissue from the same subject. Alternatively, the reference level may be a reference level of expression from a different subject or group of subjects. For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer. The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that an numerical value discussed herein may be used with the term "about" or "approximately."

II. Colorectal Cancer Staging and Treatments

Methods and compositions may be provided for treating colorectal cancer with particular applications of biomarker expression or activity levels. Based on a profile of biomarker expression or activity levels, different treatments may be prescribed or recommended for different cancer patients.

A. Cancer Staging

Colorectal cancer, also known as colon cancer, rectal cancer, or bowel cancer, is a cancer from uncontrolled cell growth in the colon or rectum (parts of the large intestine), or in the appendix. Certain aspects of the methods are provided for patients that are stage I-IV colorectal cancer patients. In particular aspects, the patient is a stage II or III patient. In a further embodiment, the patient is a stage I or II patient. In a further embodiment, the patient is a stage I, II, or III patient.

The most common staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome. Details of this system are in the graph below:

| AJCC stage | TNM stage | TNM stage criteria for colorectal cancer |
|---|---|---|
| Stage 0 | Tis N0 M0 | Tis: Tumor confined to mucosa; cancer-in-situ |
| Stage I | T1 N0 M0 | T1: Tumor invades submucosa |
| Stage I | T2 N0 M0 | T2: Tumor invades muscularis propria |
| Stage II-A | T3 N0 M0 | T3: Tumor invades subserosa or beyond (without other organs involved) |
| Stage II-B | T4 N0 M0 | T4: Tumor invades adjacent organs or perforates the visceral peritoneum |
| Stage III-A | T1-2 N1 M0 | N1: Metastasis to 1 to 3 regional lymph nodes. T1 or T2. |
| Stage III-B | T3-4 N1 M0 | N1: Metastasis to 1 to 3 regional lymph nodes. T3 or T4. |
| Stage III-C | any T, N2 M0 | N2: Metastasis to 4 or more regional lymph nodes. Any T. |
| Stage IV | any T, any N, M1 | M1: Distant metastases present. Any T, any N. |

B. Therapy

For people with localized and/or early colorectal cancer, the preferred treatment is complete surgical removal with adequate margins, with the attempt of achieving a cure. This can either be done by an open laparotomy or sometimes laparoscopically. Sometimes chemotherapy is used before surgery to shrink the cancer before attempting to remove it (neoadjuvant therapy). The two most common sites of recurrence of colorectal cancer is in the liver and lungs. In some embodiments, the treatment of early colorectal cancer excludes chemotherapy. In further embodiments, the treatment of early colorectal cancer includes neoadjuvant therapy (chemotherapy or radiotherapy before the surgical removal of the primary tumor), but excludes adjuvant therapy (chemotherapy and/or radiotherapy after surgical removal of the primary tumor.

In both cancer of the colon and rectum, chemotherapy may be used in addition to surgery in certain cases. In rectal cancer, chemotherapy may be used in the neoadjuvant setting.

In certain embodiments, there may be a decision regarding the therapeutic treatment based on biomarker expression. Chemotherapy based on antimetabolites or thymidylate synthase inhibitors such as fluorouracil (5-FU) have been the main treatment for metastatic colorectal cancer. Major progress has been made by the introduction of regimens containing new cytotoxic drugs, such as irinotecan or oxaliplatin. The combinations commonly used, e.g., irinotecan, fluorouracil, and Jeucovorin (FOLFIRI) and oxaliplatin, fluorouracil, and leucovorin (FOLFOX) can reach an objective response rate of about 50%. However, these new combinations remain inactive in one half of the patients and, in addition, resistance to treatment appear in almost all patients who were initially responders. More recently, two monoclonal antibodies targeting vascular endothelial growth factor Avastin® (bevacizumab) (Genentech Inc., South San Francisco Calif.) and epidermal growth factor receptor Erbitux® (cetuximab) (Imclone Inc. New York City) have been approved for treatment of metastatic colorectal cancer but are always used in combination with standard chemotherapy regimens. In some embodiments, the cancer therapy may include one or more of the chemical therapeutic agents including thymidylate synthase inhibitors or antimetabolites such as fluorouracil (5-FU), alone or in combination with other therapeutic agents.

For example, in some embodiments, the first treatment to be tested for response therapy may be antimetabolites or thymidylate synthase inhibitors, prodrugs, or salts thereof. In some embodiments, this treatment regimen is for advanced cancer. In some embodiments, this treatment regimen is excluded for early cancer.

Antimetabolites can be used in cancer treatment, as they interfere with DNA production and therefore cell division and the growth of tumors. Because cancer cells spend more time dividing than other cells, inhibiting cell division harms tumor cells more than other cells. Anti-metabolites masquerade as a purine (azathioprine, mercaptopurine) or a pyrimidine, chemicals that become the building-blocks of DNA. They prevent these substances becoming incorporated in to DNA during the S phase (of the cell cycle), stopping normal development and division. They also affect RNA synthesis. However, because thymidine is used in DNA but not in RNA (where uracil is used instead), inhibition of thymidine synthesis via thymidylate synthase selectively inhibits DNA synthesis over RNA synthesis. Due to their efficiency, these drugs are the most widely used cytostatics. In the ATC system, they are classified under L01B. In some embodiments, this treatment regimen is for advanced cancer. In some embodiments, this treatment regimen is excluded for early cancer.

Thymidylate synthase inhibitors are chemical agents which inhibit the enzyme thymidylate synthase and have potential as an anticancer chemotherapy. As an anti-cancer chemotherapy target, thymidylate synthetase can be inhibited by the thymidylate synthase inhibitors such as fluorinated pyrimidine fluorouracil, or certain folate analogues, the most notable one being raltitrexed (trade name Tomudex). Five agents were in clinical trials in 2002: raltitrexed, pemetrexed, nolatrexed, ZD9331, and GS7904L. Additional non-limiting examples include: Raltitrexed, used for colorectal cancer since 1998; Fluorouracil, used for colorectal cancer; BGC 945; OSI-7904L. In some embodiments, this treatment regimen is for advanced cancer. In some embodiments, this treatment regimen is excluded for early cancer.

In further embodiments, there may be involved prodrugs that can be converted to thymidylate synthase inhibitors in the body, such as Capecitabine (INN), an orally-administered chemotherapeutic agent used in the treatment of numerous cancers. Capecitabine is a prodrug, that is enzymatically converted to 5-fluorouracil in the body. In some embodiments, this treatment regimen is for advanced cancer. In some embodiments, this treatment regimen is excluded for early cancer.

If cancer has entered the lymph nodes, adding the chemotherapy agents fluorouracil or capecitabine increases life expectancy. If the lymph nodes do not contain cancer, the benefits of chemotherapy are controversial. If the cancer is widely metastatic or unresectable, treatment is then palliative. For example, a number of different chemotherapy medications may be used. Chemotherapy agents for this condition may include capecitabine, fluorouracil, irinotecan, leucovorin, oxaliplatin and UFT. Another type of agent that is sometimes used are the epidermal growth factor receptor inhibitors. In some embodiments, this treatment regimen is for advanced cancer. In some embodiments, this treatment regimen is excluded for early cancer.

In certain embodiments, alternative treatments may be prescribed or recommended based on the biomarker profile. In addition to traditional chemotherapy for colorectal cancer patients, cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing. In some embodiments, treatment with one or more of the compounds described herein is for advanced cancer. In some embodiments, treatment with one or more of the compounds described herein is excluded for early cancer.

While a combination of radiation and chemotherapy may be useful for rectal cancer, its use in colon cancer is not routine due to the sensitivity of the bowels to radiation. Just as for chemotherapy, radiotherapy can be used in the neoadjuvant and adjuvant setting for some stages of rectal cancer. In some embodiments, this treatment regimen is for advanced cancer. In some embodiments, this treatment regimen is excluded for early cancer.

In people with incurable colorectal cancer, treatment options including palliative care can be considered for improving quality of life. Surgical options may include non-curative surgical removal of some of the cancer tissue, bypassing part of the intestines, or stent placement. These procedures can be considered to improve symptoms and reduce complications such as bleeding from the tumor, abdominal pain and intestinal obstruction. Non-operative methods of symptomatic treatment include radiation therapy to decrease tumor size as well as pain medications. In some embodiments, this treatment regimen is for advanced cancer. In some embodiments, this treatment regimen is excluded for early cancer.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. In some embodiments, this treatment regimen is for advanced cancer. In some embodiments, this treatment regimen is excluded for early cancer.

Generally, the tumor cell must bear some marker that is amenable to targeting, i.e., is not present on the majority of other cells. Many tumor markers exist and any of these may be suitable for targeting. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. Markers described herein may be used in the context of the current claims for the purposes of developing a targeting moiety. For example, the targeting moiety may be one that binds the tumor marker. In some embodiments, the targeting moiety is an antibody. In further embodiments, the targeting moiety is an aptamer or aptamir.

In yet another embodiment, the treatment is a gene therapy. In certain embodiments, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell. Examples of tumor suppressor nucleic acids within this definition include, but are not limited to APC, CYLD, HIN-I, KRAS2b, p16, p19, p21, p27, p27mt, p53, p57, p73, PTEN, Rb, Uteroglobin, Skp2, BRCA-I, BRCA-2, CHK2, CDKN2A, DCC, DPC4, MADR2/JV18, MEN1, MEN2, MTS1, NF1, NF2, VHL, WRN, WTI, CFTR, C-CAM, CTS-I, zacl, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at www.cise.ufl.edu/~yyl/HTML-TSGDB/Homepage.litml. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied.

C. Monitoring

In certain aspects, the biomarker-based method may be combined with one or more other colon cancer diagnosis or screening tests at increased frequency if the patient is determined to be at high risk for recurrence or have a poor prognosis based on the biomarker described above.

The colon monitoring may include any methods known in the art. In particular, the monitoring include obtaining a sample and testing the sample for diagnosis. For example, the colon monitoring may include colonoscopy or colposcopy, which is the endoscopic examination of the large bowel and the distal part of the small bowel with a CCD camera or a fiber optic camera on a flexible tube passed through the anus. It can provide a visual diagnosis (e.g. ulceration, polyps) and grants the opportunity for biopsy or removal of suspected colorectal cancer lesions. Thus, colonoscopy or colposcopy can be used for treatment.

In further aspects, the monitoring diagnosis may include sigmoidoscopy, which is similar to colonoscopy—the difference being related to which parts of the colon each can examine. A colonoscopy allows an examination of the entire colon (1200-1500 mm in length). A sigmoidoscopy allows an examination of the distal portion (about 600 mm) of the colon, which may be sufficient because benefits to cancer survival of colonoscopy have been limited to the detection of lesions in the distal portion of the colon. A sigmoidoscopy is often used as a screening procedure for a full colonoscopy, often done in conjunction with a fecal occult blood test (FOBT). About 5% of these screened patients are referred to colonoscopy.

In additional aspects, the monitoring diagnosis may include virtual colonoscopy, which uses 2D and 3D imagery reconstructed from computed tomography (CT) scans or from nuclear magnetic resonance (MR) scans, as a totally non-invasive medical test.

The monitoring include the use of one or more screening tests for colon cancer including, but not limited to fecal occult blood testing, flexible sigmoidoscopy and colonoscopy. Of the three, only sigmoidoscopy cannot screen the right side of the colon where 42% of malignancies are found. Virtual colonoscopy via a CT scan appears as good as standard colonoscopy for detecting cancers and large adenomas but is expensive, associated with radiation exposure, and cannot remove any detected abnormal growths like standard colonoscopy can. Fecal occult blood testing (FOBT) of the stool is typically recommended every two years and can be either guaiac based or immunochemical. Annual FOBT screening results in a 16% relative risk reduction in colorectal cancer mortality, but no difference in all-cause mortality. The M2-PK test identifies an enzyme in colorectal cancers and polyps rather than blood in the stool. It does not require any special preparation prior to testing. M2-PK is sensitive for colorectal cancer and polyps and is able to detect bleeding and non-bleeding colorectal cancer and polyps. In the event of a positive result people would be asked to undergo further examination e.g. colonoscopy.

D. ROC Analysis

In statistics, a receiver operating characteristic (ROC), or ROC curve, is a graphical plot that illustrates the performance of a binary classifier system as its discrimination threshold is varied. The curve is created by plotting the true positive rate against the false positive rate at various threshold settings. (The true-positive rate is also known as sensitivity in biomedical informatics, or recall in machine learning. The false-positive rate is also known as the fall-out and can be calculated as 1–specificity). The ROC curve is thus the sensitivity as a function of fall-out. In general, if the probability distributions for both detection and false alarm are known, the ROC curve can be generated by plotting the cumulative distribution function (area under the probability distribution from − infinity to + infinity) of the detection probability in the y-axis versus the cumulative distribution function of the false-alarm probability in x-axis.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

The ROC curve was first developed by electrical engineers and radar engineers during World War II for detecting enemy objects in battlefields and was soon introduced to psychology to account for perceptual detection of stimuli. ROC analysis since then has been used in medicine, radiology, biometrics, and other areas for many decades and is increasingly used in machine learning and data mining research.

The ROC is also known as a relative operating characteristic curve, because it is a comparison of two operating characteristics (TPR and FPR) as the criterion changes. ROC analysis curves are known in the art and described in Metz C E (1978) Basic principles of ROC analysis. Seminars in Nuclear Medicine 8:283-298; Youden W J (1950) An index for rating diagnostic tests. Cancer 3:32-35; Zweig M H I, Campbell G (1993) Receiver-operating characteristic (ROC) plots: a fundamental evaluation tool in clinical medicine. Clinical Chemistry 39:561-577; and Greiner M, Pfeiffer D, Smith R D (2000) Principles and practical application of the receiver-operating characteristic analysis for diagnostic tests. Preventive Veterinary Medicine 45:23-41, which are herein incorporated by reference in their entirety.

III. Sample Preparation

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g. rectal) and one or more samples from another tissue (e.g. cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

IV. Nucleic Acid Assays

Aspects of the methods include assaying nucleic acids to determine expression or activity levels. Arrays can be used to detect differences between two samples. Specifically contemplated applications include identifying and/or quantifying differences between RNA from a sample that is normal and from a sample that is not normal, between a cancerous condition and a non-cancerous condition, or between two differently treated samples. Also, RNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes.

In addition to the use of arrays and microarrays, it is contemplated that a number of difference assays could be employed to analyze nucleic acids, their activities, and their effects. Such assays include, but are not limited to, nucleic amplification, polymerase chain reaction, quantitative PCR, RT-PCR, in situ hybridization, Northern hybridization, hybridization protection assay (HIPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

A further assay useful for quantifying and/or identifying nucleic acids is RNAseq. RNA-seq (RNA sequencing), also called whole transcriptome shotgun sequencing, uses next-generation sequencing (NGS) to reveal the presence and quantity of RNA in a biological sample at a given moment in time. RNA-Seq is used to analyze the continually changing cellular transcriptome. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

V. Protein Assays

A variety of techniques can be employed to measure expression levels of polypeptides and proteins in a biological sample. Examples of such formats include, but are not limited to, enzyme immunoassay (EIA), radioimmunoassay (RIA), Western blot analysis and enzyme linked immuno-absorbent assay (ELISA). A skilled artisan can readily adapt known protein/antibody detection methods for use in determining protein expression levels of biomarkers.

In one embodiment, antibodies, or antibody fragments or derivatives, can be used in methods such as Western blots or immunofluorescence techniques to detect biomarker expression. In some embodiments, either the antibodies or proteins are immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present disclosure. The support can then be washed with suitable buffers followed by treatment with the detectably labeled antibody. The solid phase support can then be washed with the buffer a second time to remove unbound antibody. The amount of bound label on the solid support can then be detected by conventional means.

Immunohistochemistry methods are also suitable for detecting the expression levels of biomarkers. In some embodiments, antibodies or antisera, including polyclonal antisera, and monoclonal antibodies specific for each marker may be used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art. A two-site, monoclonal-based immunoassay utilizing antibodies reactive to two non-interfering epitopes or a competitive binding assay may be employed.

Numerous labels are available and commonly known in the art. Radioisotope labels include, for example, $^{36}S$, $^{14}C$, $^{125}I$, $^{3}H$, and $^{131}I$. The antibody can be labeled with the radioisotope using the techniques known in the art. Fluorescent labels include, for example, labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques known in the art. Fluorescence can be quantified using a fluorimeter. Various enzyme-substrate labels are available and U.S. Pat. Nos. 4,275,149, 4,318,980 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzymology (Ed. J. Langone & H. Van Vunakis), Academic press, New York, 73: 147-166 (1981).

In some embodiments, a detection label is indirectly conjugated with an antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). In some embodiments, the antibody need not be labeled, and the presence thereof can be detected using a labeled antibody, which binds to the antibody.

VI. Pharmaceutical Compositions

In certain aspects, the compositions or agents for use in the methods, such as chemotherapeutic agents or biomarker modulators, are suitably contained in a pharmaceutically acceptable carrier. The carrier is non-toxic, biocompatible and is selected so as not to detrimentally affect the biological activity of the agent. The agents in some aspects of the disclosure may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VII. Kits

Certain aspects of the present disclosure also concern kits containing compositions of the disclosure or compositions to implement methods of the disclosure. In some embodiments, kits can be used to evaluate one or more nucleic acid and/or polypeptide molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more nucleic acid probes, synthetic RNA molecules or inhibitors, or any value or range and combination derivable therein. In some embodiments, there are kits for evaluating biomarker levels or activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using probes, polypeptide detecting agents, and/or inhibitors or antagonists of the disclosure for prognostic or diagnostic applications are included. Specifically contemplated are any such molecules corresponding to any biomarker nucleic acid or polypeptide.

In certain aspects, negative and/or positive control agents are included in some kit embodiments. The control molecules can be used to verify transfection efficiency and/or control for transfection-induced changes in cells.

It is contemplated that any method or composition described herein can be implemented with respect to any other method or composition described herein and that different embodiments may be combined.

Any embodiment of the disclosure relating to a polypeptide or nucleic acid is contemplated also to cover embodiments whose sequences are at least 80, 81, 82, 83, 84, 85, 86, 87, 88, 89, 90, 91, 92, 93, 94, 95, 96, 97, 98, 99% identical to the polypeptide or nucleic acid.

Embodiments of the disclosure include kits for analysis of a pathological sample by assessing a nucleic acid or polypeptide profile for a sample comprising, in suitable container means, two or more RNA probes, or a biomarker polypeptide detecting agent, wherein the RNA probes or polypeptide detecting agent detects biomarker nucleic acids or polypeptides. In some embodiments, the reagents (i.e. RNA probe and/or polypeptide detecting agent) are labeled with a detectable label. Labels are known in the art and also described herein. The kit can further comprise reagents for labeling probes, nucleic acids, and/or detecting agents. The kit may also include labeling reagents, including at least one of amine-modified nucleotide, poly(A) polymerase, and poly(A) polymerase buffer. Labeling reagents can include an amine-reactive dye.

VIII. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Identification of a miRNA Cluster with Prognostic Biomarker Potential in Colorectal Cancer Despite recent advances in colorectal cancer (CRC) treatments, approximately 30-50% of CRC patients who undergo curative resection subsequently experience tumor recurrence. Therefore, identification of reliable prognostic biomarkers that accurately select and stratify high-risk stage II & III CRC patients is paramount for individualized therapeutic strategies and ultimately improving patient outcomes. MicroRNAs (miRNAs) are small non-coding RNAs frequently dysregulated in various cancers and are emerging as promising cancer biomarkers. In this example, the inventors conducted a comprehensive miRNA expression profiling of tumors with or without tumor recurrence to identify a panel of miRNAs that are associated with tumor recurrence in CRC patients.

The inventors performed miRNA expression profiling in stage III primary CRC using multiple datasets to characterize miRNA signature and identify targets in patients with and without tumor recurrence (FIG. 1). The expression of these candidate miRNAs was validated in two independent stage II & III CRC cohorts (n=88, 107). The expression of the candidate tissue-based miRNAs were evaluated in 119 plasma specimens from patients with stage II/III CRC.

Figure 1D:
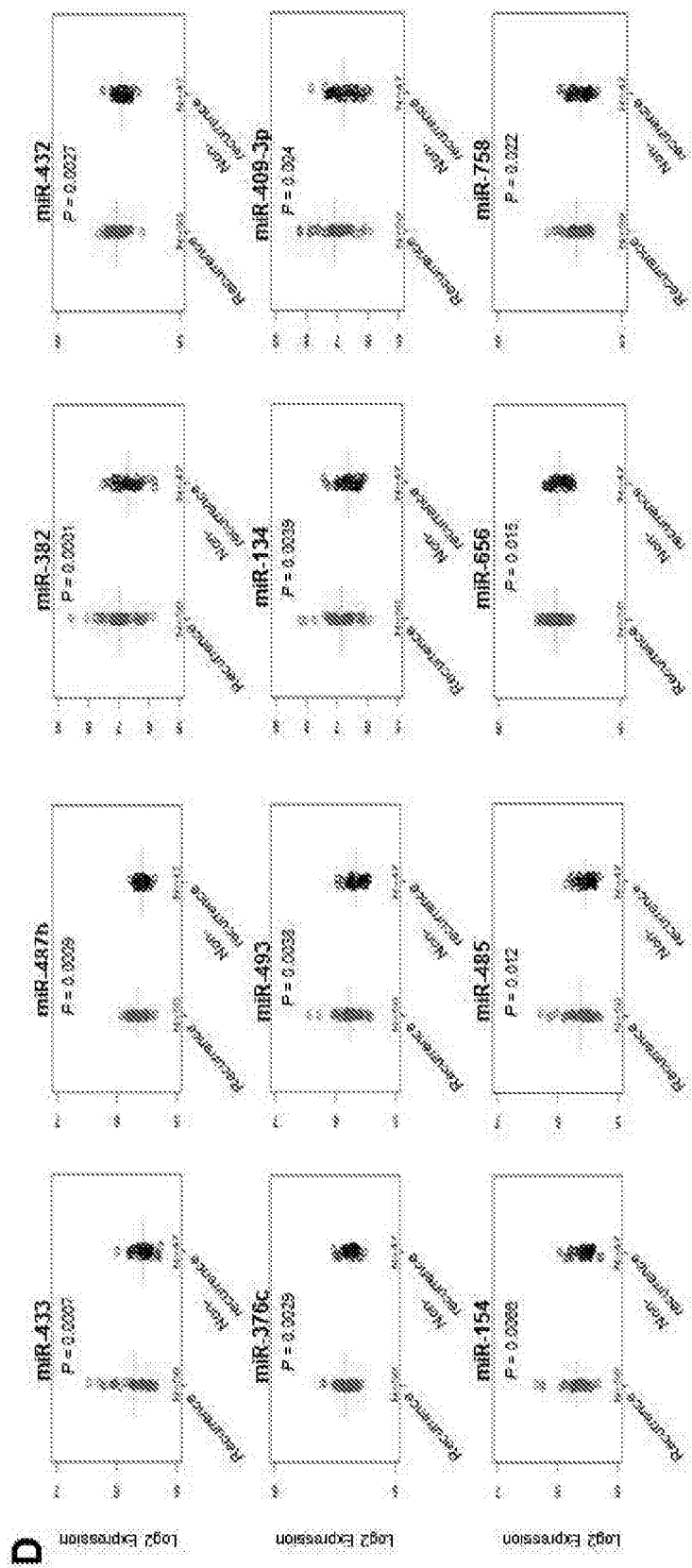
Figure 2A:
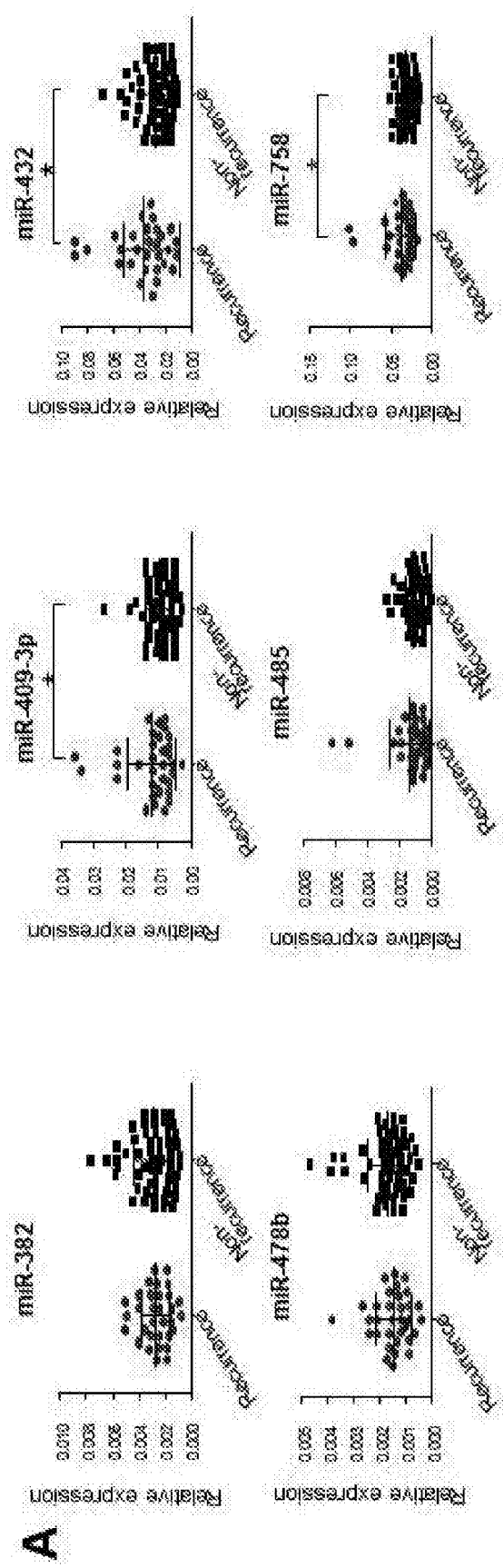
FIG. 2A-C: Relative expression of differentially expressed miRNAs in recurrent and non-recurrent colorectal cancer tissues (a). Correlation of disease free survival (DFS) and overall survival (OS) with indicated miRNA expression (b). These results are further discussed in Example 1.
Figure 2B:
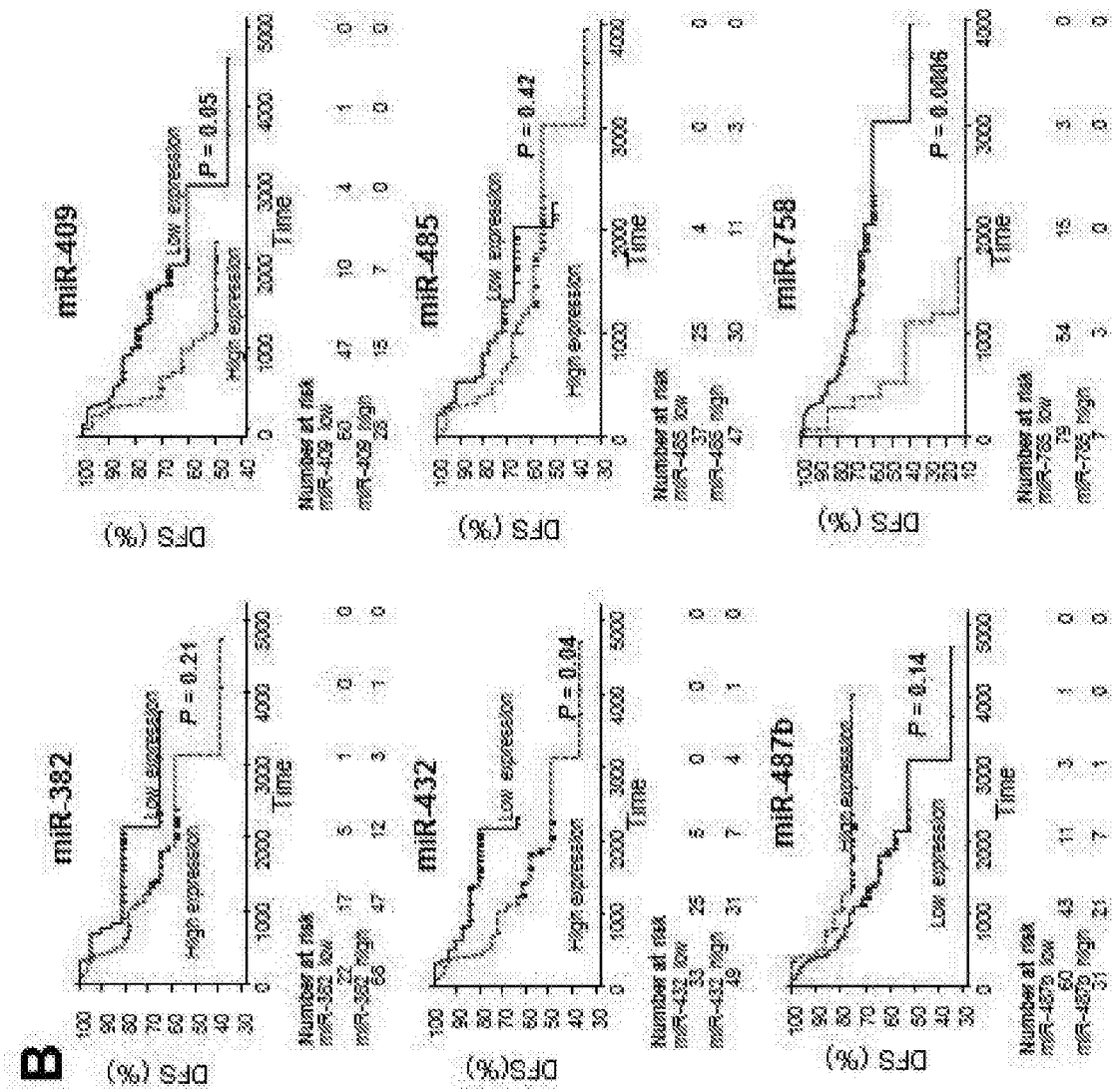
Figure 2C:
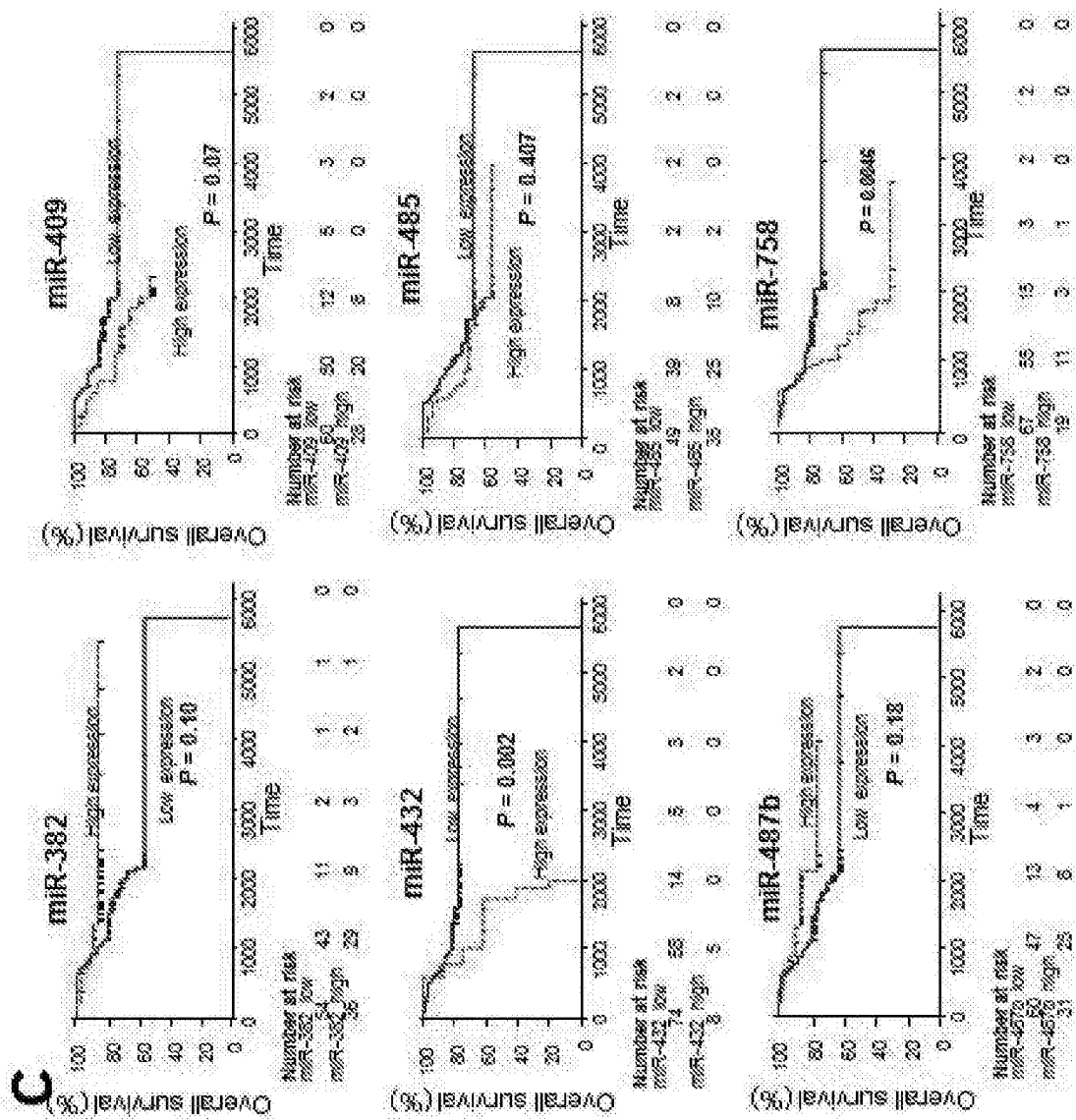

The inventors identified that 12% of differentially expressed miRNAs in tumor tissues from recurrence-positive CRC patients were clustered together and encoded by 14q32 locus. Intriguingly, all of these miRNAs were overexpressed in the tumor tissues with recurrence. Using bioinformatic and statistical approaches six differentially expressed miRNAs that mapped to this 14q32 locus were identified, and the overexpression of three miRNAs (miR-409, -432 and -758) was confirmed in the tumor tissues from stage II & III CRC patients with vs. without relapse (all $p<0.05$) (FIG. 1D, 2A). Furthermore, high expression of miR-409, miR-432 and miR-758 was associated with poor disease-free survival (DFS) ($p<0.05$, $p<0.05$ and $p<0.001$ respectively) (FIG. 2B). The inventors thereafter validated the prognostic potential of miR-758 in an independent patient cohort, and Cox regression analysis revealed that overexpression of miR-758 emerged as an independent prognostic factor for DFS (HR:2.2, 95% CI:1.0-4.9, p<0.05). Interestingly, the expression of circulating miR-758 was significantly higher in patients with vs. without recurrence in pre-operative serum samples (p<0.01).

Figure 3:
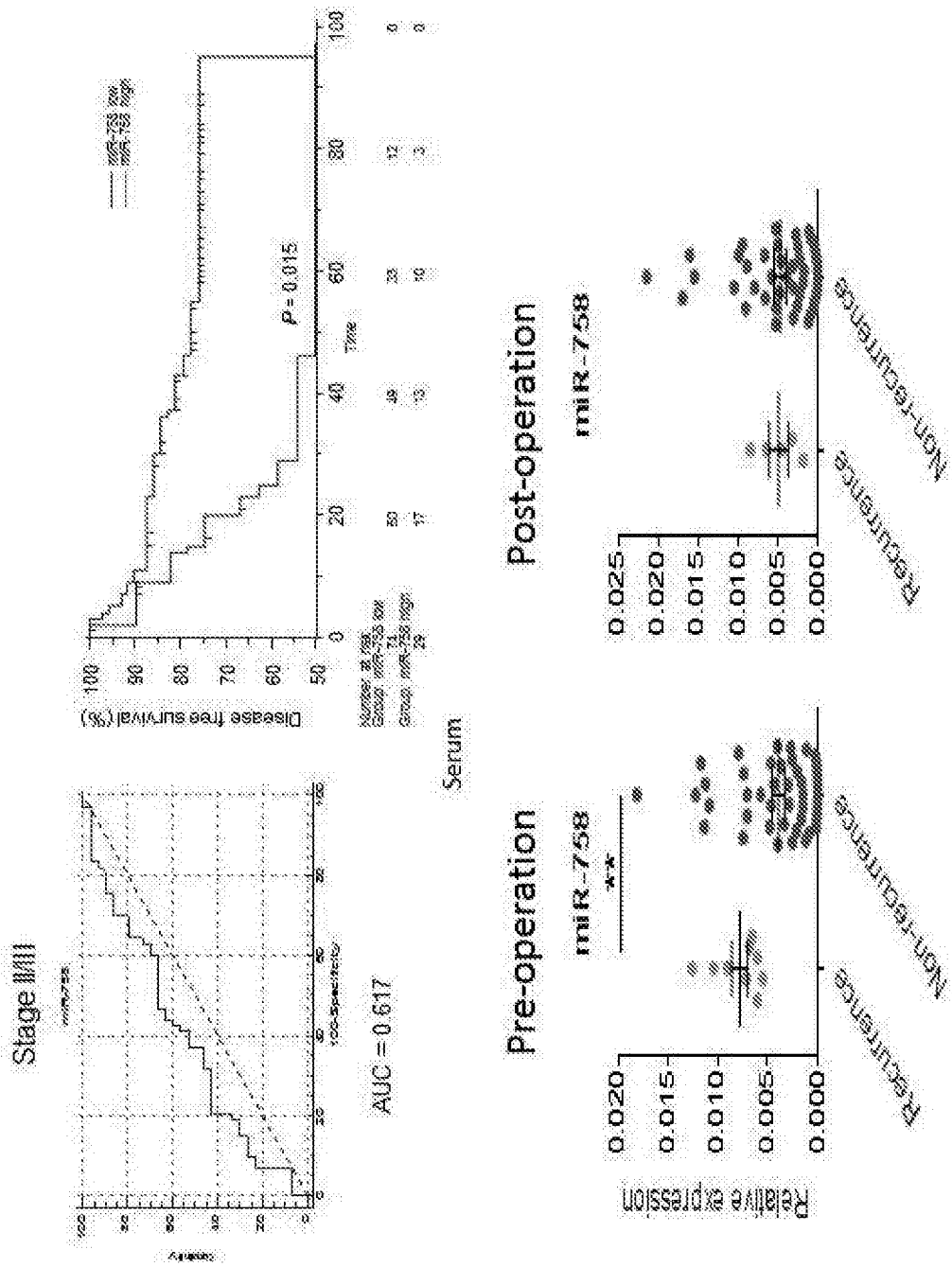
FIG. 3: ROC analysis, correlation with disease free survival, and pre-operative and post-operative serum levels of miR-758. These results are further discussed in Example 1.
Figure 4:
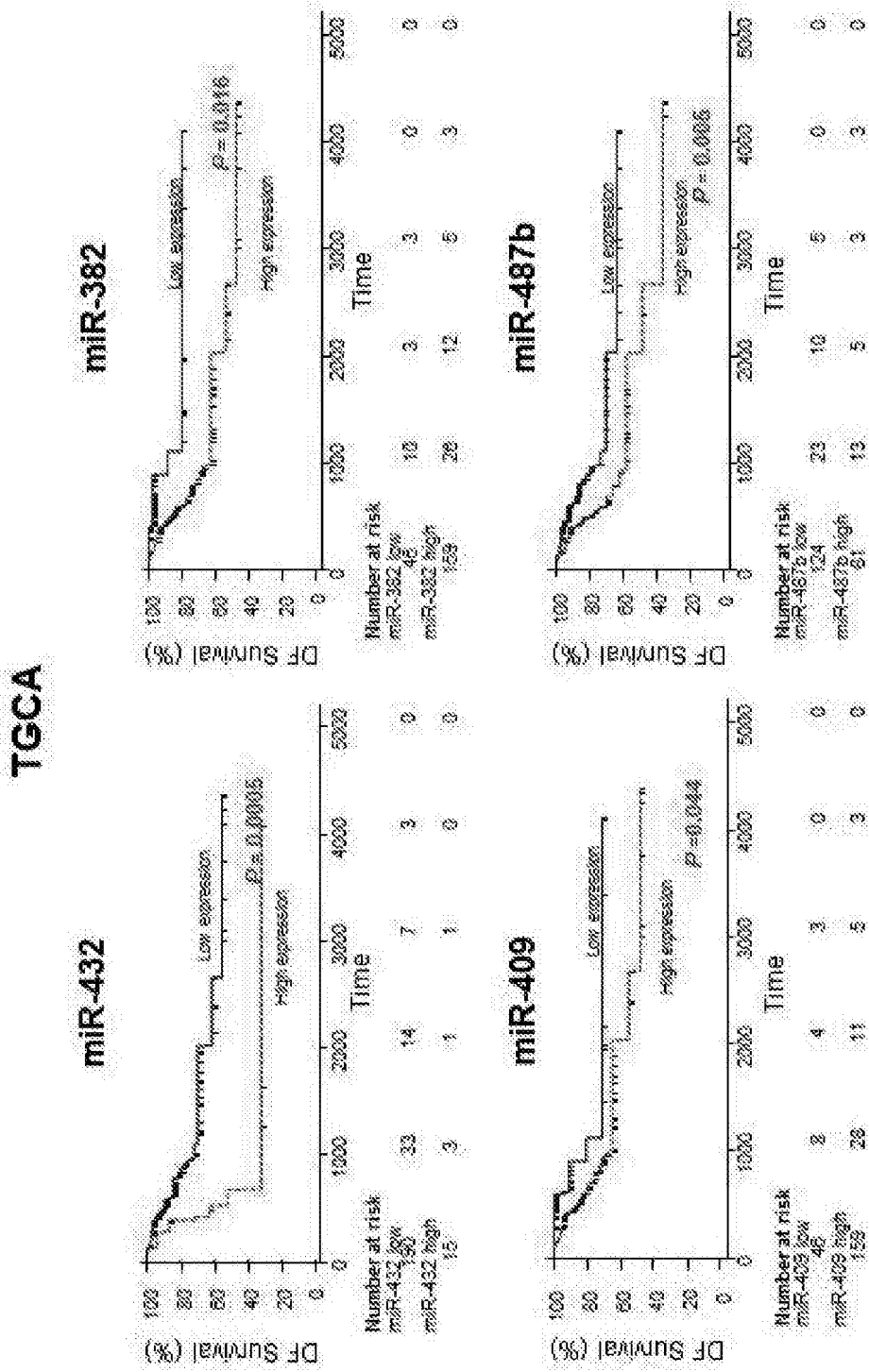
FIG. 4: Correlation of disease free survival and expression levels of various miRNAs. These results are further discussed in Example 1.

Using a comprehensive miRNA expression profiling approach, the inventors have identified a cluster of miRNAs encoded at 14q32, which is frequently overexpressed in CRC patients with tumor recurrence. In particular, miR-758 was able to identify a subgroup of stage II/III patients with high-risk of recurrence and was upregulated in post-operative plasma samples of recurrence-positive CRC patients (FIG. 3), suggesting its potential usefulness as an important biomarker for identification of high-risk patients that are candidates for more aggressive chemotherapy.

Figure 5:
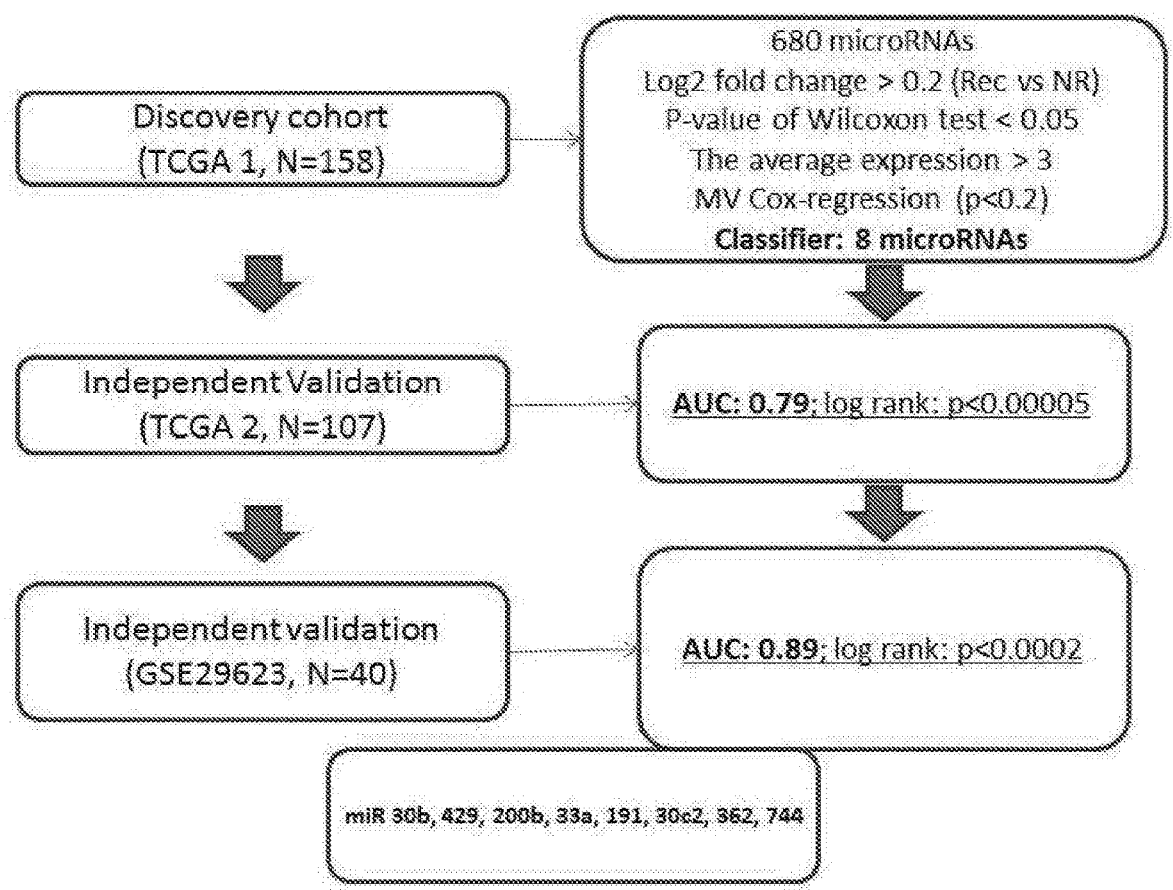
FIG. 5: Schematic of experimental design for discovery of colorectal cancer microRNA markers for prognosis—discovery from TCGA. These results are further discussed in Example 2.

Example 2—Genome-Wide Discovery and Identification of a Novel microRNA Signature for Recurrence Prediction in Colorectal Cancer Colorectal cancer (CRC) is one of the leading causes of cancer-related deaths worldwide. In 2016, there were estimated 95,270 newly diagnosed CRC cases, and 49,190 deaths from this disease in the United States. Survival of patients is closely associated with the tumor stage at the time of diagnosis as 5-year relative survival rates range from 65% for all stages, 90% for localized primary tumor, 71% for regional metastasis and 13% for distant metastasis. Post-surgery, adjuvant therapy is only recommended to those with high risk stage II, as well as stage III and IV tumors. However, approximately 40-50% of the patients undergo curative surgery only and 20-30% that are treated with adjuvant chemotherapy, eventually relapse and experience a metastatic disease and eventual death. The current gold standard TNM (Tumor, Node, Metastasis) staging for determining the prognosis of CRC patients remains inadequate at identification of high-risk stage II and III patients that have a high potential of developing tumor recurrence. MicroRNAs (miRNAs) play an important role in CRC development and are emerging as important disease biomarkers. Therefore in this example, the inventors sought to determine the prognostic potential of the miRNAs using a systematic, genome-wide biomarker discovery approach, followed by validation of biomarkers in multiple patient cohorts Three independent publicly available genome-wide miRNA expression datasets were used for miRNA biomarker discovery (n=158) and in-silico validation (n=109 and n=40) of this miRNA signature for recurrence prediction in stage II and III CRC using Cox's regression. The eight gene miRNA signature discovered from the genome-wide analysis was analytically validated in two independent patient cohorts (n=127 and n=96) using Taqman-based RT-PCR assays (FIG. 5).

Figure 6:
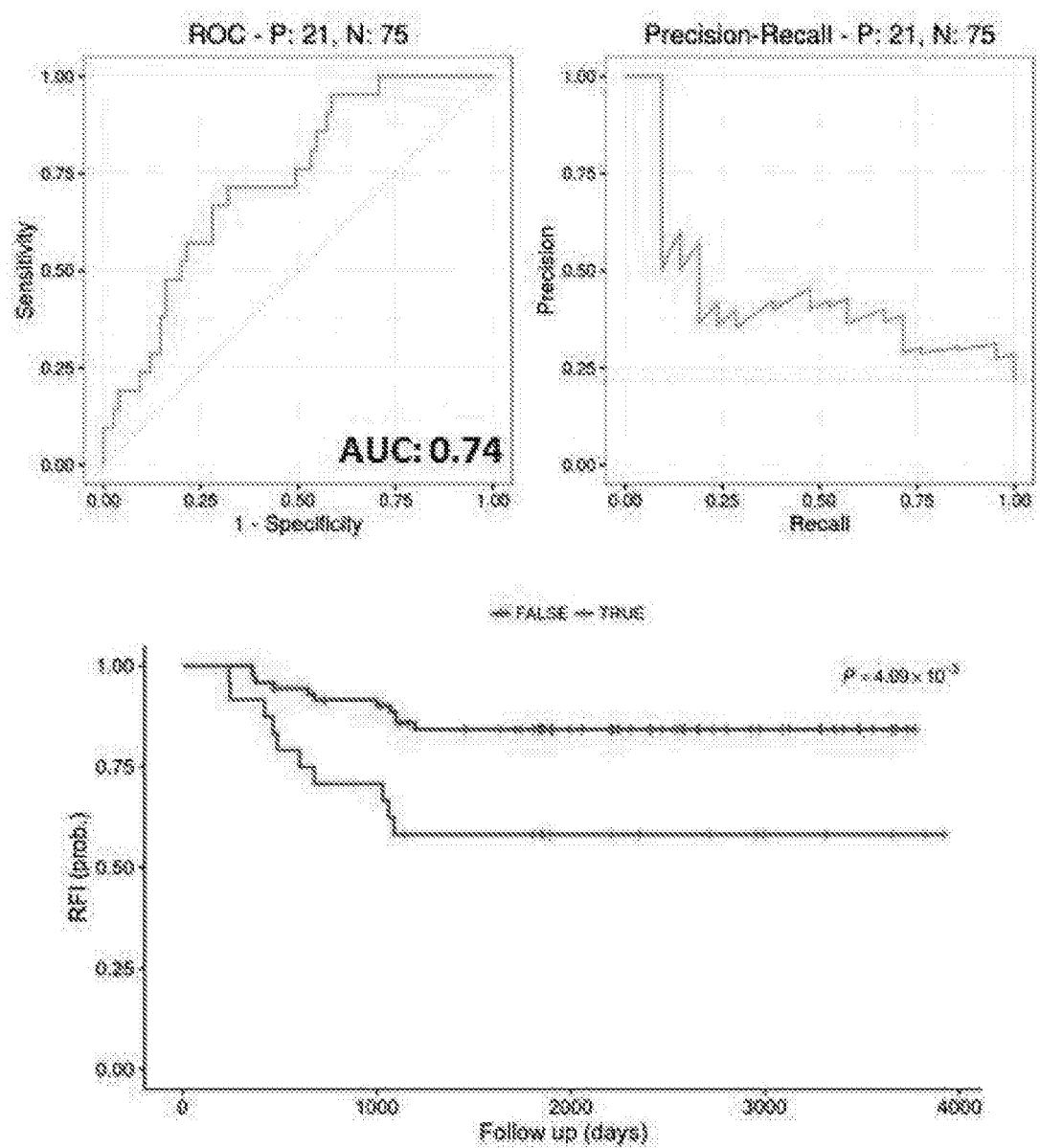
FIG. 6: Clinical validation in NCCH cohort for Stage 2 and 3 colorectal cancer tissues. These results are further discussed in Example 2.
Figure 7:
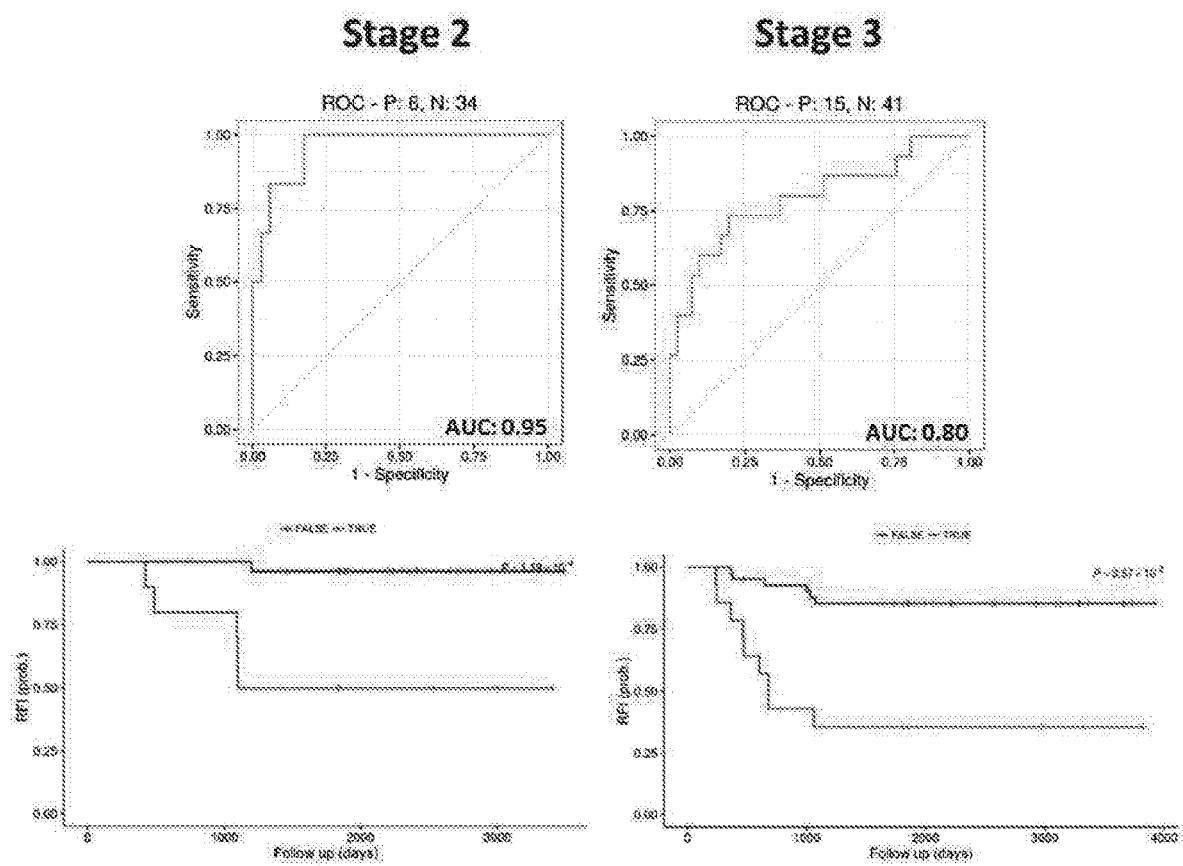
FIG. 7: Clinical validation for Stage 2 and 3 colorectal cancer tissues. These results are further discussed in Example 2.

The genome-wide comprehensive analysis led to the identification of an eight gene miRNA classifier that significantly predicted recurrence free survival (RFS) in training (log rank p=0.003) and two independent validation cohorts (log rank p<0.0001 and p=0.002). The RT-PCR based training and validation of the eight gene classifier in two independent clinical cohorts significantly associated with poor prognosis in stage II and III CRC patients (log rank p<0.004 and p<0.0001). Multivariate analyses performed in these two patient cohorts revealed that the eight gene miRNA classifier served as an independent predictor of poor prognosis in stage II and III CRC patients (FIG. 6-7).

In conclusion, the inventors have identified a novel miRNA-based classifier, which is robustly predictive of poor prognosis in patents with stage II/III CRC, and might facilitate identification and stratification of high-risk patients that are candidates for adjuvant chemotherapy and clinical surveillance.

Example 3—A Novel miRNA Signature for the Detection of Lymph Node Metastasis in Submucosal Colorectal Cancer Patients Owing to recent advances in colonoscopic techniques, majority of submucosal colorectal cancers (T1 CRCs) can now be removed by endoscopic resection. Among these, 70% of T1 CRCs are deemed as "high risk" because they meet certain pathological risk factors including the presence of lymphovascular invasion, poor differentiation, and increased depth of tumor (>1000 um). However, post-surgical pathology data indicates that in reality only 10-15% of all T1 CRCs are genuinely high risk, while all other patients undergo unnecessary surgeries. Since current pathological criteria are inadequate, availability of more robust molecular biomarkers that may help identify 'genuine high risk patients with lymph node (LN) metastasis' more accurately will reduce the burden of surgical overtreatments. Due to the growing interest in developing miRNA biomarkers, the inventors undertook this study to identify a miRNA-based diagnostic signature for detecting LN metastasis in CRC.

In a biomarker discovery step using RNA-Seq data from 15 LN-positive and 104 LN-negative T½ CRC patients, the inventors identified candidate miRNAs with >0.5 log fold change and a p<0.05. Thereafter, using a receiver operating curve (ROC) based backwards elimination approach, the inventors identified a signature of miRNAs that were differentially expresses in LN positive vs. negative CRCs. The inventors validated the performance of this miRNA signature to detect LN metastasis in 190 surgically resected CRC specimens from two independent patient cohorts by qPCR assays.

A panel of 10 differentially expressed miRNAs were identified in the discovery step, which was initially validated in a training cohort of 61 T1 CRC samples, which included 8 LN-positive cases. Using a logistic regression analysis model, the inventors deduced robust AUC values when using miRNA expression results alone (AUC=0.85, 95% CI: 0.74-0.93, p<0.001) for identifying LN-positive T1 CRCs. Thereafter using the same model parameters in an independent validation cohort of 130 T1 CRCs, which included 16 LN-positive patients, the inventors were able to successfully confirm the results from the training cohort (AUC=0.74, 95% CI:0.66-0.781, p<0.001) for the identification of high risk T1 CRC patients with lymph node metastasis.

Based upon a systematic approach, this example demonstrates report the feasibility and promise of a miRNA signature that can be used clinically for the detection of T1 CRCs with lymph node metastasis, which will reduce patient discomfort and healthcare costs.

A. Patients and Methods

1. Candidate miRNA Selection and miRNA Signature Construction

The inventors analyzed and constructed miRNA signature using miRNA seq of TCGA database. First, the inventors compared miRNA expressions between LNM positive and negative samples in 119 T1-2 CRC (positive 15 and negative 104, respectively) since T1 there were only 19 CRC samples with node information (positive 2 and negative 17, respectively). TCGA miRNA seq included 1881 miRNAs and candidate miRNAs were selected through the following analyses; (1) log 2 fold change of >0.5 between node positive and negative samples with p-value of Wilcoxon test <0.05 and (2) The average expression of >3. Then receiver operation curve (ROC) based back step elimination method was applied to construct the miRNA signature by logistic regression model.

2. Patients and Sample Collection

Total, 188 T1 CRC fresh frozen paraffin embedded (FFPE) specimens were obtained from two Japanese cohorts: 60 (LNM positive 7 and negative 53, respectively) from Kumamoto University cohort and 128 (LNM positive 20 and negative 108, respectively) from the University of Tokyo cohort. All of the samples were resected surgically and collected between 2005 and 2014 in Kumamoto University and between 2005 and 2016 in the University of Tokyo. Matched biopsy samples (FFPE), which were taken during colonoscopy before surgery, were also obtained from the University of Tokyo cohort. Exclusion criteria were as follows: (1) synchronous CRC (T1-4); (2) distant metastasis; (3) neoadjuvant chemo/radio therapy; (4) hereditary or inflammation associated CRC; and (5) non-adenocarcinoma. All of the patients underwent standard surgical procedure (resection of affected segment of colon or rectum and regional lymphadenectomy), and all of the samples were evaluated by pathologists of each institute according to AJCC TNM grading system and Japanese guidelines. Preoperative serum carcinoembrionic antigen (CEA) level was evaluated before surgery in the laboratory. CT were performed before surgery for all of the patients of the University of Tokyo cohort and their findings were evaluated by radiologists in the University of Tokyo hospital. When the size of regional LN is more than 10 mm, LNM was estimated as positive.

3. Total RNA Extraction and Real-Time Quantitative Reverse Transcription Polymerase Chain Reaction Total RNA was extracted from 10 m thick FFPE specimens using AllPrep® DNA/RNA FFPE kit (QIAGE, Hilden, Germany) according to the manufacturer's instructions. cDNA was synthesized from total RNA according to the manufacturer's recommendations (ThermoFisher Scientific, MA, USA). qRT-PCR was performed using the QuantStudio™ 7 Flex Real Time PCR System (Applied Biosystems®, Foster City, Calif.), and expression levels were evaluated with Applied Biosystems QuantStudio™ 7 Flex Real Time PCR System Software. The relative abundance of target transcripts was evaluated and normalized to the expression levels of miR-16 as internal controls using the $2^{-\Delta Ct}$ method; ΔCt means the difference of Ct values between the miRNA of interest and the normalizer. Normalized values were further log transformed and standardized. All of the primers for miRNA used in this study are purchased from ThermoFisher Scientific (MA, USA).

4. Study Design miRNA signatures to predict LNM in T1-2 CRC, which was constructed using TCGA database, were validated by in silico analyses of T1 CRC patients of TCGA database and also GSE56350 which included miRNA expression of 46 primary site and 43 LNM site evaluated by Affymetrix microarray.

Figure 10:
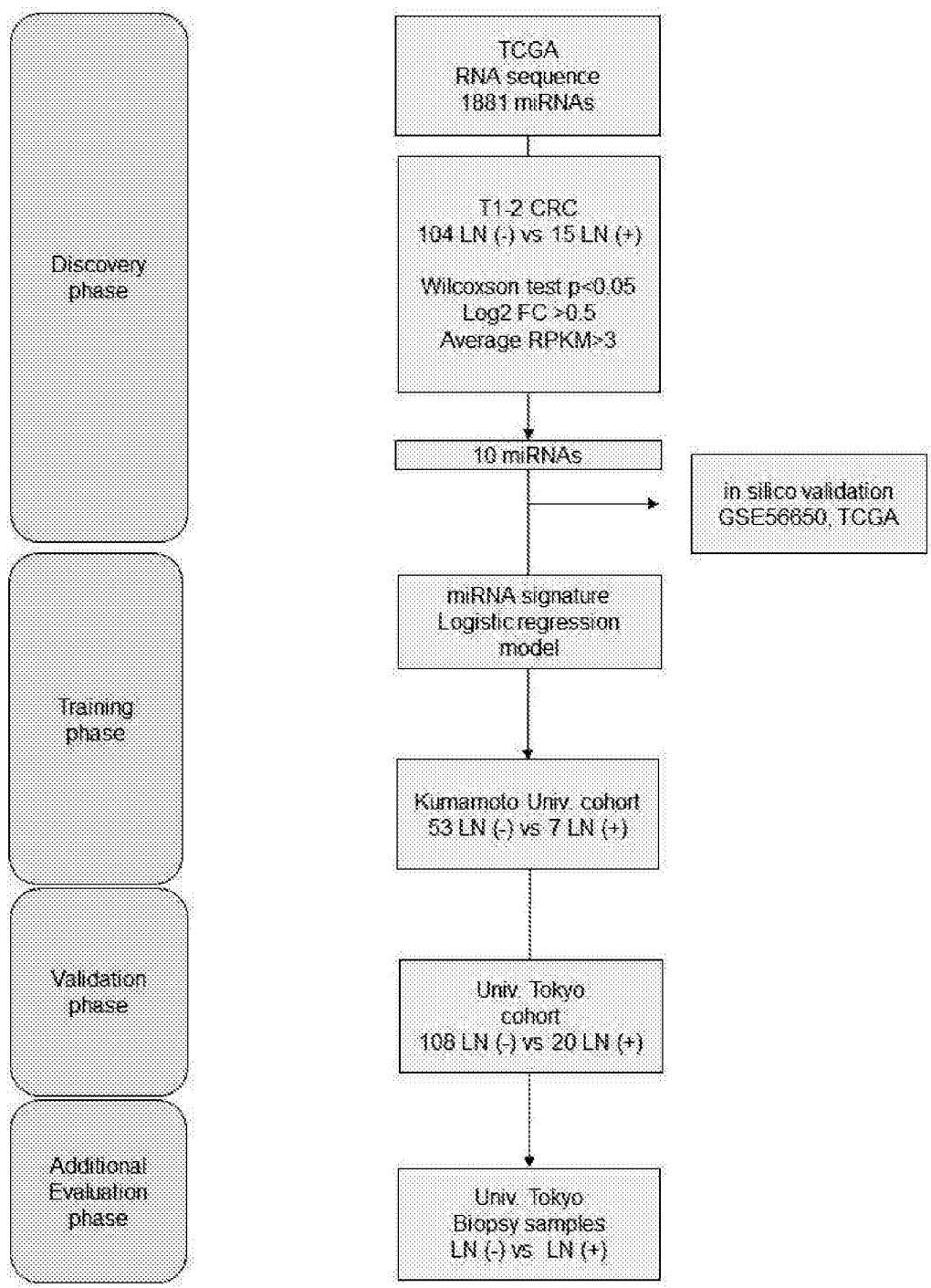
FIG. 10: Schematic diagram of miRNA biomarker discovery and analysis. These results are further discussed in Example 3.

Then, the inventors validated the predictive power of this miRNA signature in surgically resected T1 CRC FFPE samples from two individual cohorts, and compared with conventional clinicopathological factors or CT evaluation. The predictive power of this miRNA signature in biopsy samples from University of Tokyo cohort was also validated (FIG. 10).

5. Statistical Analysis

Expression levels of each miRNA were shown as mean±standard error. Mann-Whitney U test was used to evaluate the statistical difference of miRNA expressions. Several clinicopathological characteristics were compared between LNM positive and negative groups using the chi-square test or Fisher's exact test for categorical data. ROC curve and area under the curve (AUC) were used to evaluate the predictive value of each miRNA and miRNA signature for LNM. Prediction values calculated by logistic regression model using miRNA expression levels were transformed into z-score and were shown as risk score. Statistical calculations were performed using JMP Pro 11 statistical software (SAS Institute Japan, Tokyo, Japan), Medcalc version 16.1. (MedCalc Software, Belgium) and GraphPad Prism 7 (GraphPad Software Inc., CA, USA).

B. Results

1. The Discovery Phase in TCGA Database Identified Ten miRNAs to Predict LNM in T1 and 2 Colorectal Cancer Logistic regression model with ROC back step elimination method identified 10 miRNA signature that best predicts LNM in T1-2 CRC in TCGA database; mir-32, mir-181b (-1 and -2), mir-188, mir-193b, mir-195, mir-424, mir-425, mir-592, mir-3677, and mir-4326.

Figure 8A:
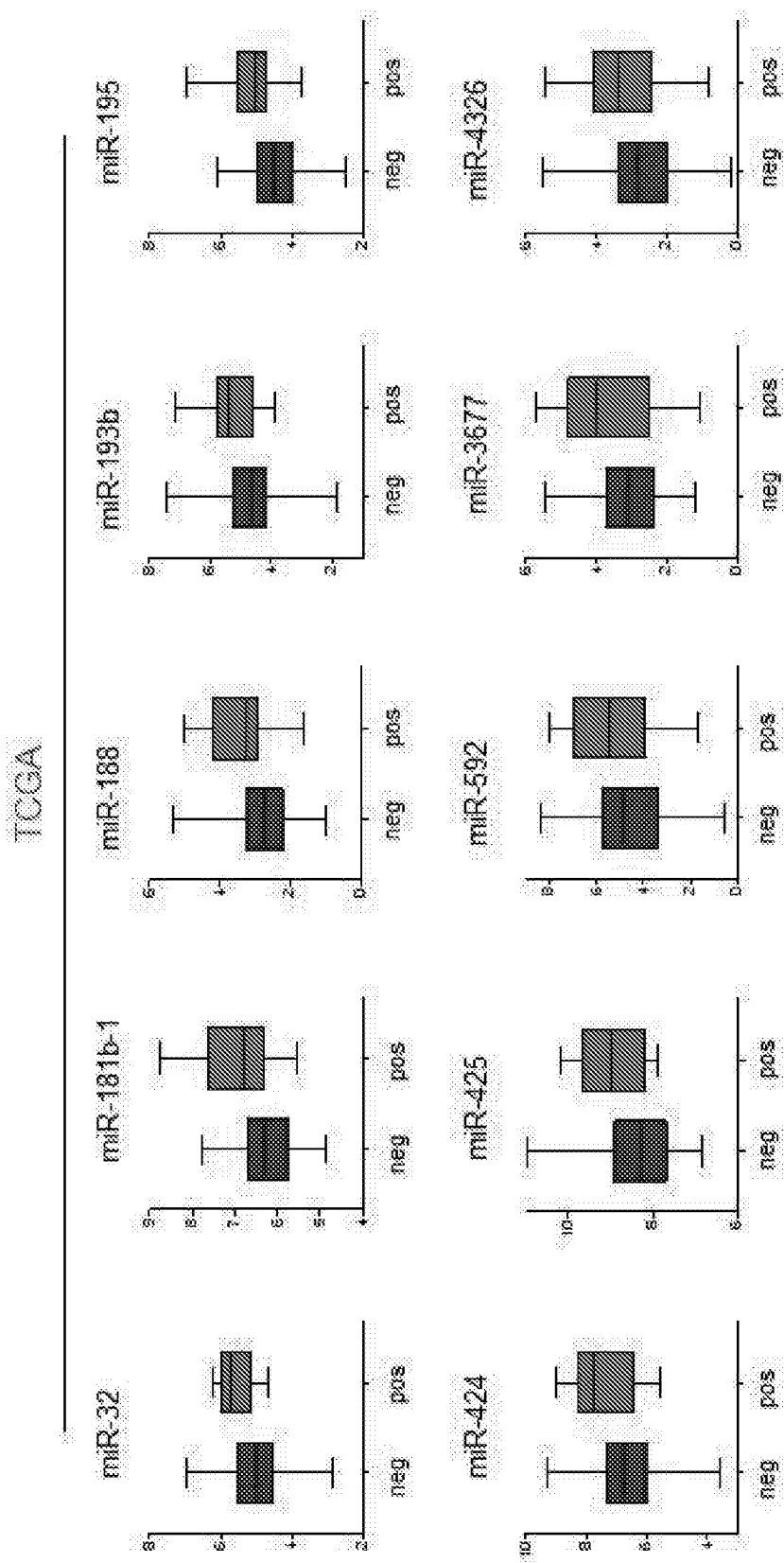
FIG. 8A-C: Analysis of miRNA expression for correlation with colorectal cancer. Shown are results of expression analysis (a), the sensitivity and specificity ROC analysis for the prediction of lymph node metastasis (LNM) of each miRNA alone (b), of the combination of mir-32, mir-181b (-1 and -2), mir-188, mir-193b, mir-195, mir-424, mir-425, mir-592, mir-3677, and mir-4326 in T1-2 CRC (10-miRNA signature; c; left panel), of the combination of mir-32, mir-181b (-1 and -2), mir-188, mir-193b, mir-195, mir-424, mir-425, mir-592, mir-3677, and mir-4326 in T1 CRC patients of the TCGA database (c; middle panel), and of the combination of mir-32, mir-181b (-1 and -2), mir-188, mir-193b, mir-195, mir-424, mir-425, and mir-592 in tissues of primary and LNM tissues (c; right panel). These results are further discussed in Example 3.
Figure 8B:
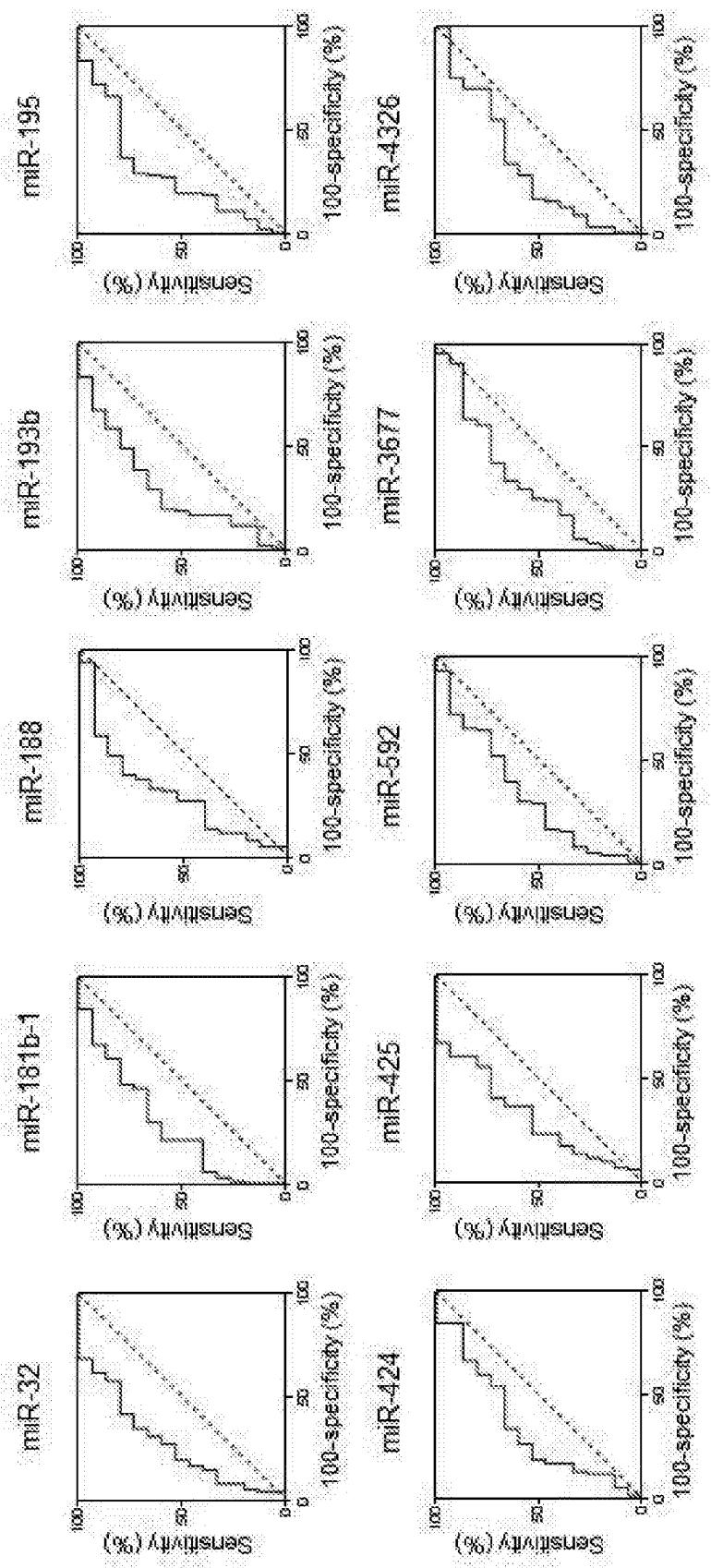
Figure 8C:
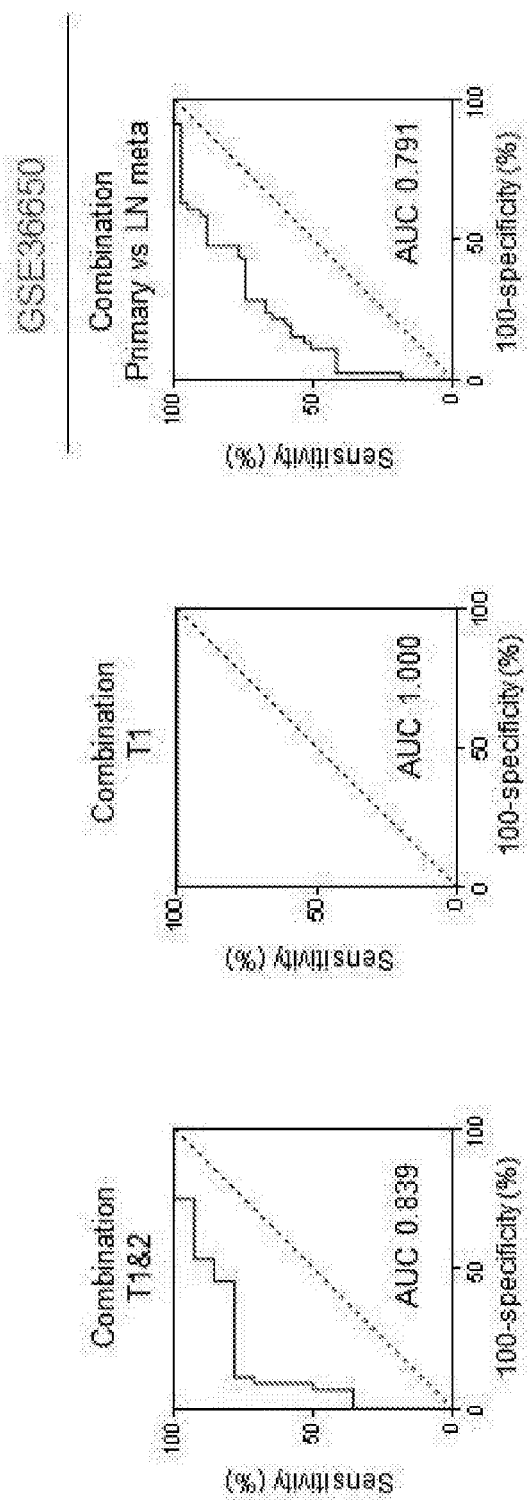

The expression of each miRNA between LNM positive and negative and ROC curves are shown in FIG. 8. All of the miRNAs were highly upregulated in LNM positive samples compared to negative samples. Although the AUC value of each miRNA individually was insufficient to predict LNM, the miRNA signature which was constructed with these 10 miRNAs showed robust AUC value of 0.839 [95% CI(confidence interval): p=] to predict LNM in T1-2 CRC.

2. In Silico Validation of miRNA Signature Confirmed Good Performance of this Model The inventors applied this model to T1 CRC patients of TCGA database including 2 LNM positive and 17 negative patients, and confirmed that this model performed well in T1 CRC patients with AUC value of 1.000 (95% CI: p=) (FIG. 8).

Then, the inventors applied this model to GSE36650, which contained miRNA expression data of Affymetrix microarray from 46 primary CRC site and 43 LNM site. Because this dataset was generated by microarray, miR-3677 and miR-4326 were not included. Therefore, a miRNA signature was constructed using the other 8 miRNAs. This 8 miRNA signature predicted LNM site with AUC of 0.791 (950% CI: p=), and this result supported the idea that this miRNA signature was associated with LNM in CRC (FIG. 8).

3. Validation in Surgically Resected Samples from Kumamoto Univ. Cohort Showed this miRNA Signature Performed Well in Clinical Samples Kumamoto Univ. cohort included 7 LNM positive and 53 LNM negative patients. The presence of lymphatic invasion was significantly more frequent in LNM positive samples than that of negative samples (p<0.001). The other clinicopathological features such as tumor depth, poorly differentiated histology, and venous invasion were not associated with LNM (p=, 0.117, and 0.338, respectively) (Table 1).

TABLE 1

Associations between LN metastasis and clinicopathological features

| Characteristics | Kumamoto Univ. (N = 60) N (%) | | | Univ. Tokyo (N = 128) N (%) | | |
|---|---|---|---|---|---|---|
| | LN negative (N = 53) | LN positive (N = 7) | P value | LN negative (N = 108) | LN positive (N = 20) | P value |
| Gender | | | 1.000 | | | 0.226 |
| Male | 34 (64) | 2 (29) | | 65 (60) | 9 (45) | |
| Female | 19 (36) | 5 (71) | | 43 (40) | 11 (55) | |
| Age (Years) | | | 0.117 | | | 1.000 |
| <65 | 20 (38) | 5 (71) | | 48 (44) | 9 (45) | |
| ≥65 | 33 (62) | 2 (29) | | 60 (56) | 11 (55) | |
| Tumor location | | | 0.182 | | | 0.608 |
| Colon | 39 (74) | 3 (43) | | 73 (68) | 12 (50) | |
| Rectum | 14 (26) | 4 (57) | | 35 (32) | 8 (40) | |
| Tumor depth (pm) | | | | | | 0.007 |
| <1000 | | | | 20 ( ) | 0 (0) | |
| ≥1000 | | | | 82 ( ) | 18 ( ) | |
| Unavailable | | | | 6 ( ) | 2 ( ) | |
| Tumor size (mm) | | | 1.000 | | | 0.647 |
| <20 | 24 | 3 | | 60 (56) | 10 (50) | |
| ≥20 | 24 | 2 | | 48 (44) | 10 (50) | |
| Unavailable | 5 | 2 | | 0 (0) | 0 (0) | |
| Tumor type | | | | | | |
| Flat/Polypoid | | | | | | |
| Depressed | | | | | | |
| Histology (Differentiation) | | | 0.117 | | | 0.579 |
| Well/Moderate | 53 (100) | 6 (86) | | 104 (96) | 19 (95) | |
| Poor | 0 (0) | 1 (14) | | 4 (4) | 1 (5) | |
| Lymphatic invasion | | | <0.001 | | | <0.001 |
| Negative | 51 (96) | 0 (0) | | 99 (92) | 10 (50) | |
| Positive | 2 (4) | 7 (100) | | 9 (8) | 10 (50) | |
| Venous invasion | | | 0.338 | | | 0.224 |
| Negative | 42 (79) | 4 (57) | | 61 (56) | 8 (40) | |
| Positive | 11 (21) | 3 (43) | | 47 (44) | 12 (60) | |
| Risk factors | | | 0.299 | | | 0.013 |
| Negative | 7 | 0 (0) | | 16 ( ) | 0 (0) | |
| Positive | 19 | 7 (100) | | 87 ( ) | 20 (100) | |
| Unavailable | 27 | 0 (0) | | 5 ( ) | 0 (0) | |
| Preoperative CEA (ng/ml) | 48 (91) | 7 (100) | 1.000 | 89 ( ) | 19 (95) | 0.302 |
| <5 | 5 (9) | 0 (0) | | 17 ( ) | 1 (5) | |
| ≥5 unavailable | 0 (0) | 0 (0) | | 2 ( | 0 (0) | |

Figure 9A:
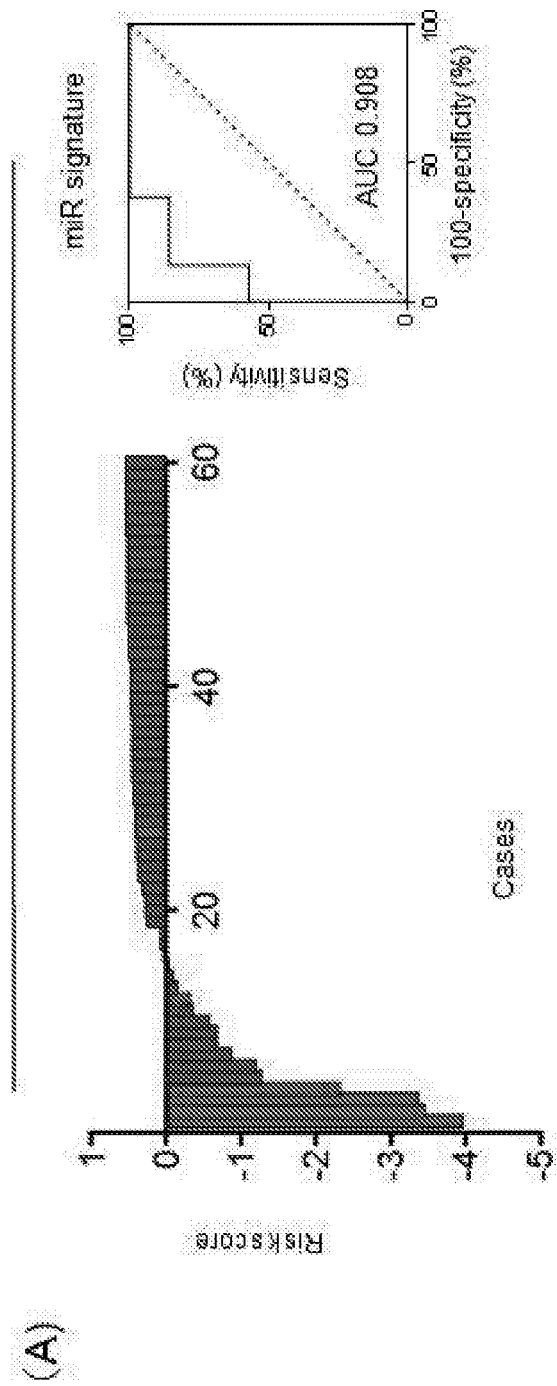
FIG. 9A-C: Analysis of miRNA expression for correlation with colorectal cancer. Shown are ROC analyses of the sensitivity/specificity of the 10-gene miRNA signature in predicting LNM in samples from the Kumamoto Univ. cohort (a; AUC=0.908) and Univ. Tokyo cohort (b; AUC=0.842). The miRNA signature was better at predicting LMN than conventional risk factors such as tumor depth, lymphatic invasion, venous invasion, and poorly histology (c; top left) or other clinical measurements such as serum CEA, CT, or tumor budding (c; top right). When combined with the conventional risk factors (tumor depth, lymphatic invasion, venous invasion, and poorly histology) using logistic regression model, this model showed better AUC value to predict LNM in T1 CRC (c; bottom left and right). These results are further discussed in Example 3.

The expression levels of each miRNA between LNM positive and negative patients are shown in FIG. 10. Consistent with the in silico analysis, the miRNA signature predicted LNM with AUC value of 0.908 (95% CI, p=), although most of the miRNAs were not statistically upregulated in LNM positive samples compared with negative samples (FIG. 9A). When combined with the conventional risk factors (lymphatic invasion, venous invasion, and poorly histology) using logistic regression model, this model showed better AUC value of 0.992 to predict LNM in T1 CRC (FIG. 9A).

4. Second Validation in Large Number of Clinical Samples from Univ. Tokyo Cohort Showed Robustness of this miRNA Signature Because Kumamoto Univ. cohort were relatively small cohort and almost all patients were classified as high risk by conventional pathological features, the inventors validated the miRNA signature in another bigger cohort which included 12.5% of risk negative and 83.6% of positive patients (3.9% were not available).

Univ. Tokyo cohort included 20 LNM positive and 108 negative patients. Tumor depth was significantly deeper and the presence of lymphatic invasion was significantly more frequent in LNM positive samples than that of negative samples (p=0.007 and <0.001, respectively). The other clinicopathological features such as poorly differentiated histology and venous invasion were not associated with LNM (p=0.579 and 0.224, respectively) (Table 1).

Figure 9B:
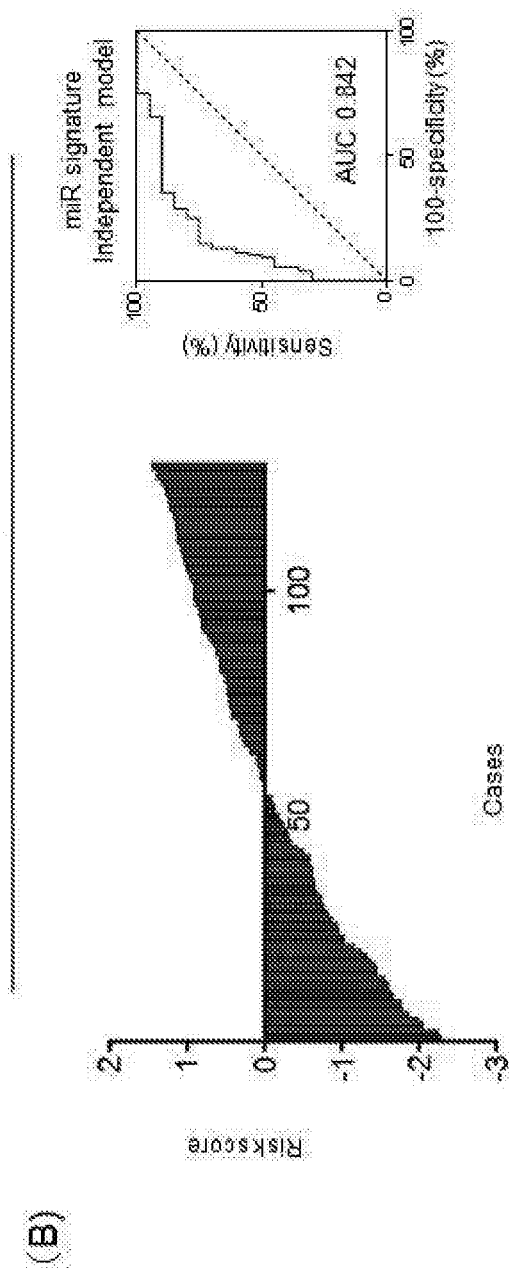
Figure 11A:
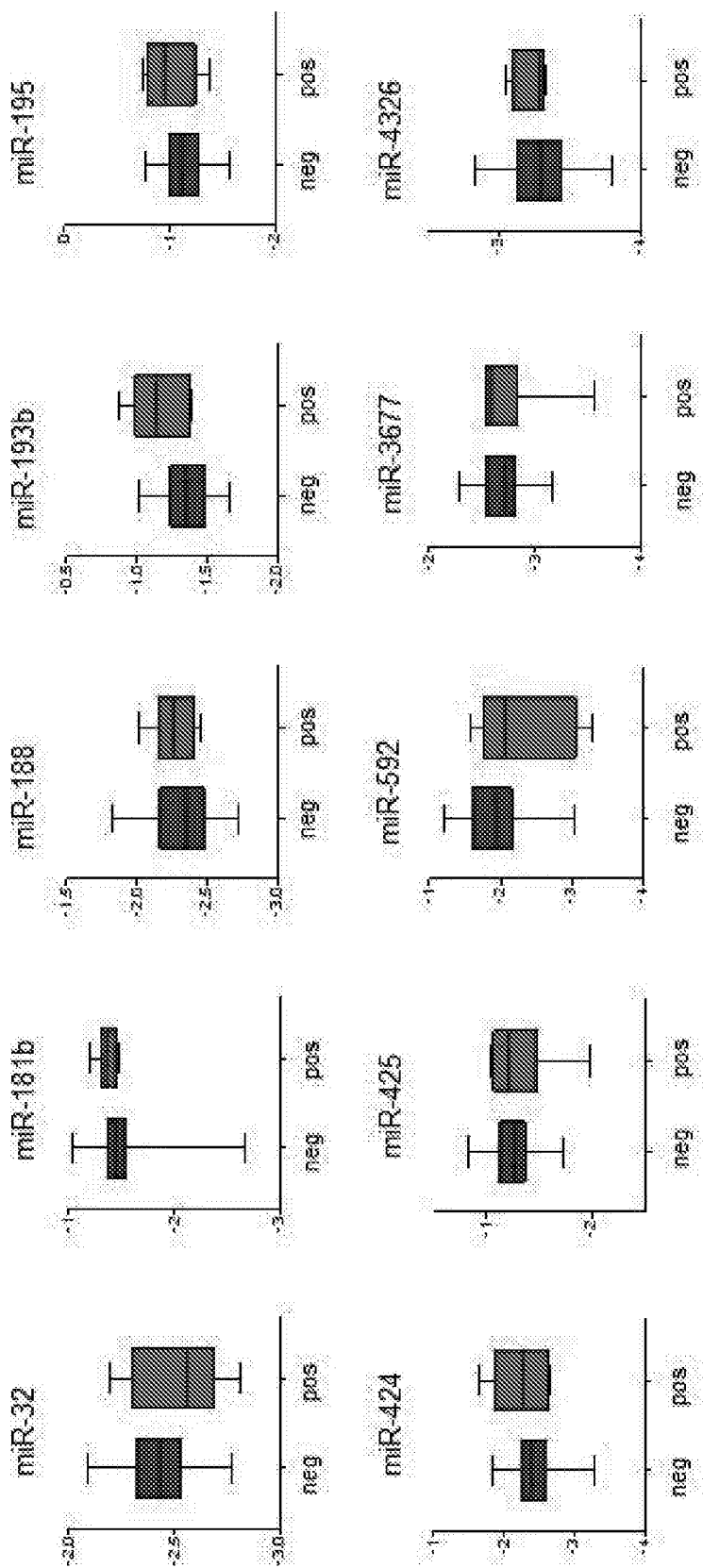
FIG. 11A-B: Kumamoto Univ. cohort. (a) Expression levels of various miRNA between LNM positive and negative samples and (b) sensitivity and specificity ROC analysis for the prediction of lymph node metastasis (LNM) of each miRNA alone from the of the Kumamoto Univ. cohort. These results are further discussed in Example 3.
Figure 11B:
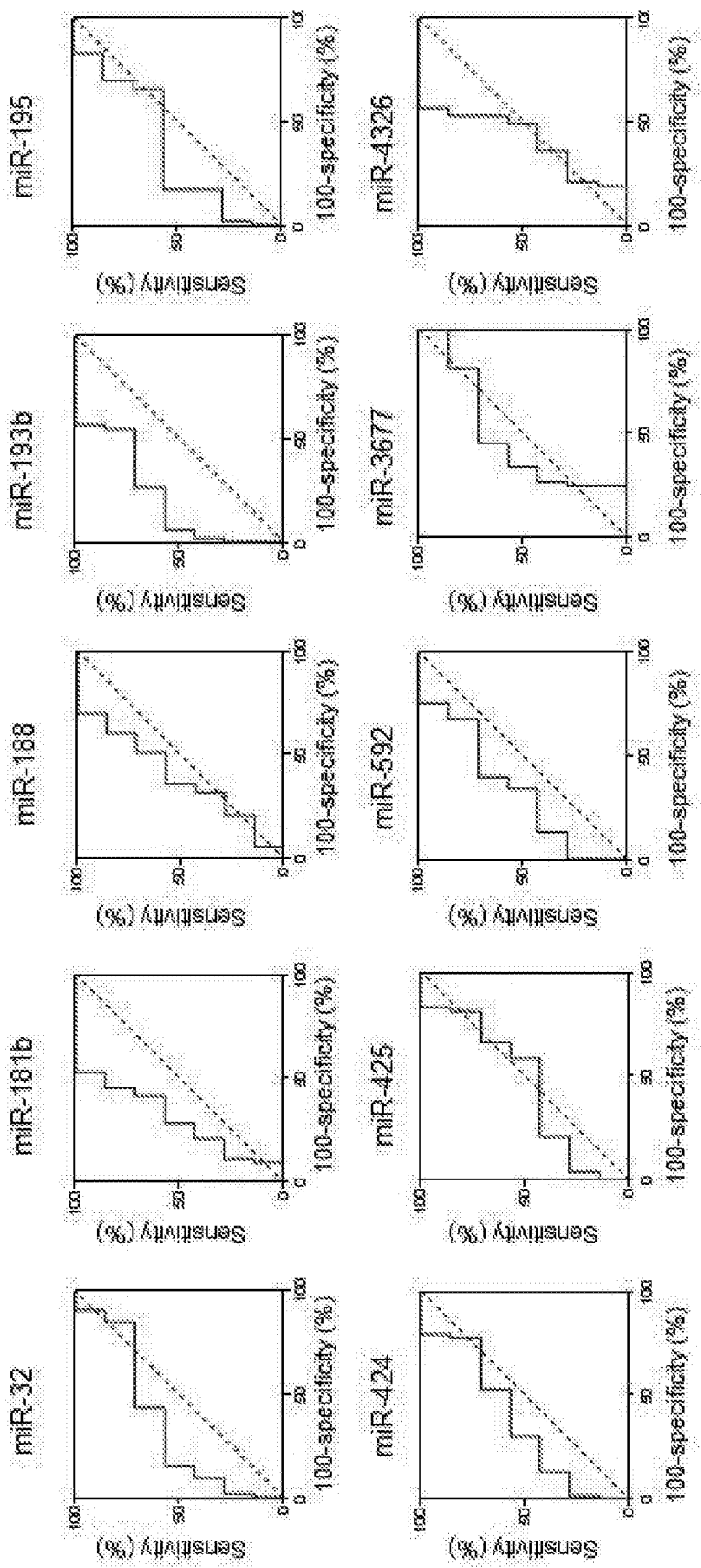
Figure 12A:
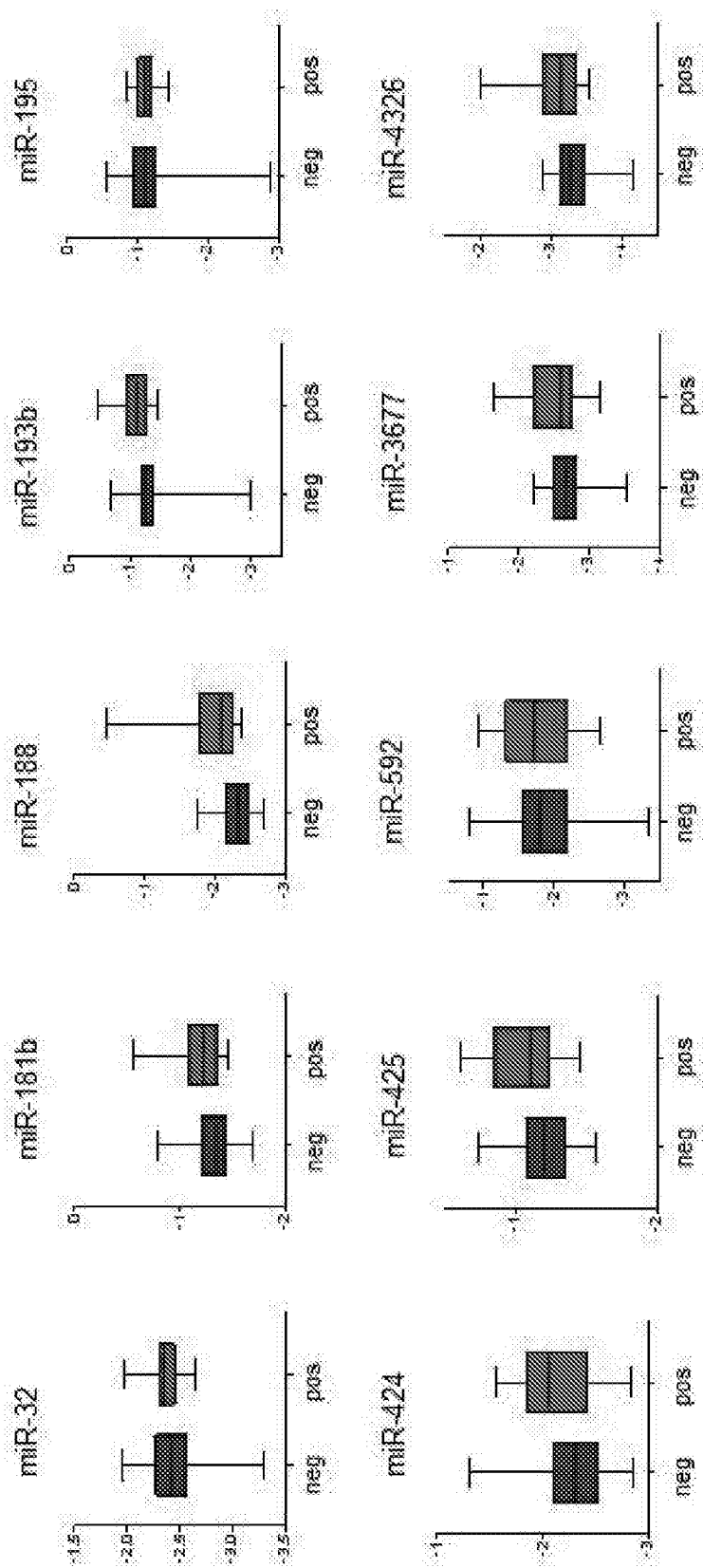
FIG. 12A-B: Univ. Tokyo cohort. (a) Expression levels of various miRNA between LNM positive and negative samples and (b) sensitivity and specificity ROC analysis for the prediction of lymph node metastasis (LNM) of each miRNA alone from the of the Univ. Tokyo cohort. These results are further discussed in Example 3.
Figure 12B:
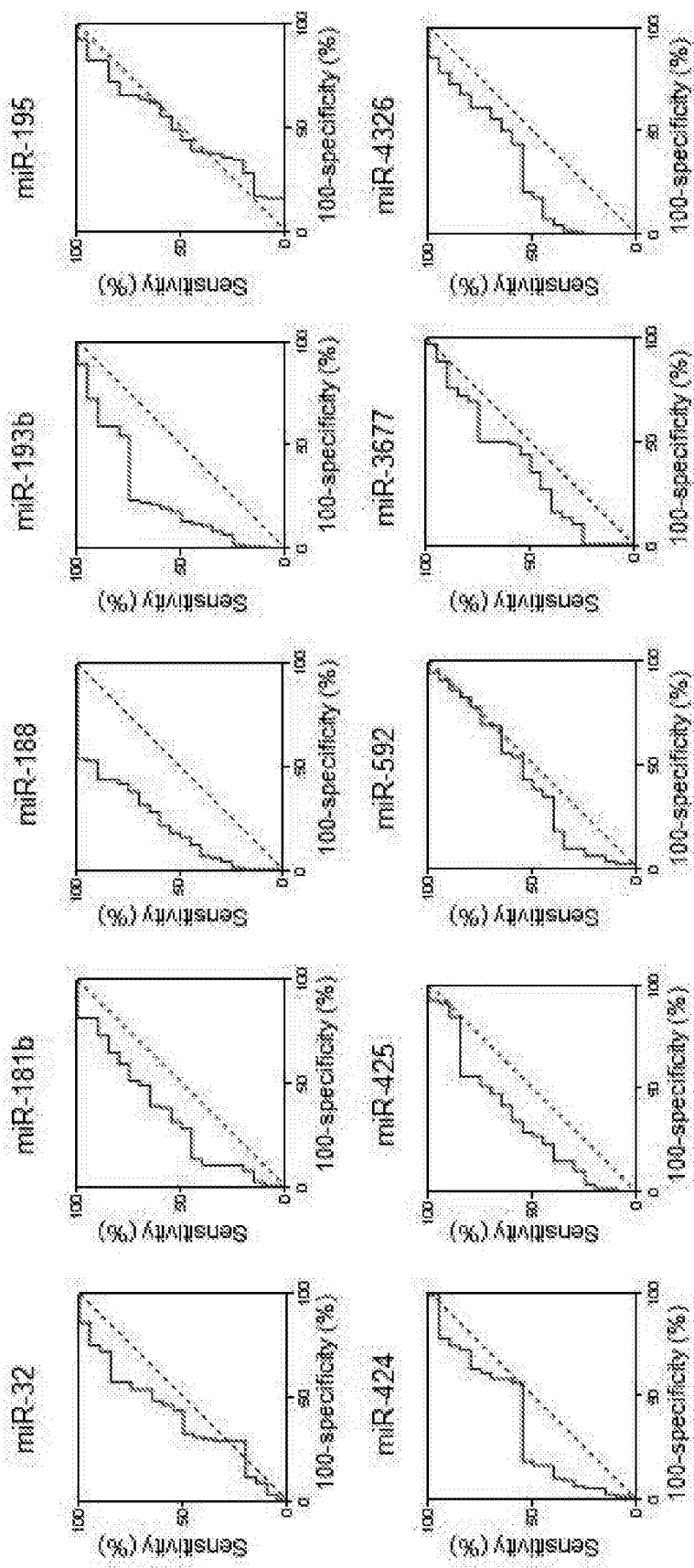
Figure 13:
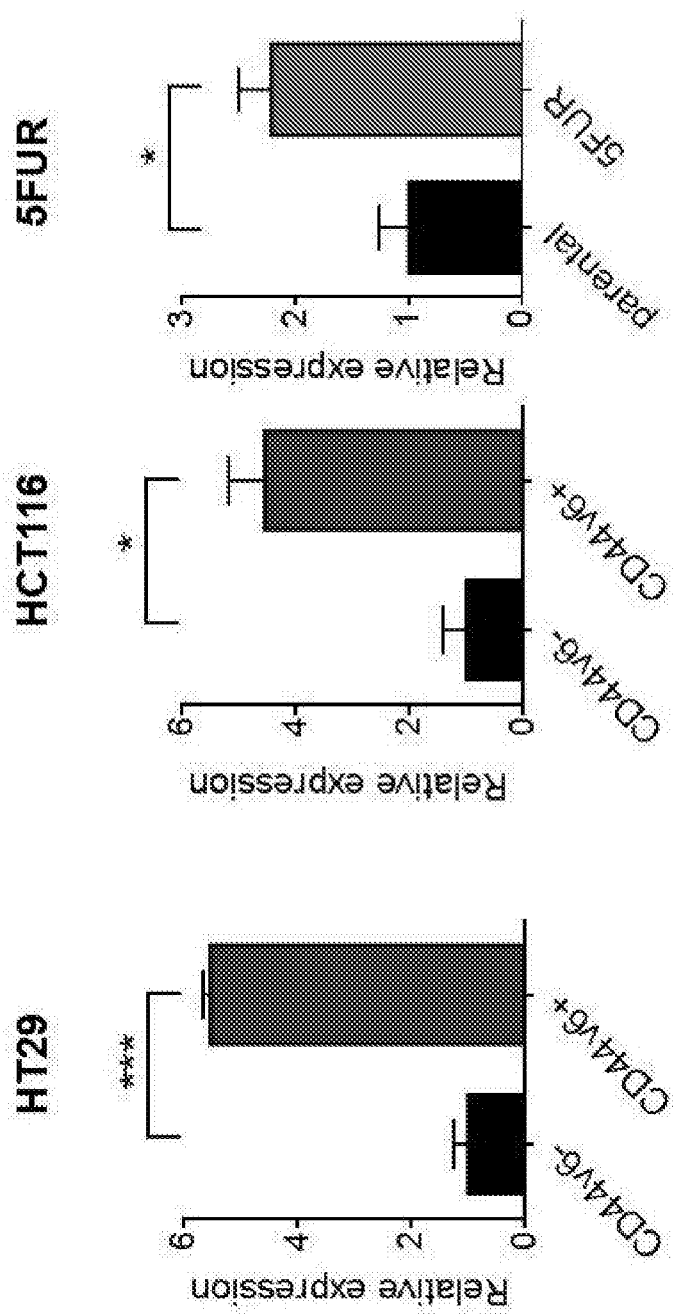
FIG. 13: Relative expression of miR-1246 in CD44v6+ colorectal cancer stem cells: HT29 (left), HCT116 (middle), and 5-FU resistant (right). These results are further discussed in Example 4.

The expression levels of each miRNA between LNM positive and negative patients are shown in FIG. 11. Consistent with the in silico analysis and that of Kumamoto Univ. cohort, the miRNA signature predicted LNM with AUC value of 0.842 (95% CI, p=) (FIG. 9B) in this large cohort as well. When combined with the conventional risk factors (tumor depth, lymphatic invasion, venous invasion, and poorly histology) using logistic regression model, this model showed better AUC value of 0.907 to predict LNM in T1 CRC (FIG. 9B).

Figure 9C:
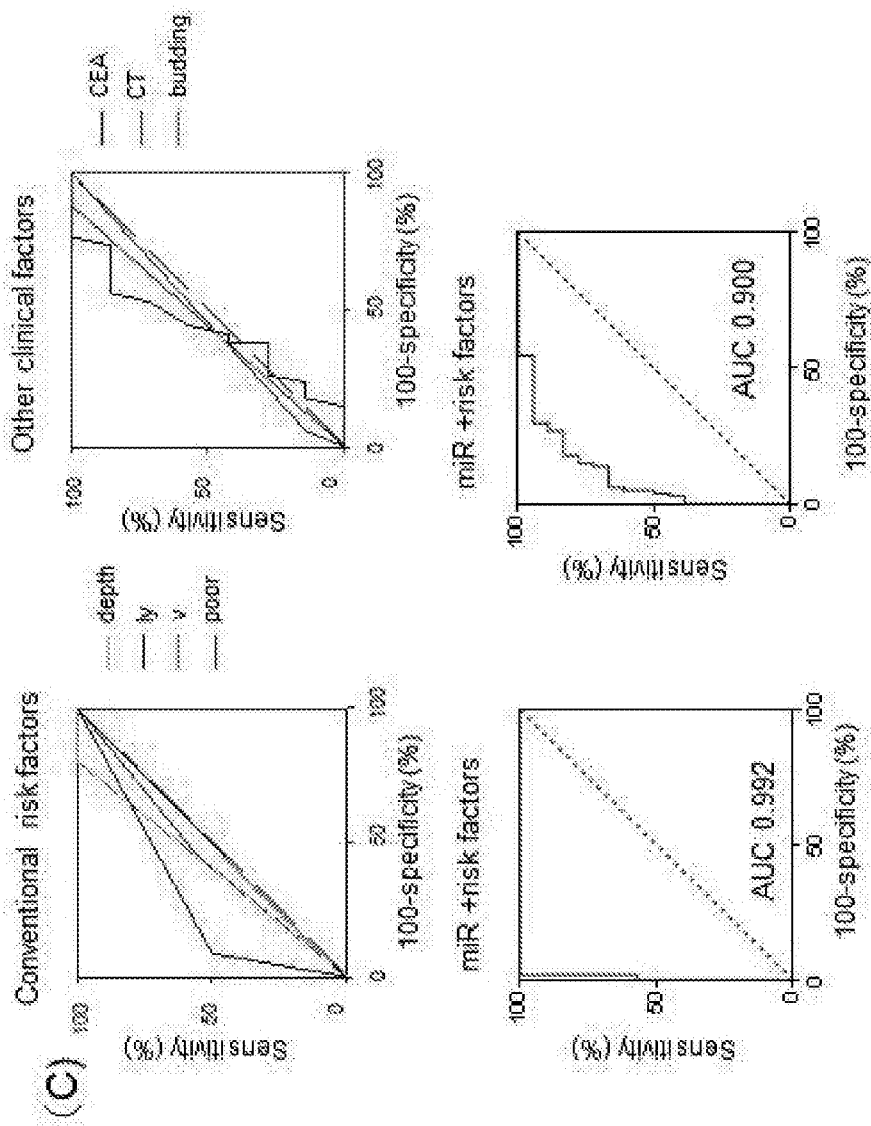

5. The Combination Model of 10 miRNA Signature with Risk Factors Improved the Prediction Power of LNM in T1 CRC The inventors further constructed LNM risk model with miRNA signature, conventional risk factors, and CT diagnosis using logistic regression model. The combination model of miRNA signature, lymphatic invasion, and CT diagnosis better predicted LNM with AUC of 0.923 (95% CI, p=) (FIG. 9C).

C. Discussion

This example demonstrations the construction of a robust miRNA signature to predict LNM in T1 CRC using comprehensive method and validated in 19 TCGA database samples and 188 of their own clinical specimens. This signature predicted LNM well with AUC of (sensitivity: and specificity: respectively).

One strength of the study described in this example was the comparison with conventional clinicopathological factors, which are the general method to predict LNM. The prediction values of conventional clinicopathological features were not sufficient, with the highest AUC being 0.70 of lymphovascular invasion (sensitivity: specificity:, respectively). This result is consistent with previous reports and highlights the deficiencies in the current methods for predicting high risk individuals. The inventors also evaluated the prediction power of preoperative CEA level, tumor budding, and CT, which are also generally evaluated in clinical practices. However, these were also insufficient, when compared to the miRNA signature described in this example. By combining miRNA signature with these clinicopathological factors using logistic regression model, the predictive power of the model increased up to AUC of 0.923 (sensitivity: specificity:).

Additionally, this example demonstrates, for the first time, the prediction power of the miRNA signature in the biopsy samples. Predicting LNM in biopsy samples would allow one to omit endoscopic treatment for the patients with high risk for LNM stratified by the miRNA signature, and this may eventually reduce the risk of endoscopic resection such as perforation or bleeding, physician's burden, and medical cost.

Example 4—Identification of a Novel Network of miRNAs that Regulate Stemness in Colorectal Cancer Accumulating evidence suggests that a subset of cancer cells also known as the "cancer stem cells" (CSCs) influence various clinical outcomes in cancer, including tumor recurrence, metastasis and resistance to chemotherapy. Recently stemness has been recognized as a dynamic state governed by epigenetic modifiers including miRNAs. Despite identification of several self-renewal associated miRNAs, their expression profiles in CSCs remain unclear. In this example, the inventors systematically characterized miRNA expression patterns in CSCs with high vs. low CD44v6 expression through RNA-Seq. Subsequently, the inventors investigated the clinical significance of a novel miRNA identified from this systematic discovery approach.

Colorectal CSCs from HCT116 and HT29 cells were grown as spheroid-derived cancer stem cells (SDCSCs). CD44v6$^+$ and CD44v6$^-$ CSCs were subdivided by FACS and characterized by small RNA-Seq. Differentially expressed miRNAs were subsequently confirmed in CD44v6$^+$ CSCs and chemoresistant cells. The expression of one such candidate, miR-1246, was assessed in a clinical patient cohort (n=144) by qRT-PCR.

Figure 14:
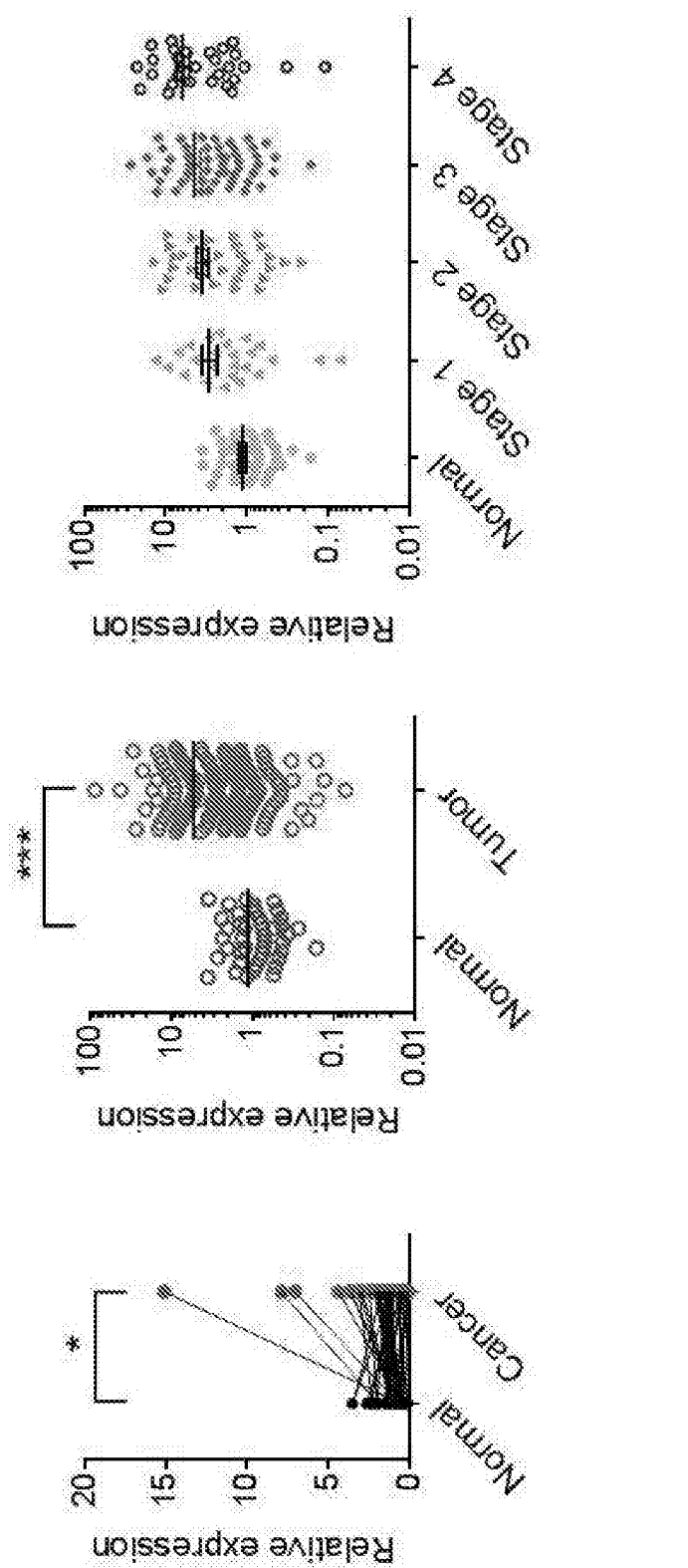
FIG. 14: The expression of miR-1246 was significantly elevated in CRC tissues compared to corresponding normal mucosa (left and middle), and this occurred in a stage-dependent manner in primary CRCs (right). These results are further discussed in Example 4.
Figure 15C:
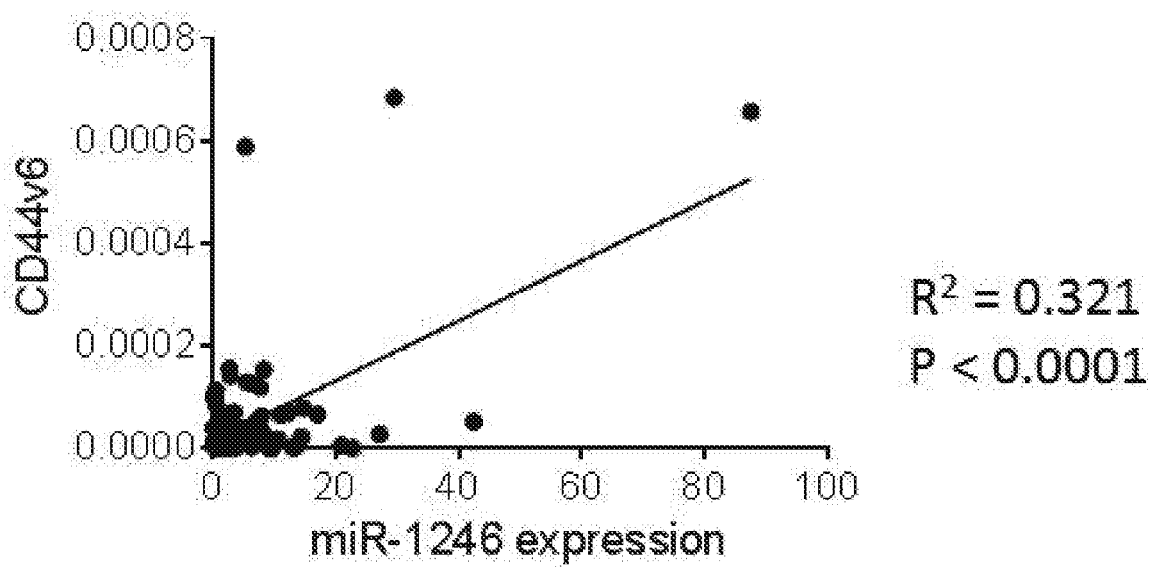

MiRNA profiling identified a unique overall pattern of CD44v6$^+$ SDCSCs indicative of high self-renewal capacity. It was noted that a panel of established self-renewal suppressive-miRNAs were downregulated (including miR-34a, 101 and 200 family) in CD44v6$^+$ CSCs, and discovered upregulation of previously unreported miRNAs (miR-1246, 3605, 3182 and 4284). KEGG pathway analysis indicated that these miRNAs regulate Akt-MAPK and Wnt signaling pathways. Subsequently, the inventors selected miR-1246 and validated its expression in CD44v6$^+$ SDCSCs and chemoresistant cells. Clinically, the expression of miR-1246 was significantly elevated in CRC tissues compared to corresponding normal mucosa, and this occurred in a stage-dependent manner in primary CRCs (FIG. 14). Furthermore, the expression of CD44v6 positively correlated with miR-1246 in CRC tissues (FIG. 15C). High miR-1246 expression resulted in poor overall and disease free survival (FIG. 15A-B).

Using a systematic and comprehensive approach, the inventors have identified a unique network of dysregulated miRNAs in CD44v6 CSCs indicative of high degree of stemness features in cancer. In particular, miR-1246 was identified to be frequently over-expressed in CSCs as well as chemoresistant cells and its expression was associated with poor prognosis in CRC patients. Collectively, the inventors have identified a unique group of previously unreported miRNAs which appear to have important mechanistic roles in CSCs and could serve as a promising predictive biomarkers for recurrence and prognosis in patients with CRC.

Example 5—Genome-Wide Analysis Revealed a Robust Gene Expression Signature to Identify Lymph Node Metastasis in Submucosal Colorectal Cancer Due to recent advances in colonoscopic techniques, submucosal colorectal cancers (T1 CRCs) can now be removed endoscopically. Among these, 70% of T1 CRCs are considered as "high risk" because they demonstrate presence of lymphovascular invasion, poor differentiation, and the depth of tumor is >1000 um. However, post-surgical pathology results suggest that only ~10-15% of all T1 CRCs are truly lymph node positive, while majority of high risk patients undergo unnecessary surgical treatments with current criteria. Since current pathological criteria have limitations, availability of molecular biomarkers that can identify 'genuine high risk patients with lymph node (LN) metastasis' will reduce the burden of surgical overtreatment. Since gene expression-based classification of CRC could identify patients with poor prognosis, the inventors sought to identify a gene expression signature which can detect T1 CRCs with LN metastasis.

Two independent publicly available genome-wide mRNA expression datasets were used for mRNA biomarker discovery (n=125) and in-silico validation (n=56). Genome-wide unbiased gene expression signature was developed from The Cancer Genome Atlas (TCGA) RNA-Seq data by comparing the expression profiles between 16 LN-positive and 109 LN-negative T½ CRC patients. In addition to the selection of most differentially expressed genes between the two groups, the inventors used (ROC) based back-step elimination methodology to identify a robust mRNA panel. The gene panel was validated in an independent publicly available dataset (n=56), followed by analytical validation in two independent T1 CRC patient cohorts (n=134 and n=67) using RT-PCR assays.

The in silico genome-wide comprehensive discovery led to the identification of an eight gene mRNA classifier that significantly predicted LN-metastasis with an AUC of 1.0, and the subsequent validation in an independent public data set resulted in an AUC of 0.93. The 8 genes include: AMT2 over-expression, MMP9 under-expression, FOXA1 under-expression, C2CD4A under-expression, RCC1 under-expression, LYZ under-expression, MMP1 over-expression, and PIGR under-expression. The RT-PCR based training and validation of this eight gene classifier in two independent clinical cohorts robustly identified LN metastasis-positive T1 CRC patients with an AUC of 0.90 (FIG. 16) and 0.89 (FIG. 19), respectively.

Figure 16:
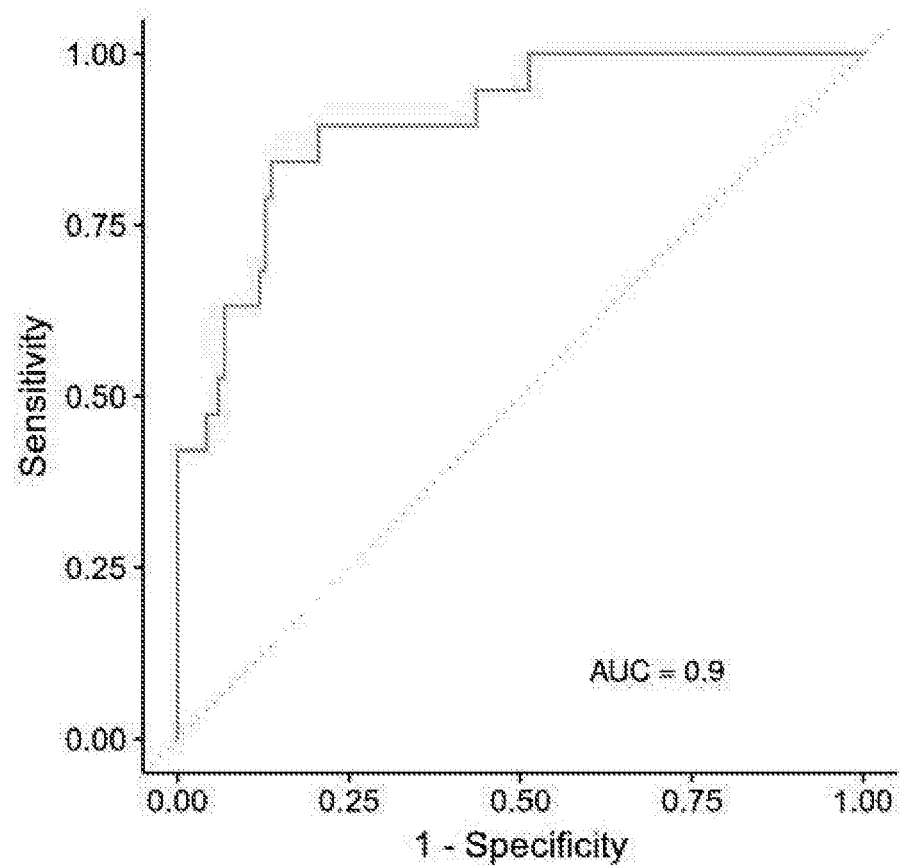
FIG. 16: Tokyo clinical cohort 1: ROC analysis. 19 LN positive and 117 LN negative samples were in the cohort. The analysis yielded an AUC value of 0.9. This analysis is further described in Example 5.
Figure 17:
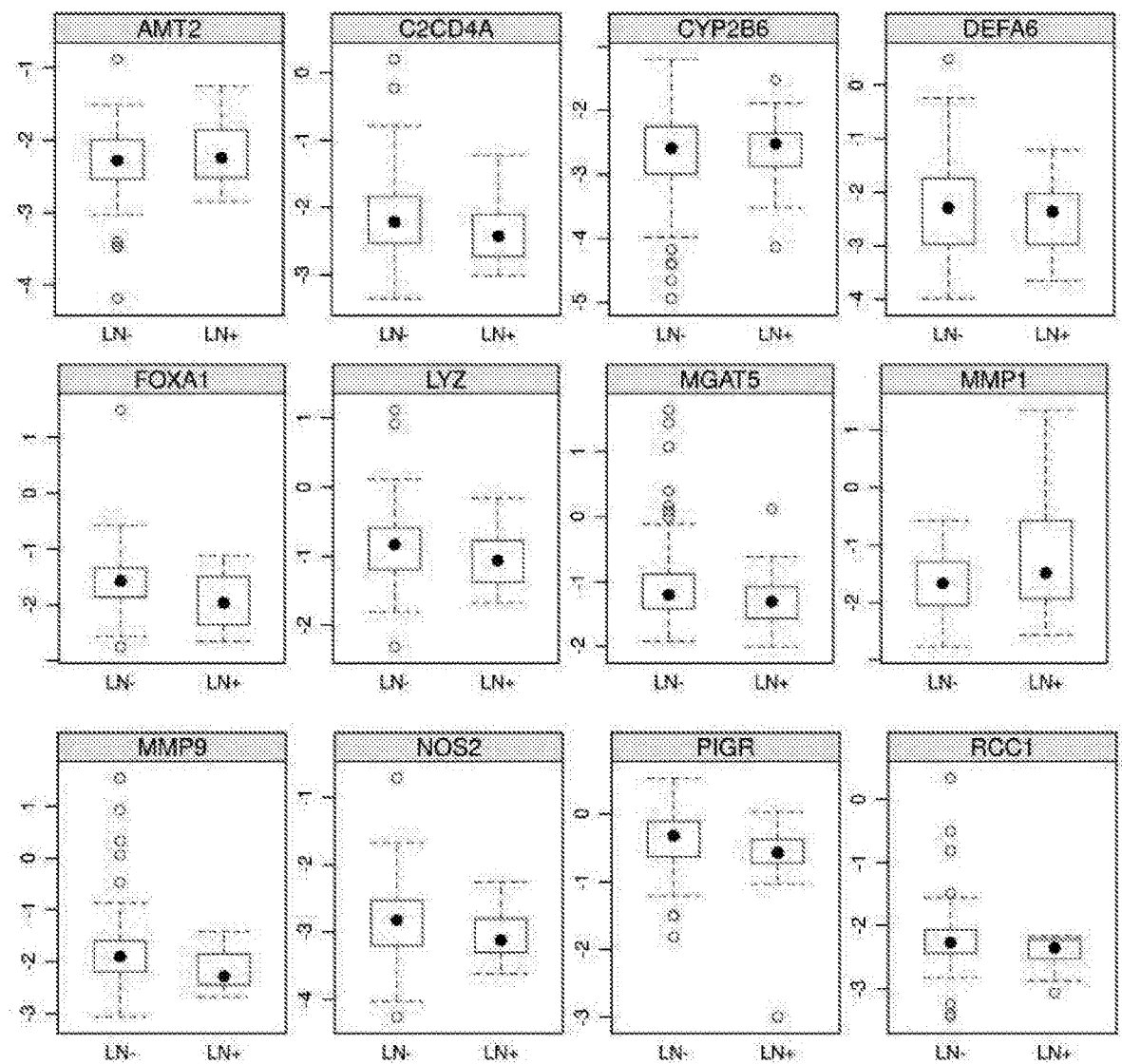
FIG. 17: Tokyo clinical cohort 1: Boxplots of mRNA normalized expression in lymph node negative (LN−) and lymph node positive (LN+) samples. This analysis is further described in Example 5.
Figure 18A:
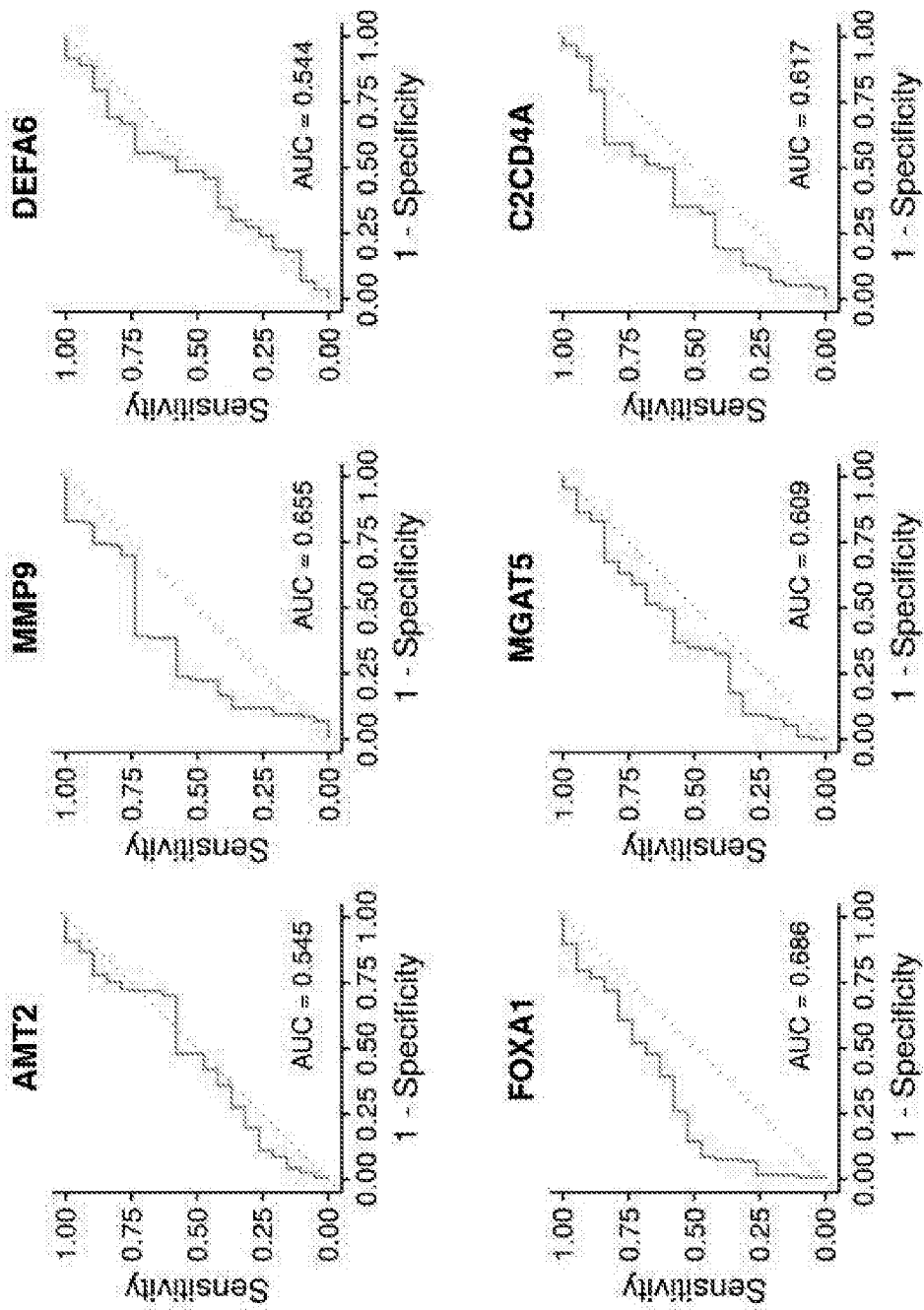
FIG. 18A-B: Tokyo clinical cohort 1: ROC curves for individual mRNAs. This analysis is further described in Example 5.
Figure 18B:
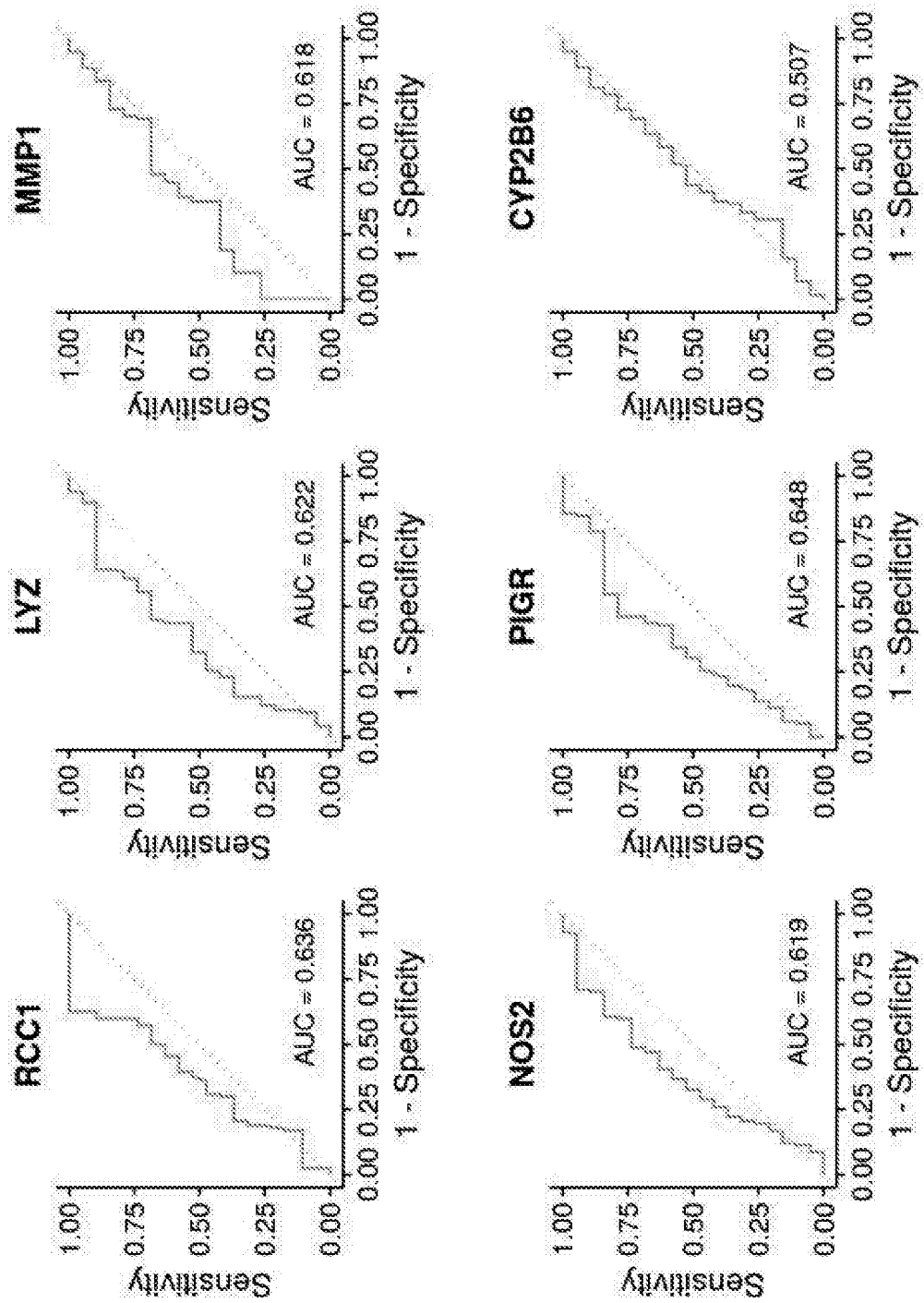
Figure 19:
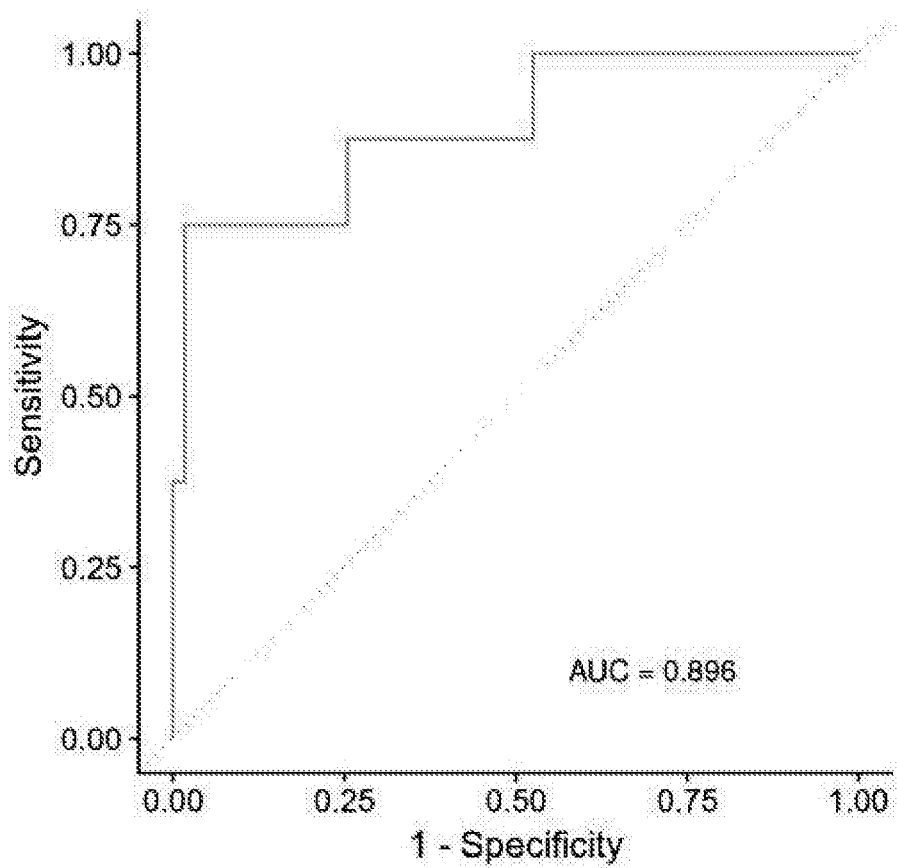
FIG. 19: Kumamoto clinical cohort 2: ROC analysis. 8 LN positive and 59 LN negative samples were in the cohort. The analysis yielded an AUC value of 0.896. This analysis is further described in Example 5.
Figure 20:
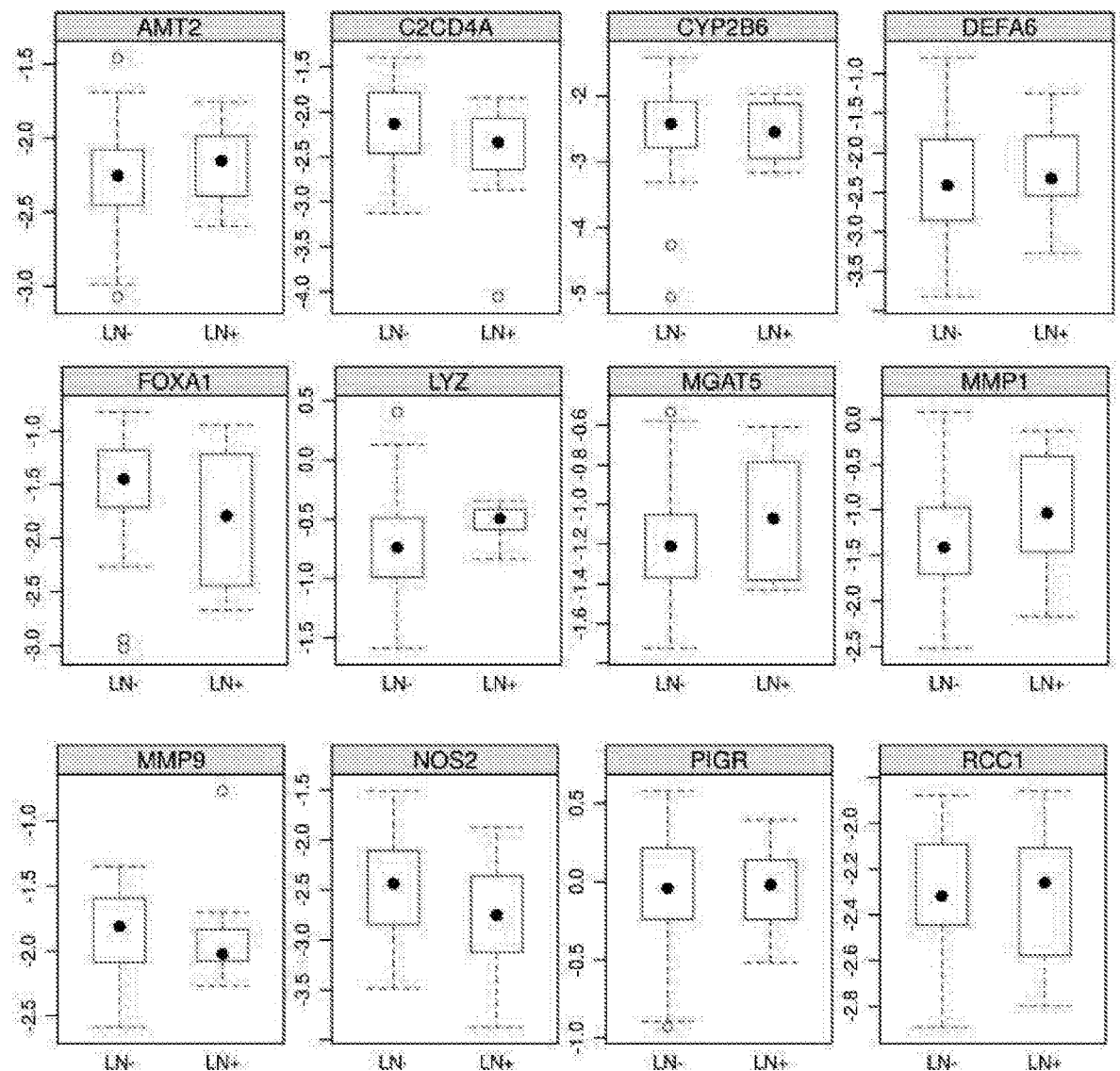
FIG. 20: Kumamoto clinical cohort 2: Boxplots of mRNA normalized expression in lymph node negative (LN−) and lymph node positive (LN+) samples. This analysis is further described in Example 5.
Figure 21A:
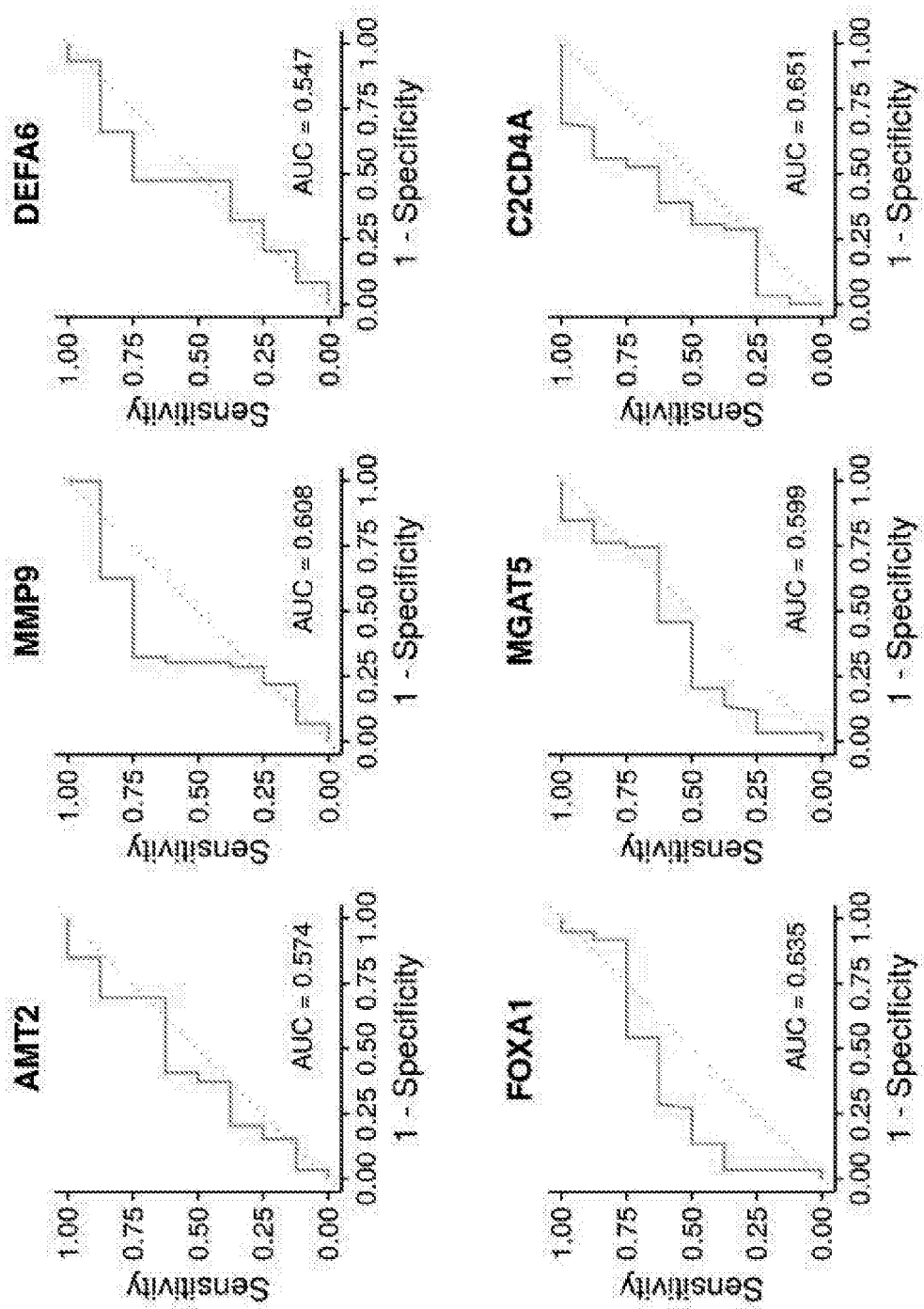
FIG. 21A-B: Kumamoto clinical cohort 2: ROC curves for individual mRNAs. This analysis is further described in Example 5.
Figure 21B:
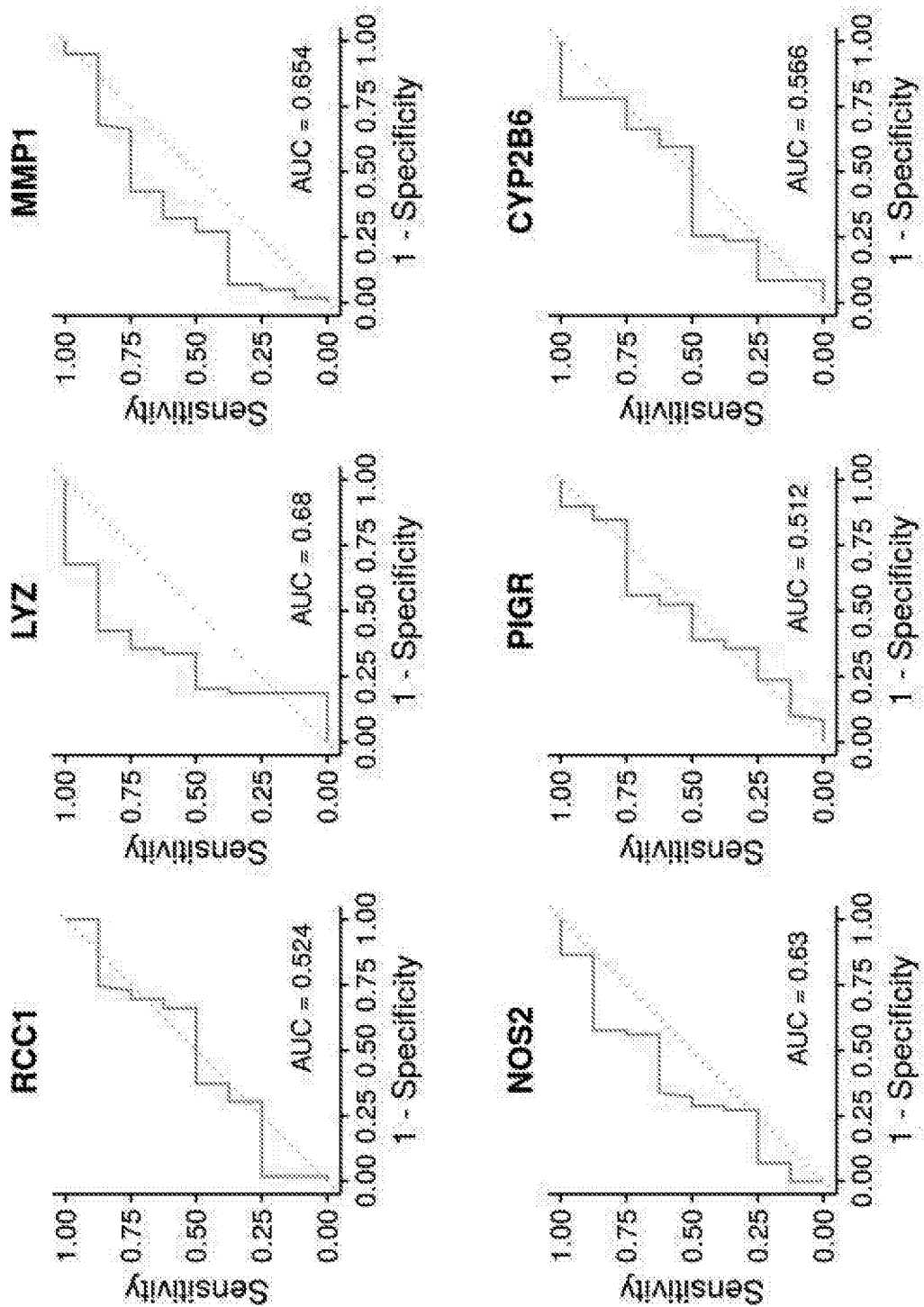
Figure 22:
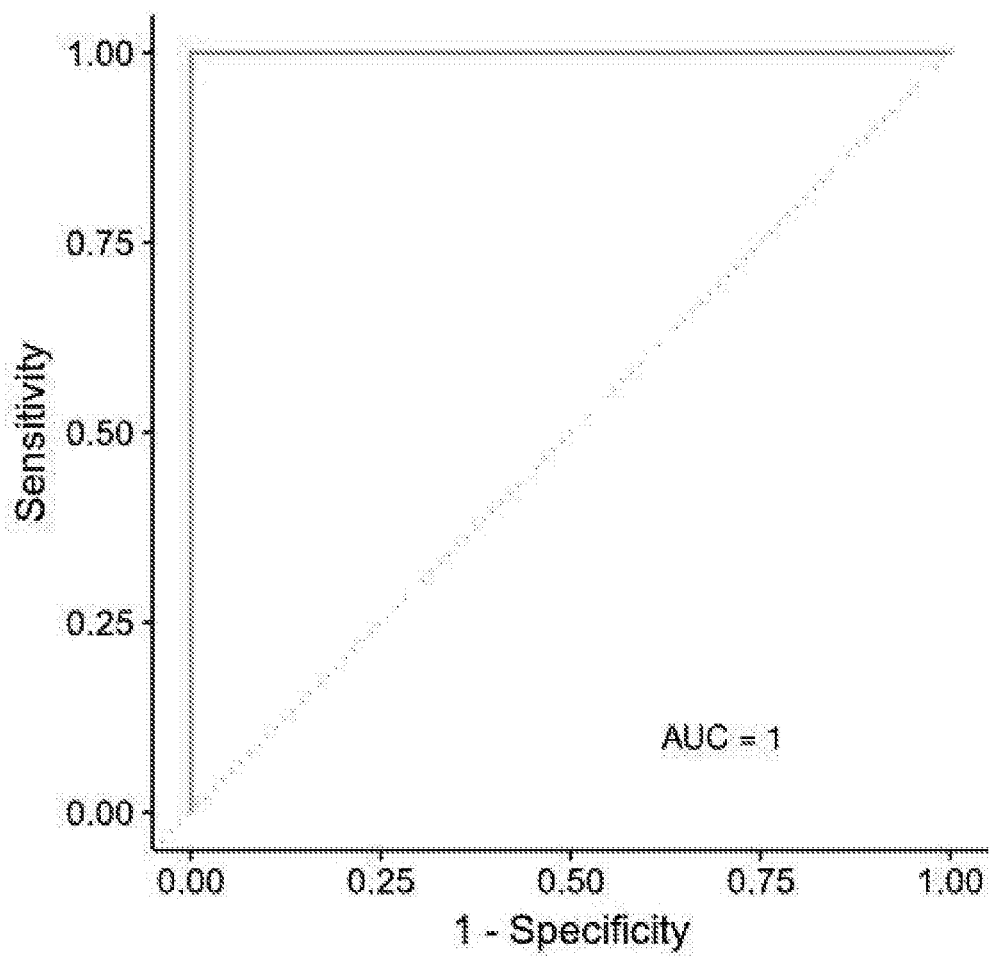
FIG. 22: TMDU clinical cohort 3: ROC analysis. 4 LN positive and 35 LN negative samples were in the cohort. The analysis yielded an AUC value of 1.0. This analysis is further described in Example 5.
Figure 23:
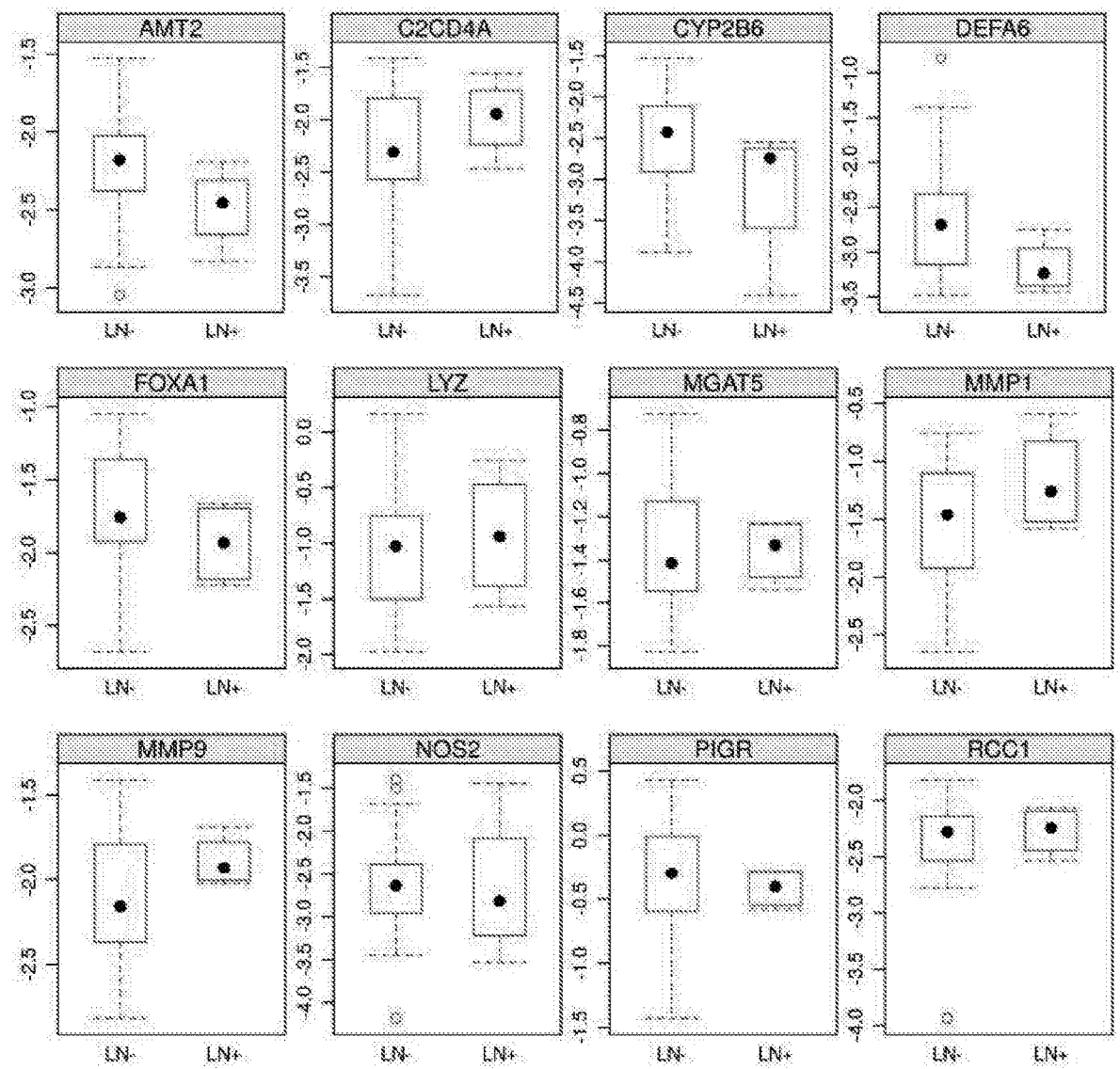
FIG. 23: TMDU clinical cohort 3: Boxplots of mRNA normalized expression in lymph node negative (LN−) and lymph node positive (LN+) samples. This analysis is further described in Example 5.
Figure 24A:
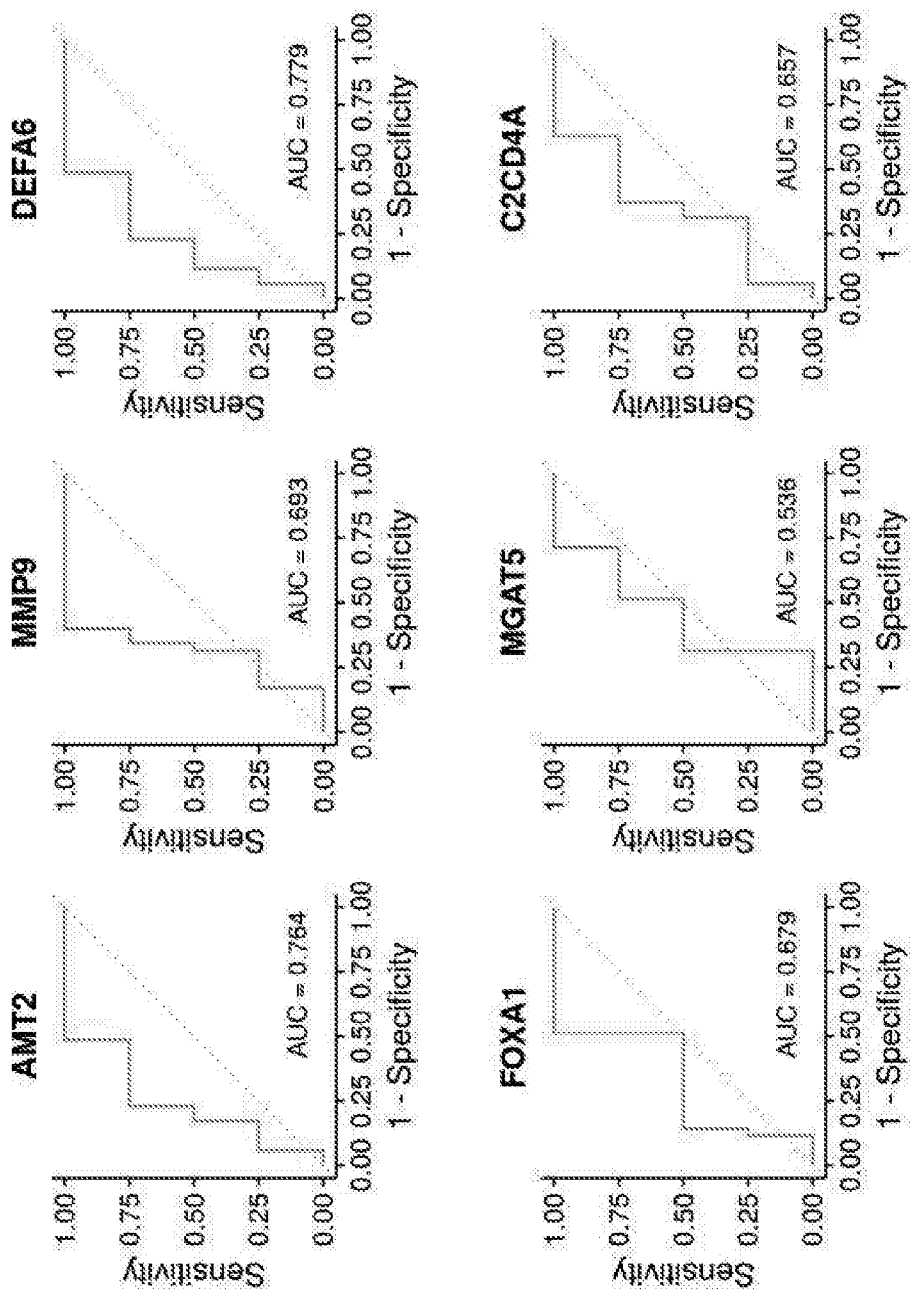
FIG. 24A-B: TMDU clinical cohort 3: ROC curves for individual mRNAs. This analysis is further described in Example 5.
Figure 24B:
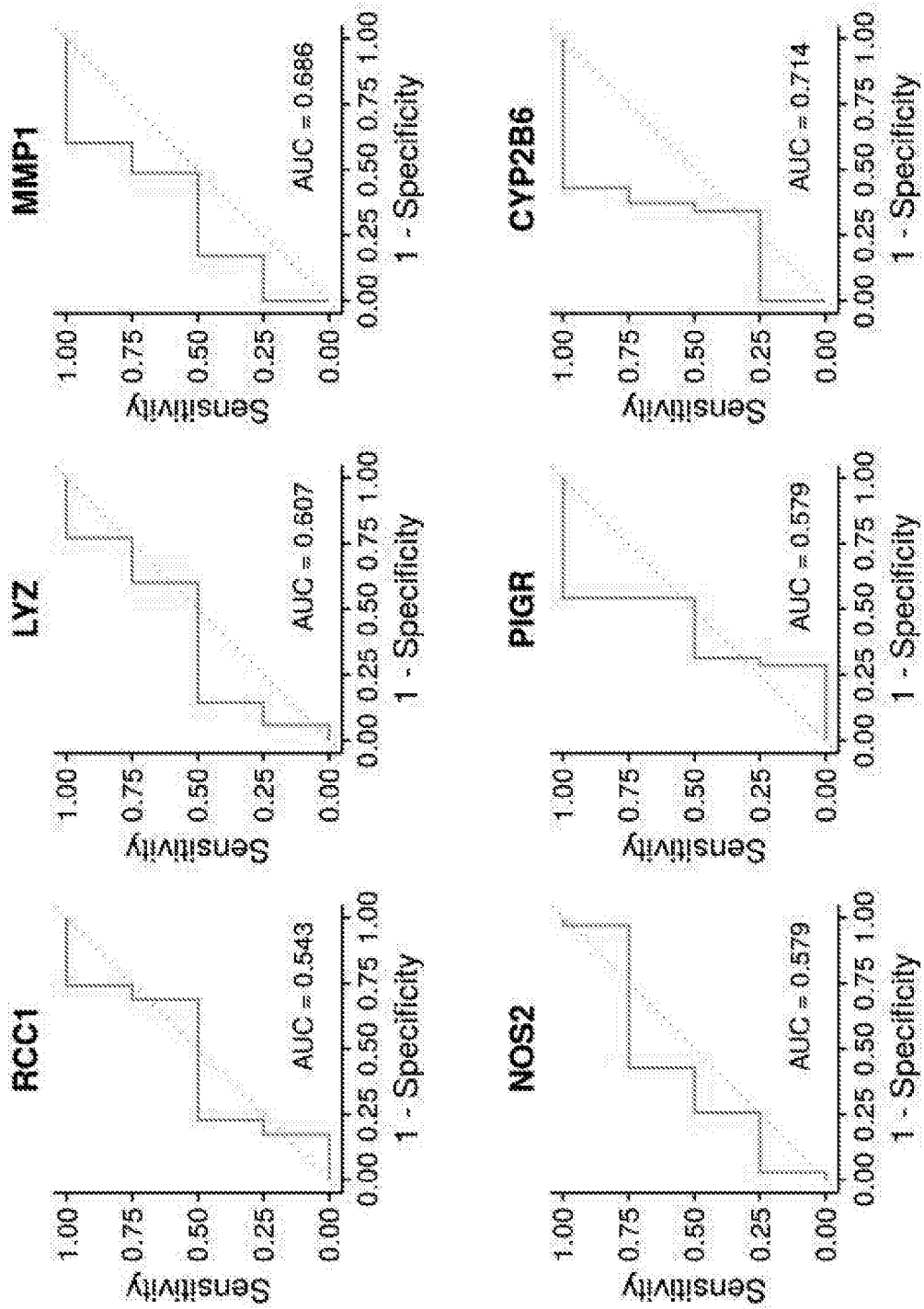

A similar analysis was done for a 12 gene classifier that included AMT2 over-expression, MMP9 under-expression, DEFA6 under-expression, FOXA1 under-expression, MGAT5 under-expression, C2CD4A under-expression, RCC1 under-expression, LYZ under-expression, MMP1 over-expression, NOS2 under-expression, PIGR under-expression, CYP2B6 over-expression. The validation was done in three separate cohorts (Tokyo, Kumamoto, and TMDU). The AUC values for these three cohorts were 0.9, 0.896, and 1.0, respectively. This analysis is shown in FIGS. 16, 19, and 22.

Figure 25A:
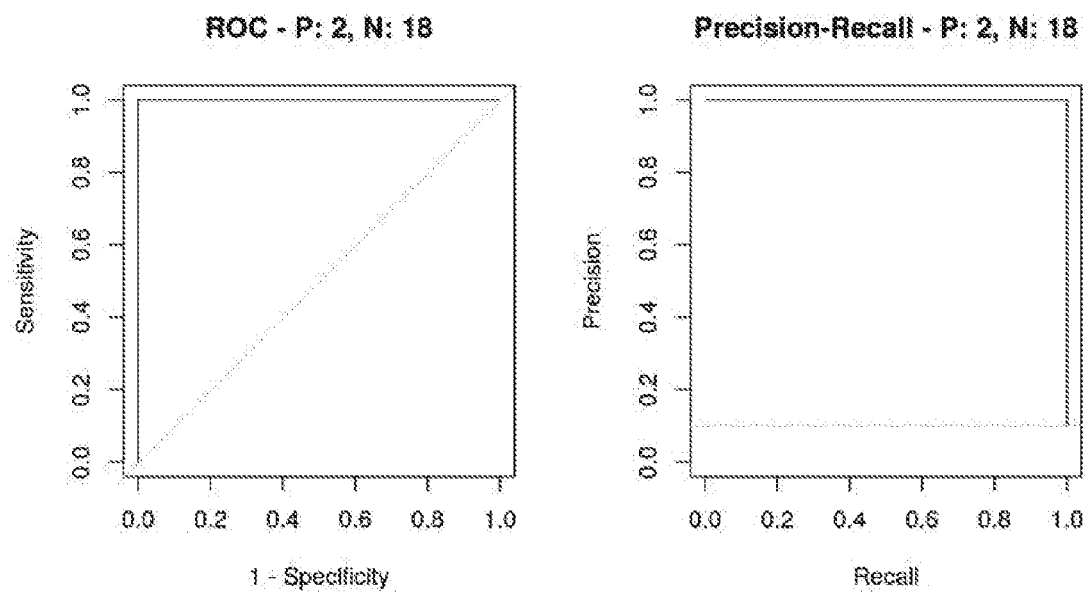
FIG. 25A-B: Validation on TCGA; ROC curves for cohort with (a) T1 CRC patients (2 LN+, 8 LN−); AUC=1.0 (ROC), 1.0 (Precision) and (b) T1 and T2 CRC patients (16 LN+, 109 LN−); AUC=0.95 (ROC), 0.85 (precision) using 16 gene classifier described in Example 5.
Figure 25B:
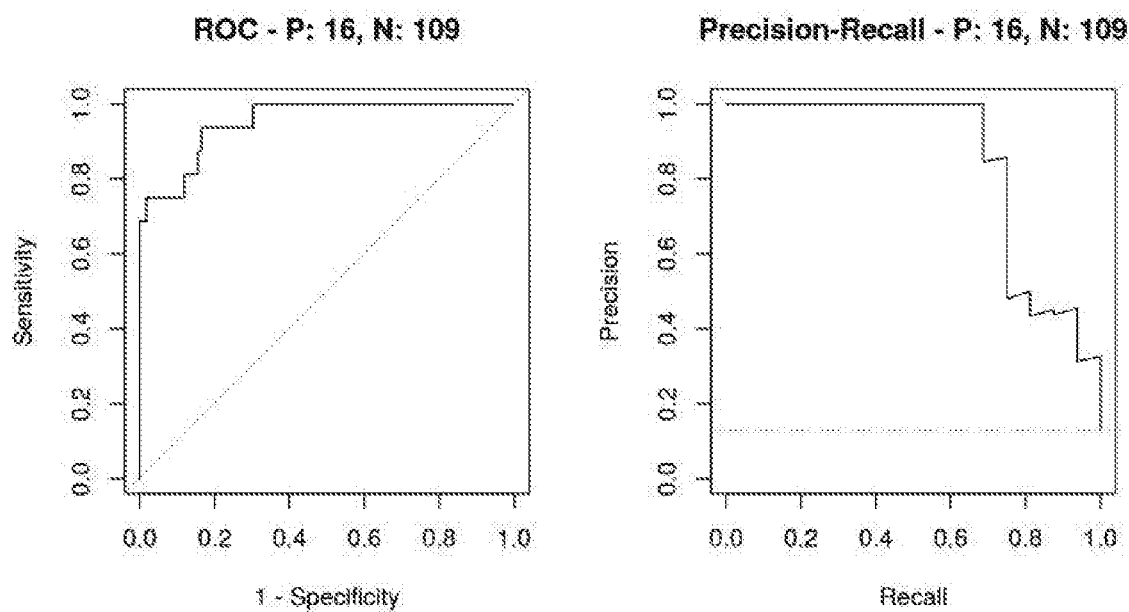
Figure 26A:
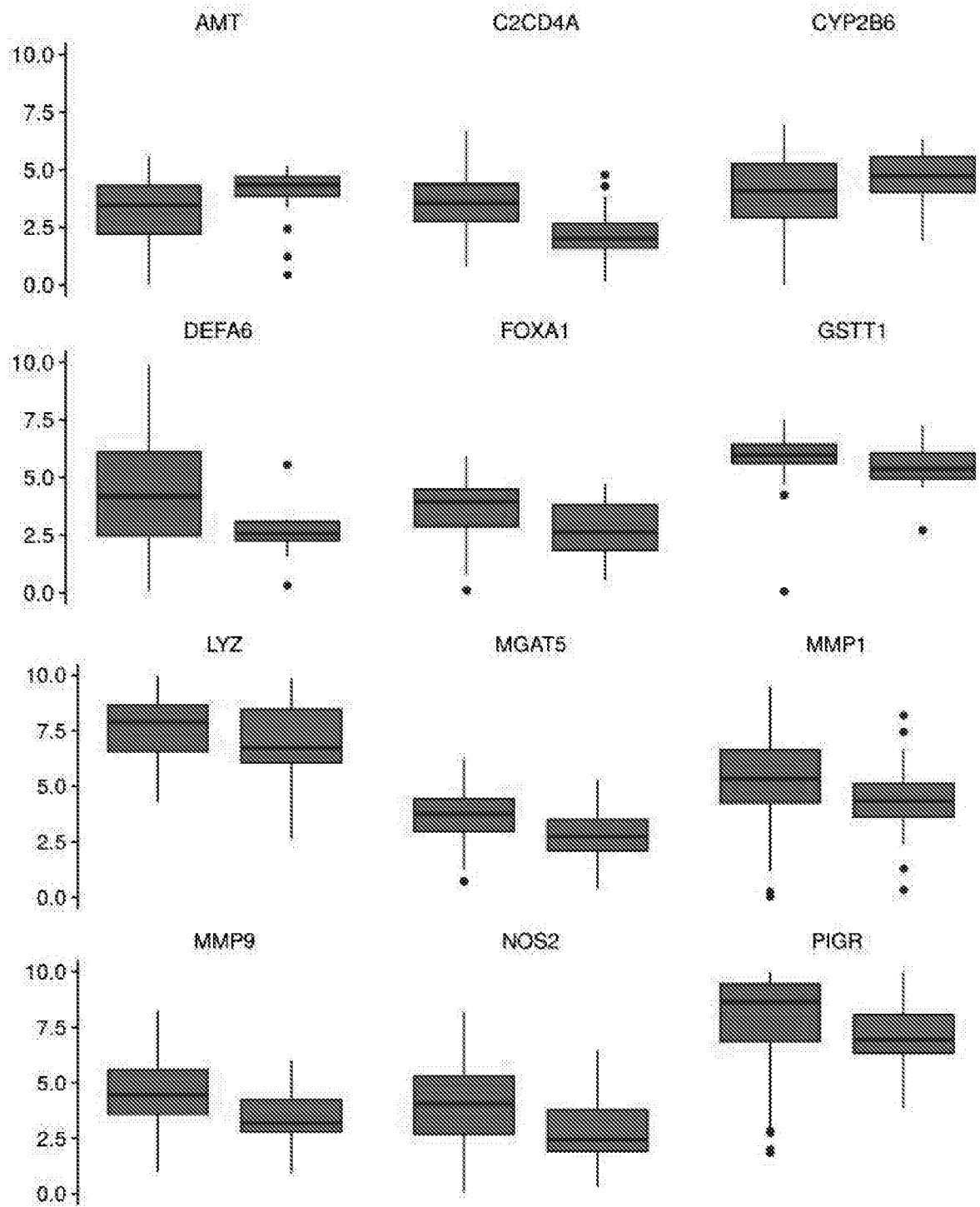
FIG. 26A-B: Boxplots of expression of indicated mRNA of LM− (left box of each graph) and LM+ (right box of each graph) samples of the 16 genes in the 16 gene classifier described in Example 5.
Figure 26B:
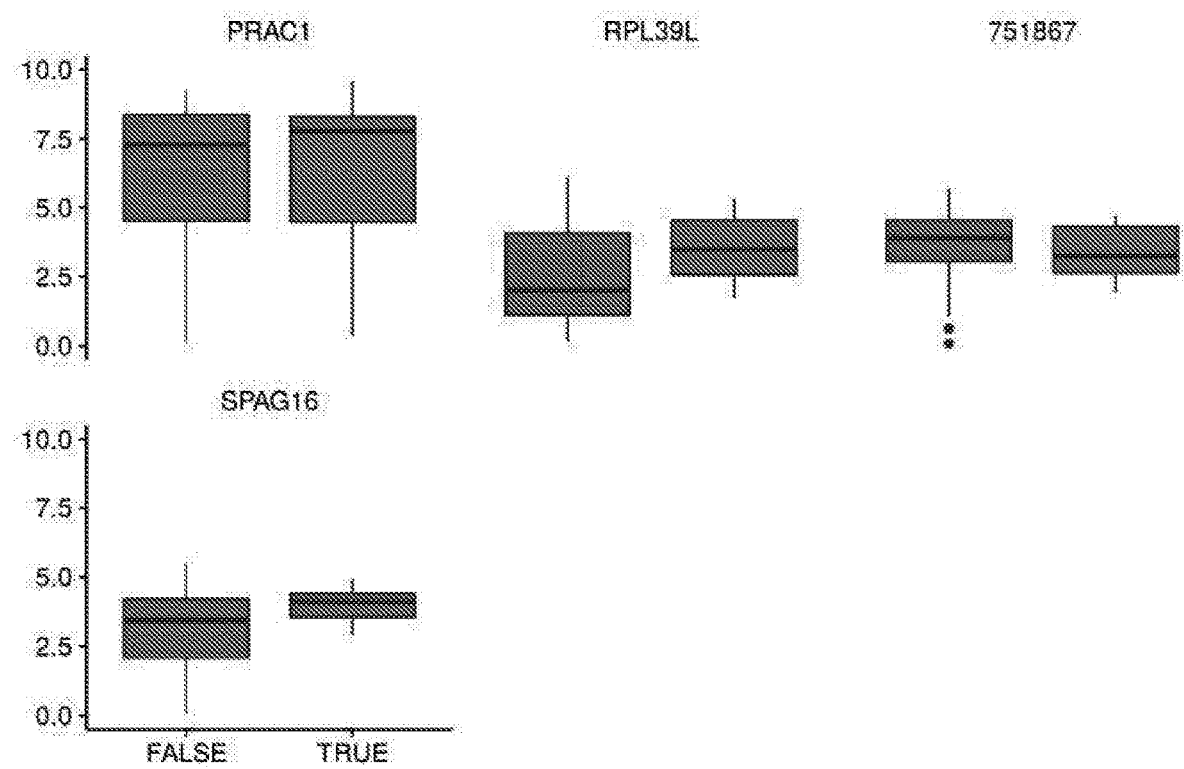
Figure 27A:
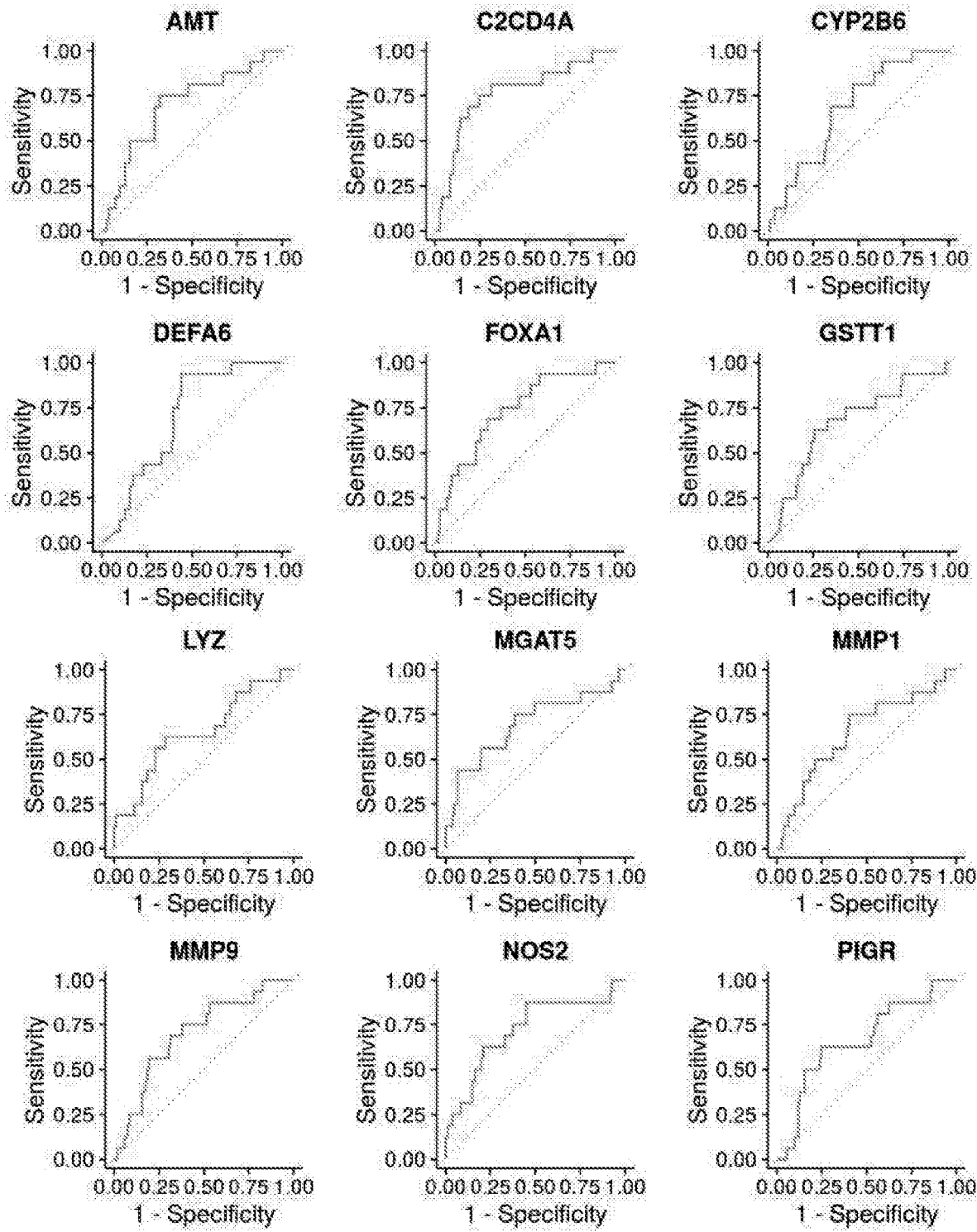
FIG. 27A-B: ROC analysis of each mRNA alone of the 16-gene classifier described in Example 5.
Figure 27B:
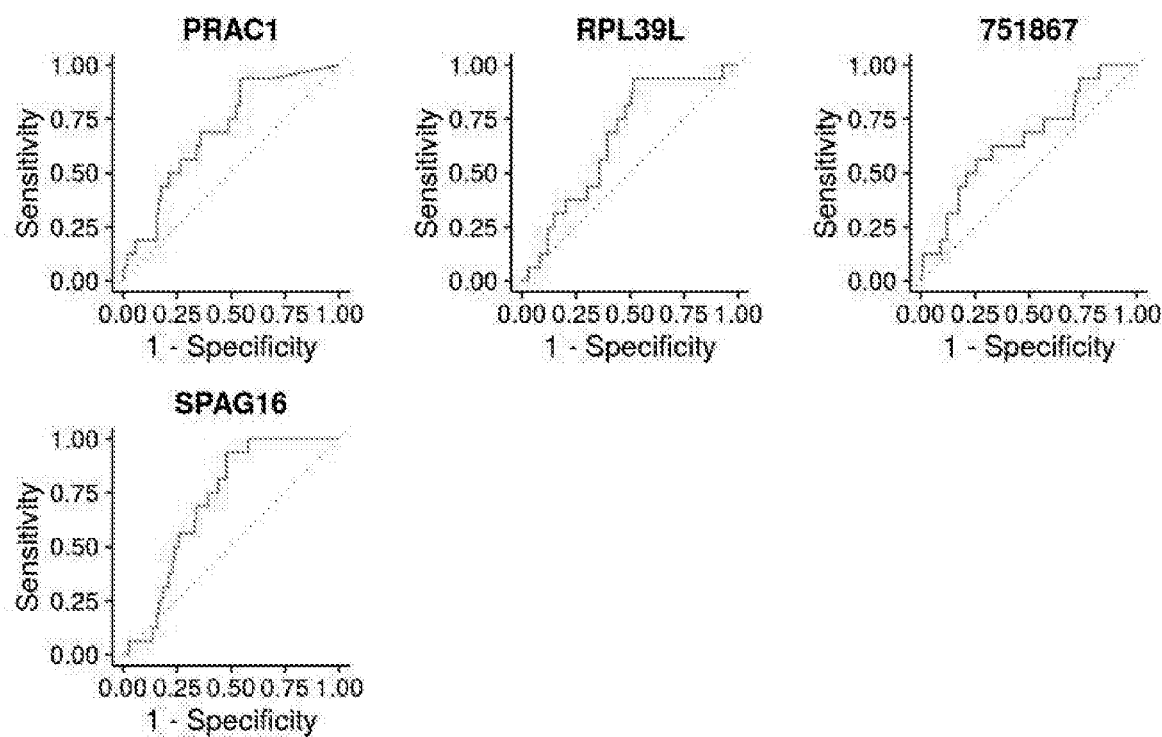
Figure 28A:
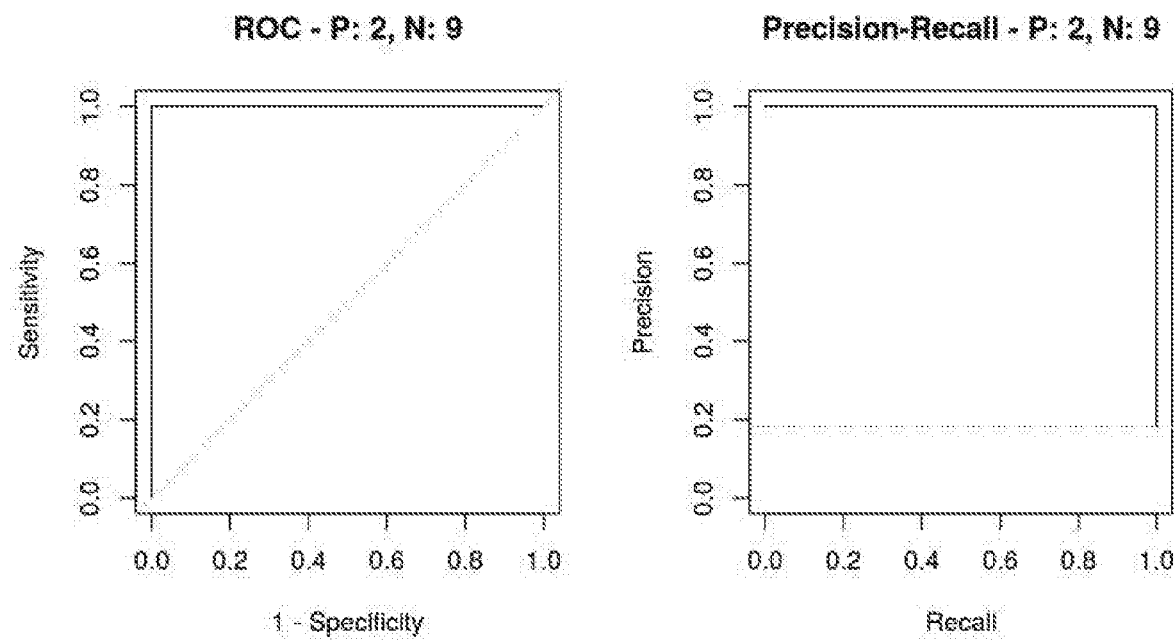
FIG. 28A-B: Validation on CIT/GSE39582: ROC curves for cohort with (a) T1&T2 CRC patients (2 LN+, 9 LN−); AUC=1.0 (ROC), 1.0 (Precision) and (b) T1 and T2 CRC patients (18 LN+, 38 LN−); AUC=0.93 (ROC), 0.85 (precision) using 15 gene classifier described in Example 5.
Figure 28B:
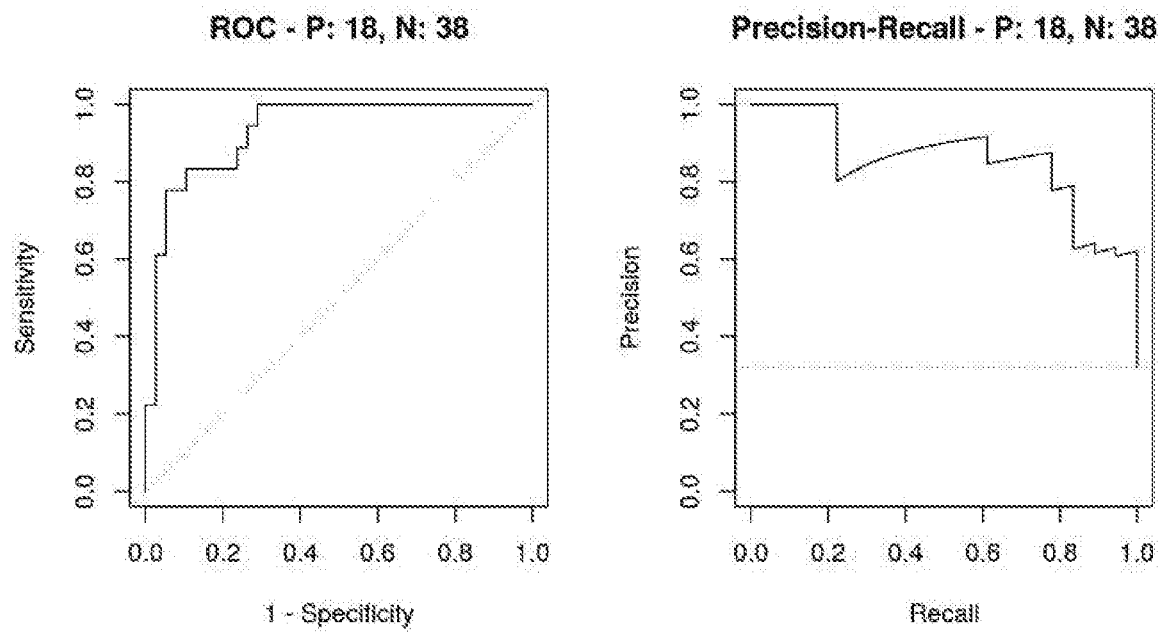
Figure 29A:
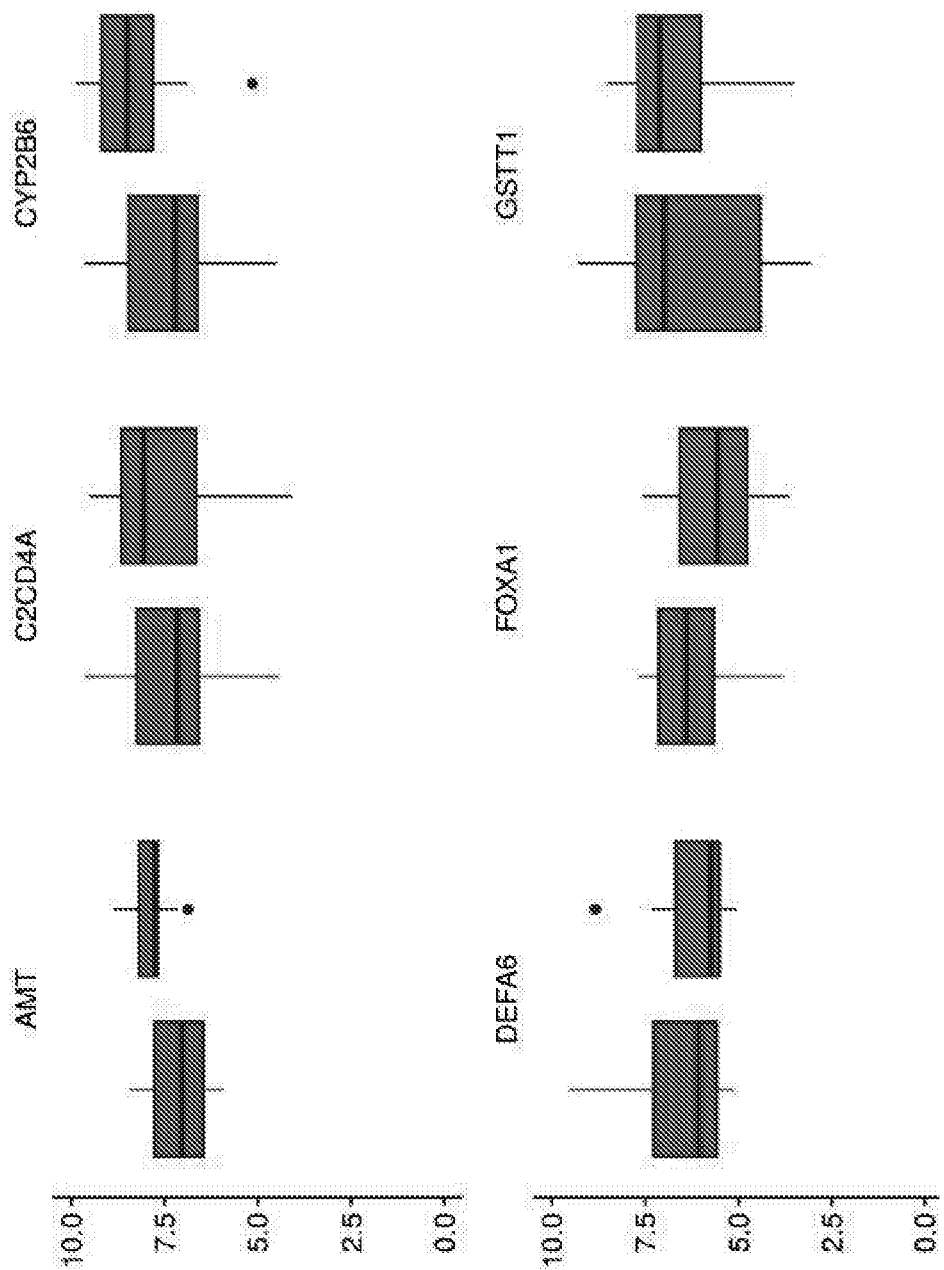
FIG. 29A-C: Boxplots of expression of indicated mRNA of LM− (left box of each graph) and LM+ (right box of each graph) samples of the 15 genes in the 15 gene classifier described in Example 5.
Figure 29B:
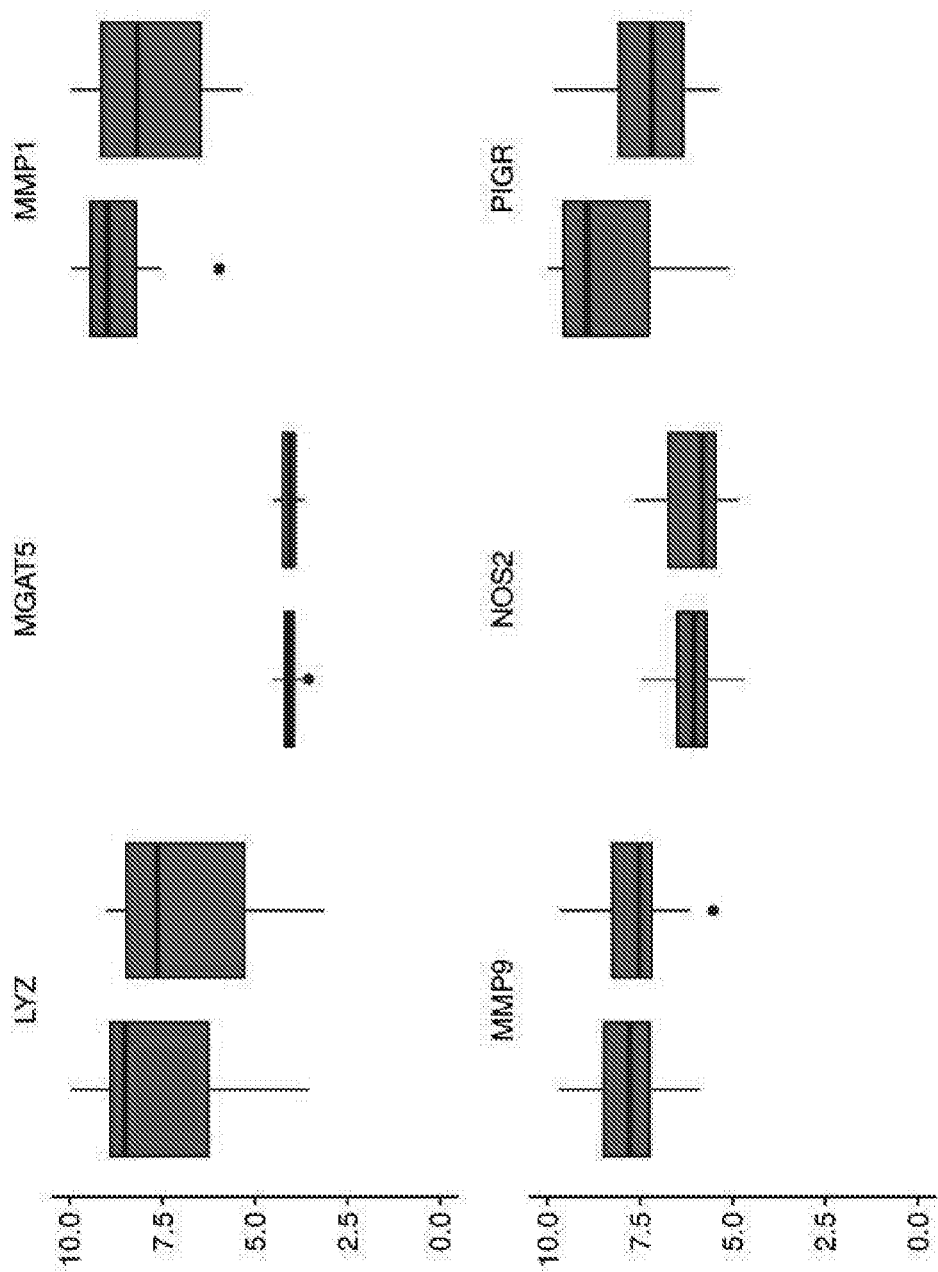
Figure 29C:
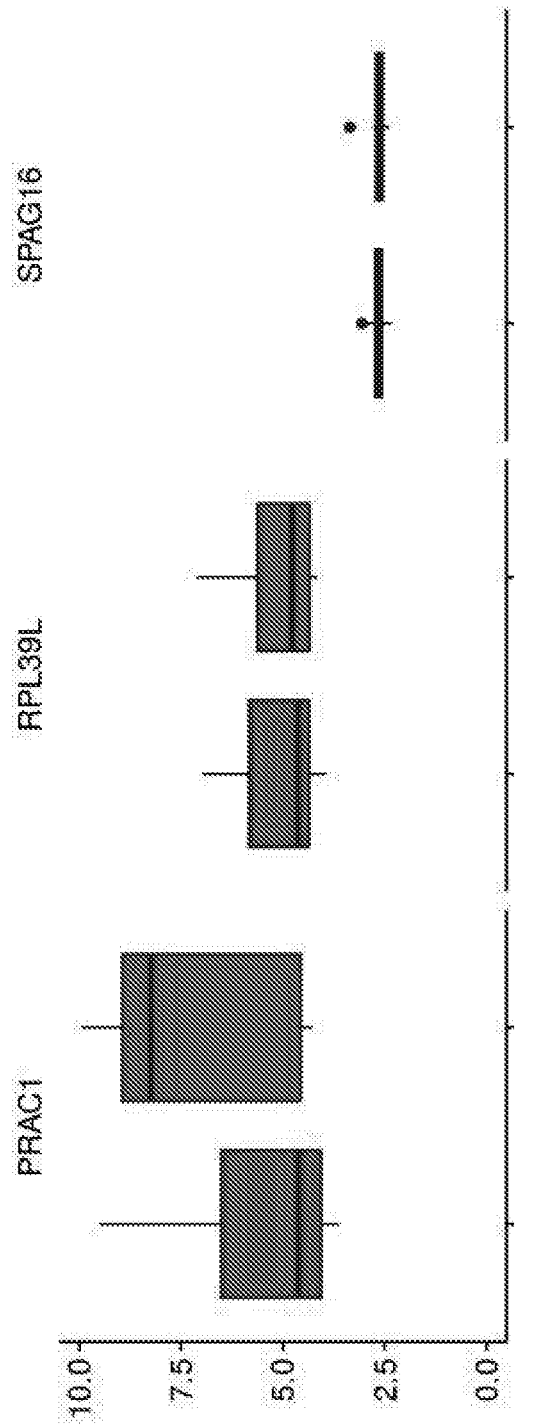
Figure 30A:
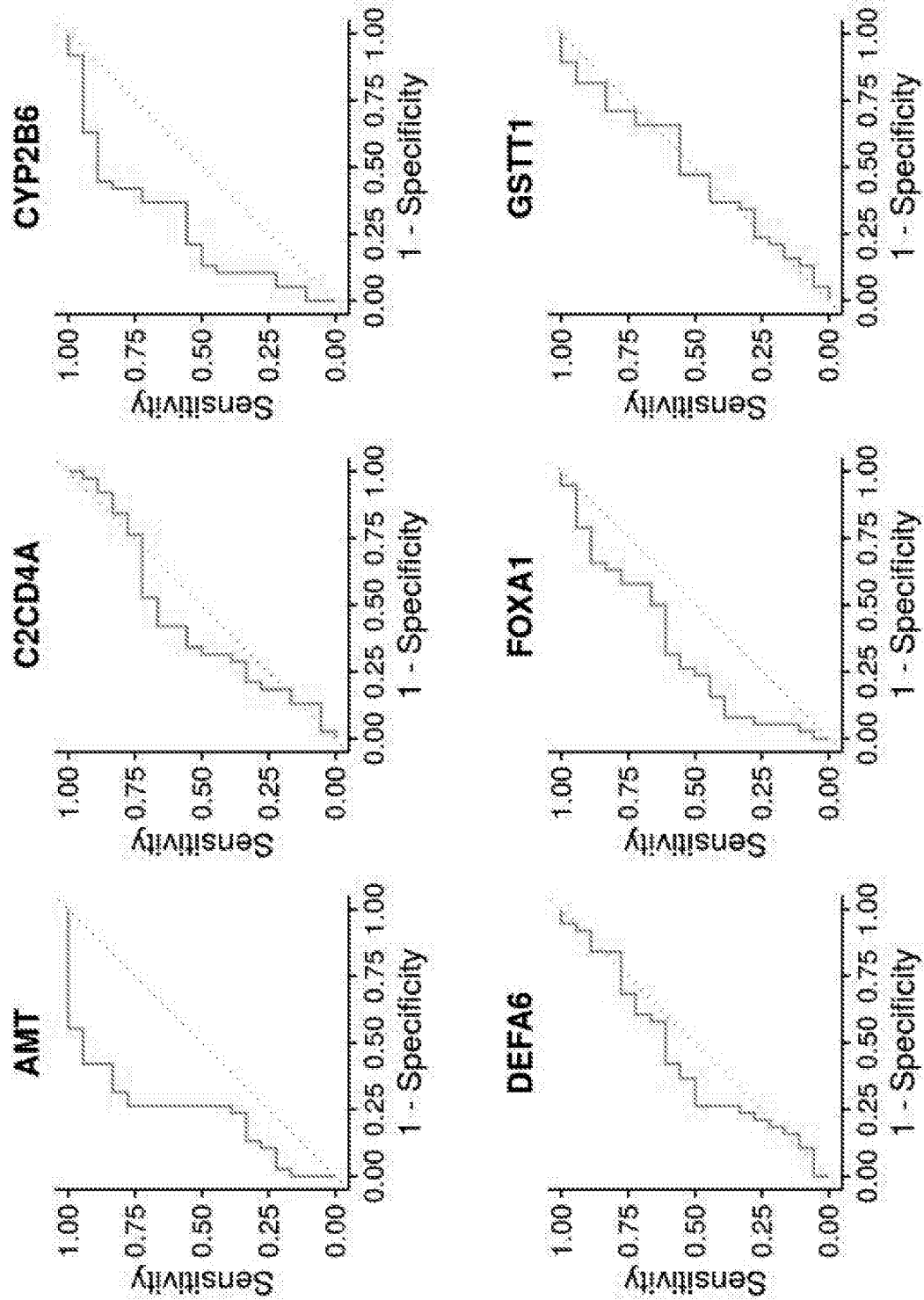
FIG. 30A-C: ROC analysis of each mRNA alone of the 15-gene classifier described in Example 5.
Figure 30B:
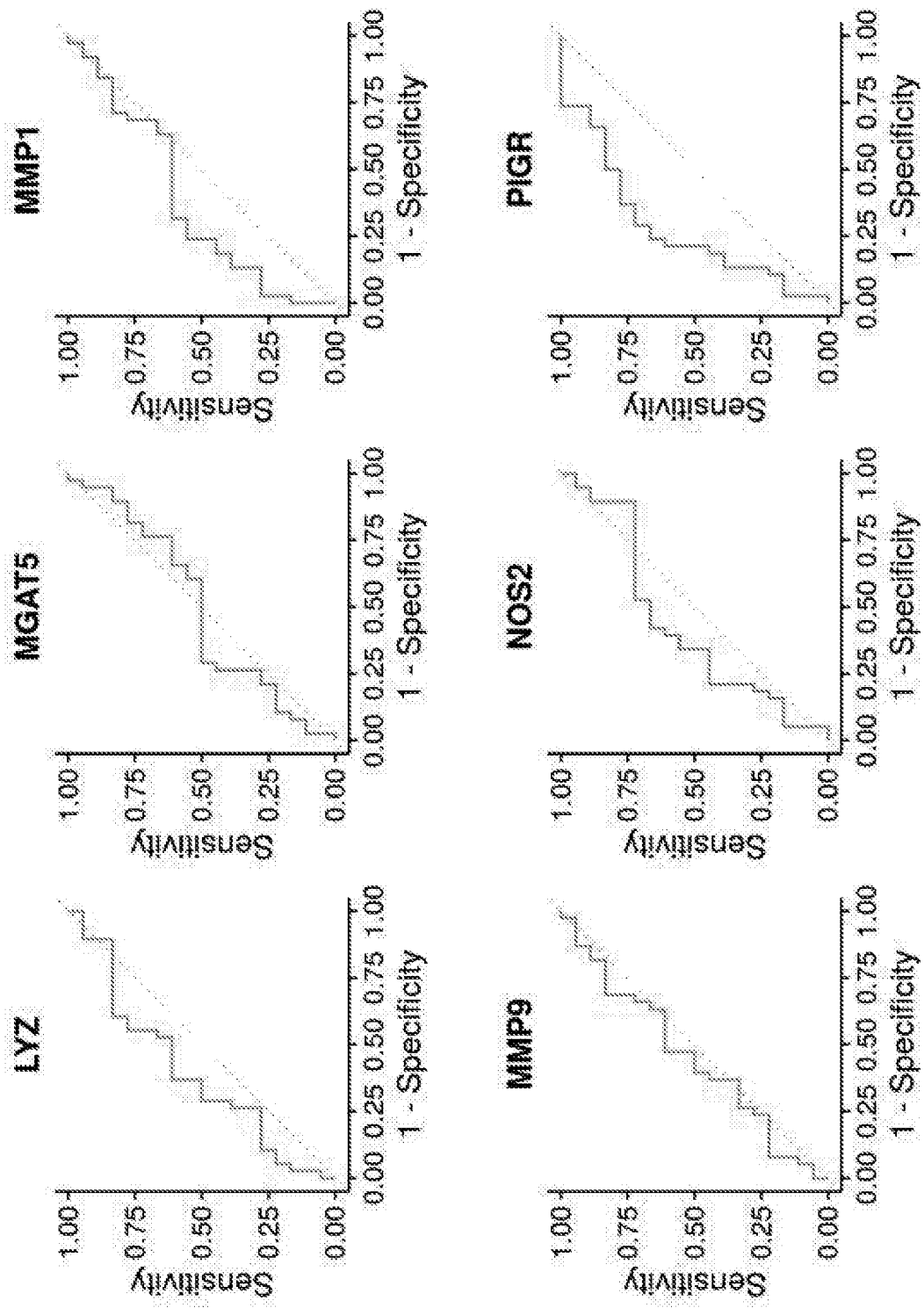
Figure 30C:
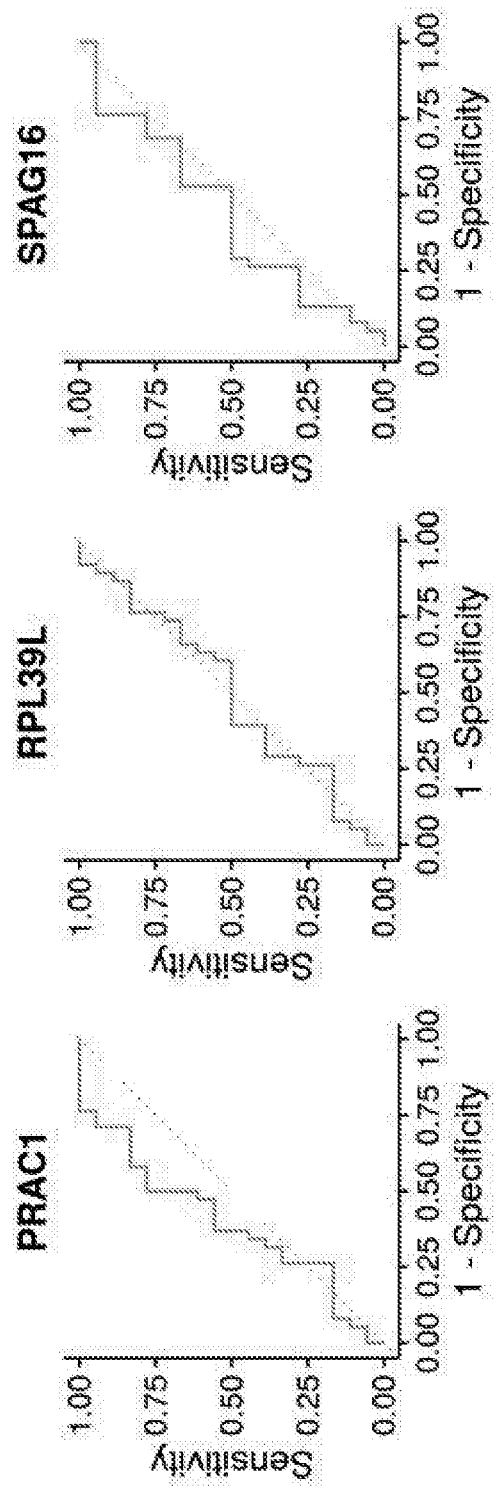

A similar analysis was done for a 16 gene classifier that included AMT, C2CD4A, CYP2B6, DEFA6, FOXA1, GSTT1, LYZ, MGAT5, MMP1, MMP9, NOS2, PIGR, PRAC1, RPL39L, RCC1, and SPAG16. This analysis is shown in FIGS. 25-27.

A similar analysis was done for a 15 gene classifier that included AMT, C2CD4A, CYP2B6, DEFA6, FOXA1, GSTT1, LYZ, MGAT5, MMP1, MMP9, NOS2, PIGR, PRAC1, RPL39L, and SPAG16. This analysis is shown in FIGS. 26-30.

Figure 31:
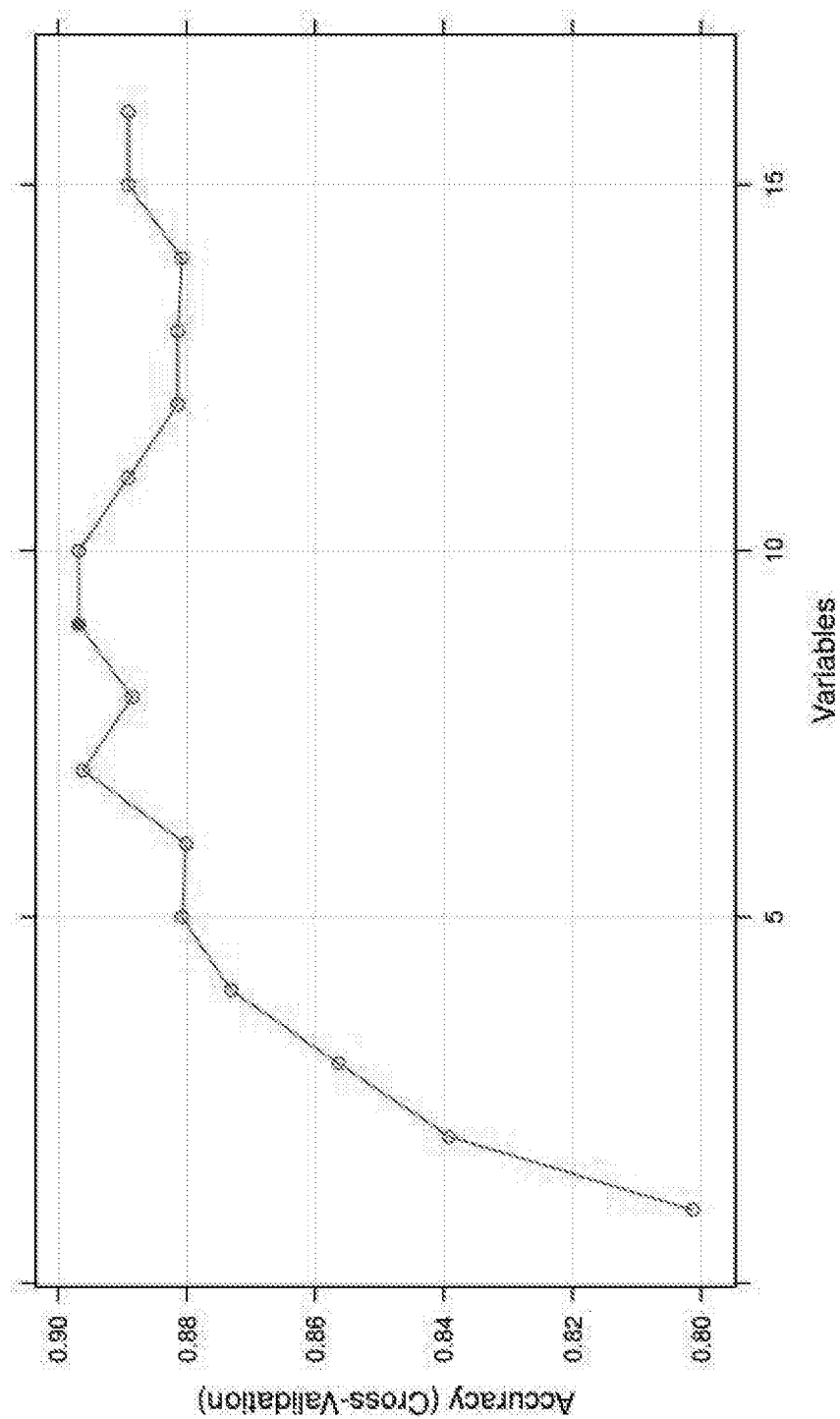
FIG. 31: Use Recursive Feature Elimination based on 5-fold cross-validation of Random Forest algorithm, 9 were kept as a 9-gene classifier. These results are further discussed in Example 5.
Figure 32A:
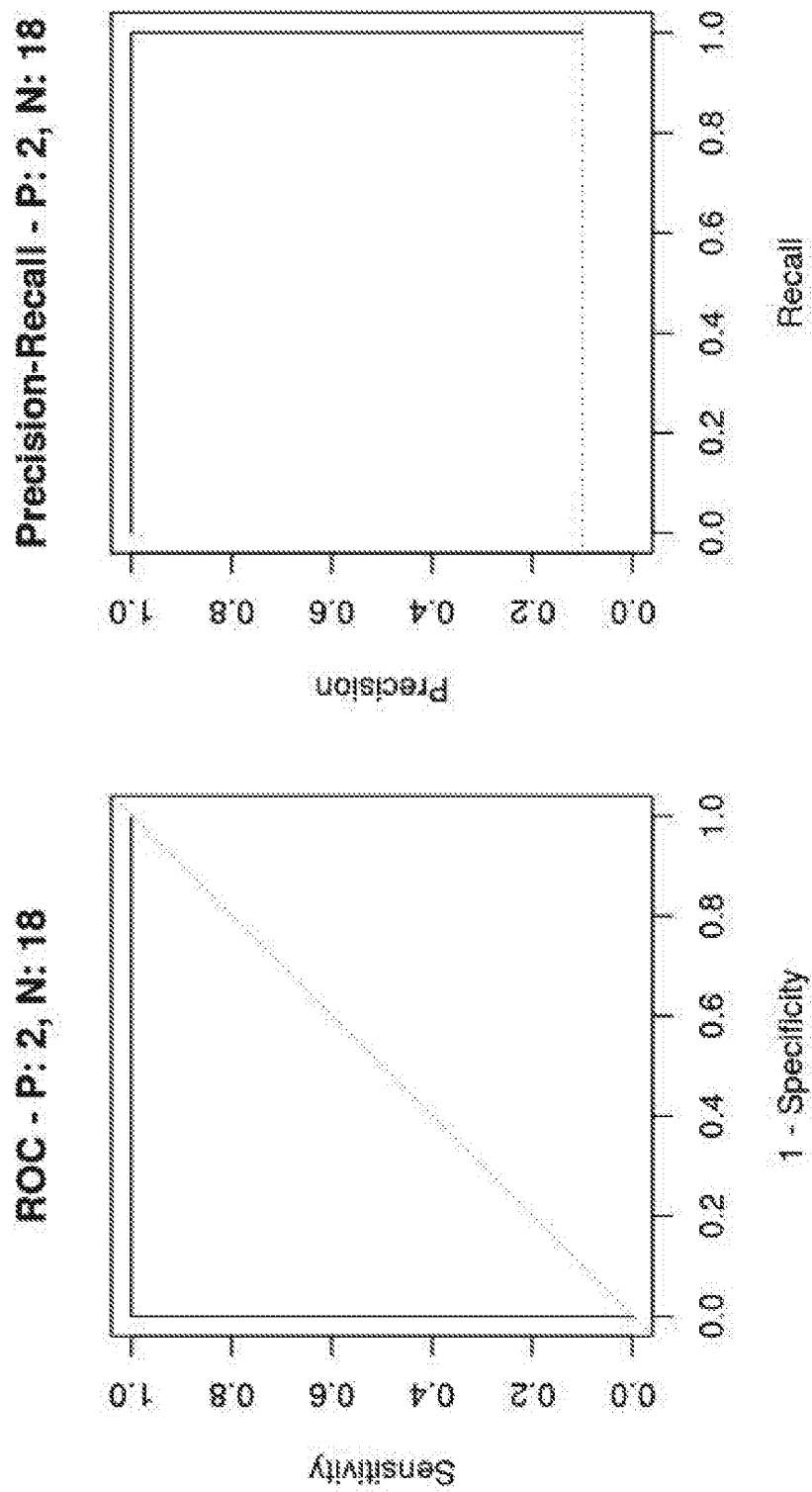
FIG. 32A-D: Validation on TCGA. ROC curves for cohort with (a) TCGA cohort with T1 CRC patients (2 LN+, 18 LN−); AUC=1.0 (ROC), 1.0 (Precision); (b) TCGA cohort with T1 and T2 CRC patients (16 LN+, 109 LN−); AUC=0.94 (ROC), 0.78 (precision); (c) CIT/GSE39582 cohort with T1 CRC patients (2 LN+, 9 LN−); AUC=1.0
Figure 32B:
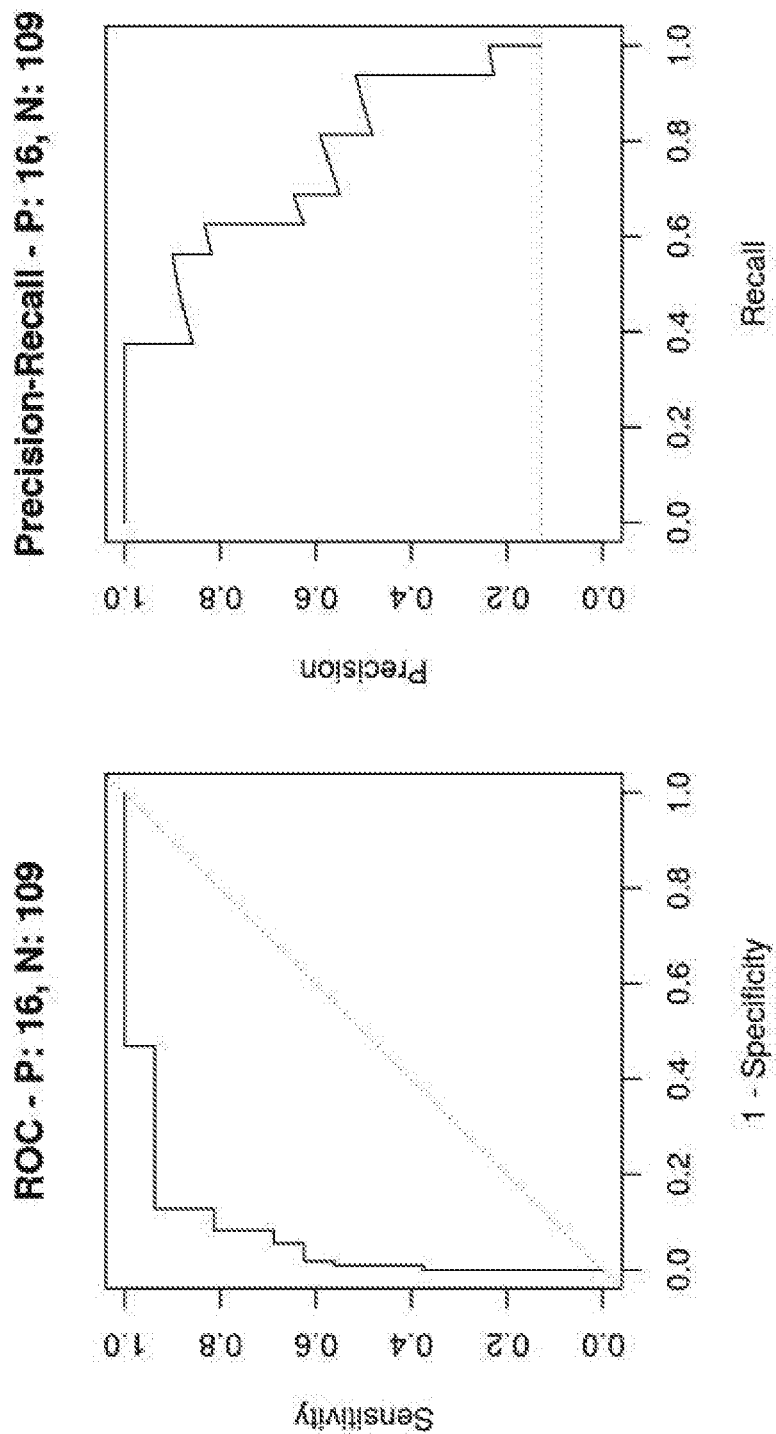
Figure 32C:
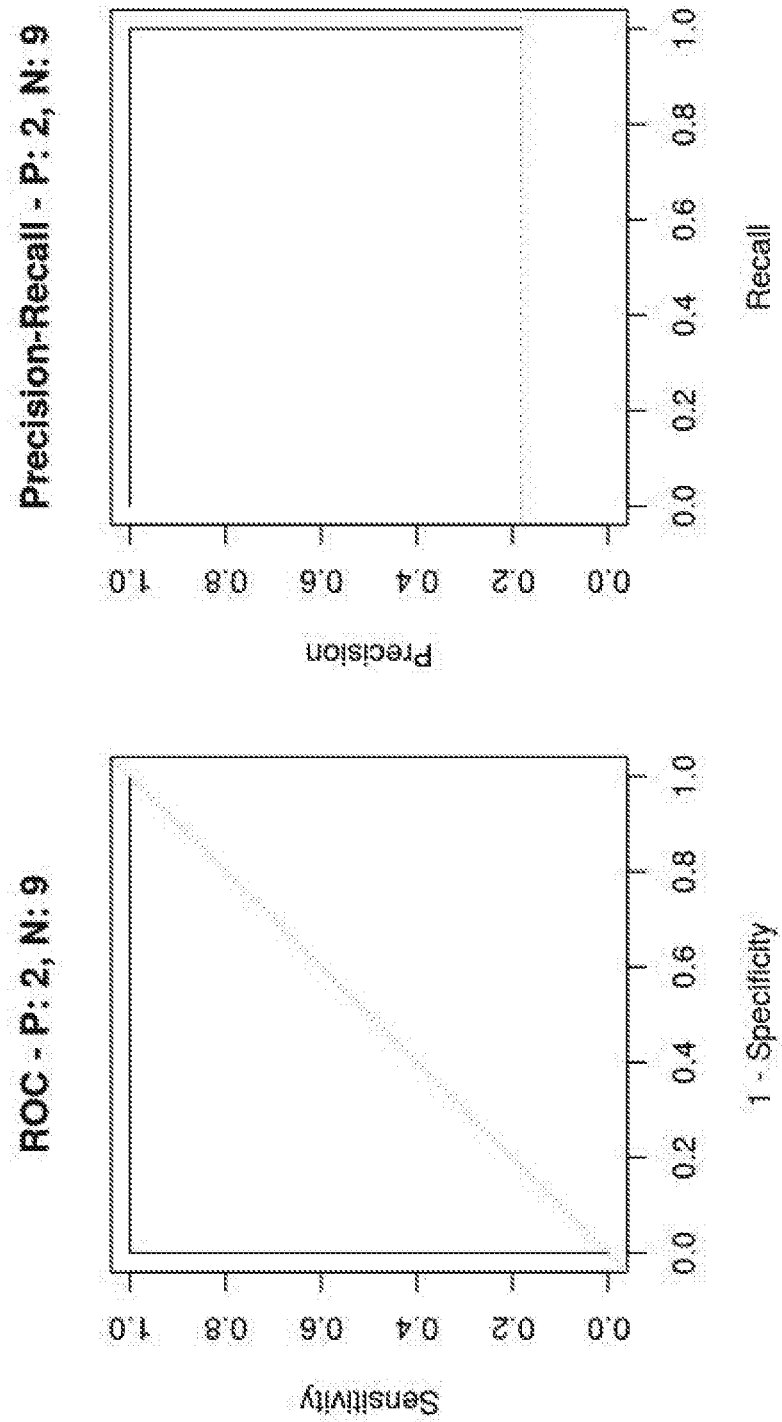
Figure 32D:
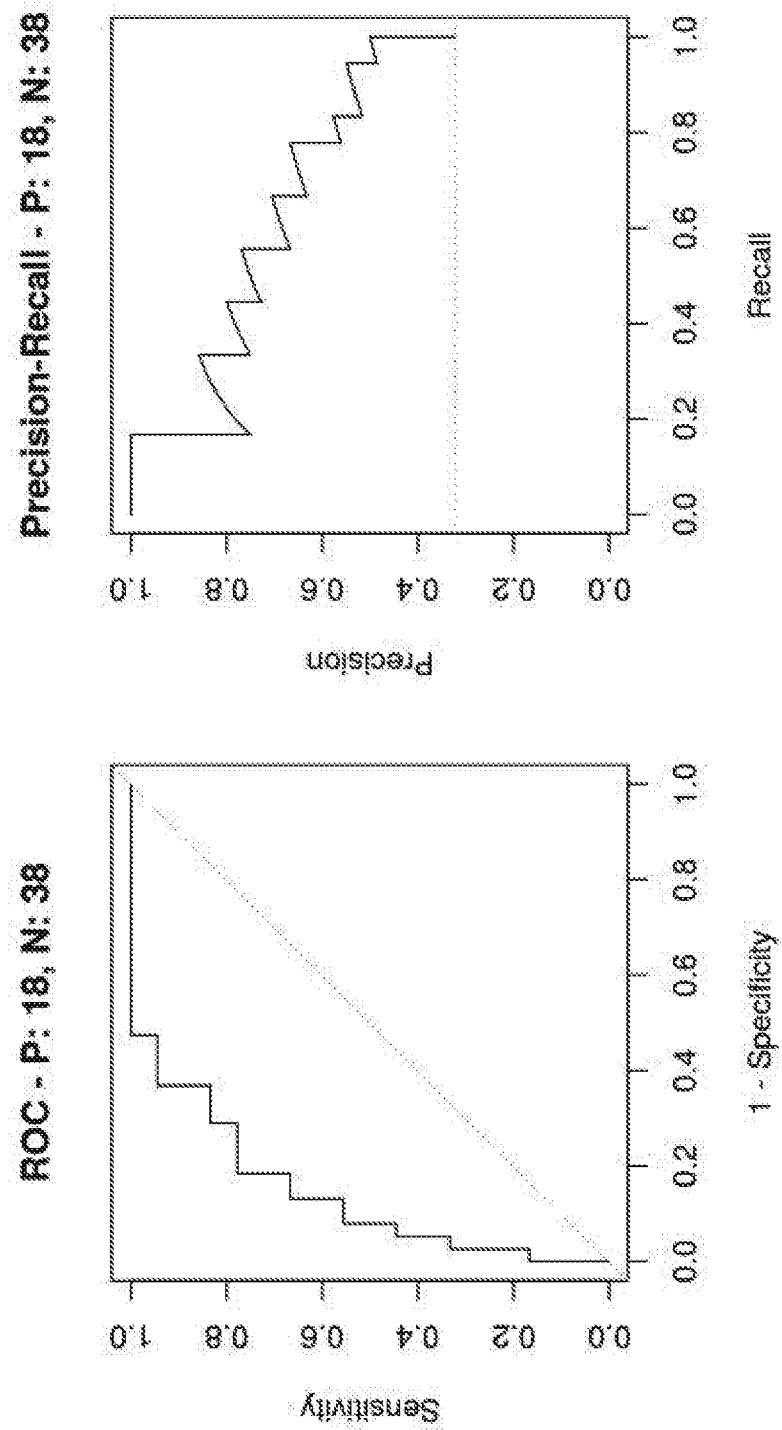

A similar analysis was done for a 9 gene classifier that included C2CD4A, DEFA6, MGAT5, MMP9, SPAG16, FOXA1, AMT, PRAC1, and RCC1. This analysis is shown in FIGS. 31-32.

In conclusion, the inventors have identified a novel mRNA-based classifier that can detect high risk T1 CRCs with Lymph node metastasis. Further validation of these biomarkers in endoscopically collected biopsies will aid in clinical decision making and improving the clinical management of such patients.

Example 6—CCAT1 and CCAT2 Long Noncoding RNAs, Located within the 8q.24.21 'Gene Desert', Serve as Important Prognostic Biomarkers in Colorectal Cancer The 8q24.21 region is often referred to as a 'gene desert' due to lack of any important protein-coding genes, highlighting the potential role of non-coding RNAs, including long non-coding RNAs (lncRNAs) located around the proto-oncogene MYC. In this Example, the inventors have firstly evaluated the clinical significance of altered expression of lncRNAs mapped to this genomic locus in CRC.

A total of 300 tissues, including 280 CRC and 20 adjacent normal mucosa specimens were evaluated for the expression of 12 lncRNAs using qRT-PCR assays. The associations between lncRNA expression and various clinicopathological features, as well as with recurrence free survival (RFS) and overall survival (OS) were analyzed in two independent cohorts.

The expression of CCAT1, CCAT1-L, CCAT2, PVT1, and CASC19 were elevated in cancer tissues (P=0.039, <0.001, 0.018, <0.001, 0.002, respectively). Among these, high expression of CCAT1 and CCAT2 was significantly associated with poor RFS (P=0.049 and 0.022, respectively) and OS (P=0.028 and 0.015, respectively). These results were validated in an independent patient cohort, in which combined expression of CCAT1 and CCAT2 expression was significantly associated with a poor RFS (HR:2.60, 95% confidence interval [CI]: 1.04-6.06, P=0.042) and a poor OS (HR:8.38, 95% CI: 2.68-37.0, P<0.001). The inventors established a RFS prediction model which revealed that combined expression of CCAT1, CCAT2 and carcinoembryonic antigen (CEA) was a significant determinant for efficiently predicting RFS in stage II (P=0.034) and stage III (P=0.001) CRC patients.

Several lncRNAs located in 8q24.21 locus are highly over-expressed in CRC. High expression of CCAT1 and CCAT2 significantly associates with poor RFS and OS. The expression of these two lncRNAs independently, or in combination, serves as important prognostic biomarkers in colorectal cancer.

A. Materials and Methods

1. Patients and Sample Collection

This study included analysis of a total of 300 fresh frozen tissue specimens, which encompassed 280 samples of primary colorectal adenocarcinoma and 20 matched corresponding normal mucosa tissues, collected from three institutes (Cohort 1; Mie University, Cohort 2; National Cancer Center Hospital, and Cohort 3; Tokyo Medical and Dental University). Patients who underwent resection of their primary tumor and were histologically confirmed to have a stage 0-IV CRC were included in this study. Details of the clinicopathological features of the patients involved in this study are shown in Table 1, and available at *Annals of Oncology* online. The flow chart for testing these 300 samples is shown in FIG. 35A.

SUPPLEMENTARY TABLE 1

Clinicopathological features of patients in this study

| Characteristics | Cohort 1 (Mie Univ.) N = 20 N (%) | Cohort 2 (NCC Hospital) N = 125 N (%) | Cohort 3 (TMD Univ.) N = 135 N (%) |
|---|---|---|---|
| Gender | | | |
| Male | 5 (33) | 70 (56) | 77 (57) |
| Female | 15 (67) | 55 (44) | 58 (43) |
| Age (Years) | | | |
| <75 | 13 (65) | — | 99 (73) |
| ≥75 | 7 (35) | — | 36 (27) |
| Tumor Location | | | |
| Right sided colon | — | 23 (18) | 36 (27) |
| Left sided colon | — | 42 (34) | 44 (33) |
| Rectum | — | 60 (48) | 55 (41) |
| Tumor Size (mm) | | | |
| <50 | — | 78 (62) | 64 (47) |
| ≥50 | — | 47 (38) | 65 (48) |
| Unavailable | | 0 (0) | 6 (4) |
| Tumor Depth | | | |
| T1-2 | — | 27 (22) | 28 (21) |
| T3-4 | — | 98 (78) | 107 (79) |
| Histology (Differentiation) | | | |
| Well/Moderate | — | 120 (96) | 126 (93) |
| Poor | — | 5 (4) | 9 (7) |
| Lymphatic Invasion | | | |
| Negative | — | 80 (64) | 59 (44) |
| Positive | — | 45 (36) | 76 (56) |
| Venous Invasion | | | |
| Negative | — | 47 (38) | 19 (14) |
| Positive | — | 78 (62) | 116 (86) |
| Lymph Node Metastasis | | | |
| Negative | — | 56 (45) | 77 (57) |
| Positive | — | 69 (55) | 58 (43) |

SUPPLEMENTARY TABLE 1-continued

Clinicopathological features of patients in this study

| Characteristics | Cohort 1 (Mie Univ.) N = 20 N (%) | | Cohort 2 (NCC Hospital) N = 125 N (%) | | Cohort 3 (TMD Univ.) N = 135 N (%) | |
|---|---|---|---|---|---|---|
| Tumor Stage | | | | | | |
| 0 | 3 | (15) | 0 | (0) | 0 | (0) |
| I | 0 | (0) | 19 | (15) | 22 | (16) |
| II | 5 | (25) | 34 | (27) | 49 | (36) |
| III | 7 | (35) | 55 | (44) | 34 | (25) |
| IV | 5 | (25) | 17 | (14) | 30 | (22) |
| Preoperative Serum CEA (ng/mL) | | | | | | |
| <5 | 5 | (33) | 77 | (62) | 76 | (56) |
| ≥5 | 15 | (67) | 48 | (38) | 59 | (44) |
| Median follow up period (Months) | — | | 69 | | 60 | |

2. Expression of lncRNAs Using Real-Time Quantitative Reverse Transcriptase Polymerase Chain Reaction Quantitative reverse transcriptase polymerase chain reaction (qRT-PCR) was performed using SYBR Green (Thermo Fisher Scientific, Waltham, Mass.). The results were normalized to the expression levels of ACTB. The sequences of the primers used in this study are listed in Table 2.

Quantitative reverse transcriptase polymerase chain reaction (qRT-PCR) was performed using the QuantStudio™ 6 Flex Real Time PCR System (Applied Biosystems®, Foster City, Calif.) and expression levels were evaluated using the QuantStudio™ 6 Flex Real Time PCR System Software. The relative abundance of target transcripts was evaluated utilizing 5 ng of cDNA and SYBR Green (Thermo Fisher Scientific, Waltham, Mass.), and the results were normalized to the expression levels of ACTB using the $2^{-\Delta Ct}$ method; ΔCt is the difference of Ct values between the lncRNA of interest and the normalizer. qRT-PCR was performed in duplicate for each sample and the mean value was used to calculate the expression levels. Normalized values were further log transformed and standardized.

SUPPLEMENTARY TABLE 2

Primer sequences

| | Forward | SEQ ID NO: | Reverse | SEQ ID NO: |
|---|---|---|---|---|
| CCAT1 | AGAAACACTATCACCTACGC | 1 | CTTAACAGGGCATTGCTAATCT | 2 |
| CCAT1-L | CCACGTGCACATATTTGAATTG | 3 | TGCATTCCCTGCTTAATACTCA | 4 |
| CCAT2 | CCCTGGTCAAATTGCTTAACCT | 5 | TTATTCGTCCCTCTGTTTTATGGAT | 6 |
| PVT1 | TTGGGTCTCCCTATGGAATG | 7 | GGAGAAGGCTCCAGGGAGTA | 8 |
| PCAT1 | TGAGAAGAGAAATCTATTGGAACC | 9 | GGTTTGTCTCCGCTGCTTTA | 10 |
| PCAT2 | CTTAAGGCACTGATGCTCTCA | 11 | GTGCTGATGCCTCTGGAAAT | 12 |
| CASC8 | TCCAGCTTTGTGCTGATGAA | 13 | CTTGCAACGTCAGTCCAAAA | 14 |
| CASC11 | CCCCAACACCTTCTTTGAAC | 15 | CGTCCAGTTGCTTTCCATC | 16 |
| CASC19 | ATTGGAGTGCCTGGGTTAGA | 17 | TTTGGACAGCACCTTGAATG | 18 |
| CASC21 | CCAGAGGAGCCAAGAGAAGA | 19 | CCAATGCTGTCCCACTCTGT | 20 |
| PRNCR1 | CCAGATTCCAAGGGCTGATA | 21 | GATGTTTGGAGGCATCTGGT | 22 |
| CCDC26 | GGTGATGTGGTGCATCTGAG | 23 | GCAACAACGGGAACTCTGAT | 24 |
| MYC | CGTCTCCACACATCAGCACAA | 25 | TCTTGGCAGCAGGATAGTCCTT | 26 |
| ACTB | AGAGCTACGAGCTGCTGAC | 27 | AGCACTGTGTTGGCGTACAG | 28 |

3. Statistical Analysis

Receiver operating characteristic (ROC) curves with Youden's Index correction were established to determine optimal cut-off values for each lncRNA as it related to recurrence-free survival (RFS) and overall survival (OS). In multivariate analyses, a Cox proportional hazard model was used to identify clinical factors with a statistically significant influence on survival. Differences with a P value of <0.05 were considered statistically significant. The inventors followed the criteria of REporting recommendations for tumor MARKer prognostic studies (REMARK) (See, for example, McShane L M et al., Nat Clin Pract Oncol 2005; 2: 416-422).

Expression levels of each lncRNA were shown as mean±standard error and were compared using the paired Mann-Whitney test. Receiver operating characteristic (ROC) curves with Youden's Index correction were established to determine optimal cut-off value for each lncRNA as it related to recurrence-free survival (RFS) and OS. Patients were divided into two groups, high and low expression groups, by means of the Youden's index related to OS, and several clinicopathological characteristics were compared between the two groups using either the chi-square test or Fisher's exact test for categorical data or the Mann-Whitney test for continuous variables. Pearson's coefficient was calculated for correlation analysis. A RFS and OS curve were established from the time of resection using the Kaplan-Meier method and differences were evaluated using the log-rank test. Multivariate analyses were performed including all variables with a P value of <0.05 in univariate analysis. In multivariate analyses, a Cox proportional hazard model was used to identify factors with a statistically significant influence on survival. Differences with a P value of <0.05 were considered statistically significant. RFS prediction models were established using a Cox-proportional hazard model using expression levels of lncRNAs and clinicopathological factors. ROC curves were established and area under the curves (AUC) were compared between the each models. All statistical calculations were performed using JMP Pro 11 statistical software (SAS Institute Japan, Tokyo, Japan) and Medcale version 16.1. (MedCalc Software, Belgium).

4. Total RNA Extraction and cDNA Synthesis

Total RNA was extracted from fresh frozen specimens using the RNeasy Mini kit (QIAGEN) according to the manufacturer's instructions. Then, cDNA was synthesized from 2 μg of total RNA using the High Capacity cDNA Reverse Transcription Kit according to the manufacturer's recommendations (Thermo Fisher Scientific, Waltham, Mass.).

B. Results

1. The Screening Phase Identified Upregulation of Specific lncRNAs in Colorectal Cancer Twelve lncRNAs mapped to the 8q24.21 locus, which possess a HUGO Gene Nomenclature Committee (HGNC) symbol, and have previously been suggested to associate with cancer progression, were selected as candidates for initial screening (FIG. 35B). The inventors compared the expression level of each of the twelve lncRNAs in a Cohort 1, comprising of 20 matched CRCs and normal mucosa (FIG. 36). Five of the twelve screened lncRNAs; CCAT1, CCAT1-L, CCAT2, pvt1 oncogene (PVT1), and cancer susceptibility candidate 19 (CASC19), were significantly up-regulated in cancer vs. normal tissues (P=0.037, <0.001, 0.017, <0.001, 0.002, respectively). The prostate cancer associated transcript 1 (PCAT1) was at or below the limit of detection in most patients, and no significant differences were observed for the other six lncRNAs (P>0.05). Based on these results, the inventors selected the five significantly up-regulated lncRNAs (CCAT1, CCAT1-L, CCAT2, PVT1, and CASC19) for further evaluation.

2. The Testing Phase Revealed that High Expression of CCAT1, CCAT2 and PVT1 Associated with Poor Recurrence Free Survival and Overall Survival in CRC Patients Next, during the testing phase, the inventors examined the expression of CCAT1, CCAT1-L, CCAT2, PVT1, and CASC19 in 125 CRC tissue specimens from Cohort 2. CCAT1-L and CASC19 could not be detected in 2 samples, and PVT1 could not in 3 samples. The expression levels of these five lncRNAs were analyzed in the context of various clinicopathological characteristics and prognosis of the patients. The detailed associations between clinicopathological characteristics and expression of each lncRNA are shown in Table 3.

TABLE 3

The associations between clinicopathological features and lncRNA expression in NCCH cohort

| Characteristics | CCAT1 | | | CCAT2 | | | CCAT1-L | | |
|---|---|---|---|---|---|---|---|---|---|
| | Low N = 70 (%) | High N = 55 (%) | P-Value | Low N = 105 (%) | High N = 20 (%) | P-Value | Low N = 105 (%) | High N=18 (%) | P-Value |
| Gender | | | 0.126 | | | 0.557 | | | 0.798* |
| Male | 35 (50) | 35 (64) | | 60 (57) | 10 (50) | | 47 (45) | 7 (39) | |
| Female | 35 (50) | 20 (36) | | 45 (43) | 10 (50) | | 58 (55) | 11 (61) | |
| Tumor Location | | | 0.614 | | | 0.811* | | | 0.611* |
| Colon | 35 (50) | 30 (55) | | 54 (51) | 11 (55) | | 56 (53) | 8 (44) | |
| Rectum | 35 (50) | 25 (45) | | 51 (49) | 9 (45) | | 49 (47) | 10 (56) | |
| Maximum Tumor Size (mm) | | | 0.800 | | | 0.615* | | | 1.000* |
| <50 | 43 (61) | 35 (64) | | 64 (61) | 14 (70) | | 100 (95) | 18 (100) | |
| ≥50 | 27 (39) | 20 (36) | | 41 (39) | 6 (30) | | 5 (5) | 0 (0) | |
| Tumor Depth | | | 0.699 | | | 0.568* | | | <0.001 |
| T1-2 | 16 (23) | 11 (20) | | 24 (23) | 3 (15) | | 16 (15) | 11 (61) | |
| T3-4 | 54 (77) | 44 (80) | | 81 (77) | 17 (85) | | 89 (85) | 7 (39) | |
| Histology (Differentiation) | | | 0.653* | | | 0.588* | | | 1.000* |
| Well/Moderate | 68 (97) | 52 (95) | | 101 (96) | 19 (95) | | 66 (63) | 11 (61) | |
| Poor | 2 (3) | 3 (5) | | 4 (4) | 1 (5) | | 39 (37) | 7 (39) | |
| Lymphatic Invasion | | | 0.940 | | | 0.447* | | | 0.288* |
| Negative | 45 (64) | 35 (64) | | 69 (66) | 11 (55) | | 65 (62) | 14 (78) | |
| Positive | 25 (36) | 20 (36) | | 36 (34) | 9 (45) | | 40 (38) | 4 (22) | |
| Venous Invasion | | | 0.080 | | | 0.314* | | | 0.034* |
| Negative | 31 (44) | 16 (29) | | 42 (40) | 5 (25) | | 35 (33) | 11 (61) | |
| Positive | 39 (56) | 39 (71) | | 63 (60) | 15 (75) | | 70 (67) | 7 (39) | |
| Lymph Node Metastasis | | | 0.016 | | | 0.220* | | | 0.799 |
| Negative | 38 (54) | 18 (33) | | 50 (48) | 6 (30) | | 47 (45) | 9 (50) | |
| Positive | 32 (46) | 37 (67) | | 55 (52) | 14 (70) | | 58 (55) | 9 (50) | |
| Distant Metastasis | | | 0.443* | | | 0.148* | | | 1.000* |
| Absent | 62 (89) | 46 (84) | | 93 (89) | 15 (75) | | 91 (87) | 16 (89) | |
| Present | 8 (11) | 9 (16) | | 12 (11) | 5 (25) | | 14 (13) | 2 (11) | |
| Stage | | | 0.020 | | | 0.324 | | | 0.610 |
| I-II | 36 (51) | 17 (31) | | 47 (45) | 6 (30) | | 44 (42) | 9 (50) | |
| III-IV | 34 (49) | 38 (69) | | 58 (55) | 14 (70) | | 61 (58) | 9 (50) | |
| Preoperative Serum CEA (ng/ml) | | | 0.745 | | | 0.617* | | | 0.795 |
| <5 | 44 (63) | 33 (60) | | 66 (63) | 11 (55) | | 64 (61) | 12 (67) | |
| ≥5 | 26 (37) | 22 (40) | | 39 (37) | 9 (45) | | 41 (39) | 6 (33) | |

TABLE 3-continued

The associations between clinicopathological features and lncRNA expression in NCCH cohort

| | PVT1 | | | CASC19 | | |
|---|---|---|---|---|---|---|
| Characteristics | Low N = 110 (%) | High N = 12 (%) | P-Value | Low N = 77 (%) | High N = 46 (%) | P-Value |
| Gender | | | 0.546* | | | 0.498 |
| Male | 50 (45) | 4 (33) | | 32 (42) | 22 (48) | |
| Female | 60 (55) | 8 (67) | | 45 (58) | 24 (52) | |
| Tumor Location | | | 0.230* | | | 0.727 |
| Colon | 59 (54) | 4 (33) | | 41 (53) | 23 (50) | |
| Rectum | 51 (46) | 8 (67) | | 36 (47) | 23 (50) | |
| Maximum Tumor Size (mm) | | | 1.000* | | | 0.759 |
| <50 | 68 (62) | 8 (67) | | 49 (64) | 28 (61) | |
| ≥50 | 42 (38) | 4 (33) | | 28 (36) | 18 (39) | |
| Tumor Depth | | | 0.135* | | | 0.029 |
| T1-2 | 22 (20) | 5 (42) | | 12 (16) | 15 (33) | |
| T3-4 | 88 (80) | 7 (58) | | 65 (84) | 31 (67) | |
| Histology (Differentiation) | | | 1.000* | | | 1.000* |
| Well/Moderate | 106 (96) | 12 (100) | | 74 (96) | 44 (96) | |
| Poor | 4 (4) | 0 (0) | | 3 (4) | 2 (4) | |
| Lymphatic Invasion | | | 0.537 | | | 0.324 |
| Negative | 70 (64) | 9 (75) | | 52 (68) | 27 (59) | |
| Positive | 40 (36) | 3 (25) | | 25 (32) | 19 (41) | |
| Venous Invasion | | | 0.365* | | | 0.283 |
| Negative | 40 (36) | 6 (50) | | 26 (34) | 20 (43) | |
| Positive | 70 (64) | 6 (50) | | 51 (66) | 26 (57) | |
| Lymph Node Metastasis | | | 1.000* | | | 0.270 |
| Negative | 51 (46) | 5 (42) | | 38 (49) | 18 (39) | |
| Positive | 59 (54) | 7 (58) | | 39 (51) | 28 (61) | |
| Distant Metastasis | | | 1.000* | | | 1.000* |
| Absent | 95 (86) | 11 (92) | | 67 (87) | 40 (87) | |
| Present | 15 (14) | 1 (8) | | 10 (13) | 6 (13) | |
| Stage | | | 1.000* | | | 0.287 |
| I-II | 48 (44) | 5 (42) | | 36 (47) | 17 (37) | |
| III-IV | 62 (56) | 7 (58) | | 41 (53) | 29 (63) | |
| Preoperative Serum CEA (ng/ml) | | | 0.534* | | | 0.871 |
| <5 | 69 (63) | 6 (50) | | 48 (62) | 28 (61) | |
| ≥5 | 41 (37) | 6 (50) | | 29 (38) | 18 (39) | |

CEA: carcinoembryonic antigen;
*Fisher's exact test

The inventors thereafter evaluated the prognostic significance of each lncRNA using the Kaplan-Meier analysis. High levels of CCAT1 and CCAT2 expression were significantly associated with poor RFS (P=0.049 and 0.022, respectively), and poor OS (P=0.028 and 0.015, respectively) (FIGS. 33A & 33B). Besides, high levels of CCAT1-L expression was significantly associated with poor RFS (P=0.048). However, expression alterations in PVT1 and CASC19 did not demonstrate a significant association with tumor recurrence (P=0.178 and P=0.087, respectively) and patient survival (P=0.113 and 0.290, respectively), as shown in FIG. 37. Accordingly, CCAT1 and CCAT2 were selected as candidate lncRNAs for further validation and evaluation of their prognostic potential in another independent patient cohort.

3. Prognostic Significance of CCAT1 and CCAT2 lncRNAs was Validated in an Independent Cohort of CRC Patients To further confirm and validate the prognostic significance of the two candidate lncRNAs, the inventors analyzed another, large, independent cohort of 135 CRC tissues (Cohort 3). The high and low categorical expression cut-off thresholds were determined using Youden's index. The associations between each lncRNA expression and clinicopathological features are shown in Table 4. RFS data was not available for 1 patient with stage III CRC and excluded from RFS analysis.

TABLE 4

The association between clinicopathological factors and lncRNAs in TMD Univ. cohort

| | CCAT1 | | | CCAT2 | | |
|---|---|---|---|---|---|---|
| Characteristics | Low N = 30 (%) | High N = 105 (%) | P-Value | Low N = 101 (%) | High N = 34 (%) | P-Value |
| Gender | | | 0.379 | | | 0.061 |
| Male | 15 (50) | 62 (59) | | 53 (53) | 10 (29) | |

TABLE 4-continued

The association between clinicopathological factors and lncRNAs in TMD Univ. cohort

| | CCAT1 | | | CCAT2 | | |
|---|---|---|---|---|---|---|
| Characteristics | Low N = 30 (%) | High N = 105 (%) | P-Value | Low N = 101 (%) | High N = 34 (%) | P-Value |
| Female | 15 (50) | 43 (41) | | 48 (48) | 24 (71) | |
| Age (Years) | | | 0.357 | | | 0.197 |
| <75 | 20 (67) | 79 (75) | | 77 (76) | 22 (65) | |
| ≥75 | 10 (33) | 26 (25) | | 24 (24) | 12 (35) | |
| Tumor Location | | | 0.114 | | | 0.730 |
| Colon | 14 (47) | 66 (63) | | 59 (58) | 21 (62) | |
| Rectum | 16 (53) | 39 (37) | | 42 (42) | 13 (38) | |
| Maximum Tumor Size (mm) | | | 0.183 | | | 0.729 |
| <50 | 17 (57) | 47 (45) | | 48 (48) | 16 (47) | |
| ≥50 | 11 (37) | 54 (51) | | 47 (47) | 18 (53) | |
| Unavailable | 2 (15) | 4 (4) | | 6 (6) | 0 (0) | |
| Tumor Depth | | | 0.799* | | | 0.339* |
| T1-2 | 7 (23) | 21 (20) | | 19 (19) | 9 (26) | |
| T3-4 | 23 (77) | 84 (80) | | 82 (81) | 25 (74) | |
| Histology (Differentiation) | | | 0.207* | | | 0.830* |
| Well/Moderate | 30 (100) | 96 (91) | | 94 (93) | 32 (94) | |
| Poor | 0 (0) | 9 (9) | | 7 (7) | 2 (6) | |
| Lymphatic Invasion | | | 0.190 | | | 0.649 |
| Negative | 10 (33) | 49 (47) | | 43 (43) | 16 (47) | |
| Positive | 20 (67) | 56 (53) | | 58 (57) | 18 (53) | |
| Venous Invasion | | | 0.565 | | | 1.000* |
| Negative | 3 (10) | 16 (15) | | 14 (14) | 5 (15) | |
| Positive | 27 (90) | 89 (85) | | 87 (86) | 29 (85) | |
| Lymph Node Metastasis | | | 0.643 | | | 0.808 |
| Negative | 16 (53) | 61 (58) | | 57 (56) | 20 (59) | |
| Positive | 14 (47) | 44 (42) | | 44 (44) | 14 (41) | |
| Distant Metastasis | | | 0.024* | | | 0.815 |
| Absent | 28 (93) | 77 (73) | | 79 (78) | 26 (76) | |
| Present | 2 (7) | 28 (27) | | 22 (22) | 8 (24) | |
| Stage | | | 0.747 | | | 0.963 |
| I-II | 15 (50) | 56 (53) | | 53 (52) | 18 (53) | |
| III-IV | 15 (50) | 49 (47) | | 48 (48) | 16 (47) | |
| Preoperative Serum CEA (ng/ml) | | | 0.642 | | | 0.649 |
| <5 | 18 (60) | 58 (55) | | 58 (57) | 18 (53) | |
| ≥5 | 12 (40) | 47 (45) | | 43 (43) | 16 (47) | |

CEA: carcinoembryonic antigen
*: Fisher's exact test

Next, the inventors evaluated the association between expression of both lncRNAs with RFS and OS. Consistent with the findings in Cohort 2, high levels of CCAT1 and CCAT2 expression were associated significantly with poor RFS (P<0.001 and 0.010, respectively) as well as poor OS (P=0.011 and 0.025, respectively) as shown in FIGS. 33C-D.

4. CCAT1 and CCAT2 Expression was an Independent Predictor of Poor RFS and OS in CRC Patients The inventors next performed univariate and multivariate analyses using the Cox proportional hazard model in the validation cohort. The univariate analysis revealed that the age (≥75) (HR:2.27, 95% CI=1.05-4.74, P=0.037), the presence of lymph node metastasis (HR:2.89, 95%₀CI=1.38-6.05, P=0.005), high pre-operative serum carcinoembryonic antigen (CEA) levels (HIR:2.98, 95% CI: 1.43-6.32, P=0.004), high CCAT1 expression (HIR:3.88, 95% CI: 1.67-8.39, P=0.003), and high CCAT2 expression (HIR: 2.55, 95% CI: 1.19-5.31, P=0.017) were significantly associated with poor RFS, while other clinicopathological factors and high CCAT1 and CCAT2 expression also demonstrated a significant association with OS as well (CCAT1 expression: HR: 4.06, 95% CI: 1.47-16.8, P=0.004, CCAT2 expression: HR: 2.04, 95% CI: 1.05-3.84, P=0.036, Table 5).

TABLE 5

Univariate analysis of RFS and OS using a Cox proportional hazard model

| | RFS | | | OS | | |
|---|---|---|---|---|---|---|
| Variables | HR | 95% CI | P-value | HR | 95% CI | P-value |
| Gender Female/Male | 1.06 | 0.50-2.20 | 0.881 | 1.18 | 0.62-2.19 | 0.611 |
| Age ≥75/<75 (Years) | 2.27 | 1.05-4.74 | 0.037 | 1.43 | 0.66-2.84 | 0.345 |

TABLE 5-continued

Univariate analysis of RFS and OS using a Cox proportional hazard model

| Variables | RFS | | | OS | | |
|---|---|---|---|---|---|---|
| | HR | 95% CI | P-value | HR | 95% CI | P-value |
| Tumor Location Rectum/Colon | 1.75 | 0.84-3.71 | 0.131 | 0.94 | 0.49-1.75 | 0.837 |
| Tumor Depth T3-4/T1-2 | 2.50 | 0.97-8.51 | 0.059 | 2.24 | 0.96-6.54 | 0.062 |
| Histology (Differentiation) Poor/Well-Moderate | 1.70 | 0.41-4.85 | 0.417 | 1.62 | 0.49-4.06 | 0.389 |
| Lymphatic Invasion Positive/Negative | 1.20 | 0.58-2.55 | 0.614 | 1.80 | 0.95-3.60 | 0.073 |
| Vascular Invasion Positive/Negative | 2.06 | 0.72-8.64 | 0.193 | 7.78 | 1.69-138 | 0.003 |
| Lymph Node Metastasis Positive/Negative | 2.89 | 1.38-6.05 | 0.005 | 4.69 | 2.41-9.82 | <0.001 |
| Stage III-IV/I-II | — | — | — | 7.09 | 3.32-17.5 | <0.001 |
| Preoperative Serum CEA ≥5/<5 (ng/mL) | 2.98 | 1.43-6.32 | 0.004 | 3.78 | 1.96-7.72 | <0.001 |
| CCAT1 expression High/Low | 3.88 | 1.67-8.39 | 0.003 | 4.06 | 1.47-16.8 | 0.004 |
| CCAT2 expression High/Low | 2.55 | 1.19-5.31 | 0.017 | 2.04 | 1.05-3.84 | 0.036 |

RFS: recurrence free survival, OS: overall survival, HR: hazard ration, CI: confidence interval, CEA: carcinoembryonic antigen.

Interestingly, multivariate analysis revealed that the expression levels of CCAT1 (HR: 2.52, 95% CI: 1.07-5.56, P=0.036) and CCAT2 (HR: 2.39, 95% CI: 1.10-5.08, P=0.029) were independent factors for predicting poor RFS and poor OS (CCAT1: HR: 5.90, 95% CI: 2.09-24.7, P<0.001 and CCAT2: HR: 2.40, 95% CI: 1.22-4.59, P=0.011; Table 1). Taken together, the inventors successfully validated the prognostic significance of both CCAT1 and CCAT2 expression as important prognostic biomarkers in multiple cohorts of CRC patients.

5. CCAT1 and CCAT2 Expression Significantly Correlated with MYC in Colorectal Cancer Since there have been suggestions that lncRNAs mapped to the 8q24.21 locus may be associated with MYC, the inventors evaluated the relationship between expression of CCAT1 and CCAT2 with MYC. The inventors evaluated MYC expression by qRT-PCR in the Cohort 3. Both CCAT1 and CCAT2 expression were significantly correlated with MYC expression (r=0.66, P<0.001 and r=0.74, P<0.001, respectively; FIG. 38, further supporting the functional and clinical relevance of these findings in colorectal cancer.

6. Combined Expression of CCAT1 and CCAT2 is a Superior Predictor for RFS and OS in CRC Patients Due to correlative functional nature of CCAT1 and CCAT2, it was sought to examine associations for their combinatorial expression in predicting RFS and OS. In this regard, the inventors categorized all patients into three groups; a) with elevated expression of both CCAT1 and CCAT2, b) with elevated expression of either CCAT1 or CCAT2, and c) with low expression of both CCAT1 and CCAT2. By performing such analysis, the inventors discovered that the patients that co-expressed high levels of CCAT1 and CCAT2 correlated with poorer RFS compared to other groups (P=0.049 both high vs. either high, P<0.001 both high vs. both low, respectively; FIG. 34A). In the case of OS, the three groups were more spread out, such that both high vs. either high (P=0.038) and both high vs. both low (P=0.002) were significantly different from one another, and demonstrated that patients with high levels of both CCAT1 and CCAT2 had the worst OS. Furthermore, multivariate analysis by combining expression levels of both CCAT1 and CCAT2 revealed that the group of patients with high co-expression of CCAT1 and CCAT2 had higher hazard ratios for RFS (HIR:2.60, 950% CI: 1.04-6.06, P=0.042) and also for OS (HR: 8.38, 950% CI: 2.68-37.0, P<0.001) compared with the both low expression group (Table 6).

TABLE 6

Multivariate analyses of RFS and OS using Cox proportional hazard model

| Variables | CCAT1 | | | CCAT2 | | | CCAT1 + CCAT2 | | |
|---|---|---|---|---|---|---|---|---|---|
| | HR | 95% CI | P-value | HR | 95% CI | P-value | HR | 95% CI | P-value |
| Multivariate analysis for RFS | | | | | | | | | |
| Age ≥75/<75 (Years) | 2.28 | 1.05-4.85 | 0.039 | 2.23 | 1.01-4.74 | 0.046 | 2.20 | 1.00-4.69 | 0.050 |
| Lymph Node Metastasis Positive/Negative | 2.30 | 1.09-4.89 | 0.029 | 2.80 | 1.31-5.98 | 0.008 | 2.86 | 1.28-6.64 | 0.011 |
| Preoperative Serum CEA ≥5/<5 (ng/mL) | 2.49 | 1.17-5.35 | 0.017 | 2.60 | 1.23-5.59 | 0.013 | 2.67 | 1.24-5.85 | 0.013 |

TABLE 6-continued

Multivariate analyses of RFS and OS using Cox proportional hazard model

| Variables | CCAT1 | | | CCAT2 | | | CCAT1 + CCAT2 | | |
|---|---|---|---|---|---|---|---|---|---|
| | HR | 95% CI | P-value | HR | 95% CI | P-value | HR | 95% CI | P-value |
| LncRNA expression High/Low | 2.52 | 1.07-5.56 | 0.036 | 2.39 | 1.10-5.08 | 0.029 | 2.60 | 1.04-6.06 | 0.042 |
| Multivariate analysis for OS | | | | | | | | | |
| Vascular Invasion Positive/Negative | 3.73 | 0.75-67.7 | 0.124 | 3.84 | 0.76-69.9 | 0.116 | 3.97 | 0.78-72.5 | 0.107 |
| Lymph Node Metastasis Positive/Negative | 0.65 | 0.25-2.22 | 0.447 | 0.66 | 0.25-2.26 | 0.469 | 0.60 | 0.22-2.06 | 0.375 |
| Stage III-IV/I-II | 9.07 | 2.31-31.2 | 0.003 | 7.86 | 2.01-26.8 | 0.005 | 9.94 | 2.52-34.5 | 0.002 |
| Preoperative Serum CEA ≥5/<5 (ng/mL) | 2.26 | 1.15-4.73 | 0.017 | 2.25 | 1.14-4.71 | 0.019 | 2.27 | 1.15-4.77 | 0.017 |
| LncRNA expression High/Low | 5.90 | 2.09-24.7 | <0.001 | 2.40 | 1.22-4.59 | 0.011 | 8.38 | 2.68-37.0 | <0.001 |

RFS: recurrence free survival, OS: overall survival, HR: hazard ration, CI: confidence interval, CEA: carcinoembryonic antigen 7. A RFS Prediction Model Highlighted the Prognostic Potential of CCAT1 and CCAT2 in Colorectal Cancer The inventors constructed a RFS prediction model with various combinations of parameters including serum CEA and the expression levels of CCAT1 and CCAT2 using the Cox proportional hazard model, in which the area under the curves (AUCs) for each variable were compared by constructing ROCs for 5 years' recurrence in 80 stage I-III CRC patients (53 non-recurrence with follow-up >5 years and 27 recurrence within 5 years) (FIG. 34B). The combination of CCAT1, CCAT2 and CEA expression yielded the greatest AUC of 0.793 (95% CI: 0.687-0.876). Thereafter, the inventors evaluated the RFS using this model in stage II and stage III CRC patients separately. This model efficiently distinguished RFS in both stage II and stage III CRC patients by employing the Kaplan-Meier curve analysis (P=0.034 and 0.001, respectively, FIG. 34C).

C. Discussion

In the current example, the inventors, for the first time, have performed a comprehensive investigation on the clinical significance of lncRNAs mapped to the 8q.24.21 locus 'gene desert', in CRC. It was found that five of the twelve lncRNAs in this locus were upregulated in CRC, and among them, high expression of CCAT1 and CCAT2 significantly associated with poor RFS and OS in CRC patients, in two independent cohorts. This example provides first clinical validation to suggest that CCAT1 and CCAT2 play an essential role in CRC progression, which may in part me mediated through their interactions with MYC.

Following a potentially curative surgery, approximately 30% of CRC patients will often eventually develop metastases, in spite of adjuvant therapies, such as chemotherapy and radiochemotherapy. Although adjuvant chemotherapy provides significant survival benefit in stage III patients, its clinical significance is stage II CRCs remains controversial, since 20-30% of these patients eventually experience tumor relapse. Recently, it was suggested that a subset of stage II CRC patients may benefit from adjuvant chemotherapy, but a priori identification of such patients remains presents a clinical challenge. In this example, the inventors have established a RFS prediction model using a Cox-proportional hazard analysis by utilizing the expression levels of CCAT1 and CCAT2 with serum CEA. It was demonstrated that the combination of CCAT1, CCAT2 and CEA expression levels were the best predictors of RFS. In addition, the model predicted RFS not only in stage III CRC patients, but in stage II CRC patients as well. Hence, the prognostic biomarkers identified in this study, and the novel RFS prediction model may serve as an actionable approach for clinical decision-making for adjuvant therapy in stage II CRC patients.

In conclusion, several lncRNAs located in 8q24.21 are highly expressed in CRC and may be associated with carcinogenesis or tumor progression. Among these overexpressed lncRNAs, the inventors identified that CCAT1 and CCAT2 are associated with tumor recurrence and poor prognoses, and evaluating the expression of these two lncRNAs may provide useful, actionable, biomarkers for predicting tumor recurrence or prognosis in CRC patients.

Example 7—Plasma Levels of piRNAs as Biomarkers for Prognosis and Predicting Tumor Recurrence in Colorectal Cancer Patients Accumulating evidence in recent years indicates that small non-coding RNAs (sncRNAs), such as miRNAs, lncRNAs, snoRNAs and piwi-interacting RNAs (piRNAs), play a central role in many diseases, including cancer. In this regard, although the mechanistic role piRNAs play in cancer pathogenesis continues to evolve, it is believed that they may function just like miRNAs in causing transcriptional repression of gene targets or by inducing hypermethylation of specific tumor suppressor genes. Considering their small size and stability in biological fluids, and lack of any reports for their role as disease biomarkers in cancer, the inventors undertook this study to systematically and comprehensively evaluate the piRNA expression patterns and their biomarker potential in tissue and plasma specimens from colorectal cancer (CRC) patients.

The inventors performed a discovery phase by performing statistical analysis on RNA-Seq data from TCGA, to identify differentially expressed piRNAs between early (stage I/II) vs. late (stage IV) CRCs. Thereafter the inventors evaluated the clinical significance of these piRNAs in 405 surgically resected tissue and 145 plasma samples from two, independent patient cohorts (testing: n=202, validation: n=203) by quantitative PCR, and analyzed the results with various clinicopathological features and patient survival.

The inventors identified a panel of 3 piRNAs (piR61919, piR30652, and piR31111), which were significantly up-regulated in cancer vs. matched normal tissues in CRC patients. Kaplan-Meier curves revealed that high piR61919 and piR30652 expression were significantly associated with poor overall survival (p<0.001 and 0.016, respectively), and these results were subsequently validated in an independent validation cohort (p=0.016 and 0.005, respectively). More importantly, high levels of piR61919 and piR30652 in plasma specimens significantly associated with poor recurrence free survival (p=0.029 and <0.001, respectively) in stage II-III CRC patients. A Cox regression model which included combined expression levels of piR61919 and piR30652 revealed a robust AUC value of 0.779 to predict 5 years' recurrence in stage II-III CRC patients.

The inventors, for the first time, demonstrate that piR61919 and piR30652 expression levels in tissue, but more intriguingly in plasma, may serve as novel and clinically useful biomarkers to predict prognosis and tumor recurrence in CRC.

Example 8: Gene-Specific 5hmC Levels as Biomarkers for Disease Progression and Survival in Colorectal Cancer Aberrant DNA demethylation, constitutes an important epigenetic alteration in various diseases including cancer. Active demethylation of methylated cytosine (5mC) involves TET genes-mediated generation of intermediates such as 5hmC, 5fC and 5caC (FIG. 39). Among these intermediaries, 5hmC is relatively abundant in human genome and is pivotal in cellular functioning because of its association with DNA repair genes and other DNA binding proteins. Recent reports have suggested global depletion of 5hmC levels in multiple cancers. However, since alterations in 5hmC content on a gene-specific level has important functional consequences and potential clinical significance, the inventors undertook the present study to examine and compare global and gene-specific 5hmC levels in colorectal cancer (CRC) and their prognostic implications.

Global 5hmC levels were measured in matched tumor and adjacent normal samples in two CRC patient cohorts (n=25 and 100) by ELISA. The gene expression data (shown as log fold change of 5hmC for the two cohorts are shown in FIGS. 40-42 and 46-47. Eight candidate genes were selected for gene-specific 5hmC level measurements based on publicly available datasets and their functional role in CRC pathogenesis (P2RX4, PTAFR, CRISPLD2, FKBP4, PDE4DIP, VHL, TGFBI and SFRP2). Gluc-MS-qPCR was performed for gene-specific 5hmC measurement. Wilcoxon signed rank test along with survival analyses were performed, and TCGA dataset was analyzed for expression profiles of significantly altered genes.

Global 5hmC levels were significantly lower in cancer vs. normal tissues in CRC patients (p<0.001). Stage-wise decrease in gene-specific 5hmc levels (trend test p values <0.001 for P2RX4, SFRP2, CRISPLD2 and FKBP4) was observed. While the inventors did not observe any prognostic role of global 5hmC levels, lower 5hmC levels in P2RX4, CRISPLD2 and FKBP4 were significantly associated with poor overall survival (p=0.02, p=0.02 and p=0.006 respectively) (FIGS. 43 & 48). Furthermore multivariate Cox regression analysis showed FKBP4 to be an independent prognostic factor for overall survival (p=0.008). Lower levels of gene-specific 5hmC content significantly correlated in patients with distant metastasis (CRISPLD2, p=0.008; FKBP4, p=0.004), while lower global 5hmC content together with 5hmC levels of two candidate genes were associated with liver metastasis (Global 5hmC, p=0.04; CRISPLD2, p=0.009 and FKBP4, p=0.01) (FIG. 45). A large majority of lymph node positive samples (31/40) had significantly lower levels of P2RX5-specific 5hmC (p=0.02). TCGA dataset showed reduced expression of P2RX4, CRISPLD2 and SFRP2 (p<0.001; p=0.008; p<0.001 respectively), which corroborated with the hypothesis.

ROC curves were conducted for the association of the biomarkers with poor prognosis in colorectal cancer. The AUC values are shown below:

| Biomarker | AUC |
| --- | --- |
| Global 5 hmC modification | 0.75 |
| P2RX4 5 hmC modification | 0.81 |
| SFRP2 5 hmC modification | 0.76 |
| CRISPLD2 5 hmC modification | 0.79 |
| FKBP4 5 hmC modification | 0.66 |
| Combination of global, P2RX4, CRISPLD2, and FKBP4 | 0.89 |
| Combination of global, P2RX4, SFRP2, CRISPLD2, and FKBP4 | 0.92 |

Global 5hmC levels were significantly lower in CRC tissues compared to normal specimen. In particular, gene-specific 5hmC levels emerged as superior prognostic biomarkers in CRC patients, and may serve as important clinical tools for determining patient survival and improving patient management.

Example 9: ITGBL1 is a Novel Epithelial Mesenchymal Transition-Associated Prognostic Biomarker in Colorectal Cancer Colorectal cancer (CRC) ranks as the third leading cancer worldwide, and its incidence continues to rise gradually, highlighting the need to stratify the risk of recurrence after curative surgery. Recently, several genes have been identified which appear to associate with metastasis, as they mediate epithelial-to-mesenchymal transition (EMT) in cancer. This study aimed to identify novel EMT and cancer recurrence-associated biomarkers through systematic and comprehensive discovery and validated strategy in multiple, independent CRC cohorts.

Two independent gene expression microarray datasets (n=173 and n=307 respectively) were used to identify novel metastasis-recurrence biomarkers for CRC. Following carefully selection and prioritization of biomarkers, the inventors selected a candidate gene and validated its performance as a recurrence marker in a large testing cohort (n=566), and two independent clinical validation cohorts (n=201, n=475, respectively). To confirm the protein expression of ITGBL1 in cancer, immunohistochemistry (IHC) was performed in paired 33 primary CRCs and adjacent normal mucosa, as well as a subset of liver and lung metastases tissues. In addition, we used Gene Set Enrichment Analysis (GSEA) to determine the functional role of ITGBL1 in CRC.

During the discovery step, gene expression profiles from differentially expressed genes between recurrence positive and negative primary CRCs, as well as evaluation of the metastatic sites compared with primary CRC, identified ITGBL1 as a most promising candidate biomarker. High expression of ITGBL1 associated with poor overall survival (OS) in stage I-IV patients and worse disease-free survival (DFS) in stage I-III patients. Subgroup validation of these results in two large and independent patient cohorts confirmed these findings and demonstrated that high ITGBL1 expression correlated with shorter DFS in stage II and III CRC patients. In addition, high ITGBL1 expression emerged as an independent prognostic factor for DFS in stage II and III patients. IHC analysis revealed that both early stage CRCs and adjacent normal colonic mucosa displayed low ITGBL1 expression, while ITGBL1 expression gradually increased from tumor surface to the invasive front in late stage cancer, indicating that ITGBL1 may facilitate EMT process and promote a more aggressive phenotype in CRC.

High expression of ITGBL1 in primary tumors was associated with tumor recurrence in CRC patients after curative surgery. Collectively, we have identified ITGBL1 as a novel EMT-associated biomarker which could be used for risk stratification for metastatic potential in CRC.

Example 10: piRACC, a Novel Oncogenic piRNA, Promotes Tumor Progression and Predicts Unfavorable Prognosis in Colorectal Cancer Colorectal cancer (CRC) constitutes a major heath burden in most western countries. Very recent and relatively limited evidence indicates that piwi-interacting RNAs (piRNAs) play crucial roles in several types of cancers. However, the biological involvement of piRNAs in colorectal carcinogenesis remains elusive. In this study, the inventors performed systematic piRNA expression profiling between CRC and paired normal tissues by small RNA-Seq, and identified piRNA DQ570994 (named as piRACC for piRNA Associated with Colorectal Cancer), as a novel, differentially expressed piRNA in CRC. piRACC was found to be frequently overexpressed in CRC tissues from multiple independent patient cohorts (with a 5.49-7.0 fold increase and P<0.01 in each cohort). To interrogate the clinical significance of piRACC in CRC, the inventors evaluated its expression level in 771 CRC patients from a TCGA dataset, a clinical testing cohort and a validation cohort. The overexpression of piRACC was significantly associated with several known clinicopathological risk factors (advanced T-stage, P=0.0008 and P=0.0434 in testing and validation cohort respectively; lymph node involvement, P=0.025 and P=0.0025 in testing and validation cohort respectively; and distant metastasis, P=0.0319 and P=0.0027 in testing and validation cohort respectively), and furthermore, patients with high expression of piRACC had a shorter overall survival compared to those with low expression of piRACC (HR=2.387, P=0.0026 in testing cohort; HR=3.208, P=0.0002 in validation cohort). Multivariate Cox's regression analysis demonstrated that high piRACC expression was an independent predictor for poor overall survival in CRC (HR=1.965, P=0.0298 in testing cohort; HR: 2.9347, P=0.0025 in validation cohort). The inventors supported these findings by performing a series of functional assays and demonstrated that piRACC exerts its oncogenic function through promotion of cell survival, migration and invasion as well as suppression of apoptosis. Consistent with its aggressive biological and clinical phenotype, the inventor's microarray data revealed a subset of genes regulated by piRACC are enriched in cancer-related pathways as indicated by Ingenuity Pathways Analysis (IPA). By using bioinformatics approaches, nine tumor suppressor genes (ATF3, BTG1, DUSP5, FAS, NFKBIA, UPP1, SESN2, TP53INP1 and MDX1) were predicted to be direct potential targets of piRACC due to sequence complementarity. The regulation of the expression of these target genes by piRACC was subsequently validated in CRC cell lines and inversely associated with piRACC expression in CRC tissues. In conclusion, this example, for the first time, has provided evidence for a novel piRNA (piRACC), which promotes CRC pathogenesis and may be an important prognostic biomarker in CRC.

Colorectal cancer (CRC) constitutes a major public heath burden, being the third most commonly diagnosed cancer and the fourth cause of cancer death worldwide. Interestingly, recent reports showed the incidence of colorectal cancer in Asian countries, which were previously considered as low rate, has increased dramatically in last two decades. Considering the mortality and burden of this disease, it is imperative to investigate the prevention and treatment strategies for the management of this malignancy.

CRC develops as a consequence of genetic and epigenetic alterations, which occur with tumor initiation and progression. Due to the molecular heterogeneity, the prognosis and response to chemotherapy between individual patients can vary largely. However, current guidelines selected "risk" patients solely based on clinicopathological factors and intraoperative findings, suggesting potential risk for under or over-treatment for CRC patients. Therefore, readouts of disease biology by novel molecular targets would be of great value in prognosis assessment and/or cancer treatment.

The goals of the study set forth in this example were to systematically and comprehensively interrogate the molecular contributions of the piRNA super family members in colorectal cancer, identify specific piRNAs that aberrantly expressed between tumor and normal tissues, and decipher whether these candidate piRNAs may have translational relevance as clinically relevant disease biomarkers. In addition, to support the clinical findings, the functional and mechanistic role of piRNAs in human colorectal cancer will also be investigated.

A. Methods

1. Patients and Study Design

To identify CRC-associated piRNA, the inventors prepared small RNA sequencing libraries from 4 frozen cancer tissues and paired normal mucosa (NM) specimens, which were collected at the Mie University, Japan. To confirm the expression level of candidate piRNA between cancer and normal tissues, the inventors measured their expression levels in matched cancer and normal frozen tissues from 3 different cohorts of Mie University, Japan (n=20), Shanghai Tenth People's Hospital, China (n=20) and Okayama University Medical Hospital, Japan (n=18). To investigate the prognostic value of candidate piRNAs in CRC, the inventors analyzed piRACC expression pattern in three different cohorts of a combined total of 771 CRC patients from TCGA dataset, clinical testing cohort and validation cohort. The expression profile of piRNAs from TCGA database (n=387) was characterized by Martinez et al. (*Sci Rep* 5, 10423 (2015)). The inventors then analyzed candidate piRNAs expression in clinical testing cohort (n=195, Shanghai Tenth People's Hospital) and a subsequent validation cohort (n=189, Okayama University Medical Hospital). Both testing and validation cohort are FFPE samples. Micro-dissection was performed to enrich tumor cells from the FFPE samples and the baseline characteristic of these patient cohorts is described in Table 1. To further understand the mechanistic correlation of piRNA expression in CRC, the inventors determined its expression pattern in the context of its target genes in fresh frozen samples (n=159). Written informed consent was obtained from all patients and the study was approved by the institutional review boards of all participating institutions. All CRC patients were followed up for survival for at least 5 years duration from their date of surgery. Patients treated with radiotherapy or chemotherapy before surgery were excluded from the study.

3. piRNA Quantification by qRT-PCR

Expression of identified piRNAs (DQ593356, DQ596309, DQ593752 and DQ570994) was analyzed using Custom TaqMan small RNA assays (Applied Biosystems,

TABLE 1

Clinicopathological characteristic and piRACC expression in testing and validation cohort

| | Testing cohort | | | | Validation cohort | | | |
|---|---|---|---|---|---|---|---|---|
| | Cases | Low | High | P[c] | Cases | Low | High | P[c] |
| Gender | | | | | | | | |
| Male | 91 | 45 | 46 | 0.9391 | 110 | 52 | 58 | 0.4255 |
| Female | 104 | 52 | 52 | | 79 | 42 | 37 | |
| Age | | | | | | | | |
| ≤69[a]/66[b] | 100 | 55 | 45 | 0.133 | 100 | 45 | 55 | 0.1687 |
| >69766[b] | 95 | 42 | 53 | | 89 | 49 | 40 | |
| Tumor location | | | | | | | | |
| Distal | 150 | 82 | 68 | *0.0123 | 121 | 55 | 66 | 0.1174 |
| Proximal | 45 | 15 | 30 | | 68 | 39 | 29 | |
| Histological type | | | | | | | | |
| Well/moderate | 175 | 90 | 85 | 0.0566 | 180 | 90 | 90 | 0.7456 |
| Poor | 18 | 5 | 13 | | 9 | 4 | 5 | |
| Unknown | 2 | — | — | | — | — | — | |
| Pathological T category | | | | | | | | |
| pT1-3 | 48 | 34 | 14 | **0.0008 | 154 | 82 | 72 | *0.0434 |
| pT4 | 147 | 63 | 84 | | 35 | 12 | 23 | |
| Lymph node metastasis | | | | | | | | |
| Negative | 132 | 73 | 59 | *0.025 | 85 | 53 | 32 | **0.0025 |
| Positive | 63 | 24 | 39 | | 100 | 40 | 60 | |
| Unknown | — | — | — | | 4 | — | — | |
| Distant metastasis | | | | | | | | |
| Negative | 187 | 96 | 91 | *0.0319 | 143 | 80 | 63 | **0.0027 |
| Positive | 8 | 1 | 7 | | 46 | 14 | 32 | |
| Stage | | | | | | | | |
| I | 29 | 21 | 8 | **0.006 | 28 | 18 | 10 | **0.0052 |
| II | 99 | 51 | 48 | | 53 | 33 | 20 | |
| III | 59 | 24 | 35 | | 62 | 29 | 33 | |
| IV | 8 | 1 | 7 | | 46 | 14 | 32 | |

[a]The median age of testing cohort is 69.
[b]The median age of validation cohort is 66.
[c]Pearson chi-squared testing was used - compare the correlation between piRACC expression and clinical variables.
*P < 0.05;
**P < 0.01.

2. Small RNA-Seq Analysis

For RNA-seq, 1 μg of total RNA was used for library preparation with Illumina TruSeq small RNA sample preparation Kit. Linker sequences were trimmed off from the 50 nucleotide raw sequences by using fastx_clipper with at least 8 basepair match. All the trimmed sequences must be not shorter than 9 nucleotides long. Next, the trimmed sequences were filtered by human miRNAs reported by mirBase. The remaining small RNAs that could be mapped to human genome hg38 were matched to known piRNAs collected from piRNA bank (found on the web at pirnabank.ibab.ac.in) and pirbase (see for example, the world wide web at regulatoryrna.org/database/piRNA/) databases. DESeq was employed to identify differentially expressed piRNAs in colorectal cancer patients (with ≥2 fold change and P-value≤0.01).

Foster City, Calif., USA), and U6 expression was used as an endogenous control for data normalization, as described previously. The average expression levels of tissue piRNAs were normalized against U6 using the $2^{-\Delta Ct}$ method.

4. Gene Expression Analysis by Quantitative Reverse Transcription Polymerase Reaction (qRT-PCR)

The qRT-PCR assays were performed using QuantStudio 6 Flex Real-Time PCR System (Applied Biosystems Foster City, Calif.). 500 ng of total RNA was converted to cDNA using High-Capacity cDNA Reverse Transcription Kit (Applied Biosystems, Foster City, Calif.). Real-time PCR was thereafter performed using Fast SYBR Green Master Mix (Applied Biosystems, Foster City, Calif.). The relative expression of target genes was determined by $2^{-\Delta Ct}$ method. GAPDH were used as normalizers. The primer sequences used are shown in Table 2:

TABLE 2

Primers sequence

| Gene | Forward (5'→3') | SEQ ID NO: | Reverse (5'→3') | SEQ ID NO: |
|---|---|---|---|---|
| MXD1 | GCTGAACATGGTTATGCCTCC | 29 | AGCCCGTCTATTCTTCTCCATTTC | 30 |
| DUSP5 | TCCTGAGTGTTGCGTGGATG | 31 | GGGCCACCCTGGTCATAAG | 32 |
| BTG1 | GGAGCTGCTGGCAGAACATTA | 33 | GTGCTGCCTGTCCAATCAGA | 34 |
| TP53INP1 | CTCACGGGCACAGAAGTGGAA | 35 | ATCCACTGGGAAGGGCGAA | 36 |
| FAS | GTACGGAGTTGGGGAAGCTC | 37 | ACAGACGTAAGAACCAGAGGT | 38 |
| SENS2 | TCGCTCTCCTCCTTCGTGTT | 39 | TCAAAGCCCCAGAGTTGTTC | 40 |
| NFKBIA | CCCCTACACCTTGCCTGTG | 41 | CACGTGTGGCCATTGTAGTTG | 42 |
| UPP1 | GAGTGGGCTTGGTGAGGTG | 43 | CAGGACCCGTCAGAGGAGAG | 44 |
| ATF3 | GCCGAAACAAGAAGAAGGAGA | 45 | TCGTTCTTGAGCTCCTCAATC | 46 |
| GAPDH | TGTAGTTGAGGTCAATGAAGGG | 47 | ACATCGCTCAGACACCATG | 48 |

5. Cell Lines, RNA Oligos, Antisense and Transfection

HCT116 and SW480 were obtained from the American Type Culture Collection (ATCC, Rockville, Md.) and cultured in Iscove's modified Dulbecco's medium (Invitrogen, Carlsbad, Calif.) supplemented with 10% fetal bovine serum (FBS) and antibiotics (100 U/ml penicillin and 100 g/ml streptomycin) at 37° C. in 5% humidified C02 atmosphere. These cell lines were periodically authenticated using a panel of genetic and epigenetic biomarkers.

For the overexpression of piRACC in CRC cell lines, HCT116 and SW480 were transfected in biological triplicate with either a single-stranded RNA oligos (5'AGC CCU GAU GAU GCC CAC UCC UGA GC-3' (SEQ ID NO:49) with 2'-O-methylated 3'-end) or a single-stranded scrambled RNA control (5'-UCA CAA CCU CCU AGA AAG AGU AGA-3' (SEQ ID NO:50) with 2'-O-methylated 3'-end). For the inhibition of piRACC in CRC cell lines, the antisense were designed as described previously. The 2'-O-Me-modified antisense sequence was 5'-CUUA GCT CAG GAG TGG GCA TCA TCA GGG CT ACCUU-3', (SEQ ID NO:51) while negative scrambled control was 5'-CUUA TC aGG ACT gCT ACt GGT GcG GAC gCG ACCUU-3' (SEQ ID NO:52).

For the transfections, colorectal cancer cells were transfected with RNA oligos or antisense at a final concentration of 100 nmol/L using Lipofectamine RNAi MAX(Invitrogen) and Opti-MEM (Gibco) according to the manufacturer's instructions.

6. MTT and Colony Formation Assay

MTT (3-(4,5-dimethylthiazol-2-yl)-2,5-diphenyltetrazolium bromide) assay (Sigma, St. Louis, Mo., USA) was used to evaluate cell proliferation. Cells were seeded at 1×10³ cells per well in 96 well plates. MTT was added at 0 h-, 24-, 48h-, 72h-hour time-points. Absorbance was read at 570 nm using Infinite 200 Pro multi-reader (Tecan Group Ltd, Morrisville, N.C.). For colony formation assay, 500 cells were seeded in each well of 6 well plates and incubated for 10 days. The colonies were stained with crystal violet and counted.

7. Cell Invasion, Migration and Apoptosis Assay

Migration and invasion assays were performed using Boyden chambers (Corning, Corning, N.Y.) using 8 µm-size pore membrane coated with matrigel (for invasion assays) or without matrigel (for migration assays). Transfected cells in serum-free medium were seeded onto each insert at a density of 2×105 cells/insert, with culture medium containing 10% FBS in the bottom well. Following 24h incubation, non-invading cells were removed by scraping the top of the membrane. Invaded cells on the bottom of the membrane were then fixed and stained using diff-quick staining kit (Thermo Scientific, Rockford, Ill.). Stained cells were counted using a light microscope. For apoptosis assays, Muse Annexin V and dead cell kit (Millipore, Billerica, Mass.) were used according to the manufacturer's instructions.

8. Immunofluorescence (IF)

For IF, cells were fixed by 4% paraformaldehyde for 15 min, washed with PBS and blocking buffer (3% FBS, 1% heat-inactivated sheep serum, 0.1% Triton X-100), and then incubated overnight at 4° C. in primary antibodies against Ki-67 (Santa Cruz, Dallas, Tex.) Fluorescent Alexa Fluor 488- conjugated secondary antibodies (Thermo Scientific, Rockford, Ill.) were used for detection. The ki-67 staining intensity was semi-quantified as − for negative staining, ± for very weak staining, + for weak staining and ++ for strong staining.

9. Microarray Preparation and Analysis

To investigate regulatory role of piRACC on whole-genome mRNAs, HCT116 cells were treated with or without piRACC antisense, and subsequently performed Affymetrix GeneChip Human gene 2.0 ST array. The microarray probe intensity values (CEL files) were background-corrected and normalized by Robust Multiarray Average (RMA) method. Comparison analysis was performed by using limma package to assess the differentiation expression of mRNAs. The genes with ≥1.5 fold change and P-value≤0.01 were selected as differentially expressed. GO analysis was performed in DAVID for the differentially expressed genes to evaluate the enrichment of certain functions. To get insights into piRACC related disease and function networks, QIAGEN's Ingenuity Pathway Analysis (see for example, qiagen.com/ingenuity on the world wide web) was performed.

10. Targets Prediction

To predict the potential targets of piRACC, Miranda v3.3a and RNA22 was used to search for targets against all human transcripts.

11. Statistical Analysis

All statistical analyses were performed using GraphPad Prism version 6.0 or Medcalc version 12.3 programs. Data were expressed as Mean±SD. Statistical differences between groups were determined by Wilcoxon's signed rank test, the $\chi^2$ test or Mann-Whitney U test. Kaplan-Meier analysis and log-rank test was used to estimate and compare survival rates of CRC patients with high and low piRACC expression. ROC curves were established to determine the cutoff values to discriminate patients with or without death. The Cox's proportional hazards models were used to estimate hazard ratios (HRs) for death. All P values were 2-sided, and those less than 0.05 were considered statistically significant.

B. Results

1. Identification of Cancer-Related piRNAs in CRC

The inventors found the mRNA and protein level of PIWIL1 and PIWIL4, two major PIWI protein members, were significantly overexpressed in CRC tissues compared to normal tissues, suggesting piRNAs may be dysregulated and involved in CRC development (Table 3 and FIG. 57). Therefore, small RNA-seq analysis was performed to identify CRC-associated piRNA. The small RNA sequencing libraries were prepared from 4 cancer tissues and paired normal mucosa (NM) specimens. The results showed that 4 piRNAs (DQ593356, DQ596309, DQ593752 and DQ570994) were differentially expressed between cancer and normal tissues (with ≥2 fold change and P value ≤0.01). The expression level of these piRNAs was subsequently validated in a subset of 20 cancer and paired NM specimens from the same cohort. However, similar results were only obtained from DQ570994 and DQ596309 (FIG. 51A). Due to cohort difference and tumor heterogeneity, the expression level of DQ570994 and DQ596309 was further confirmed in 2 additional independent cohorts. Although no significant differences in the expression of DQ596309 was observed, DQ570994 was consistently higher in cancer versus normal tissues, with a 5.49-fold increase (P<0.01) and 7.0 fold change (P<0.01) in each cohort, respectively (FIG. 51B), suggesting piRNA DQ570994 was a potential onco-piRNA in colorectal cancer. The inventors thus named this piRNA as piRACC, an abbreviation of piRNA DQ570994 associated with colorectal cancer.

TABLE 3

| | mRNA level (Oncomine-TCGA) | | Protein level (Protein Atlas) | |
|---|---|---|---|---|
| | Colon adeno-carcinoma vs Normal | Rectal adeno-carcinoma vs Normal | Cancer | Normal Rectal Colon |
| PIWIL1 | | | | |
| Fold Change | 2.465 | 2.240 | 9/12 high | Low in rectal and colon |
| P | $4.12 \times 10^{-9}$ | $7.18 \times 10^{-8}$ | | |

TABLE 3-continued

| | mRNA level (Oncomine-TCGA) | | Protein level (Protein Atlas) | |
|---|---|---|---|---|
| | Colon adeno-carcinoma vs Normal | Rectal adeno-carcinoma vs Normal | Cancer | Normal Rectal Colon |
| PIWIL2 | | | | |
| Fold Change | 1.190 | 1.267 | NA | NA |
| P | 0.068 | 0.223 | | |
| PIWIL3 | | | | |
| Fold Change | 1.005 | 1.046 | NA | NA |
| P | 0.465 | 0.375 | | |
| PIWIL4 | | | | |
| Fold Change | 1.523 | 1.691 | 3/12 high; 2/12 medium | Medium in Rectal; low in colon |
| P | $1.47 \times 10^{-6}$ | $3.26 \times 10^{-8}$ | | |

Figure 52A:
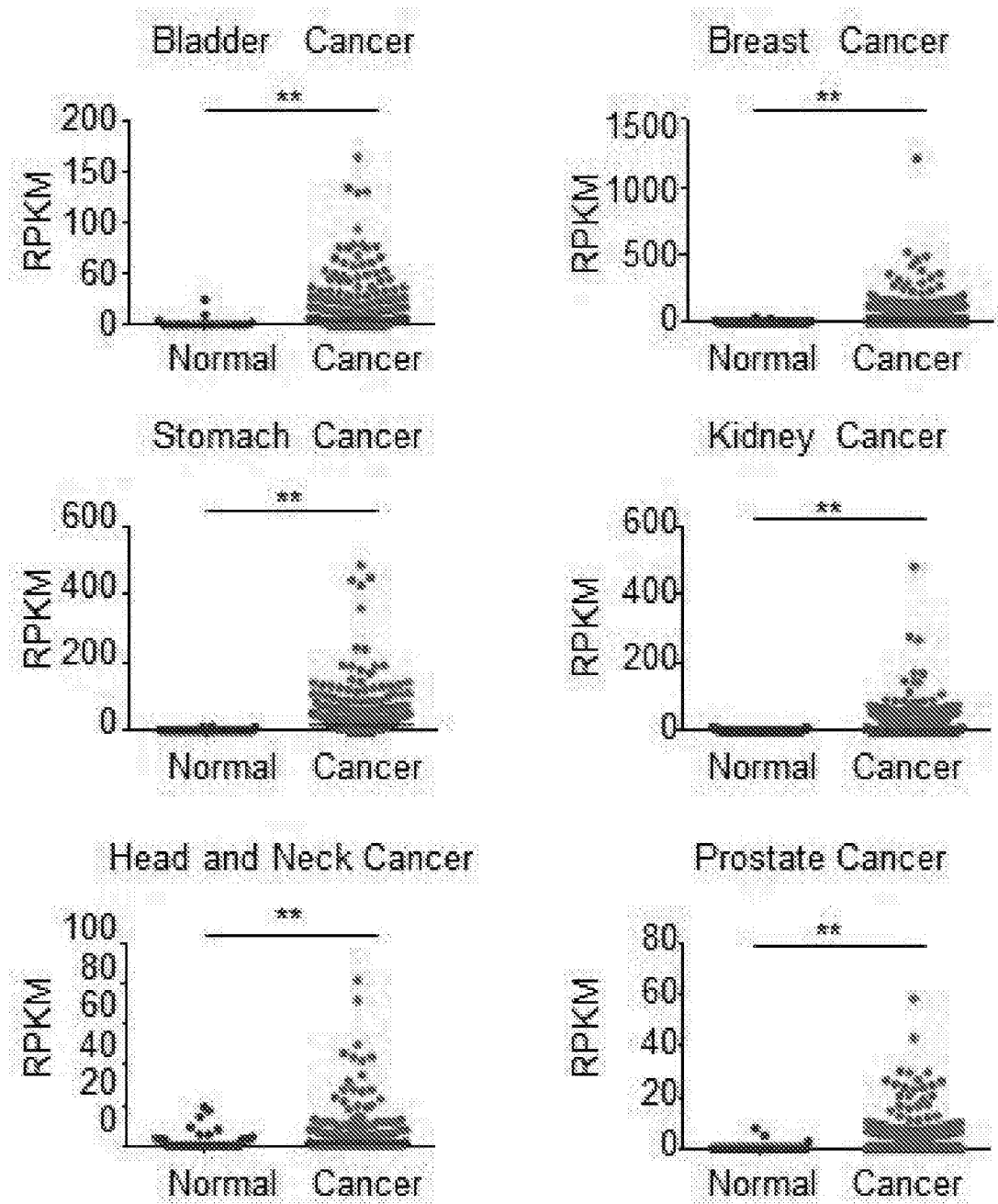
Figure 52B:
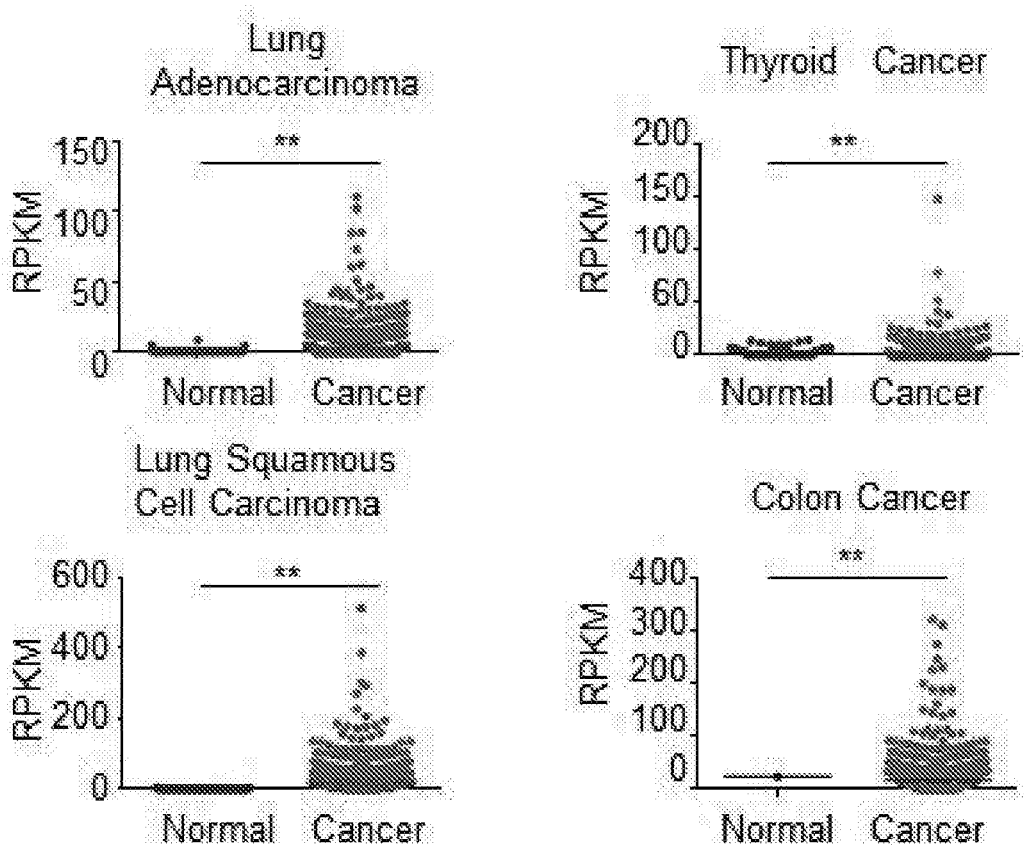

In particular, it was noticed that piRACC was not only overexpressed in CRC but also exhibited pan-cancer pattern expression. In the TCGA datasets, it was found that the expression of piRACC was upregulated in various type of cancer such as lung, breast, stomach, bladder, kidney and prostate cancer, highlighting its important key role in carcinogenesis (FIG. 52A-B).

2. Strong Expression of piRACC Correlates with Known Risk Clinicopathological Factors of CRC The inventors next examined the expression patterns of piRACC with regard to their clinical significance in testing cohort (n=195). The overexpression of piRACC occurred in a stage dependent manner (P=0.006, Table 1). The distal colon or rectal tumor showed higher expression level of piRACC compared to proximal tumor (P=0.0123). Furthermore, higher expression of piRACC was found in cancer tissues with poor differentiation (P=0.0566), advanced T stage (P=0.0008), lymph node metastasis (P=0.025) and distant metastasis (P=0.0319), suggesting that piRACC plays a crucial role in the cancer development.

To further validate the correlation between piRACC expression and clinicopathological variables, the inventors interrogated these associations in an additional cohort (n=189). The inventors were able to successfully validate that the upregulated piRACC is associated with advanced T-stage (P=0.0434), lymph node (P=0.0025) and distant metastasis (P=0.0027). Collectively, the analyses showed evidence that expression of piRACC is overabundant in tumors with high risk clinicopathological features.

3. High Expression of piRACC Associates with Poor Prognosis in Colorectal Cancer Patients To interrogate the impact of piRACC expression on prognosis in CRC patients, piRACC expression pattern were analyzed in three different cohorts of a combined total of 771 CRC patients from the TCGA datasets, clinical testing cohort and validation cohort. In the TCGA dataset, piRACC-high expression group showed a strong tendency to be associated with poor OS (P=0.0802, HR=1.604; FIG. 52C). Therefore, the prognostic potency of piRACC was examined in a testing cohort of high quality tissues with complete follow-up clinical data. As expected, piRACC-high expression group significantly correlated with poor OS (P=0.0026, HR=2.387; FIG. 52D), suggesting piRACC could be used as prognostic biomarker for CRC patients. To further confirm the prognostic of piRACC in CRC patient survival, this association was investigated in an additional cohort. In agreement with other results, piRACC-high expression groups demonstrated shorter OS (P=0.0002, HR=3.208; FIG. 52D), highlighting its clinical relevance as independent prognostic biomarker in CRC patients. Furthermore, multivariate cox's regression analysis revealed that high piRACC expression was an independent predictor for poor prognosis in both clinical testing and validation cohort (HR: 1.965, 95% CI: 1.0683 to 3.6144, P=0.0298, HR: 2.9347, 95% CI: 1.4584 to 5.9057, P=0.0025, respectively, Table 4). Taken together, these findings elucidate that overexpression of piRACC has clinical significance, and can serve as potential prognostic biomarker in CRC patients.

FIG. 53B, inhibition of piRACC in HCT116 and SW480 cells demonstrated significantly reduced number of colonies compared to control cells, while up-regulation of piRACC markedly increased colonies. In line with above findings, inhibition of piRACC significantly reduces the percent of Ki-67 strong positive colon cancer cells, suggesting that piRACC functions as a positive regulator of cell survival (FIG. 53C).

Since high expression of piRACC is associated with lymph node and distant metastasis, it was assumed that piRACC may regulate cell migration and invasion as well. As illustrated in FIG. 53D and, inhibition of piRACC

TABLE 4

Univariate and multivariate analysis for predictors of overall survival in testing and validation cohort

| | Univariate survival analysis | | | Multivariate survival analysis | | |
|---|---|---|---|---|---|---|
| | HR | 95% CI | P | HR | 95% CI | P |
| Testing cohort | | | | | | |
| Gender(Male) | 0.8471 | 0.4948-1.4500 | 0.545 | | | |
| Age(>69) | 1.9063 | 1.0970-3.3125 | *0.0221 | | | |
| Tumor location (Proximal) | 2.3263 | 1.3379-4.0449 | **0.0028 | | | |
| Histological type (Poor) | 2.1597 | 1.0165-4.5887 | *0.0452 | 1.945 | 0.9003-4.2019 | 0.0905 |
| T classification (pT4) | 2.6736 | 1.2045-5.9346 | *0.0156 | 2.1501 | 0.9431-4.9017 | 0.0687 |
| Node involvement (Present) | 1.6608 | 0.9700-2.8434 | 0.0644 | 1.3642 | 0.7813-2.3820 | 0.2748 |
| Distant metastasis (Present) | 4.8339 | 2.0511-11.3923 | **0.0003 | 4.796 | 1.9696-11.6786 | **0.0006 |
| piRACC expression level (High) | 2.387 | 1.3300-4.2838 | **0.0035 | 1.965 | 1.0683-3.6144 | *0.0298 |
| Validation cohort | | | | | | |
| Gender(Male) | 1.1471 | 0.7592-1.7334 | 0.5145 | | | |
| Age(>69) | 1.077 | 0.6065-1.9124 | 0.8002 | | | |
| Tumor location (Proximal) | 0.7355 | 0.3972-1.3619 | 0.3284 | | | |
| Histological type (Poor) | 3.7535 | 1.4754-9.5487 | **0.0055 | 3.4914 | 1.2996-9.3799 | *0.0132 |
| T classification (pT4) | 3.61 | 2.0014-6.5114 | **<0.0001 | 2.2202 | 1.1551-4.2673 | *0.0167 |
| Node involvement (Present) | 1.921 | 1.2479-2.9573 | **0.003 | 1.2908 | 0.5790-2.8776 | 0.5326 |
| Distant metastasis (Present) | 8.1136 | 4.4863-14.6739 | **<0.0001 | 4.7427 | 2.3622-9.5220 | **<0.0001 |
| piRACC expression level (High) | 3.208 | 1.6989-6.0578 | **0.0003 | 2.9347 | 1.4584-5.9057 | **0.0025 |

HR: Hazard ratio;
*P < 0.05;
**P < 0.01.

4. piRACC has Multiple Functional Roles in Colorectal Cancer Cells to Promote Tumor Progression Since high expression of piRACC indicates aggressive clinical behavior in CRC patients, it was questioned whether piRACC affects biological characteristics. Several functional assays were performed to determine phenotypic alterations following overexpression or inhibition of piRACC in colon cancer cell. MTT assay was employed to determine the proliferation rates of colon cancer cells transfected with piRACC oligos or antisense. The results showed inhibition of piRACC had a pronounced suppression effect on the proliferation of HCT116 and SW480 cells, and in contrast, overexpression of piRACC enhanced cell proliferation (FIG. 53A). Meanwhile, colony formation assays were performed to evaluate the effect of piRACC on the colony-forming ability of single cells in vitro. As shown in significantly suppressed cell migration and invasion capabilities of both HCT116 and SW480 cells compared to the control cells.

Figure 53E:
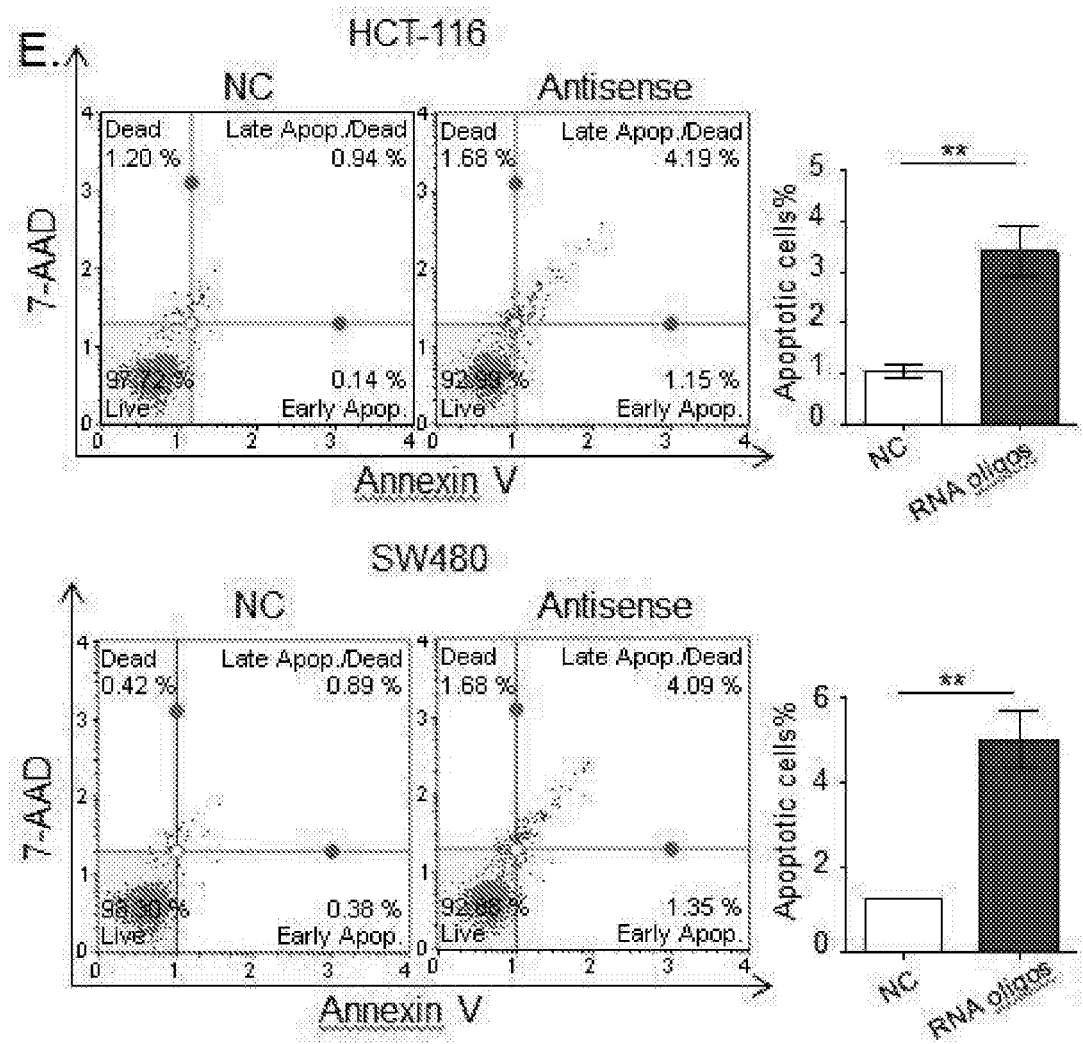

Resistance of programmed cell death is recognized as one of the cancer hallmarks to contribute to tumor metastasis. Based on the clinical data, it was hypothesized that piRACC also plays a key role in apoptosis resistance in colorectal cancer. In line with the hypothesis, inhibition of piRACC significantly induces apoptosis in HCT116 and SW480 cells (FIG. 53E). Collectively, the data showed newly discovered piRACC exert oncogenic function in CRC through promotion of cell survival, migration and invasion as well as suppression of apoptosis.

5. piRACC Affects Multiple Cancer-Related Pathways Involved in Cell Proliferation, Cell Death and Apoptosis To address the oncogenic mechanism of piRACC in CRC, the impact of piRACC on transcriptomes in CRC cell lines was investigated. HCT116 cells were treated with or without piRACC antisense and subsequently performed microarray analysis. It was found that a total of 244 mRNAs were detected to be differentially expressed with fold change ≥1.5 and P≤0.01. Notably, 168 genes were found upregulated, while 76 genes were downregulated in piRACC-inhibited cells compared to control cells.

KEGG pathway analysis showed the up-regulated genes are enriched in p53 pathway, MAPK pathway and cancer pathway (FIG. 55C). Strikingly, the top 10 GO term enrichment analysis for upregulated genes favored cell death or apoptosis, cell proliferation, protein metabolic process and protein (FIG. 55D)., while the downregulated genes were enriched with genes related to chromatin assembly and catalytic activity (FIG. 58).

In order to get insights into disease and function networks, Ingenuity Pathway Analysis (IPA) was performed based on the microarray data. The results disclosed that activated p53 pathway, which was induced by piRACC inhibition, led to cell apoptosis, necrosis, cell death, contact growth inhibition, senescence of cells, and inhibited cell proliferation, colony formation (FIG. 54C). Furthermore, IPA showed the piRACC acts as important regulator in cell death and survival (data not shown). Based on these findings, these biological process and molecular function could contribute to the development of CRC.

6. Identification of piRACC Target mRNAs in CRC

A growing body of studies showed piRNAs have the capabilities to bind to diverse mRNAs and form specific RNA silencing complexes (pi-RISC), leading to RNA repression via imperfect base-pairing between the two RNAs. The inventors thereafter searched potential target sites of piRACC from the upregulated genes. miRANDA and RNA22 tool was used, applying stringent thermodynamic parameters and binding energy thresholds, to predict biologically relevant RNA-RNA interactions. It was found that there are 9 potential targets complementary to piRACC. The examples of piRNA:RNA complementarities identified by this approach are shown in FIG. 55A and FIGS. 59-60. These genes have been reported to be involved in key cellular processes in CRC, including cell death and survival, cell cycle, DNA replication and repair or cell-cell communication (Table 5). The inventors further performed qPCR to confirm the expression change of target genes after piRACC overexpression or knockdown in HCT116 and SW480 cells and were able to successively validate these findings, highlighting that piRACC serves as a master oncogenic regulator in CRC.

TABLE 5

The function of piRACC targets and their expression in CRC

| Gene | Expression* | Function** | Process** | Component** |
|---|---|---|---|---|
| MXD1 | down | RNA polymerase II core promoter proximal region sequence-specific DNA binding protein binding protein dimerization activity transcription cofactor activity transcription corepressor activity transcription factor activity, sequence-specific DNA binding transcriptional repressor activity, RNA polymerase II core promoter proximal region sequence-specific binding | cell proliferation multicellular organism development negative regulation of transcription from RNA polymerase II promoter transcription, DNA-templated | nuclear chromatin nucleus |
| DUSP5 | down | MAP kie tyrosine/serine/threonine phosphae activity phosphae activity protein binding protein tyrosine phosphae activity protein tyrosine/serine/threonine phosphae activity protein tyrosine/serine/threonine phosphae activity | MAPK cascade activation of MAPK activity dephosphorylation endoderm formation inactivation of MAPK activity peptidyl-threonine dephosphorylation peptidyl-tyrosine dephosphorylation protein dephosphorylation | nucleoplasm |
| BTG1 | down | enzyme binding kie binding protein binding transcription cofactor activity | cell migration negative regulation of cell growth negative regulation of cell proliferation positive regulation of angiogenesis positive regulation of endothelial cell differentiation positive regulation | cytoplasm cytoplasm nucleus nucleus |

TABLE 5-continued

The function of piRACC targets and their expression in CRC

| Gene | Expression* | Function** | Process** | Component** |
|---|---|---|---|---|
| | | | of fibroblast apoptotic process positive regulation of myoblast differentiation positive regulation of myoblast differentiation regulation of transcription, DNA-templated | |
| TP53INP1 | down | antioxnt activity protein binding | apoptotic process autophagic cell death autophagosome assembly cell cycle arrest cellular oxnt detoxification cellular response to cellular response to ethanol cellular response to hydroperoxide cellular response to methyl methanesulfonate negative regulation of cell migration negative regulation of cell proliferation positive regulation of apoptotic signaling pathway positive regulation of autophagy positive regulation of transcription, DNA-templated regulation of apoptotic process regulation of signal transduction by p53 class mediator response to heat response to stress transcription, DNA-templated | PML body autophagosome cytoplasm cytoplasmic vesicle cytosol nucleoplasm nucleus |
| FAS | down | identical protein binding kie binding protease binding protein binding protein complex binding receptor activity signal transducer activity tumor necrosis factor-activated receptor activity | B cell mediated immunity activation of cysteine-type endopeptse activity involved in apoptotic process activation of cysteine-type endopeptse activity involved in apoptotic signaling pathway activation-induced cell death of T cells aging apoptotic process apoptotic signaling pathway brain development cellular response to cobalt ion cellular response to estrogen stimulus cellular response to glucose stimulus cellular response to hydrogen peroxide | CD95 death-inducing signaling complex apical dendrite apical plasma membrane cell surface cytoplasm cytosol death-inducing signaling complex external side of plasma membrane extracellular exosome extracellular space integral component of plasma membrane membrane raft neuron projection neuronal cell |

TABLE 5-continued

The function of piRACC targets and their expression in CRC

| Gene | Expression* | Function** | Process** | Component** |
|---|---|---|---|---|
| | | | cellular response to hydrostatic pressure | body nucleus |
| | | | cellular response to hyperoxia | nucleus perinuclear |
| | | | cellular response to hypoxia | region of cytoplasm |
| | | | cellular response to interleukin-1 | plasma membrane |
| | | | cellular response to lithium ion | plasma membrane |
| | | | cellular response to mechanical stimulus | plasma membrane |
| | | | cellular response to phenylalanine | |
| | | | chordate embryonic development | |
| | | | circadian rhythm | |
| | | | dendrite regeneration | |
| | | | extrinsic apoptotic signaling pathway | |
| | | | extrinsic apoptotic signaling pathway in absence of ligand | |
| | | | extrinsic apoptotic signaling pathway via death domain receptors | |
| SESN2 | down | leucine binding oxidoreduce activity, acting on peroxide as acceptor protein binding sulfiredoxin activity NOT sulfiredoxin activity | DNA damage response, signal transduction by p53 class mediator autophagy cellular oxnt detoxification NOT cellular oxnt detoxification cellular oxnt detoxification cellular response to amino acid stimulus cellular response to leucine cellular response to oxtive stress fatty acid beta-oxtion glucose ort mitochondrial DNA metabolic process negative regulation of TORC1 signaling negative regulation of cell growth negative regulation of translation in response to endoplasmic reticulum stress positive regulation of macroautophagy positive regulation of protein localization to nucleus positive regulation of transcription from RNA polymerase II promoter in response to oxtive stress protein kie B signaling | colocalizes_with ATG1/ULK1 kie complex colocalizes_with GATOR2 complex colocalizes_with TORC2 complex cytoplasm cytosol mitochondrion colocalizes_with nucleotide-activated protein kie complex nucleus |

TABLE 5-continued

The function of piRACC targets and their expression in CRC

| Gene | Expression* | Function** | Process** | Component** |
|------|-------------|------------|-----------|-------------|
| | | | reactive oxygen species metabolic process regulation of cAMP-dependent protein kie activity regulation of gluconeogenesis involved in cellular glucose homeosis regulation of protein phosphorylation regulation of response to reactive oxygen species response to glucose response to insulin positive regulation of NF-kappaB transcription factor activity positive regulation of cellular protein metabolic process positive regulation of cholesterol efflux positive regulation of transcription from RNA polymerase II promoter positive regulation of transcription from RNA polymerase II promoter protein ort into nucleus, translocation regulation of NF-kappaB ort into nucleus | |
| UPP1 | down | uridine phosphorylase activity | UMP salvage cellular response to glucose starvation nucleobase-containing compound metabolic process nucleotide catabolic process pyrimidine nucleoside catabolic process pyrimidine nucleoside salvage uridine catabolic process | cytosol |
| ATF3 | down | RNA polymerase II core promoter proximal region sequence-specific DNA binding RNA polymerase II regulatory region sequence-specific DNA binding identical protein binding protein binding protein heterodimerization activity protein homodimerization activity transcription corepressor | PERK-mediated unfolded protein response cellular response to amino acid starvation gluconeogenesis negative regulation of ERK1 and ERK2 cascade negative regulation of transcription from RNA polymerase II promoter positive regulation of TRAIL-activated | CHOP-ATF3 complex nucleolus nucleoplasm nucleus |

TABLE 5-continued

The function of piRACC targets and their expression in CRC

| Gene | Expression* | Function** | Process** | Component** |
|------|-------------|------------|-----------|-------------|
| | | activity transcription factor activity, RNA polymerase II core promoter proximal region sequence-specific binding transcription factor activity, sequence-specific DNA binding transcription regulatory region DNA binding transcription regulatory region sequence-specific DNA binding transcriptional activator activity, RNA polymerase II transcription regulatory region sequence-specific binding transcriptional repressor activity, RNA polymerase II core promoter proximal region sequence-specific binding | apoptotic signaling pathway positive regulation of cell proliferation positive regulation of transcription from RNA polymerase II promoter positive regulation of transcription from RNA polymerase II promoter in response to endoplasmic reticulum stress regulation of transcription from RNA polymerase II promoter in response to arsenic-containing substance skeletal muscle cell differentiation transcription from RNA polymerase II promoter | |

*To compare the expression of target genes in cancer and normal tissues, Oncomine database was analyzed (Rhodes, D. R., et al. ONCOMINE: a cancer microarray database and integrated data-mining platform. Neoplasia, 2004 6, 1-6).
**The function of target gene was provided by Gene Ontology Annotation (UniProt-GOA) Database To further validate the in vitro results that piRACC regulated those tumor suppressors, the expression correlation between piRACC and its target genes in colorectal cancer tissues was investigated. The results indicated that the expression of these targets were all negatively associated with piRACC expression in CRC (P<0.05; FIG. 56). Moreover, several genes have strong inverse correlation with piRACC including MXD1, BTG1 and FAS, suggesting their expression level are probably tightly synchronized with piRACC function.

C. Discussion

Colorectal cancer is one of the most common cancers worldwide. Therefore, elucidating the molecular mechanisms underlying CRC progression is critical for the development of new biomarkers or treatment for the management of patients with this deadly malignancy. Herein, the inventors, for the first time, report piRACC as a novel oncogenic piRNA in CRC. The inventors have made several novel observations in this study. First, the inventors have discovered that piRACC is frequently overexpressed in CRC tissues from different cohorts, and this overexpression associated with several known risk clinicopathological factors. Second, this data revealed that patients with high expression of piRACC had shorter survival compared to those with low level of piRACC, highlighting its applicability as a promising prognostic biomarker in CRC. Third, this is the first study to demonstrate the biological relevance of this piRACC as a tumor-promoting noncoding RNA in CRC. Fourth, microarray analysis showed piRACC regulates several key cancer pathways, supporting its oncogenic role in CRC. Finally, the inventors discovered several important tumor suppressors as direct targets of piRACC, and their expression were observed inversely correlated with the expression of piRACC, suggesting piRACC promotes CRC development through inhibition of these target genes at transcriptional level.

It is believed that there are no previous studies reporting the clinical significance of piRNAs in CRC. In this example, the inventors, for the first time, demonstrate that piRNAs are highly expressed in colorectal cancer by small RNA-seq analysis. Notably, piRACC was found to be consistently overexpressed in colorectal cancer tissues across different cohorts, highlighting its important role in CRC development. Notwithstanding its overexpression in cancer, it was also found that piRACC is a strong disease associated biomarker, whose overexpression correlates with known risk clinicopathological features such as tumor depth, tumor differentiation and metastasis. Furthermore, another major finding is that piRACC was a robust prognostic biomarker for survival prediction in CRC patients. These findings may help to understand the mechanisms of piRNA in metastasis and progression of CRC, and suggest novel small RNA molecules as biomarkers or therapeutic targets.

To better understand the clinical value of piRACC in CRC, its biological significance for its contribution to colorectal carcinogenesis should be considered. The functional experiments of this example provide convincing evidence to support for the associations of piRACC with aggressive clinical phenotype, where piRACC promote CRC cells survival, migration and invasion as well as suppression of apoptosis. Consistent with this paradigm, the microarray analysis clearly showed that piRACC affects cancer-related pathways and functions as oncogenic regulator in downstream gene network. Accordingly, these results successfully proved the assumption, whereby the overexpression of piRACC affects gene regulatory network for CRC and results in its aggressive phenotype both biologically and clinically.

To further decipher the mechanic role of piRACC in CRC, potential targets were identified. By using bioinformatics approach, nine 'functionally relevant' cancer-related genes were identified. Interestingly, these nine candidates are involved in key tumor suppressive pathway and inversely correlated with piRACC expression, supporting the oncogenic role of piRACC in CRC. Surprisingly, piRACC was found not only binds to exon region but also intro region. Recent study reported that piRNA is able to bind to pre-mRNA intron and subsequently leads to the decay of targeted pre-mRNA through nuclear exosomes, suggesting that piRACC may use similar mechanism to downregulate target genes. Furthermore, the inventors observed that piRACC could targets 3'UTR, CDS or 5'UTR region via perfect or imperfect base-pairing between the two RNAs, by a mechanism that closely resembles that of nature antisense, siRNA or miRNA. Although a number of possible scenarios could account for the interaction between piRACC and its targets, the inventors clearly demonstrated the expression of these targets was significantly changed after gain or loss of piRACC in CRC cell lines.

Taken together, these findings implicate piRACC as a potential modulator of colorectal carcinogenesis, a function possibly linked to piRACC dependent mRNA degradation of its downstream targets. However, the precise mechanism for the interaction between piRACC and its targets merits further investigation. The inventors believe that, to the best of their knowledge, that this study represents the first evidence of piRACC as prognostic biomarkers in CRC. Since piRNAs are abundant in cancer tissues, with improving profiling platforms and availability of tumor samples with extensive clinical annotations, it will be helpful to identify new CRC related piRNAs, further the understanding of their mechanistic and prognostic contributions to this disease.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and the publications referred to throughout the specification, to the extent that they provide exemplary procedural or other details supplementary to those set forth herein, are specifically incorporated herein by reference.

Siegel R L, Miller K D, Jemal A. Cancer statistics, 2016. CA: a cancer journal for clinicians 2016; 66: 7-30.

Duffy M J. Carcinoembryonic antigen as a marker for colorectal cancer: is it clinically useful?Clin Chem 2001; 47: 624-630.

Aragane H, Sakakura C, Nakanishi M et al. Chromosomal aberrations in colorectal cancers and liver metastases analyzed by comparative genomic hybridization. International journal of cancer 2001; 94: 623-629.

Ghadimi B M, Grade M, Liersch T et al. Gain of chromosome 8q23-24 is a predictive marker for lymph node positivity in colorectal cancer. Clinical cancer research: an official journal of the American Association for Cancer Research 2003; 9: 1808-1814.

Douglas E J, Fiegler H, Rowan A et al. Array comparative genomic hybridization analysis of colorectal cancer cell lines and primary carcinomas. Cancer research 2004; 64: 4817-4825.

Pomerantz M M, Ahmadiyeh N, Jia L et al. The 8q24 cancer risk variant rs6983267 shows long-range interaction with MYC in colorectal cancer. Nature genetics 2009; 41: 882-884.

Grisanzio C, Freedman M L. Chromosome 8q24-Associated Cancers and MYC. Genes & cancer 2010; 1: 555-559.

Ling H, Vincent K, Pichler M et al. Junk DNA and the long non-coding RNA twist in cancer genetics. Oncogene 2015; 34: 5003-5011.

Lujambio A, Lowe S W. The microcosmos of cancer. Nature 2012; 482: 347-355.

Gibb E A, Brown C J, Lam W L. The functional role of long non-coding RNA in human carcinomas. Molecular cancer 2011; 10: 38.

McShane L M, Altman D G, Sauerbrei W et al. REporting recommendations for tumor MARKer prognostic studies (REMARK). Nat Clin Pract Oncol 2005; 2: 416-422.

Ling H, Spizzo R, Atlasi Y et al. CCAT2, a novel noncoding RNA mapping to 8q24, underlies metastatic progression and chromosomal instability in colon cancer. Genome research 2013; 23: 1446-1461.

Xiang J F, Yin Q F, Chen T et al. Human colorectal cancer-specific CCAT1-L lncRNA regulates long-range chromatin interactions at the MYC locus. Cell research 2014; 24: 513-531.

Takahashi Y, Sawada G, Kurashige J et al. Amplification of PVT-1 is involved in poor prognosis via apoptosis inhibition in colorectal cancers. British journal of cancer 2014; 110: 164-171.

Kim T, Cui R, Jeon Y J et al. Long-range interaction and correlation between MYC enhancer and oncogenic long noncoding RNA CARLo-5. Proceedings of the National Academy of Sciences of the United States of America 2014; 111: 4173-4178.

Sur I K, Hallikas O, Vaharautio A et al. Mice lacking a Myc enhancer that includes human SNP rs6983267 are resistant to intestinal tumors. Science 2012; 338: 1360-1363.

Tuupanen S, Yan J, Turunen M et al. Characterization of the colorectal cancer-associated enhancer MYC-335 at 8q24: the role of rs67491583. Cancer Genet 2012; 205: 25-33.

Takatsuno Y, Mimori K, Yamamoto K et al. The rs6983267 SNP is associated with MYC transcription efficiency, which promotes progression and worsens prognosis of colorectal cancer. Ann Surg Oncol 2013; 20: 1395-1402.

Haller D G. An overview of adjuvant therapy for colorectal cancer. Eur J Cancer 1995; 31A: 1255-1263.

O'Connor E S, Greenblatt D Y, LoConte N K et al. Adjuvant chemotherapy for stage II colon cancer with poor prognostic features. J Clin Oncol 2011; 29: 3381-3388.

Sonnenberg, A., Delco, F. & Inadomi, J. M. Cost-effectiveness of colonoscopy in screening for colorectal cancer. *Ann Intern Med* 133, 573-584 (2000).

Pourhoseingholi, M. A. Increased burden of colorectal cancer in Asia. *World J Gastrointest Oncol* 4, 68-70 (2012).

Ferlay, J., et al. Estimates of worldwide burden of cancer in 2008: GLOBOCAN 2008. *Int J Cancer* 127, 2893-2917 (2010).

Reimers, M. S., Zeestraten, E. C., Kuppen, P. J., Liefers, G. J. & van de Velde, C. J. Biomarkers in precision therapy in colorectal cancer. *Gastroenterol Rep (Oxf)* 1, 166-183 (2013).

Wilkes, G. M. Metastatic colorectal cancer: management challenges and opportunities. *Oncology (Williston Park)* 25, 32-44 (2011).

Weng, W., Feng, J., Qin, H., Ma, Y. & Goel, A. An update on miRNAs as biological and clinical determinants in colorectal cancer: a bench-to-bedside approach. *Future Oncol* 11, 1791-1808 (2015).

Stiegelbauer, V., et al. MicroRNAs as novel predictive biomarkers and therapeutic targets in colorectal cancer. *World J Gastroenterol* 20, 11727-11735 (2014).

Moyano, M. & Stefani, G. piRNA involvement in genome stability and human cancer. *J Hematol Oncol* 8, 38 (2015).

Mei, Y., Clark, D. & Mao, L. Novel dimensions of piRNAs in cancer. *Cancer Lett* 336, 46-52 (2013).

Siddiqi, S. & Matushansky, I. Piwis and piwi-interacting RNAs in the epigenetics of cancer. *J CellBiochem* 113, 373-380 (2012).

Thorenoor, N. & Slaby, O. Small nucleolar RNAs functioning and potential roles in cancer. *Tumour Biol* 36, 41-53 (2015).

Fu, Y., Lee, I., Lee, Y. S. & Bao, X. Small Non-coding Transfer RNA-Derived RNA Fragments (tRFs): Their Biogenesis, Function and Implication in Human Diseases. *Genomics Inform* 13, 94-101 (2015).

Carmell, M. A., et al. MIWI2 is essential for spermatogenesis and repression of transposons in the mouse male germline. *Dev Cell* 12, 503-514 (2007).

Deng, W. & Lin, H. miwi, a murine homolog of piwi, encodes a cytoplasmic protein essential for spermatogenesis. *Dev Cell* 2, 819-830 (2002).

Kuramochi-Miyagawa, S., et al. Mili, a mammalian member of piwi family gene, is essential for spermatogenesis. *Development* 131, 839-849 (2004).

Ross, R. J., Weiner, M. M. & Lin, H. PIWI proteins and PIWI-interacting RNAs in the soma. *Nature* 505, 353-359 (2014).

Yan, Z., et al. Widespread expression of piRNA-like molecules in somatic tissues. *Nucleic Acids Res* 39, 6596-6607 (2011).

Lee, E. J., et al. Identification of piRNAs in the central nervous system. *RNA* 17, 1090-1099 (2011).

Rajasethupathy, P., et al. A role for neuronal piRNAs in the epigenetic control of memory-related synaptic plasticity. *Cell* 149, 693-707 (2012).

Martinez, V. D., et al. Unique somatic and malignant expression patterns implicate PIWI-interacting RNAs in cancer-type specific biology. *Sci Rep* 5, 10423 (2015).

Kozomara, A. & Griffiths-Jones, S. miRBase: annotating high confidence microRNAs using deep sequencing data. *Nucleic Acids Res* 42, D68-73 (2014).

Kozomara, A. & Griffiths-Jones, S. miRBase: integrating microRNA annotation and deep-sequencing data. *Nucleic Acids Res* 39, D152-157 (2011).

Okugawa, Y., et al. Clinical significance of SNORA42 as an oncogene and a prognostic biomarker in colorectal cancer. *Gut* (2015).

Hur, K., et al. Identification of a metastasis-specific MicroRNA signature in human colorectal cancer. *J Natl Cancer Inst* 107(2015).

Han, T. S., et al. MicroRNA-29c mediates initiation of gastric carcinogenesis by directly targeting ITGB1. *Gut* 64, 203-214 (2015).

Horwich, M. D. & Zamore, P. D. Design and delivery of antisense oligonucleotides to block microRNA function in cultured *Drosophila* and human cells. *Nat Protoc* 3, 1537-1549 (2008).

Wang, Z., Liu, N., Shi, S., Liu, S. & Lin, H. The Role of PIWIL4, an Argonaute Family Protein, in Breast Cancer. *J Biol Chem* 291, 10646-10658 (2016).

Krishnan, P., et al. Piwi-interacting RNAs and PIWI genes as novel prognostic markers for breast cancer. *Oncotarget* (2016).

Navarro, A., et al. The significance of PIWI family expression in human lung embryogenesis and non-small cell lung cancer. *Oncotarget* 6, 31544-31556 (2015).

Al-Janabi, O., et al. Piwi-like 1 and 4 gene transcript levels are associated with clinicopathological parameters in renal cell carcinomas. *Biochim Biophys Acta* 1842, 686-690 (2014).

Chen, C., Liu, J. & Xu, G. Overexpression of PIWI proteins in human stage III epithelial ovarian cancer with lymph node metastasis. *Cancer Biomark* 13, 315-321 (2013).

Rhodes, D. R., et al. ONCOMINE: a cancer microarray database and integrated data-mining platform. *Neoplasia* 6, 1-6 (2004).

Uhlen, M., et al. Proteomics. Tissue-based map of the human proteome. *Science* 347, 1260419 (2015).

Uhlen, M., et al. Towards a knowledge-based Human Protein Atlas. *Nat Biotechnol* 28, 1248-1250 (2010).

Uhlen, M., et al. A human protein atlas for normal and cancer tissues based on antibody proteomics. *Mol Cell Proteomics* 4, 1920-1932 (2005).

Ponten, F., Jirstrom, K. & Uhlen, M. The Human Protein Atlas—a tool for pathology. *J Pathol* 216, 387-393 (2008).

Glinsky, G. V., Glinsky, V. V., Ivanova, A. B. & Hueser, C. J. Apoptosis and metastasis: increased apoptosis resistance of metastatic cancer cells is associated with the profound deficiency of apoptosis execution mechanisms. *Cancer Lett* 115, 185-193 (1997).

Zhang, P., et al. MIWI and piRNA-mediated cleavage of messenger RNAs in mouse testes. *Cell Res* 25, 193-207 (2015).

Zhong, F., et al. A SnoRNA-derived piRNA interacts with human interleukin-4 pre-mRNA and induces its decay in nuclear exosomes. *Nucleic Acids Res* 43, 10474-10491 (2015).

Watanabe, T. & Lin, H. Posttranscriptional regulation of gene expression by Piwi proteins and piRNAs. *Mol Cell* 56, 18-27 (2014).

Weick, E. M. & Miska, E. A. piRNAs: from biogenesis to function. *Development* 141, 3458-3471 (2014).

Ishizu, H., Siomi, H. & Siomi, M. C. Biology of PIWI-interacting RNAs: new insights into biogenesis and function inside and outside of germlines. *Genes Dev* 26, 2361-2373 (2012).

Cheng, J., et al. piR-823, a novel non-coding small RNA, demonstrates in vitro and in vivo tumor suppressive activity in human gastric cancer cells. *Cancer Lett* 315, 12-17 (2012).

Cheng, J., et al. piRNA, the new non-coding RNA, is aberrantly expressed in human cancer cells. *Clin Chim Acta* 412, 1621-1625 (2011).

What is claimed is:

1. A method for treating a patient having colorectal cancer comprising: administering adjuvant therapy to the patient; wherein the patient was determined to have an increased expression level of miR-32, miR-181b-1, miR-188, miR-193b, miR-195, miR-424, miR-425, miR-592, miR-3677, and miR-4326 in a colorectal cancer biopsy sample; wherein the expression is increased in comparison to the expression levels of the same miRNAs in colorectal cancer tissue samples obtained from patients without lymph node metastasis.

2. The method of claim 1, wherein the method further comprises measuring expression levels of the miRNAs in the colorectal cancer biopsy sample.

3. The method of claim 2, wherein the method further comprises comparing the expression levels of the miRNAs in the colorectal cancer biopsy sample to the expression levels of the same miRNAs in colorectal cancer tissue samples obtained from patients without lymph node metastasis.

4. The method of claim 2, wherein the method further comprises calculating a risk score based on the expression levels of the miRNAs in the colorectal cancer biopsy sample.

5. The method of claim 4, wherein the risk score is compared to a cut-off value.

6. The method of claim 1, wherein the patient has Stage I, II, III, or IV colorectal cancer.

7. The method of claim 1, wherein the expression levels are normalized.

8. The method of claim 1, wherein the adjuvant therapy comprises cetuximab, 5-fluorouracil, oxaliplatin, irinotecan, bevacizumab, panitumumab, afibercept, leucovorin, and/or radiotherapy.

9. The method of claim 1, wherein the method further comprises surgical resection of a primary tumor or metastatic tumor.

10. The method of claim 1, wherein the patient was determined to have one or more risk factors selected from poorly differentiated tissues, increased tumor depth; lymphatic invasion, and venous invasion.

* * * * *